United States Patent
Li et al.

(10) Patent No.: US 11,815,514 B2
(45) Date of Patent: Nov. 14, 2023

(54) METHODS AND COMPOSITIONS RELATED TO TOXICITY ASSOCIATED WITH CELL THERAPY

(71) Applicants: Juno Therapeutics, Inc., Seattle, WA (US); Fred Hutchinson Cancer Center, Seattle, WA (US)

(72) Inventors: He Li, Seattle, WA (US); Mark J. Gilbert, Seattle, WA (US); David Maloney, Seattle, WA (US); Stanley R. Riddell, Seattle, WA (US); Cameron J. Turtle, Seattle, WA (US)

(73) Assignees: Juno Therapeutics, Inc., Seattle, WA (US); Fred Hutchinson Cancer Research Center, Seattle, WA (US)

( * ) Notice: Subject to any disclaimer, the term of this patent is extended or adjusted under 35 U.S.C. 154(b) by 713 days.

(21) Appl. No.: 15/781,089

(22) PCT Filed: Dec. 2, 2016

(86) PCT No.: PCT/US2016/064865
§ 371 (c)(1),
(2) Date: Jun. 1, 2018

(87) PCT Pub. No.: WO2017/096331
PCT Pub. Date: Jun. 8, 2017

(65) Prior Publication Data
US 2019/0277858 A1    Sep. 12, 2019

Related U.S. Application Data

(60) Provisional application No. 62/417,284, filed on Nov. 3, 2016, provisional application No. 62/263,612, filed on Dec. 4, 2015.

(51) Int. Cl.
*G01N 33/68* (2006.01)
*A61K 39/00* (2006.01)

(52) U.S. Cl.
CPC ...... *G01N 33/6863* (2013.01); *A61K 39/0011* (2013.01); *G01N 33/6866* (2013.01); *G01N 33/6869* (2013.01); *A61K 2039/5156* (2013.01); *A61K 2039/5158* (2013.01)

(58) Field of Classification Search
CPC .......... G01N 33/6863; G01N 33/6869; G01N 33/6866; A61K 39/0011; A61K 2039/5156; A61K 2039/5158
See application file for complete search history.

(56) References Cited

U.S. PATENT DOCUMENTS

| | | |
|---|---|---|
| 4,235,871 A | 11/1980 | Papahadjopoulos et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 5,019,369 A | 5/1991 | Presant et al. |
| 5,087,616 A | 2/1992 | Myers et al. |
| 5,200,084 A | 4/1993 | Liberti et al. |
| 5,219,740 A | 6/1993 | Miller et al. |
| 5,591,827 A | 1/1997 | Brakenhoff et al. |
| 6,040,177 A | 3/2000 | Riddell et al. |
| 6,207,453 B1 | 3/2001 | Maass et al. |
| 6,410,319 B1 | 6/2002 | Raubitschek et al. |
| 6,451,995 B1 | 9/2002 | Cheung et al. |
| 7,070,995 B2 | 7/2006 | Jensen |
| 7,235,240 B2 | 6/2007 | Grabstein et al. |
| 7,265,209 B2 | 9/2007 | Jensen |
| 7,354,762 B2 | 4/2008 | Jensen |
| 7,446,179 B2 | 11/2008 | Jensen et al. |

(Continued)

FOREIGN PATENT DOCUMENTS

| | | |
|---|---|---|
| EP | 2537416 | 11/2014 |
| EP | 2 277 543 | 12/2015 |

(Continued)

OTHER PUBLICATIONS

Shimabukuro-Vornhagen, A., et al. Cytokine release syndrome. Journal for ImmunoTherapy of Cancer, 2018, 6:56, p. 1-14.*
Siebert, J.C. et al. Monitoring cytokine profiles during immunotherapy. Immunotherapy, 2010, 2(6):799-816).*
Siebert et al. Immunotherapy, 2010, 2(6):799-816 (Year: 2010).*
Vajdos et al. Comprehensive Functional Maps of the Antigen binding Site of an Anti-ErbB2 Antibody Obtained with Shotgun Scanning Mutagenesis. J Mol Biol. Jul. 5, 2002;320(2):415-28 (Year: 2002).*
Brown et al. Tolerance to Single, but Not Multiple, Amino Acid Replacements in Antibody VH CDR2. J Immunol. May 1996; 156(9):3285-91 (Year: 1996).*
Guido et al. Virtual Screening and Its Integration with Modern Drug Design Technologies. Curr Med Chem. 2008; 15(1):37-46 (Year: 2008).*

(Continued)

*Primary Examiner* — Vanessa L. Ford
*Assistant Examiner* — Sandra Dillahunt
(74) *Attorney, Agent, or Firm* — MORRISON & FOERSTER LLP

(57) ABSTRACT

Provided are methods, kits and compositions related to toxicity associated with administration of cell therapy for the treatment of diseases or conditions, e.g., cancer, including methods for use in predicting and treating a toxicity. In some embodiments, the toxicity is a neurotoxicity or cytokine release syndrome (CRS), such as a severe neurotoxicity or a severe CRS. The methods generally involve detecting a parameter of a biomarker or individually a parameter of each biomarker in a panel of biomarkers, such as a concentration, amount or activity, and comparing the detected parameter to a reference value for the parameter to determine if the subject is at risk for developing the toxicity, such as neurotoxicity or CRS or severe neurotoxicity or severe CRS. In some embodiments, the methods further involve administering an agent or therapy for treating, ameliorating, preventing, delaying and/or attenuating the development of the toxicity, such as neurotoxicity or CRS, such as severe neurotoxicity or severe CRS.

31 Claims, 43 Drawing Sheets
Specification includes a Sequence Listing.

(56) References Cited

U.S. PATENT DOCUMENTS

| | | | |
|---|---|---|---|
| 7,446,190 B2 | 11/2008 | Sadelain et al. | |
| 7,446,191 B2 | 11/2008 | Jensen | |
| 7,514,444 B2 | 4/2009 | Honigberg et al. | |
| 8,008,309 B2 | 8/2011 | Honigberg et al. | |
| 8,324,353 B2 | 12/2012 | Jensen | |
| 8,339,645 B2 | 12/2012 | Nakawaki | |
| 8,389,282 B2 | 3/2013 | Sadelain et al. | |
| 8,476,284 B2 | 7/2013 | Honigberg et al. | |
| 8,479,118 B2 | 7/2013 | Lyndersay et al. | |
| 8,497,277 B2 | 7/2013 | Honigberg et al. | |
| 8,697,711 B2 | 4/2014 | Honigberg et al. | |
| 8,703,780 B2 | 4/2014 | Honigberg et al. | |
| 8,735,403 B2 | 5/2014 | Honigberg et al. | |
| 8,754,090 B2 | 6/2014 | Buggy et al. | |
| 8,754,091 B2 | 6/2014 | Honigberg et al. | |
| 8,802,374 B2 | 8/2014 | Jensen | |
| 8,822,647 B2 | 9/2014 | Jensen | |
| 8,911,993 B2 | 12/2014 | June et al. | |
| 8,957,079 B2 | 2/2015 | Honigberg et al. | |
| 8,999,999 B2 | 4/2015 | Buggy et al. | |
| 9,125,889 B2 | 9/2015 | Buggy et al. | |
| 9,181,257 B2 | 11/2015 | Honigberg et al. | |
| 9,296,753 B2 | 3/2016 | Smyth et al. | |
| 2002/0131960 A1* | 9/2002 | Sadelain | G01N 33/56977 424/93.21 |
| 2003/0170238 A1* | 9/2003 | Gruenberg | A61K 39/395 424/144.1 |
| 2011/0003380 A1* | 1/2011 | Miltenyi | C12M 47/04 435/325 |
| 2013/0149337 A1* | 6/2013 | Cooper | A61K 39/001124 424/209.1 |
| 2013/0287748 A1* | 10/2013 | June | A61K 39/0011 424/93.21 |
| 2014/0271635 A1* | 9/2014 | Brogdon | C07K 14/70503 424/133.1 |

FOREIGN PATENT DOCUMENTS

| | | |
|---|---|---|
| WO | WO-1992/008796 | 5/1992 |
| WO | WO-1994/028143 | 12/1994 |
| WO | WO-2000/14257 | 3/2000 |
| WO | WO-2010/033140 | 3/2009 |
| WO | WO-2009/072003 | 6/2009 |
| WO | WO-2012/129514 | 9/2012 |
| WO | WO-2013/071154 | 5/2013 |
| WO | WO-2013/123061 | 8/2013 |
| WO | WO-2013/126726 | 8/2013 |
| WO | WO-2013/166321 | 11/2013 |
| WO | WO-2014/011984 | 1/2014 |
| WO | WO-2014/031687 | 2/2014 |
| WO | WO-2014/055668 | 4/2014 |
| WO | WO-2015/136298 | 9/2015 |
| WO | WO-2017/165571 | 9/2017 |
| WO | WO-2018/093591 | 5/2018 |
| WO | WO-2018/223101 | 12/2018 |

OTHER PUBLICATIONS

Clark et al. Discovery and Development of Janus Kinase (JAK) Inhibitors for Inflammatory Diseases. J. Med. Chem., 2014, 57 (12), pp. 5023-5038 (Year: 2014).*

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

Bork. Powers and Pitfalls in Sequence Analysis: The 70% Hurdle. Genome Research, 2000, 10:398-400 (Year: 2000).*

Aagaard et al. RNAi therapeutics: Principles, prospects and challenges. Advanced Drug Delivery Reviews 59 (2007) 75-86 (Year: 2007).*

Warzocha et al. Antisense Strategy: Biological Utility and Prospects in the Treatment of Hematological Malignancies. Leukemia and Lymphoma, 1997; 24(3-4): 267-281 (Year: 1997).*

Maude et al. Managing Cytokine Release Syndrome Associated With Novel T Cell-Engaging Therapies. Cancer J. 2014; 20(2): 119-122 (Year: 2014).*

Lee et al. Current concepts in the diagnosis and management of cytokine release syndrome. Blood, Jul. 10, 2014; 124(2): 188-195 (Year: 2014).*

Grupp et al. CD19-redirected chimeric antigen receptor t (CART19) cells induce a cytokine release syndrome (CRS) and induction of treatable macrophage activation syndrome (MAS) that can be managed by the IL-6 antagonist tocilizumab (TOC). Blood, 2012; 120(21) (Year: 2012).*

Bonifant et al. Toxicity and management in CAR T-cell therapy. Molecular Therapy—Oncolytics (2016) 3, 16011 (Year: 2016).*

Vajdos et al. J Mol Biol. Jul. 5, 2002;320(2):415-28 (Year: 2002).*

Brown et al. J Immunol. May 1996; 156(9):3285-91 (Year: 1996).*

Guido et al. Curr Med Chem. 2008; 15(1):37-46 (Year: 2008).*

Clark et al J. Med. Chem., 2014, 57 (12), pp. 5023-5038 (Year: 2014).*

Bowie et al. Science, 1990, 247:1306-1310 (Year: 1990).*

Burgess et al. J. Cell Biol. 111:2129-2138, 1990 (Year: 1990).*

Lazar et al. Mol. Cell. Biol., 8:1247-1252, 1988 (Year: 1988).*

Bork. Genome Research, 2000, 10:398-400 (Year: 2000).*

Aagaard et al. Advanced Drug Delivery Reviews 59 (2007) 75-86 (Year: 2007).*

Warzocha et al. Leukemia and Lymphoma, 1997; 24(3-4): 267-281 (Year: 1997).*

Shimabukuro-Vonrhagen et al., J. ImmunoTherapy Cancer, 2018, 6:56, p. 1-14 (Year: 2018).*

Lee et al. Blood, 2014, 124(2):188-195 (Year: 2014).*

Maude et al. Cancer J. 2014; 20(2): 119-122 (Year: 2014).*

Lee et al. Blood. Jul. 10, 2014; 124(2): 188-195 (Year: 2014).*

Grupp et al. Blood, 2012; 120(21) (Year: 2012).*

Bonifant et al. Molecular Therapy—Oncolytics (2016) 3, 16011 (Year: 2016).*

Turtle et al. Blood 2015; 126 (23): 3773 (Year: 2015).*

Alonso-Camino et al., "CARbodies: Human Antibodies Against Cell Surface Tumor Antigens Selected From Repertoires Displayed on T Cell Chimeric Antigen Receptors," Mol Ther ucleic Acids (2013) 2(5):e93.

Barret et al., "Chimeric Antigen Receptor Therapy for Cancer," Annual Review of Medicine (2014) 65:333-347.

Barret et al., "Interleukin 6 Is Not Made by Chimeric Antigen Receptor T Cells and Does Not Impact Their Function," Abstract 654. Presented at ASH 58th Annual Meeting San Diego, CA (Dec. 3-6, 2016).

Basu et al., "Use of a novel hemoadsorption device for cytokine removal as adjuvant therapy in a patient with septic shock with multi-organ dysfunction: A case study," Indian J Crit Care Med (2014) 18(12):822-824.

Baum et al., "Retrovirus Vectors: Toward the Plentivirus?" Mol Ther (2006) 13(6):1050-1063.

Boris-Lawrie., "Recent advances in retrovirus vector technology," Curr Opin Genet (1993) 3:102-109.

Brash et al., "Strontium phosphate transfection of human cells in primary culture: stable expression of the simian virus 40 large-T-antigen gene in primary human bronchial epithelial cells," Mol Cell Biol (1987) 7:2031-2034.

Brentjens et al., "CD19-targeted T cells rapidly induce molecular remissions in adults with chemotherapy-refractory acute lymphoblastic leukemia," Sci Transl Med (2013) 5(177):177ra38.

Burns et al., "Vesicular stomatitis virus G glycoprotein pseudotyped retroviral vectors: concentration to very high titer and efficient gene transfer into mammalian and nonmammalian cells," PNAS (1993) 90(17):8033-8037.

(56) References Cited

OTHER PUBLICATIONS

Carlens et al., "Ex vivo T lymphocyte expansion for retroviral transduction: influence of serum-free media on variations in cell expansion rates and lymphocyte subset distribution," Exp Hematol (2000) 28(10):1137-1146.

Cavaletti et al., "Chemotherapy-induced peripheral neurotoxicity," Nature Reviews Neurology (2010) 6:657-666.

Cavalieri et al., "Human T lymphocytes transduced by lentiviral vectors in the absence of TCR activation maintain an intact immune competence," Blood (2003) 102(2):497-505.

Cheadle et al., "Chimeric antigen receptors for T-cell based therapy," Methods Mol Biol (2012) 907:645-666.

Chicaybam et al., "An Efficient Low Cost Method for Gene Transfer to T Lymphocytes," PLoS ONE (2013) 8(3):e60298.

Cho et al., "Human mammalian cell sorting using a highly integrated micro-fabricated fluorescence-activated cell sorter (µFACS)," Lap Chip (2010) 10:1567-1573.

Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175:5799-5808.

Cooper et al., "T-cell clones can be rendered specific for CD19: toward the selective augmentation of the graft-versus-B—lineage leukemia effect," Blood (2003) 101:1637-1644.

Davila et al., "CD19 CAR-Targeted T Cells Induce Long-Term Remission and B Cell Aplasia in an Immunocompetent Mouse Model of B Cell Acute Lymphoblastic Leukemia," PLoS ONE (2013) 8(4):e61338.

Davila et al., "Efficacy and Toxicity Management of 19-28z CAR T Cell Therapy in B Cell Acute Lymphoblastic Leukemia," Sci Transl Med (2014) 6(224):224ra25.

Dobber et al., "The in vivo effects of neutralizing antibodies against IFN-gamma, IL-4, or IL-10 on the humoral immune response in young and aged mice," Cell Immunol (1995) 160(2):185-192.

Dupont et al., "Validation and comparison of luminex multiplex cytokine analysis kits with ELISA: determinations of a panel of nine cytokines in clinical sample culture supernatants," J Reprod Immunol. (2005) 66(2):175-191.

Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.

Fleischmann et al., "Safety of extended treatment with anakinra in patients with rheumatoid arthritis," Ann Rheum Dis (2006) 65(8):1006-1012.

Frecha et al., "Advances in the Field of Lentivector-based Transduction of T and B Lymphocytes for Gene Therpy," Mol Ther (2010) 18(10):1748-1757.

Godin et al., "Microfluidics and photonics for Bio-System-on-a-Chip: a review of advancements in technology towards a microfluidic flow cytometry chip," J Biophotonics (2008) 1(5):355-376.

Gong et al., "An Antagonist of Monocyte Chemoattractant Protein 1 (MCP-1) Inhibits Arthritis in the MRL-lpr Mouse Model," J Exp Med (1997) 186(1):131-137.

Grupp et al., "Chimeric antigen receptor-modified T cells for acute lymphoid leukemia," N Engl J Med. Apr. 18, 2013;368(16):1509-1518.

Hackett et al., "A transposon and transposase system for human application," Mol Ther (2010) 18(4):674-683.

Hannum et al., "Interleukin-1 receptor antagonist activity of a human interleukin-1 inhibitor," Nature (1990) 343:336-340.

Hermans et al., "The Vital assay: a versatile fluorometric technique for assessing CTL- and NKT-mediated cytotoxicity against multiple targets in vitro and in vivo," J Immunol Methods (2004) 285(1):25-40.

Huang et al., "DNA transposons for modification of human primary T lymphocytes," Methods Mol Biol (2009) 506:115-126.

Hudecek et al., "Receptor affinity and extracellular domain modifications affect tumor recognition by ROR1-specific chimeric antigen receptor T cells," Clin Cancer Res (2013) 19(12):3153-3164.

Hunter et al., "Neutralizing anti-IL-10 antibody blocks the protective effect of tapeworm infection in a murine model of chemically induced colitis," J Immunol (2005) 174(11):7368-7375.

Johnston et al., "Biolistic transformation: microbes to mice," Nature (1990) 346:776-777.

Klebanoff et al., "Sorting through subsets: Which T cell populations mediate highly effective adoptive immunotherapy?" J Immunother (2012) 35(9):651-660.

Kochenderfer et al., "B-cell depletion and remissions of malignancy along with cytokine-associated toxicity in a clinical trial of anti-CD19 chimeric-antigen-receptor-transduced T cells," Blood (2012) 119:2709-2720.

Kochenderfer et al., "Construction and preclinical evaluation of an anti-CD19 chimeric antigen receptor," J Immunother (2009( 32(7):689-702.

Kochenderfer et al., "Treating B-cell cancer with T cells expressing anti-CD19 chimeric antigen receptors," Nat Rev Clin Oncol (2013) 10(5):267-276.

Koste et al., "T-cell receptor transfer into human T cells with ecotropic retroviral vectors," Gene Therapy (2014) 21:533-538.

Lee et al., "Current Concepts in the Diagnosis and Management of Cytokine Release Syndrome," Blood (2014) 124(2): 188-195.

Li et al., "Directed evolution of human T-cell receptors with picomolar affinities by phage display," Nat Biotechnol (2005) 23(3):349-354.

Lupton et al., "Dominant positive and negative selection using a hygromycin phosphotransferase-thymidine kinase fusion gene," Mol and Cell Biol (1991) 11(6):3374-3378.

Manuri et al., "piggyBac Transposon/Transposase System to Generate CD19-Specific T Cells for the Treatment of B-Lineage Malignancies," Hum Gene Ther (2010) 21(4):427-437.

Martinez-Lopez et al. "Prognostic value of deep sequencing method for minimal residual disease detection in multiple myeloma," Blood. 2014;123(20):3073-3079.

Mesa et al., "Ruxolitinib," Nature Reviews Drug Disovery (2012) 11(2):103-104.

Miller et al., "Improved retroviral vectors for gene transfer and expression," Biotechniques (1989) 7(9):980-982.

Miller, "Retrovirus packaging cells," Hum Gene Ther (1990) 1(1):5-14.

Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.

Muller et al., "Amino-substituted thalidomide analogs: Potent inhibitors of TNF-α production," Bioorganic & Medicinal Chemistry Letters (1999) 9(11):1625-1630.

Ozmen et al., "Mouse soluble IFN gamma receptor as IFN gamma inhibitor. Distribution, antigenicity, and activity after injection in mice," J Immunol (1993) 150(7):2698-2705.

Park et al., "Treating cancer with genetically engineered T cells," Trends Biotechnol (2011) 29(11):550-557.

Parkhurst et al., "Characterization of Genetically Modified T-Cell Receptors that Recognize the CEA:691-699 Peptide in the Context of HLA-A2.1 on Human Colorectal Cancer Cells," Clin Cancer Res (2009) 15(1):169-180.

Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant," Human Gene Therapy (1992) 3:319-338.

Rosenberg et al., "Cell transfer immunotherapy for metastatic solid cancer—what clinicians need to know," Nat Rev Clin Oncol (2011) 8(10):577-585.

Rossi et al., "Phase 1 Biomarker Analysis of the ZUMA-1 (KTE-C19-101) Study: A Phase 1-2 Multi-Center Study Evaluating the Safety and Efficacy of Anti-CD19 CAR T Cells (KTE-C19) in Subjects with Refractory Aggressive Non-Hodgkin Lymphoma (NHL)," Blood (2015) 126:2730.

Ruella et al., "Kinase Inhibitor Ibrutinib Prevents Cytokine-Release Syndrome after Anti-CD19 Chimeric Antigen Receptor T Cells (CART) for B Cell Neoplasms," Abstract 2159. Presented at ASH 58th Annual Meeting San Diego, CA (Dec. 3-6, 2016).

(56) References Cited

OTHER PUBLICATIONS

Sadelain et al., "The basic principles of chimeric antigen receptor (CAR) design," Cancer Discov (2013) 3(4):388-398.
Scarpa et al., "Characterization of recombinant helper retroviruses from Moloney-based vectors in ecotropic and amphotropic packaging cell lines," Virology (1991) 180(2):849-852.
Shahrara et al., "Inhibition of Monocyte Chemoattractant Protein-1 Ameliorates Rat Adjuvant-Induced Arthritis," J Imunol (2008) 180:3447-3456.
Sharma et al., "Efficient Sleeping Beauty DNA Transposition From DNA Minicircles," Molec Ther Nucl Acids (2013) 2:e74.
Szoka et al., "Comparative properties and methods of preparation of lipid vesicles (liposomes)," Annu Rev Biophys Bioeng (1980) 9:467-508.
Teachey et al., "Biomarkers Accurately Predict Cytokine Release Syndrome (CRS) after Chimeric Antigen Receptor (CAR) T Cell Therapy for Acute Lymphoblastic Leukemia (ALL)," Blood (2015) 126(23):1334.
Terakura et al., "Generation of CD19-chimeric antigen receptor modified CD8+ T cells derived from virus-specific central memory T cells," Blood (2012) 119(1):72-82.
Themeli et al., "Generation of tumor-targeted human T lymphocytes from induced pluripotent stem cells for cancer therapy," Nat Biotechnol (2013) 31(10):928-933.
Tsukahara et al., "CD19 target-engineered T-cells accumulate at tumor lesions in human B-cell lymphoma xenograft mouse models," Biochem Biophys Res Commun (2013) 438(1):84-89.
Turtle et al. "Biomarkers of Cytokine Release Syndrome and Neurotoxicity after CD19 CAR-T Cells and Mitigation of Toxicity by Cell Dose." Abstract #1852. Presented at ASH, San Diego, CA (Dec. 3, 2016).
Turtle et al., "Addition of Fludarabine to Cyclophosphamide Lymphodepletion Improves In Vivo Expansion of CD19 Chimeric Antigen Receptor-Modified T Cells and Clinical Outcome in Adults with B Cell Acute Lymphoblastic Leukemia," Blood (2015) 126(23):3773.
Turtle et al., "CD19 CAR-T cells of defined CD4+:CD8+ composition in adult B cell ALL patients," J Clinical Investigation (2016) 126(6):2123-2138.
Turtle et al., "Engineered T cells for anti-cancer therapy," Engineered T cells for anti-cancer therapy, Curr Opin Immunol (2012) 24(5):633-639.
Turtle et al., "Immunotherapy with CD19-specific chimeric antigen receptor-modified T cells of defined subset composition for NHL and CLL," Presentation. Presented at ASH, San Diego, CA (Dec. 6, 2015) 16 pages.
Turtle et al., "Immunotherapy of non-Hodgkin's lymphoma with a defined ratio of CD8+ and CD4+ CD19-specific chimeric antigen receptor-modified T cells," Sci Trasl Med (2016) 8(355):355ra116.
Van Tedeloo et al., "High-level transgene expression in primary human T lymphocytes and adult bone marrow CD34+ cells via electroporation-mediated gene delivery," Gene Therpay (2000) 7(16):1431-1437.
Varela-Rohena et al., "Control of HIV-1 immune escape by CD8 T cells expressing enhanced T-cell receptor," Nat Med (2008) 14:1390-1395.
Verhoeyen et al., "Lentiviral vector gene transfer into human T cells," Methods Mol Biol (2009) 506:97-114.
Wadhwa et al., "Receptor mediated glycotargeting," J Drug Target (1995) 3(2):111-127.
Wang et al., "Phenotypic and Functional Attributes of Lentivirus Modified CD19-specific Human CD8+ Central Memory T Cells Manufactured at Clinical Scale," J Immunother (2012) 35(9):689-701.
Wigler et al., "Transfer of Purified Herpes Virus Thymidine Kinase Gene to Cultured Mouse Cells," Cell 2:223, 1977.
Wu et al., "Adoptive T-cell therapy using autologous tumor-infiltrating lymphocytes for metastatic melanoma: current status and future outlook," Cancer J (2012) 18(2):160-175.
Xu et al., "Cytokine release syndrome in cancer immunotherapy with chimeric antigen receptor engineered T cells.," Cancer Lett (2014) 343(2):172-178.
Taraseviciute et al., "Creation of the First Non-Human Primate Model That Faithfully Recapitulates Chimeric Antigen Receptor (CAR) T cell-mediated Cytokine Release Syndrome (CRS) and Neurologic Toxicity Following B Cell-directed CAR-T Cell Therapy," Blood (2016) 128:651.

* cited by examiner

Days after CAR-T cell infusion

Days after CAR-T cell infusion

Grade 0   Grade 1-3   Grade 4-5

Grade 0    Grade 1-3    Grade 4-5

Grade 0   Grade 1-3   Grade 4-5

METHODS AND COMPOSITIONS RELATED TO TOXICITY ASSOCIATED WITH CELL THERAPY

CROSS-REFERENCE TO RELATED APPLICATIONS

This application is a U.S. National Stage of International Application No. PCT/US2016/064865 filed Dec. 2, 2016, which claims priority from U.S. provisional application No. 62/263,612, filed Dec. 4, 2015, entitled "Methods and Compositions Related to Toxicity Associated with Cell Therapy," and U.S. provisional application No. 62/417,284, filed Nov. 3, 2016, entitled "Methods and Compositions Related to Toxicity Associated with Cell Therapy," the contents of which are incorporated by reference in their entirety.

STATEMENT OF GOVERNMENT INTEREST

This invention was made with government support under CA136551 awarded by the National Institutes of Health. The government has certain rights in the invention.

INCORPORATION BY REFERENCE OF SEQUENCE LISTING

The present application is being filed along with a Sequence Listing in electronic format. The Sequence Listing is provided as a file entitled 735042004500SeqList.txt, created May 31, 2018, which is 17,781 bytes in size. The information in the electronic format of the Sequence Listing is incorporated by reference in its entirety.

FIELD

The present disclosure provides methods, kits and compositions related to toxicity associated with administration of cell therapy for the treatment of diseases or conditions, e.g., cancer, including methods for use in predicting and treating a toxicity. In some embodiments, the toxicity is a neurotoxicity or cytokine release syndrome (CRS), such as a severe neurotoxicity or a severe CRS. The methods generally involve detecting a parameter of a biomarker or individually a parameter of each biomarker in a panel of biomarkers, such as a concentration, amount or activity, and comparing the detected parameter to a reference value for the parameter to determine if the subject is at risk for developing the toxicity, such as neurotoxicity or CRS or severe neurotoxicity or severe CRS. In some embodiments, the methods further involve administering an agent or therapy for treating, ameliorating, preventing, delaying and/or attenuating the development of the toxicity, such as neurotoxicity or CRS, such as severe neurotoxicity or severe CRS.

BACKGROUND

Various methods are available for adoptive cell therapy using engineered cells expressing recombinant receptors, such as chimeric antigen receptor (CARs). Improved methods are needed, for example, to reduce the risk of toxicity and/or to increase efficacy, for example, by increasing exposure of the subject to the administered cells, for example, by improving expansion and/or persistence of the administered cells. Provided are methods, compositions, and articles of manufacture that meet such needs.

SUMMARY

Provided in some embodiments are methods of ameliorating the development of toxicity, such as severe neurotoxicity or severe CRS, in a subject following administration of an adoptive cell therapy, e.g. CAR-T cell therapy. In some aspects, the methods involve detecting a parameter for a biomarker or, individually, for of each biomarker in a panel of biomarkers in a biological sample. In some cases, the biological sample is derived from a subject at a time at which the subject does or did not exhibit a physical sign or symptom of severe neurotoxicity or severe CRS. In some aspects, the parameter is detected directly in the biological sample, or indirectly in a test sample obtained from the biological sample. In some embodiments, the method involves comparing the detected parameter for the biomarker or each of the biomarkers in the panel, individually, to a reference value for the parameter. In some cases, the comparison indicates whether the subject is or is not at risk for developing a toxicity and/or indicates a degree of risk for developing a toxicity. In some instances the toxicity is neurotoxicity or severe neurotoxicity. In some instances the toxicity is or is related to cytokine release syndrome (CRS) or severe CRS. In some embodiments, if the comparison indicates that the subject is at risk for developing the toxicity and/or indicates that the risk is above a threshold level, the method involves administering to the subject an agent or therapy that is capable of treating, preventing, delaying, or attenuating the development of the toxicity.

In some embodiments, the parameter for the biomarker or each of the panel of biomarkers, individually, is a concentration, amount, level, relative concentration, relative amount, or activity. In some cases, the parameter for the biomarker or each of the panel of biomarkers, individually, is a concentration, amount, level, relative concentration, or relative amount.

In some instances, the comparison to the reference value, or each of the comparisons to each of the reference values, thereby determines a relative value for the parameter, as compared to the reference value. In some aspects, the relative value or combination thereof indicates whether the subject is at risk. In some cases, the relative value is a percentage or fold increase or percentage or fold decrease, compared to the reference value, or is an indication that the parameter is at, within, above, or below the reference value. In some embodiments, the reference value contains a range of values. In some cases, the relative value is an indication that the detected parameter is within the range or is not within the range.

In some embodiments, at the time of the detection, comparison or administration, the subject has received or is receiving a cell therapy for treating a disease or condition in the subject. In some cases, the cell therapy is associated with or is capable of inducing the toxicity. In some aspects, the cell therapy is adoptive cell therapy. In some instances, the cell therapy includes administration of a dose of cells expressing a recombinant receptor to treat a disease or condition in the subject.

Provided herein in some aspects are methods of treatment involving administering to a subject having a disease or condition a cell therapy containing a dose of cells expressing a recombinant receptor. In some aspects, the methods involve detecting a parameter for a biomarker or, individually, for each biomarker in a panel of biomarkers in a biological sample. In some cases, the biological sample is derived from a subject at a time at which the subject does not or did not exhibit a physical sign or symptom of a toxicity, such as severe neurotoxicity or severe CRS. In some aspects, the parameter is detected directly in the biological sample, or indirectly in a test sample obtained from the biological sample. In some embodiments, the method involves comparing the detected parameter for the biomarker, or each of the biomarkers in the panel, to a reference value for the parameter. In some cases, the comparison indicates whether the subject is or is not at risk for developing a toxicity and/or indicates a degree of risk for developing a toxicity. In some instances the toxicity is neurotoxicity or severe neurotoxicity. In some instances the toxicity is CRS or severe CRS. In some embodiments, if the comparison indicates that the subject is at risk for developing the toxicity and/or indicates that the risk is above a threshold level, the method involves administering to the subject an agent or therapy that is capable of treating, preventing, delaying, or attenuating the development of the toxicity.

In some embodiments, the subject does not exhibit a physical sign or symptom of neurotoxicity or CRS or does not exhibit a physical sign or symptom of severe neurotoxicity or CRS at the time of the detection, the comparison or the administering of the agent or therapy.

Provided herein in some embodiments are methods of diagnosing or predicting a risk for developing neurotoxicity or CRS associated with cell therapy in a subject. In some cases, the methods involve detecting a level, amount, relative amount, concentration, or relative concentration of a biomarker, or of each biomarker in a panel of biomarkers, in a biological sample derived from a subject that has been administered a cell therapy for treatment of a disease or condition in the subject. In some aspects, the biomarker or each biomarker is detected directly in the biological sample, or is detected indirectly in a test sample obtained from the biological sample. In some instances, the biological sample is or has been derived from the subject no more than three days after the administration of the cells. In some embodiments, the method involves comparing the detected level, amount, relative amount, concentration or relative concentration of the biomarker or of each of the panel of biomarkers to a reference value, thereby determining a comparison value for the biomarker or panel of biomarkers. In some cases, the comparison indicates whether the subject is at risk for developing severe neurotoxicity or CRS and/or a degree of risk for developing severe neurotoxicity or CRS. In some aspects, if the comparison value or combination thereof indicates that the subject is at risk for developing severe neurotoxicity or CRS, the method thereby diagnoses or predicts a risk for neurotoxicity or CRS and/or a level of risk thereof.

In some embodiments, the parameter for the biomarker or the parameter for one or more or each of the panel of biomarkers, individually, is a peak serum level of the biomarker within a defined period of time, which optionally is within 1, 2, 3, 4, 5, 6, 7, 8, 9, 10, 12, 15, 18, 21, 24, 27 and/or 30 days after administration of the cell therapy, or a first administration or dose thereof, or after the initiation of any of the foregoing, wherein the peak serum level is the highest serum level of the biomarker within the defined period.

In some embodiments, the subject does not exhibit a physical sign or symptom of neurotoxicity or CRS or does not exhibit a physical sign or symptom of severe neurotoxicity or CRS at the time of the detection, comparison, diagnosing or predicting.

In some cases, the biological sample is obtained or has been obtained from the subject no more than 3 days after administration of the cell therapy, or a first administration of the cell therapy, or a first administration or dose thereof or after the initiation of any of the foregoing. In some instances, the biological sample is obtained or has been obtained from the subject no more than 2 days after administration of the cell therapy, or a first administration or dose thereof, or after the initiation of any of the foregoing. In some aspects, the biological sample is obtained or has been obtained from the subject no more than 1 day after administration of the cell therapy or a first administration or dose thereof to the subject, or greater than 4 hours after the initiation of any of the foregoing. In some embodiments, the biological sample is obtained or has been obtained from the subject greater than 4 hours after administration of the cell therapy or greater than 4 hours after the first administration or dose thereof to the subject, or greater than 4 hours after the initiation of any of the foregoing.

In some embodiments, the toxicity is neurotoxicity, and/or the toxicity is severe neurotoxicity and/or the severe neurotoxicity is a grade 3 or higher neurotoxicity. In some embodiments, the toxicity is CRS, and/or the toxicity is severe CRS and/or the severe CRS is a grade 3 or higher CRS.

In some embodiments, the cell therapy involves administration of a dose of cells expressing a recombinant receptor. In some cases, the dose of cells contains a number of cells between about $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive. In some embodiments, the dose of cells comprises a number of cells between about such as between about $1 \times 10^5$ cells/kg and $5 \times 10^7$ cells/kg, $2 \times 10^5$ cells/kg and $2 \times 10^7$ cells/kg, $2 \times 10^5$ cells/kg and $1 \times 10^7$ cells/kg, $2 \times 10^5$ cells/kg and $5 \times 10^6$ cells/kg, $2 \times 10^5$ cells/kg and $2 \times 10^6$ cells/kg or $2 \times 10^5$ cells/kg and $1 \times 10^6$ cells/kg, each inclusive.

In some cases, the method further involves, if the subject is predicted to be at a risk for or diagnosed with the toxicity, altering the treatment of the cell therapy. In some aspects, altering the treatment includes discontinuing the treatment of the cell therapy, administering a different cell therapy for treating the disease or condition, administering a treatment for treating the disease or condition other than the cell therapy, administering subsequent dose of cells in combination with a second therapeutic agent or treatment for the treatment of the disease or condition, administering a subsequent dose of cells that is decreased compared to the prior dose of cells, or decreasing the frequency of administration of the cell therapy.

In some embodiments, the method further involves, if the subject is diagnosed with or predicted to be at a risk for, or predicted to be at risk for above the threshold level, developing the toxicity, administering an agent that treats toxicity, e.g., neurotoxicity or CRS, and/or an agent that prevents, delays, or attenuates the development of or risk for developing toxicity, e.g. neurotoxicity or CRS.

In some embodiments, the biomarker or one or more or all of the panel of biomarkers include a cytokine or a plurality of cytokines.

In some embodiments, the cytokine or the plurality of cytokines is selected from among transforming growth factor beta (TGF-beta), interleukin 6 (IL-6), interleukin 10 (IL-10), interleukin 15 (IL-15), interferon gamma (IFN-gamma) and monocyte chemoattractant protein-1 (MCP-1).

In some cases, the panel of biomarkers includes at least 2 cytokines or at least 3 cytokines. In some embodiments, the at least two biomarkers include IL-15 and IL-6. In some instances, the biomarker or panel of biomarkers includes IL-6. In some embodiments, the biomarker or biomarkers include the panel and the parameter for each of the biomarkers in the panel is detected simultaneously or sequentially, in the same biological sample or test sample, or in different test samples obtained from the subject or the biological sample.

In some embodiments, the reference value is based on, or has been predetermined using information obtained from assessment of a ROC curve of the one or more biomarkers in a population of diseased subjects having a cancer treated with a cell therapy. In some cases, the reference value is a value, e.g., a threshold value, and/or a value of optimal sensitivity and/or specificity, which can be established based on the Youden Index.

In some embodiments, the reference value for the parameter, or the combination of the reference values for the parameter for each of the panel of biomarkers, has been selected to or does provide a sensitivity or net sensitivity of greater than 0.50, greater than 0.60, greater than 0.70, greater than 0.80, greater than 0.90 or greater than 0.95. In some cases, the reference value for the parameter, or the combination of the reference values for the parameter for each of the panel of biomarkers, has been selected to or does provide a specificity or net specificity of greater than 0.50, greater than 0.60, greater than 0.70, greater than 0.80, greater than 0.90 or greater than 0.95. In some aspects, the reference value for the parameter, or the combination of the reference values for the parameter for each of the panel of biomarkers, has been selected to or does provide an area under the curve (AUC) in a ROC analysis for the biomarker or panel of biomarkers of greater than 0.80, greater than 0.85, greater than 0.90 or greater than 0.95.

In some embodiments, the reference value for the parameter, or the combination of the reference values for the parameter for each of the panel of biomarkers, is selected to provide a sensitivity or net sensitivity of greater than 0.80, greater than 0.85, greater than 0.90 or greater than 0.95. In some cases, the reference value for the parameter, or the combination of the reference values for the parameter for each of the panel of biomarkers, is selected to provide a specificity or net specificity of greater than 0.60, greater than 0.70, greater than 0.80, greater than 0.90 or greater than 0.95. In some instances, the reference value for the parameter, or the combination of the reference values for the parameter for each of the panel of biomarkers, is selected to provide an AUC in a ROC analysis of greater than 0.85, greater than 0.90 or greater than 0.95.

In some aspects, the disease or condition is a cancer. In some cases, the disease or condition is a leukemia or lymphoma. In some instances, the disease or condition is a non-Hodgkin lymphoma (NHL).

In some embodiments, the biomarker or panel of biomarkers includes one or a combination of cytokines, including at least one cytokine selected from among TGF-beta, IL-6 and IL-15. In some cases, if the parameter for the cytokine or, in the case of the combination, for at least one, at least two, or at least three of the cytokines selected from among TGF-beta, IL-6 and IL-15, individually, meet a classification selected from: i) for TGF-beta, less than the TGF-beta reference value; ii) for IL-6, greater than the IL-6 reference value; and/or iii) for IL-15, greater than the IL-15 reference value, then the comparison indicates that the subject is at risk for the toxicity and/or that the risk is above the threshold level of risk.

In some aspects, the at least one, at least two, or at least three of the cytokines is at least two of the cytokines. In some instances, the at least one, at least two, or at least three of the cytokines is at least three of the cytokines.

In some embodiments, the biomarker or panel of biomarkers includes the panel of biomarkers. In some such embodiments, the panel of biomarkers includes a first and second cytokine, the first and second cytokine being: TGF-beta and IL-6, TGF-beta and IL-15, or IL-6 and IL-15. In some aspects, if the detected parameter for each of the first and second cytokines, individually, meets the classification, then the comparison indicates that the subject is at risk for the toxicity and/or that the risk is above the threshold level of risk. In some cases, if the detected parameters for both the first and second cytokines do not meet the classification, then the comparison indicates that the subject is at risk for the toxicity and/or that the risk is above the threshold level of risk. In some instances, if the detected parameter for only one of the first and second cytokines does not meet the classification, the method further involves detecting a parameter for at least a third biomarker in a biological sample derived from the subject. In some such instances, the biological sample is or has been derived from the subject no more than three days after the administration of the cells. In some aspects, the method further involves comparing the detected parameter for the third biomarker to a third reference value, thereby indicating whether the subject is at risk for developing severe neurotoxicity and/or a degree of risk for developing severe neurotoxicity.

In some embodiments, the third biomarker is a cytokine selected from among TGF-beta, IL-6 and IL-15 and is different from the first and second cytokines. In some cases, if the detected parameter for the third cytokine meets the classification, the subject is identified or is diagnosed or predicted to be at risk for developing the toxicity, e.g., neurotoxicity, e.g., severe neurotoxicity. In some instances, if the detected parameter for the third cytokine does not meet the classification, the subject is identified or is diagnosed or predicted not to be at risk for developing the toxicity, e.g., neurotoxicity or severe neurotoxicity.

In some embodiments, a parameter of each of TGF-beta, IL-6 and IL-15 are detected. In some aspects, if the detected parameter for all three cytokines meet the classification, the subject is identified or is diagnosed or predicted to be at risk of the toxicity, e.g., neurotoxicity. In some cases, if the detected parameter for at least two of the cytokines meet the classification, the subject is identified or is diagnosed or predicted to be at risk for the toxicity, e.g., neurotoxicity. In some embodiments, if the detected parameter for only one of the cytokines meets the classification, the subject is identified or is diagnosed or predicted not to be at risk for the toxicity, e.g., neurotoxicity.

In some cases, the parameter, or the parameter for each of the biomarkers in the panel, individually, is a concentration of the biomarker, or relative concentration of the biomarker, and the reference value for the parameter is a reference concentration.

Provided herein in some embodiments are methods of ameliorating the development of toxicity in a subject. In some cases, the method involves detecting a concentration or relative concentration of each of a panel of cytokines in a biological sample derived from a subject. In some instances, the panel includes one, two, or three of TGF-beta, IL-6 and IL-15. In some cases the detecting includes detection of the concentration or relative concentration directly in the biological sample or indirectly, by detection in a test sample obtained from the biological sample. In some aspects, the biological sample is obtained or has been obtained from the subject no more than 1 day, 2 days or 3 days after administration of the cell therapy, or a first administration or dose thereof, or after initiation of any of the foregoing. In some instances, the method includes comparing the concentration or relative concentration of each of the cytokines in the panel to a reference value for each respective concentration of cytokine. In some cases, if the detected concentration or relative concentration of the two or three of the cytokines individually meet a classification, the subject is identified or is diagnosed or predicted to be at risk for developing neurotoxicity, e.g., severe neurotoxicity. In some embodiments, the classification is selected from: i) for TGF-beta, less than the TGF-beta reference value; ii) for IL-6, greater than the IL-6 reference value; and/or iii) for IL-15, greater than the IL-15 reference value. In some aspects, if the concentration or relative concentration of at least two of the cytokines do not meet the classification, the subject is identified or is diagnosed or predicted not to be at risk for developing toxicity, e.g., neurotoxicity.

In some embodiments, the disease or condition is a non-Hodgkin lymphoma (NHL).

Provided herein in some aspects are methods of ameliorating the development of toxicity in a subject. In some cases, the method involves detecting a concentration or relative concentration of each of a panel of cytokines in a biological sample derived from a subject. In some instances, the panel includes one, two, or three of IL-6, IL-15 and MCP-1. In some cases, the detecting includes detection of the concentration or relative concentration directly in the biological sample or indirectly, by detection in a test sample obtained from the biological sample. In some aspects, the biological sample is obtained or has been obtained from the subject no more than 1 day, 2 days or 3 days after administration of the cell therapy, or a first administration or dose thereof, or after initiation of any of the foregoing. In some embodiments, the method includes comparing the concentration or relative concentration of each of the cytokines in the panel to a reference value for each respective concentration of cytokine. In some aspects, if the detected concentration or relative concentration of the two or three of the cytokines individually meet a classification, the subject is identified or is diagnosed or predicted to be at risk for developing neurotoxicity, e.g., severe neurotoxicity. In some embodiments, the classification is selected from: i) for MCP-1, greater than the MCP-1 reference value; ii) for IL-6, greater than the IL-6 reference value; and/or iii) for IL-15, greater than the IL-15 reference value. In some aspects, if the concentration or relative concentration of at least two of the cytokines do not meet the classification, the subject is identified or is diagnosed or predicted not to be at risk for developing toxicity, e.g., neurotoxicity.

In some embodiments, the method further includes, if the comparison indicates that the subject is at risk for developing toxicity, e.g., neurotoxicity, e.g., severe neurotoxicity, and/or indicates that the risk is above a threshold level, administering to the subject an agent or therapy that is capable of treating, preventing, delaying, or attenuating the development of toxicity, e.g., neurotoxicity.

In some aspects, the disease or condition is acute lymphoblastic leukemia (ALL).

In some embodiments, the TGF-beta reference value is within a range from or from about 5.5 pg/mL to about 15.00 pg/mL (log 2 scale) or from or from about 45 pg/mL to about 33000 pg/mL. In some cases, the IL-6 reference value is within a range from or from about 2.6 pg/mL to 5.4 pg/mL (log 2 scale) or from or from about 6.00 pg/mL to about 41.0 pg/mL. In some aspects, the IL-15 reference value is within a range from or from about 6.1 pg/mL to about 7.1 pg/mL (log 2 scale) or from or from about 69.0 pg/mL to about 135.0 pg/mL.

In some embodiments, the TGF-beta reference value is within a range from or from about 10.00 pg/mL to about 15.00 pg/mL (log 2 scale) or from or from about 20000 pg/mL to about 33000 pg/mL; or is at least or at least about 10.00 pg/mL, 11.00 pg/mL, 12.00 pg/mL, 13.00 pg/mL, 14.00 pg/mL or 15.00 pg/mL, each on a log 2 scale; or is at least or at least about 20000 pg/mL, 22000 pg/mL, 24000 pg/mL, 26000 pg/mL, 28000 pg/mL, 30000 pg/mL or 32000 pg/mL; or is or is about 25000±100 pg/mL or is or is about 14.0±1.0 pg/mL on a log 2 scale.

In some embodiments, the IL-6 reference value is within a range from or from about 3.5 pg/mL to 5.4 pg/mL (log 2 scale) or from or from about 12 pg/mL to 41 pg/mL; or is at least or at least about 3.5 pg/mL, 4.0 pg/mL, 4.5 pg/mL, 4.8 pg/mL, 5.0 pg/mL, 5.2 pg/mL or 5.4 pg/mL, each on log 2 scale; or is at least or at least about 12 pg/mL, 18 pg/mL, 24 pg/mL, 30 pg/mL or 36 pg/mL; or is or is about 15.2±1.0 pg/mL and/or is or is about 3.9±1.0 pg/mL.

In some embodiments, the IL-15 reference value is a within a range from or from about 6.0 pg/mL to 7.1 pg/mL (log 2 scale) or from or from about 74 pg/mL to 135 pg/mL; or is at least or at least about 6.0 pg/mL, 6.2 pg/mL, 6.4 pg/mL, 6.6 pg/mL, 6.8 pg/mL or 7.0 pg/mL, each on log 2 scale; or is at least or at least about 74 pg/mL, 80 pg/mL, 90 pg/mL, 100 pg/mL, 110 pg/mL, 120 pg/mL or 130 pg/mL, or is or is about 6.2±1.0 on a log 2 scale or is or is about 76±4.0 pg/mL.

In some cases, the method further includes detecting a parameter for IL-10 or IFN-gamma in a sample from the subject, wherein the biological sample is or has been derived from the subject no more than three days after the administration of the cells. In some instances, the method further includes identifying the subject as at risk of developing neurotoxicity if the detected parameter of IL-10 and/or IFN-gamma meets a classification selected from: iv) for IL-10, greater than a IL-10 reference value; or v) a for IFN-gamma, greater than a IFN-gamma reference value.

In some embodiments, the IL-10 reference value is at least or at least about 3.0 pg/mL (log 2 scale) or is at least or at least about 10.0 pg/mL; or is or is about 3.5±1.0 pg/mL on log 2 scale or is or is about 11.0±1.0 pg/mL.

In some aspects, the IFN-gamma reference value is at least or at least about 4.0 pg/mL (log 2 scale) or is at least or at least about 18.0 pg/mL; or is or is about 4.2±1.0 pg/mL on log 2 scale or is or is about 19.0±1.0 pg/mL.

In some embodiments, the disease or condition is acute lymphoblastic leukemia (ALL).

In some aspects, the one or more biomarkers include a cytokine selected from among IL-6, IL-15 and MCP-1. In some instances, the subject is identified or is diagnosed or predicted to be at risk for developing the toxicity if the detected parameter of at least one of the cytokines meets a classification selected from: i) for IL-6, greater than the IL-6 reference value; ii) a for IL-15, greater than the IL-15 reference value; and/or iii) a for MCP-1, greater than the MCP-1 reference value.

In some embodiments, the subject is identified or is diagnosed or predicted to be at risk for developing severe neurotoxicity if the parameters detected for at least two of the cytokines meet the classification or if the parameters detected for at least three of the cytokines meet the classification.

In some embodiments, the one or more biomarkers include a first and second cytokine selected from among IL-15 and IL-6, IL-15 and MCP-1 and IL-6 and MCP-1. In some cases, if the parameter detected for the first and second cytokines meet the classification, the subject is identified or is diagnosed or predicted to be at risk for developing severe neurotoxicity. In some aspects, if the parameter detected for both the first and second cytokines do not meet the classification, the subject is identified or predicted not to be at risk for developing severe neurotoxicity.

In some cases, if the parameter detected for only one of the first and second cytokines does not meet the classification, the method further involves detecting a parameter for at least a third biomarker in a biological sample derived from the subject. In some aspects, the biological sample is or has been derived from the subject no more than three days after the administration of the cells. In some embodiments, the method includes comparing the detected parameter for the third biomarker to a reference value. In some such embodiments, the comparison or the method thereby indicates whether the subject is at risk for developing severe neurotoxicity and/or a degree of risk for developing severe neurotoxicity.

In some embodiments, the third biomarker is a cytokine such as MCP-1, IL-6 or IL-15 and is different from the first and second cytokines. In some instances, if the detected parameter for the third cytokine meets the classification, the subject is identified or predicted to be at risk for developing severe neurotoxicity. In some embodiments, if the detected parameter for the third cytokine does not meet the classification, the subject is identified or predicted not to be at risk for developing neurotoxicity.

In some embodiments, the first cytokine is IL-15, the second cytokine is IL-6 and the third cytokine is MCP-1.

In some embodiments, each of IL-15, IL-6 and MCP-1 are detected. In some cases, if the detected parameter for all three cytokines meet the classification, the subject is identified or is diagnosed or predicted to be at risk for developing severe neurotoxicity. In some instances, if the detected parameter for at least two of the cytokines meet the classification, the subject is identified or is diagnosed or predicted to be at risk for neurotoxicity. In some cases, the two cytokines are IL-15 and IL-6 or IL-15 and MCP-1. In some embodiments, if the parameter for only one of the cytokines meets the classification, the subject is not identified or is diagnosed predicted to be at risk for developing neurotoxicity.

In some embodiments, the IL-6 reference value is within a range, or is a range, from or from about 2.0 pg/mL to 4.0 pg/mL (log 2 scale) or from or from about 6.00 pg/mL to 12.0 pg/mL. In some cases, the IL-15 reference value is within a range, or is a range, from or from about 5.0 pg/mL to 6.5 pg/mL (log 2 scale) or from or from about 40.0 pg/mL to 90.0 pg/mL. In some embodiments, the MCP-1 reference value is within a range, or is a range, from or from about 7.00 pg/mL to 12.0 pg/mL (log 2 scale) or from or from about 700 pg/mL to 1400 pg/mL.

In some embodiments, the IL-6 reference value is at least or at least about 3.0 pg/mL or 4.0 pg/mL, each on a log 2 scale; or is at least or at least about 8.0 pg/mL, 9.0 pg/mL, 10.0 pg/mL, 11.0 pg/mL or 12.0 pg/mL; or is or is about $3.0\pm1.0$ pg/mL on a log 2 scale or is or is about $10.5\pm1.0$ pg/mL In some aspects, the IL-15 reference value is within a range from or from about 6.0 pg/mL to 6.5 pg/mL (log 2 scale) or from or from about 70 pg/mL to 90 pg/mL; or is at least or at least about 6.0 pg/mL, 6.1 pg/mL, 6.2 pg/mL, 6.3 pg/mL, 6.4 pg/mL or 6.5 pg/mL, each on a log 2 scale; or is at least or at least about 70 pg/mL, 75 pg/mL, 80 pg/mL, 85 pg/mL or 90 pg/ml; or is or is about $6.0\pm1.0$ pg/mL on a log 2 scale or is or is about $81\pm4$ pg/mL In some cases, the MCP-1 reference value is within a range from or from about 9.0 pg/mL to 12.0 pg/mL (log 2 scale) or from or from about 1000 pg/mL to 1400 pg/mL; or is at least or at least about 9.0 pg/mL, 10.0 pg/mL, 11.0 pg/mL or 12.0 pg/mL, each on log 2 scale; or is at least or at least about 1000 pg/mL, 1100 pg/mL, 1200 pg/mL, 1300 pg/mL or 1400 pg/mL; or is or is about $10.0\pm1.0$ pg/mL on a log 2 scale or is or is about $1200\pm100$ pg/mL.

In some embodiments, the toxicity is CRS, and/or the toxicity is severe CRS and/or the severe CRS is a grade 3 or higher CRS, or grade 4 or higher CRS.

In some of any such embodiments, the provided methods include a method of ameliorating the development of toxicity in a subject that includes detecting a concentration or relative concentration of each of a panel of biomarkers, the panel comprising one or more of IL-15, IL-6, IL-8, IL-10, soluble TNF receptor type 1 (sTNFR1), IFN-gamma and ferritin, in a biological sample derived from a subject, the detecting comprising detection of the concentration or relative concentration directly in the biological sample or indirectly, by detection in a test sample obtained from said biological sample, wherein the biological sample is obtained or has been obtained from the subject no more than 1 day, 2 days or 3 days after administration of the cell therapy, or a first administration or dose thereof, or after initiation of any of the foregoing. In some embodiments, the methods include comparing the concentration or relative concentration of each of the biomarkers in the panel to a reference value for each respective concentration of biomarker, wherein: if the detected concentration or relative concentration of the one or more of the biomarkers individually is higher than the reference value, the subject is identified or is diagnosed or predicted to be at risk for developing CRS, which optionally is severe CRS.

In some embodiments, the biomarker or one or more or each of the panel of biomarkers, individually, is or comprises IL-15, IL-6, IL-8, IL-10, IFN-gamma, soluble TNF receptor type I (sTNFR1) or ferritin. In some embodiments, the biological sample is obtained or has been obtained from the subject at or about 1 day after administration of the cell therapy, or a first administration or dose thereof, or after initiation of any of the foregoing. In some embodiments, the reference level is an average level of a group of subjects receiving the same treatment for the same indication, and/or such subjects that do not develop the toxicity, which optionally is severe CRS or grade 3 or higher CRS. In some embodiments, the disease or condition is a non-Hodgkin lymphoma (NHL) or acute lymphoblastic leukemia (ALL).

In some embodiments, the accuracy of the identification or prediction is greater than 80%, greater than 85%, greater than 90%, or greater than 95%.

In some embodiments, the agent that treats toxicity, e.g., neurotoxicity, or prevents, delays, or attenuates the development of or risk for developing the toxicity, is a steroid, is an antagonist or inhibitor of a cytokine receptor selected from among IL-6 receptor, CD122 receptor (IL-2R/IL-15Rbeta) and CCR2, or is an inhibitor of a cytokine selected from among IL-6, IL-15 and MCP-1. In some aspects, the antagonist or inhibitor is selected from among an antibody or antigen-binding fragment, a small molecule, a protein or peptide and a nucleic acid.

In some embodiments, the agent is selected from among tocilizumab, siltuximab, sarilumab, clazakizumab, olokizumab (CDP6038), elsilimomab, ALD518/BMS-945429, sirukumab (CNTO 136), CPSI-2634, ARGX-109, FE301, FM101, Hu-Mik-β-1, tofacitinib, ruxolitinib, CCX140-B, R0523444, BMS CCR2 22, INCB 3284 dimesylate, JNJ27141491 and RS 504393 adalimumab, certolizumab pegol, golimumab, lenalidomide, ibrutinib or acalabrutinib.

In some aspects, the agent is tocilizumab. In some such aspects, the tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.

In some cases, the agent is a corticosteroid, e.g., glucocorticoid. In some embodiments, the corticosteroid is dexamethasone or prednisone. In some embodiments, the agent is a steroid that is administered in an equivalent dosage amount of from or from about 1.0 mg to 20 mg dexamethasone per day, 1 mg to 10 mg dexamethasone per day, or 2.0 mg to 6.0 mg dexamethasone per day, each inclusive. In some aspects, the agent is a steroid that is administered intravenously or orally.

In some embodiments, the subject is treated with the agent within 3 days, within 2 days or within 1 day after administration of the cell therapy.

In some embodiments, the method involves administering the agent, and further includes, after administration of the agent, monitoring the efficacy of the agent on the treatment, prevention, delay, or attenuation of toxicity, e.g., neurotoxicity. In some such embodiments, monitoring the efficacy involves detecting a parameter for the biomarker or for one or more of the panel of biomarkers, e.g., cytokines, in a subsequent biological sample obtained from the subject following administration of the agent to the subject. In some cases, the detecting of the parameter for the biomarker or each of the panel of biomarkers includes detection directly in the biological sample or detection indirectly, in a test sample obtained from the subsequent biological sample.

In some embodiments, the method includes comparing the subsequent parameter for the biomarker, or parameter of one or more or each of the biomarkers, individually, to a reference value. In some cases, the reference value is a value for the parameter present in a prior sample from the subject or to a baseline sample prior to the administration of the agent. In some aspects, the agent is deemed or considered to have been or be efficacious if the subsequent parameter improves based on the comparison, and/or if the parameter is not deemed to be altered to a value that is more predictive of the development of neurotoxicity than the level, amount, relative amount, concentration, or relative concentration present in the prior sample or baseline sample. In some embodiments, the method includes monitoring the efficacy on the treatment, prevention, delay, or attenuation of severe neurotoxicity or grade 3 or higher neurotoxicity and the parameter is predictive of the development of severe neurotoxicity or grade 3 or higher neurotoxicity.

In some embodiments, the biomarker is a cytokine that is selected from among IL-15, IL-6, IL-10, IFN-gamma and MCP-1, and treatment with the agent is considered to be efficacious if the subsequent parameter of the cytokine is about the same or is the same or is less than the parameter present in a prior sample or the baseline sample. In some cases, the biomarker is TGF-beta, and treatment with the agent is considered to be efficacious if the subsequent parameter for the cytokine is about the same or is the same or is greater than the parameter detected in a prior sample or the baseline sample.

In some embodiments, the provided methods include monitoring the efficacy on the treatment, prevention, delay, or attenuation of severe CRS or grade 3 or higher CRS and the parameter is predictive of the development of severe CRS or grade 3 or higher CRS. In some embodiments, the biomarker or one or more or each of the panel of biomarkers, individually, is or comprises IL-15, IL-6, IL-8, IL-10, IFN-gamma, soluble TNF receptor type 1 (sTNFR1) or ferritin, and treatment with the agent is considered to be efficacious if the subsequent parameter of the cytokine is about the same or is the same or is less than the parameter present in a prior sample or the baseline sample.

In some embodiments, if the treatment is not deemed to be efficacious, the method further involves continuing treatment with the agent, increasing the dosage of the agent, increasing the frequency of administration of the agent or administering a different agent for treating, preventing, delaying, or attenuating the risk for developing neurotoxicity.

In some aspects, the physical signs or symptoms associated with toxicity, e.g., severe neurotoxicity, include confusion, delirium, expressive aphasia, obtundation, myoclonus, lethargy, altered mental status, convulsions, seizure-like activity, seizures (such as confirmed by electroencephalogram [EEG]), encephalopathy, dysphasia, tremor, choreoathetosis, symptoms that limit self-care, symptoms of peripheral motor neuropathy, symptoms of peripheral sensory neuropathy or combinations thereof. In some cases, the physical signs or symptoms associated with toxicity, e.g., severe neurotoxicity, are associated with grade 3, grade 4 or grade 5 neurotoxicity. In some embodiments, the physical signs or symptoms associated with toxicity, e.g., severe neurotoxicity, manifest greater than or greater than about or about 5 days after cell therapy, 6 days after cell therapy or 7 days after cell therapy.

In some embodiments, the method ameliorates toxicity, e.g., neurotoxicity, e.g., severe neurotoxicity and/or reduces the physical signs or symptoms of severe neurotoxicity compared to a subject in which severe neurotoxicity is treated after the subject exhibits a physical sign or symptom of neurotoxicity and/or compared to a subject in which severe neurotoxicity is treated greater than 5 days, greater than 6 days or greater than 7 days after administration of the cell therapy. In some cases, the treated subject does not exhibit grade 3 or higher neurotoxicity or a majority of treated subjects do not exhibit grade 3 or higher neurotoxicity.

In some embodiments, the physical signs or symptoms associated with toxicity, optionally severe CRS, are selected from among acute inflammatory response and/or endothelial organ damage, fever, rigors, chills, hypotension, dyspnea, acute respiratory distress syndrome (ARDS), encephalopathy, ALT/AST elevation, renal failure, cardiac disorders, hypoxia, neurologic disturbances, and death, neurological complications such as delirium, seizure-like activity, confusion, word-finding difficulty, aphasia, and/or becoming obtunded, or fatigue, nausea, headache, seizure, tachycardia, myalgias, rash, acute vascular leak syndrome, liver function impairment, and renal failure and combinations thereof; and/or the physical signs or symptoms associated with toxicity, optionally severe CRS, are associated with grade 3, grade 4 or grade 5 CRS; and/or the physical signs or symptoms associated with toxicity, optionally severe CRS, manifest greater than or greater than about or about 5 days after cell therapy, 6 days after cell therapy or 7 days after cell therapy.

In some embodiments, the recombinant receptor binds to, recognizes or targets an antigen associated with the disease or condition. In some aspects, the recombinant receptor is a T cell receptor or a functional non-T cell receptor. In some instances, the recombinant receptor is a chimeric antigen receptor (CAR).

In some embodiments, the CAR contains an extracellular antigen-recognition domain that specifically binds to the antigen and an intracellular signaling domain containing an ITAM. In some cases, the intracellular signaling domain can contain an intracellular domain of a CD3-zeta (CD3) chain. In some embodiments, the CAR further contains a costimulatory signaling region, which can contain a signaling domain of CD28 or 4-1BB.

In some embodiments, the dose of cells contains T cells. In some embodiments, the T cells are $CD4^+$ or CD8+.

In some aspects, the biological sample is a bodily fluid or a tissue. In some cases, the bodily fluid includes whole blood, serum or plasma.

In some aspects, detecting the parameter for the biomarker or individually for one or more of each of the panel of biomarkers includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more biomarkers are detected by an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay.

In some embodiments, the parameter for at least one of the one or more biomarkers is determined using a binding reagent that specifically binds to at least one biomarker. In some cases, the binding reagent is an antibody or antigen-binding fragment thereof, an aptamer or a nucleic acid probe.

Provided herein in some aspect are kits, such as kits containing reagents for detecting a parameter for at least two cytokines. The at least two cytokines may include, in some instances, transforming growth factor beta (TGF-beta), interleukin 6 (IL-6), interleukin 10 (IL-10), interleukin 15 (IL-15), interferon gamma (IFN-gamma) or monocyte chemoattractant protein-1 (MCP-1). In some aspects, the kit includes instructions for detecting the parameter for the at least two cytokines. In some cases, the at least two cytokines include one or more of IL-6 and IL-15, TGF-beta and IL-6, TGF-beta and IL-15, IL-6 and IL-15 or IL-15 and MCP-1. In some embodiments, the parameter is a concentration or relative concentration.

In some embodiments, the kit contains reagents for detecting the parameters for only two cytokines. In other aspects, the kit contains reagents for detecting the parameters at least three cytokines. In some cases, the three cytokines include one or more of TGF-beta, IL-6 and IL-15 or are IL-6, IL-15 and MCP-1.

In some embodiments, the kit includes reagents for detecting a parameter for at least two biomarkers selected from among interleukin 15 (IL-15), interleukin 6 (IL-6), interleukin 10 (IL-10), interleukin 8 (IL-8), interferon gamma (IFN-gamma), ferritin and soluble TNF receptor type 1 (sTNFR1); and, optionally, instructions for detecting the parameter for at least two biomarkers, wherein the parameter is optionally a concentration or relative concentration.

In some cases, the reagents include components for performing an in vitro assay to detect the parameters for at least two cytokines. In some aspects, the in vitro assay is an immunoassay, an aptamer-based assay, a histological or cytological assay, or an mRNA expression level assay. In some embodiments, the in vitro assay is an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay. In some embodiments, the reagent includes a binding reagent that specifically binds the cytokine. In some instances, the binding reagent is an antibody or antigen-binding fragment thereof, an aptamer or a nucleic acid probe.

Provided herein in some embodiments are combinations, such as those containing reagents for detecting a parameter (e.g., level or concentration) of at least two cytokines. In some aspects, the at least two cytokines include one, two, or three of transforming growth factor beta (TGF-beta), interleukin 6 (IL-6), interleukin 10 (IL-10), interleukin 15 (IL-15), interferon gamma (IFN-gamma) or monocyte chemoattractant protein-1 (MCP-1). Also included in the combination in some aspects is an agent that treats, prevents, delays, or attenuates the development of severe neurotoxicity and/or severe CRS. In some cases, the at least two cytokines are IL-6 and IL-15, TGF-beta and IL-6, TGF-beta and IL-15, IL-6 and IL-15 or IL-15 and MCP-1.

In some embodiments, the combination includes reagents for detecting a parameter, optionally a level or concentration, of at at least two biomarkers selected from among interleukin 15 (IL-15), interleukin 6 (IL-6), interleukin 10 (IL-10), interleukin 8 (IL-8), interferon gamma (IFN-gamma), ferritin and soluble TNF receptor type 1 (sTNFR1); and an agent that treats, prevents, delays, or attenuates the development of severe CRS.

In some cases, the combination includes reagents for detecting only two cytokines. In some aspects, the combination includes reagents for detecting at least three cytokines. In some such aspects, the three cytokines are TGF-beta, IL-6 and IL-15 or are IL-6, IL-15 and MCP-1.

In some embodiments, the reagents include components for performing an in vitro assay to detect the at least two cytokines. In some cases, the in vitro assay is an immunoassay, an aptamer-based assay, a histological or cytological assay, or an mRNA expression level assay. In some instances, the in vitro assay is an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay. In some embodiments, the reagent includes a binding reagent that specifically binds the cytokine. In some cases, the binding reagent is an antibody or antigen-binding fragment thereof, an aptamer or a nucleic acid probe.

In some embodiments, the agent that treats, prevents, delays, or attenuates the development of or risk for developing severe neurotoxicity and/or severe CRS is a steroid, is an antagonist or inhibitor of a cytokine receptor such as IL-6 receptor, CD122 receptor (IL-2R/IL-15Rbeta) and CCR2, or is an inhibitor of a cytokine such as IL-6, IL-15 or MCP-1. In some embodiments, the antagonist or inhibitor is an antibody or antigen-binding fragment, a small molecule, a protein or peptide or a nucleic acid. In some cases, the agent is tocilizumab, siltuximab, sarilumab, clazakizumab, olokizumab (CDP6038), elsilimomab, ALD518/BMS-945429, sirukumab (CNTO 136), CPSI-2634, ARGX-109, FE301, FM101, Hu-Mik-r3-1, tofacitinib, ruxolitinib, CCX140-B, R0523444, BMS CCR2 22, INCB 3284 dimesylate, JNJ27141491, or RS 504393, adalimumab, certolizumab pegol, golimumab, lenalidomide, ibrutinib or acalabrutinib.

In some such cases, the agent is tocilizumab. In some such cases, the agent is siltuximab.

In some embodiments, the combination is formulated for single dosage administration of an amount from or from about 75 mg to 750 mg, 150 mg to 600 mg, 200 mg to 400 mg or 300 mg to 700 mg or in an amount that is at least or at least about 75 mg, 100 mg, 200 mg, 300 mg, 400 mg, 500 mg, 600 mg or 700 mg.

In some embodiments, the agent is a steroid that is a corticosteroid. In some embodiments, the corticosteroid is a glucocorticoid. In some cases, the corticosteroid is a cortisone, dexamethasone, hydrocortisone, methylprednisolone, prednisolone or prednisone.

In some aspects, the combination is formulated for single dosage administration or multiple dosage administration. In some embodiments, the combination is formulated for administration of an equivalent dosage amount of from or from about 1.0 mg to 20 mg dexamethasone per day, 1 mg to 10 mg dexamethasone per day, or 2.0 mg to 6.0 mg dexamethasone per day, each inclusive. In some cases, the steroid is formulated for intravenous or oral administration.

BRIEF DESCRIPTION OF THE DRAWINGS

FIG. 2A represents a ROC curve for IL-15. FIG. 2B represents a ROC curve for TGF-β. FIG. 2C represents a ROC curve for IL-6. FIG. 2D represents a ROC curve for IFN-γ. FIG. 2E represents a ROC curve for IL-10.

FIG. 3A shows a ROC curve for the combination of IL-15 and TGF-β. FIG. 3B shows a ROC curve for the combination of IL-6 and TGF-β. FIG. 3C shows a ROC curve for the combination of IL-15, IL-6 and TGF-β.

FIG. 4A represents a ROC curve for IL-15. FIG. 4B represents a ROC curve for MCP-1. FIG. 4C represents a ROC curve for IL-6.

FIG. 8A), absolute blood neutrophil count (ANC)/4 (FIG. 8B), blood monocyte count/4 (FIG. 8C), heart rate (beats/min; FIG. 8D), blood platelet count/μL (FIG. 8E), and blood levels of ferritin (ng/mL;

FIG. 8F), albumin (g/dL; FIG. 8G), fibrinogen (mg/dL; FIG. 8H) and C-reactive protein (mg/L; FIG. 8I). ** represents $p<0.01$ and * represents $p<0.05$, in non-parametric tests.

FIG. 10A represents a ROC curve for IL-6. FIG. 10B represents a ROC curve for MCP-1. FIG. 10C represents a ROC curve for IL-10. FIG. 10D represents a ROC curve for IL-15.

FIG. 11A represents subjects with CLL. Results are shown for groups that exhibited marrow response, the IWCLL overall response rate (complete response (CR)+partial response (PR)), Grades 2-5 neurotoxicity, or Grades 2-5 CRS. FIG. 11B represents subjects with NHL. Results are shown for groups that exhibited complete response, overall response rate (ORR; CR+PR), Grades 2-5 neurotoxicity, or Grades 2-5 CRS. FIG. 11C represents subjects with ALL. Results are shown for groups that exhibited complete response, Grades 2-5 neurotoxicity, or Grades 2-5 CRS.

FIG. 11A shows a failure plot over time of first time to fever, among subjects with ALL, NHL or CLL, after treatment with anti-CD19 CART cell infusion. Results are shown for groups of subjects who were observed to exhibit Grade 0 CRS, Grade 1-3 CRS or Grade 4-5 CRS following the treatment. FIG. 11B shows a plot of median time to fever over 38° C. and onset of grade 3 or higher neurotoxicity over time, among subjects with ALL, NHL or CLL, after treatment with anti-CD19 CAR T cell infusion. Results are shown for groups of subjects that exhibited a fever of over 38° C. (n=94) and for subjects who exhibited grade 3 or higher neurotoxicity (n=28).

FIG. 13B), heart rate (beats/min; FIG. 13C), systolic blood pressure (mm Hg; FIG. 13D), diastolic blood pressure (mm Hg; FIG. 13E), respiratory rate (breaths/min; FIG. 13F), total blood protein (g/dL; FIG. 13G), blood albumin levels (g/dL, FIG. 13H), and weight change from baseline (kg, FIG. 13I). ** represents $p<0.0001$ and * represents $p<0.05$.

FIG. 14A), fibrinogen (mg/dL; FIG. 14B), prothrombin time (PT; sec; FIG. 14C), activated partial thromboplastin time (aPTT; sec; FIG. 14D), and platelet count (1000/4; FIG. 14E). ** represents $p<0.05$.

FIG. 15A), monocyte count (1000/μL; FIG. 15B), eosinophil count (1000/μL; FIG. 15C), hemoglobin (g/dL; FIG. 15D) and hematocrit percentage (%; FIG. 15E). ** represents $p<0.0001$ and * represents $p<0.05$.

FIG. 16A), alanine aminotransferase (ALT; units/L; FIG. 16B), alkaline phosphatase (ALP; units/L; FIG. 16C), total bilirubin (mg/dL; FIG. 16D) and blood urea nitrogen (BUN; mg/dL; FIG. 16E). ** represents $p<0.05$.

DETAILED DESCRIPTION

Figure 1A:
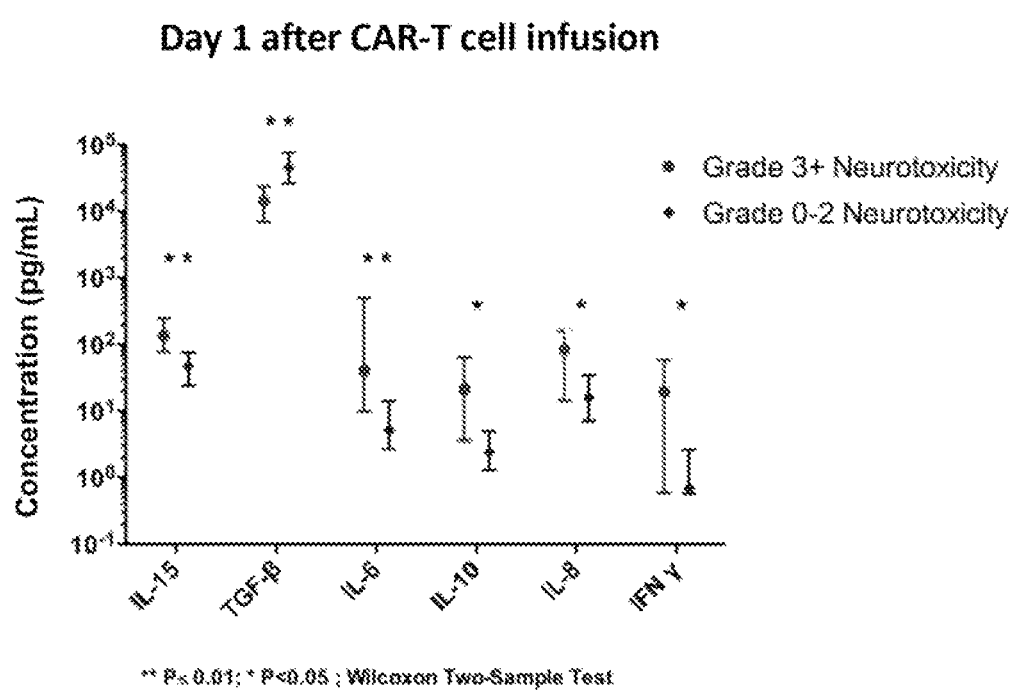
FIG. 1A shows values of various biomarkers as measured at day 1 following administration of cell therapy.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. OVERVIEW OF BIOMARKERS PREDICTIVE OF TOXICITY TO ADOPTIVE CELL THERAPY

Provided are methods for assessing the risk of development of toxicity in a subject, such as predicting whether a risk for developing a toxicity exists, and/or is above a threshold level or value, for example, one that indicates intervention should occur. In some embodiments, provided are methods for ameliorating the development of toxicity in a subject in which a risk for developing the toxicity exists (for example, as determined by the provided methods for assessing), such as treating, ameliorating, preventing, delaying and/or attenuating the development of the toxicity, for example, by administering an agent. In some embodiments, the administration of the agent is carried out at a time during which the subject does not exhibit outwardly visible or physical signs or symptoms of the toxicity or does not exhibit severe such signs or symptoms, and/or otherwise without the provided assessment methods would not have been indicated as a candidate for treatment by such agent. In some embodiments, the toxicity is related to or is cytokine release syndrome (CRS), such as is a severe CRS, for example, a grade 3 or higher CRS or a grade 4 or higher CRS. In some embodiments, the toxicity is related to or is neurotoxicity, such as a severe neurotoxicity, for example a grade 3 or higher neurotoxicity.

In some embodiments, the methods include detecting a parameter for a biomarker or, individually, a panel of biomarkers in a biological sample from a subject, and comparing such parameter to a reference value for each of the detected parameters to determine if the subject is at risk for developing a toxicity, such as CRS or a neurotoxicity, including severe CRS or severe neurotoxicity. In some embodiments, the parameter is the concentration, amount, level, relative concentration, relative amount or activity of the biomarker or each of the panel of biomarkers being assessed. Generally, the level of the parameter of the biomarker or the panel of biomarkers is indicative of risk for developing a toxicity, such as severe CRS or severe neurotoxicity. In some embodiments, the parameter can be detected directly in the biological sample. In some embodiments, the parameter can be detected indirectly. In some embodiments, the subject is a subject who has the potential to develop toxicity or who is known to be a likely candidate to develop the toxicity, for example, because such toxicity is known to be associated with a particular treatment or treatments.

In some embodiments, the subject has been or is receiving a therapy, such as a cell therapy, for example, for treating a disease or condition in a subject. For example, in some embodiments, the cell therapy is an adoptive cell therapy, including a therapy involving administration of cells expressing chimeric receptors specific for a disease or disorder of interest, such as chimeric antigen receptors (CARs) and/or other recombinant antigen receptors, as well as other adoptive immune cells and adoptive T cell therapies. In some embodiments, the adoptive cell therapy includes administration of a dose of cells expressing a recombinant receptor, such as a CAR or other recombinant antigen receptor. In some embodiments, chimeric receptors, such chimeric antigen receptor, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Adoptive cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. In certain contexts, available approaches to adoptive cell therapy may not always be entirely satisfactory. In some contexts, optimal efficacy can depend on the ability of the administered cells to recognize and bind to a target, e.g., target antigen, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states (such as effector, long-lived memory, less-differentiated, and effector states), to provide effective and robust recall responses following clearance and re-exposure to target ligand or antigen, and avoid or reduce exhaustion, anergy, terminal differentiation, and/or differentiation into a suppressive state.

In some aspects, the provided embodiments are based on observations that the efficacy of adoptive cell therapy may be limited by the development of toxicity in the subject to whom such cells are administered, which toxicity in some cases can be severe. For example, in some cases, administering a dose of cells expressing a recombinant receptor, e.g. a CAR, can result in toxicity or risk thereof, such as CRS or neurotoxicity, including, in some cases, severe CRS or severe neurotoxicity. In some cases, while a higher dose of such cells can increase the efficacy of the treatment, for example, by increasing exposure to the cells such as by promoting expansion and/or persistence, they may also result in an even greater risk of developing atoxicity or a more severe toxicity. Also, in some cases, subjects with a higher disease burden also may be at a greater risk for developing a toxicity or a more severe toxicity.

Certain available methods for treating or ameliorating toxicity may not always be entirely satisfactory. Many such approaches focus, for example, on targeting downstream effects of toxicity, such as by cytokine blockade, and/or delivering agents such as high-dose steroids which can also eliminate or impair the function of administered cells. Additionally, such approaches often involve administration of such interventions only upon detection of physical signs or symptoms of toxicity, which, in some cases, may develop upon development of severe toxicity in the subject. Many of these other approaches also do not prevent other forms of toxicity such as neurotoxicity, which can be associated with adoptive cell therapy. In some cases, such therapies are administered only after a subject presents with a physical sign or symptom of a toxicity. In some cases, this is at a time where such symptoms are severe, and that therefore may require even harsher or more extreme treatments (e.g. higher dosages or an increased frequency of administration) to ameliorate or treat the toxicity.

The use of certain alternative approaches does not provide satisfactory solutions to such issues. For example, an approach that included treatment of all or a large subset of subjects administered a treatment such as a cell therapy (e.g., larger than the subset of subjects that will ultimately develop toxicity or are at or above a certain level of risk therefor), regardless of risk or with a threshold of risk that is too low, may not be satisfactory. For example, a subject administered with a cell therapy with an agent or therapy for ameliorating or preventing a toxicity (e.g. steroid). For example, such approaches in which the treatment was administered concurrently with the administration of the cells, or within a window of time after administration of cells, but before the development of a physical sign or symptom or severe sign or symptom, at least without the appropriate level of risk assessment, may not be satisfactory. For example, not all subjects administered with a cell therapy will or do develop a toxic outcome, or develop such a toxic outcome that requires intervention. Thus, such alternatives in some contexts would involve needlessly treating certain subjects in which such treatment may be unwarranted. Further, in some cases, such agents and therapies (e.g. steroids) are themselves associated with toxic side effects. Such side effects may be even greater at the higher dose or frequency in which is it necessary to administer or treat with the agent or therapy in order to treat or ameliorate the severity of the toxicity that can result from cell therapy. In addition, in some cases, an agent or therapy for treating a toxicity may limit the efficacy of the cell therapy, such as the efficacy of the chimeric receptor (e.g. CAR) expressed on cells provided as part of the cell therapy (Sentman (2013) Immunotherapy, 5:10).

The provided methods offer advantages over available approaches and alternative solutions for addressing, predicting, and treating or preventing, the risk of toxic outcomes. In particular, the provided methods in some embodiments result in the identification of only those subjects predicted to be at risk or above a particular threshold risk level for developing toxicity, such as one related to a cell therapy. Thus, the provided methods in some embodiments permit intervention in toxic outcomes in only a subset of subjects that are more likely to develop toxicity. In many cases, this avoids treating the toxicity in all subjects being administered the cell therapy, which as described above may be unwarranted if many of the subjects would never have developed the toxicity and/or can result in significant side effects itself.

Further, the provided methods in some embodiments also provide advantages associated with the feature that the risk of developing toxicity, such as CRS (e.g. severe CRS) or neurotoxicity (e.g. severe neurotoxicity), can be predicted early, such as early after administration or initiation of a treatment such as a cell therapy, or after administration or initiation of a first dose of cell therapy. Thus, in some cases, those subjects that are predicted to be at risk of and/or are more likely to be at risk for developing toxicity (e.g. CRS or neurotoxicity, such as severe CRS or severe neurotoxicity) can receive an intervention early and generally before a physical sign or symptom of the toxicity, e.g. severe toxicity, has developed that would otherwise lead to an intervening treatment. In some cases, the ability to intervene early in the treatment of a toxic outcome or the potential of a toxic outcome can mean that a reduced dosage of an agent for treating or ameliorating the toxicity can be given and/or a decreased frequency of administration of such agent or therapy can be given.

In some embodiments, the provided methods are based on observations that certain biomarkers, such as certain cytokine biomarkers, are significantly altered as early as day 1 after administration of an adoptive cell therapy, e.g. CAR-T cell therapy in those patients who later developed a severe toxicity, e.g. grade 3 or higher, CRS or neurotoxicity. Thus, such biomarkers as described herein can be used in predictive methods to identify subjects that are likely or more likely to develop a severe toxicity to the cell therapy in order to be able to intervene earlier in the treatment of the subject to reduce later severe toxicity. Such methods can inform rational strategies for early intervention and thereby facilitate the safe and effective clinical application of adoptive cell therapy, such as CAR-T cell therapy.

In some embodiments, the provided methods can predict the risk of developing toxicity, such as neurotoxicity (e.g. severe neurotoxicity), or CRS (e.g. severe CRS), generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing.

In some embodiments, the provided methods include administration of an agent for ameliorating a toxic outcome (e.g. an agent for ameliorating neurotoxicity or CRS), such as after the predictive methods are carried out, at a dosage that is reduced or less than the dosage of such agent administered to a subject at a time when a physical sign or symptom has developed and/or at a time that is greater than 3 days (e.g. greater than 3 to 14 days, such as greater than 3, 4, 5, 6, 7, 8, 9, 10, 11, 12, 13 or 14 days) after administration or initiation of a cell therapy or after administration or initiation of a first dose of cell therapy. In some embodiments, the reduction in the dose is at least 1.2-fold, 1.3-fold, 1.4-fold, 1.5-fold, 2-fold, 3-fold, 4-fold, 5-fold, 6-fold, 7-fold, 8-fold, 9-fold or 10-fold.

In some embodiments, the provided methods include administration of the agent at a frequency in a dosage cycle or regimen that is decreased compared to the frequency of administration of an agent in a dosage cycle or regimen of such agent that is initiated at a time when a physical sign or symptom has developed and/or at a time that is greater than 3 days (e.g. greater than 3 to 14 days, such as greater than 3, 4, 5, 6, 7, 8, 9, 10, 11, 12, 13 or 14 days) after administration or initiation of a cell therapy or after administration or initiation of a first dose of cell therapy. In some embodiments, where a reference regimen or cycle of treatment of an agent (e.g. steroid) involves administration for 3 days, the decrease in the frequency of administration can be to administration for 1 day or for 2 days.

In some embodiments, if the subject is predicted to be at a risk for or diagnosed with toxicity (e.g. neurotoxicity, such as severe neurotoxicity and/or CRS, such as sCRS), the treatment with cell therapy is altered. For example, if the subject is identified as at risk for developing toxicity (e.g. neurotoxicity, such as severe neurotoxicity and/or CRS, such as sCRS), treatment with cell therapy may be discontinued. In some aspects, alteration of the treatment may include administering a different cell therapy for treating the disease or condition or administering a treatment for treating the disease or condition other than the cell therapy. In some instances, alteration of the cell therapy includes administering a subsequent dose of cells in combination with a second therapeutic agent that treats the disease or condition. In some cases, following identification of risk for developing toxicity (e.g. neurotoxicity, such as severe neurotoxicity and/or CRS, such as sCRS) in a subject, the treatment is altered to include administration of a subsequent dose of cells that is decreased compared to the prior dose of cells or the frequency of administration of the cell therapy is decreased.

In some aspects, the method further includes, after administration of the agent or therapy for ameliorating or treating toxicity (e.g. neurotoxicity, such as severe neurotoxicity and/or CRS, such as sCRS), monitoring the efficacy of the agent on the treatment, prevention, delay, or attenuation of the toxicity (e.g. neurotoxicity, such as severe neurotoxicity and/or CRS, such as sCRS). In some cases, monitoring the efficacy includes determining a subsequent detected parameter of the biomarker or each biomarker in a panel of biomarkers, which optionally are the one or more biomarkers (e.g. cytokines), in a subsequent biological sample from the subject that is or has been obtained following administration of the agent to the subject, thereby measuring a subsequent detected parameter for the biomarker or for each of the biomarkers in a panel. In some cases, the method includes comparing the subsequent detected parameter of each biomarker, optionally each cytokine, to a detected parameter of the biomarker present in a prior sample or to a baseline sample prior to the administration of the agent. In some instances, the agent is considered to be efficacious if the subsequent detected parameter is not altered to a value that is more predictive of the development of toxicity (e.g. neurotoxicity, such as severe neurotoxicity and/or CRS, such as sCRS) than the detected parameter present in the prior sample or baseline sample.

In some embodiments, if the treatment is not efficacious, the method further includes continuing treatment with the agent, increasing the dosage of the agent, increasing the frequency of administration of the agent or administering a different agent for treating, preventing, delaying, or attenuates the risk for developing neurotoxicity, such as severe neurotoxicity and/or CRS, such as sCRS.

II. METHODS OF ASSESSING BIOMARKERS RELATED TO TOXICITY

Among the provided methods are methods of treatment, methods for ameliorating the development of toxicity in a subject or methods of diagnosing or predicting a risk for developing toxicity associated with cell therapy in a subject that involves assessing or detecting biomarkers that are associated with the toxicity, e.g., neurotoxicity, such as severe neurotoxicity and/or CRS, such as severe CRS. In some embodiments, the methods involve assessing or detecting one or a panel of biomarkers and/or parameters, and comparing the parameters to a particular reference value, e.g., those associated with a risk for developing toxicity. In some embodiments, the methods also involve administering an agent or a therapy that can treat, prevent, delay and/or attenuate development of the toxicity, e.g., based on the assessment and comparison of the biomarkers.

In some aspects, the method includes obtaining a biological sample for detecting the parameter (e.g. concentration, amount, level or activity) and/or assessing the presence of and/or or detecting the parameter (e.g. concentration, amount, level or activity) in a biological sample generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing. In some aspects, the method can predict (e.g. via comparison to a reference value for the biomarker or each of the biomarkers in a panel of biomarkers) the risk of developing toxicity (e.g. neurotoxicity, such as severe neurotoxicity and/or CRS, such as severe CRS) in a subject early administration of the cell therapy, or a first administration or dose thereof, or after the initiation of any of the foregoing, such as generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing. In some embodiments, the method includes administering to the subject an agent or therapy to ameliorate or treat the risk of developing toxicity in the subject, generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing.

In some embodiments, the biomarkers or each biomarker in a panel comprise a cytokine and/or other serum or blood factor, such as any as described. In some embodiments, the biomarker or each biomarker in a panel is a cytokine, which, in some cases, can be a chemokine. In some embodiments, the biomarkers or each biomarker in a panel comprises a soluble receptor. In some embodiments, the biomarkers or each biomarker in a panel comprises a soluble serum protein. Exemplary biomarkers or panel of biomarkers is described below.

In some embodiments, the one or more biomarkers include two or more biomarkers, e.g., cytokines. In some aspects, the two or more biomarkers are measured simultaneously from the same sample. In other aspects, the two or more biomarkers are measured or sequentially from the same sample or from different samples from the subject. In some embodiments, the level, amount, concentration or other parameter of the biomarker or the panel of biomarkers are indicative of the risk of developing neurotoxicity, such as severe neurotoxicity and/or CRS, such as sCRS.

In some embodiments, a panel of biomarkers is assessed, detected or measured that includes at least a first and second biomarker. In some embodiments, if the detected parameters of the first and second biomarkers is altered compared to a biomarker in a control, e.g. a level of such biomarker or panel of biomarkers in normal subjects or subjects having a meet a defined classification or threshold level, such as described, the subject is identified or is diagnosed or predicted to be at risk for developing toxicity (e.g. neurotoxicity, such as severe neurotoxicity and/or CRS, such as severe CRS). In some such aspects, if the detected parameters of both the first and second biomarkers do not meet the classification, the subject is identified or is diagnosed or predicted not to be at risk for developing toxicity (e.g. neurotoxicity, such as severe neurotoxicity and/or CRS, such as severe CRS). In some cases, if the detected parameter of only one of the first and second biomarkers does not meet the classification, the method can further include measuring a parameter of at least a third biomarker, that alone or together with the other biomarkers in the panel is indicative of risk for developing a toxicity (e.g. neurotoxicity, such as severe neurotoxicity and/or CRS, such as severe CRS). In some embodiments, the third biomarker can be compared to a reference value for the biomarker, such as based on a classification scheme, to thereby determine whether the subject is at risk for developing a toxicity (e.g. neurotoxicity, such as severe neurotoxicity and/or CRS, such as severe CRS). In some embodiments, the third biomarker is a biomarker that is different from the first and second biomarkers. In some such aspects, if the detected parameter of the third biomarker meets the classification, the subject is identified or is diagnosed or predicted to be at risk for developing toxicity (e.g. neurotoxicity, such as severe neurotoxicity and/or CRS, such as severe CRS). In some cases, if the detected parameter of the third biomarker does not meet the classification, the subject is identified or is diagnosed or predicted not to be at risk for developing toxicity (e.g. neurotoxicity, such as severe neurotoxicity and/or CRS, such as severe CRS).

In some embodiments, the toxicity is severe neurotoxicity. In some embodiments, the toxicity is neurotoxicity; in some embodiments, it is severe neurotoxicity. In some embodiments, the toxicity is CRS, such as severe CRS.

In some embodiments, the biomarker(s), e.g., the factor, such as the cytokine or chemokine or receptor thereof, or biomarker(s) comprise one or more of, e.g., 2-3 or more of, transforming growth factor beta (TGF-beta), interleukin 6 (IL-6), interleukin 10 (IL-10), interleukin 15 (IL-15), interferon gamma (IFN-gamma), or monocyte chemoattractant protein-1 (MCP-1); or IL-6, IFN-γ, IL-15, IL-2, IL-18, and/or TIM3, and/or ferritin and/or CRP. In some embodiments, the biomarker(s) comprise one or more of, e.g., 2-3 or more of, IFN-γ, IL-2, IL-6, IL-8, IL-10, IL-15, IL-2 receptor alpha (IL-2Ra), monocyte chemoattractant protein-1 (MCP-1), tumor necrosis factor receptor p55 (TNFRp55), tumor necrosis factor receptor p75 (TNFRp75), T-cell immunoglobulin and mucin-domain containing-3 (TIM-3), B cell-activating factor belonging to TNF family (BAFF), macrophage inflammatory protein 1 beta (MIP-1 (3), C-reactive protein (CRP), IL-18, soluble IL-6 receptor (sIL-6R) and ferritin. In some embodiments, the biomarkers include one or more of, e.g., one, two, or three of, IL-6, IFNγ, IL-15, IL-8 and IL-10; and/or include one or more of, e.g., one, two, or three of, IL-6, ferritin and C-reactive protein (CRP), and optionally additionally IFNγ. In some embodiments, the biomarkers include one or more of, e.g., one, two, three or four of, IL-6, MCP-1, IL-10 and IL-15. In some aspects of such embodiment, the toxicity is CRS and/or the disease or condition is a leukemia, such as an ALL, or a lymphoma, such as an NHL.

In some embodiments, the cytokine or cytokines can be transforming growth factor beta (TGF-beta), interleukin 6 (IL-6), interleukin 10 (IL-10), interleukin 15 (IL-15), interferon gamma (IFN-gamma) or monocyte chemoattractant protein-1 (MCP-1). In some embodiments, the cytokine or cytokines can be IL-8, IL-18 and/or IL-2. In some embodiments, the biomarker or biomarkers can be ferritin, C-reactive protein (CRP) and/or soluble TNF receptor type 1 (sTNFR1). As described, such biomarkers, e.g., cytokines, have been found to be associated with or predictive of developing toxicity, e.g. neurotoxicity, such as severe neurotoxicity and/or CRS, such as severe CRS, in subjects that have received or are receiving cell therapy. In some embodiments, such subjects can have a disease or condition that is a cancer, such as a leukemia or lymphoma. In some embodiments, the subject has a non-Hodgkin lymphoma (NHL) or an acute lymphoblastic leukemia (ALL) or a chronic lymphocytic leukemia (CLL), In some embodiments, the subject has NHL, and the cytokine or cytokines in a panel can be transforming growth factor beta (TGF-beta), interleukin 6 (IL-6), interleukin 10 (IL-10), interleukin 15 (IL-15), interferon gamma (IFN-gamma), such as generally at least two or three of TGF-beta, IL-6 or IL-15. In some embodiments, the subject has ALL, and the cytokine or cytokines in a panel can be interleukin 6 (IL-6), interleukin 15 (IL-15) or monocyte chemoattractant protein-1 (MCP-1), such as generally at least two or three of such cytokines.

In some embodiments, the subject has NHL or ALL, and the biomarker and biomarkers in a panel can be interleukin-15 (IL-15), interleukin-6 (IL-6), interleukin-2 (IL-2), interferon gamma (IFN-gamma), C-reactive protein (CRP) and/or ferritin, such as generally at least two or three of IL-15, IL-6, IL-2, IFN-gamma, CRP and/or ferritin. In some embodiments, the subject has NHL or ALL, and the biomarker and biomarkers in a panel can be interleukin-15 (IL-15), interleukin-6 (IL-6), interleukin-8 (IL-8), interleukin-10 (IL-10), soluble TNF receptor type 1 (sTNFR1) and/or interferon gamma (IFN-gamma), such as generally at least two or three of IL-15, IL-6, IL-8, IL-10, sTNFR1 and/or IFN-gamma.

In some embodiments, the subject has NHL, ALL or CLLL, and the biomarker and biomarkers in a panel can be IFN-γ, IL-2, IL-6, IL-8, IL-10, IL-15, IL-2Ra, MCP-1, TNFRp55, TNFRp75, TIM3, BAFF, MIP-1β, CRP, IL-18, sIL-6R and/or ferritin, such as generally at least two or three or four of IL-6, MCP-1, IL-10 and IL-15.

In some embodiments, the parameters include clinical and laboratory parameters and/or biomarkers. In some embodiments, the clinical and laboratory parameters and/or biomarkers include one or more of body temperature (° C.), absolute blood neutrophil count (ANC), blood monocyte count, heart rate, blood platelet count, and blood levels of ferritin, albumin, fibrinogen and C-reactive protein. In some embodiments, the parameters include exposure of administered cells, e.g., exposure of administered cells that are CD4$^+$ or CD8$^+$ or total exposure of administered cells. In some embodiments, exposure is determined by area under the curve (AUC) of the administered cells over a defined period of time, e.g., 0-28 days after administration of the cell therapy, or a first administration or dose thereof, or after the initiation of any of the foregoing. In some embodiments, the parameters can be used singly or in combination with other parameters and/or biomarkers, such as in a panel of biomarkers.

In some embodiments, the parameters include vital signs, hemodynamic parameters and/or biomarkers, such as parameters that indicate hemodynamic instability or capillary leak, e.g., hypoalbumenia. In some embodiments, the vital signs, hemodynamic parameters and/or biomarkers include one or more of absolute maximum temperature (° C.), heart rate (beats/min), systolic blood pressure (mm Hg), diastolic blood pressure (mm Hg), respiratory rate (breaths/min), total blood protein (g/dL), blood albumin levels (g/dL), and weight change from baseline (kg). In some embodiments, the parameters include temperature (° C.), heart rate (beats/min), respiratory rate (breaths/min), total blood protein (g/dL) and blood albumin levels (g/dL).

In some embodiments, the parameters include factors and/or biomarkers involved in coagulation, such as biomarkers associated with coagulopathy or requirement for transfusion. In some embodiments, the factors and/or biomarkers include one or more of levels of D-dimer (µg/mL), fibrinogen (mg/dL), prothrombin time (PT; sec), activated partial thromboplastin time (aPTT; sec), platelet count (1000/µL) and transfusion requirements. In some embodiments, the parameters include levels of D-dimer (µg/mL), prothrombin time (PT; sec), activated partial thromboplastin time (aPTT; sec), and platelet count (1000/µL).

In some embodiments, the parameters include blood counts, e.g., blood cell counts, such as measurements that indicate cytopenia, e.g., monocytopenia or low eosinophils. In some embodiments, the blood counts include one or more of neutrophil count (1000/µL), monocyte count (1000/µL), eosinophil count (1000/µL), hemoglobin (g/dL) and hematocrit percentage (%). In some embodiments, the parameters include neutrophil count (1000/µL), monocyte count (1000/µL) and eosinophil count (1000/µL).

In some embodiments, the parameters include hepatic and renal factors and/or biomarkers, such as factors or biomarkers that indicate hepatic and renal dysfunction. In some embodiments, the hepatic and renal factors and/or biomarkers include one or more of levels of aspartate transaminase (AST; units/L), alanine aminotransferase (ALT; units/L), alkaline phosphatase (ALP; units/L), total bilirubin (mg/dL) and blood urea nitrogen (BUN; mg/dL). In some embodiments, the parameters include aspartate transaminase (AST; units/L) and total bilirubin (mg/dL).

In some aspects of the provided methods, a subject is determined to be at risk of developing toxicity (e.g. neurotoxicity, such as severe neurotoxicity and/or CRS, such as severe CRS) by a comparison of the parameter (e.g. concentration, amount, level or activity) of the biomarker or, individually, each of the biomarkers to a reference value of the corresponding parameter for the biomarker or each biomarker. In some embodiments, the comparison indicates whether the subject is or is not at risk for developing toxicity, e.g., neurotoxicity and/or CRS, and/or indicates a degree of risk for developing said toxicity. In some embodiments, the reference value is one that is a threshold level or cut-off at which there is a good predictive value (e.g. accuracy, sensitivity, specificity and/or AUC) that such toxicity will occur or is likely to occur either alone or in combination with one or more biomarkers in the panel. In some cases, such reference value can be or is predetermined or known prior to performing the method, such as from a plurality of subjects previously treated with a cell therapy and assessed for the correlation of the parameter of the biomarker or, individually, each of the biomarkers in a panel to the presence of a toxic outcome (e.g. the presence of neurotoxicity, such as severe neurotoxicity and/or CRS, such as severe CRS).

In some embodiments, a parameter of a biomarker (e.g. TGF-beta) that is lower than the reference value of the corresponding parameter is associated with a positive prediction of a risk of toxicity (alone or in conjunction with assessment of the other biomarkers in the panel). In some embodiments, a parameter of a biomarker (e.g. IL-6, IL-15, IL-10, IFN-gamma or MCP-1) that is higher or greater than the reference value of the corresponding parameter is associated with a positive prediction of a risk of toxicity (alone or in conjunction with assessment of the other biomarkers in the panel).

In some embodiments, the method includes assessment or detection of each biomarker in a panel. e.g. comprising two or more biomarkers as described, and comparison to a reference value for each of said biomarkers in the panel relative to a classification scheme that provides a good predictive value (e.g. accuracy, sensitivity, specificity and/or AUC) that such toxicity will occur or is likely to occur. In some embodiments, the method includes a classification scheme that prioritizes or sets, among the combination of biomarkers, those that must, individually, meet the reference value. Generally, at least two or at least three biomarkers from among a panel of biomarkers must meet the classification scheme. Thus, in some embodiments, it is understood that each biomarker in the panel need not meet the reference value in the classification or scheme in order for toxicity (e.g. neurotoxicity, such as severe neurotoxicity and/or CRS, such as severe CRS) to be predicted. Exemplary classification schemes are described, such as exemplary classification schemes for predicting neurotoxicity, such as severe neurotoxicity and/or CRS, such as severe CRS.

In some embodiments, the reference level is an average level of a group of subjects receiving the same treatment, e.g., for the same indication, and/or such subjects that do not develop the toxicity outcome, such as do not develop grade 3 or higher neurotoxicity or grade 3 or higher CRS. In some embodiments, the reference level is calculated and/or determined using statistical, clinical, and/or other analytical methods or tests, e.g., determination mean, median, accuracy, sensitivity, specificity, integral, AUC, univariate and multivariate logistic regression, receiver operating characteristic (ROC) and/or any of the other analysis or test methods described herein.

In some embodiments, the parameters assessed are peak serum levels, concentrations and/or activity of the biomarker or a panel of biomarkers, e.g., cytokines, within a defined period of time, e.g., the peak level within 1, 2, 3, 4, 5, 6, 7, 8, 9, 10, 12, 15, 18, 21, 24, 27 and/or 30 days or more after administration of the cell therapy, or a first administration or dose thereof, or after the initiation of any of the foregoing. In some embodiments, the peak serum level is the highest serum level of the biomarker within the defined period. In some embodiments, the parameters assessed are peak levels, concentrations and/or activity of the biomarker or a panel of biomarkers, e.g., cytokines, within a relatively short period of time following the administration of the cell therapy, e.g., the peak level within 4, 8, 12, 24, 36 or 48 hours after, administration of the cell therapy, or a first administration or dose thereof, or after the initiation of any of the foregoing.

In some embodiments, the parameters assessed are levels, concentrations and/or activity of the biomarker or a panel of biomarkers, e.g., cytokines, at or around a defined time point, e.g., the level measured at a time point generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing. In some embodiments, the parameter assessed is an integral over time of particular levels, concentrations and/or activity of the biomarker or panel of biomarkers, such as those determined by area under the curve (AUC; defined integral) of a plot of levels, concentrations and/or activity, over a defined period of time, e.g., over 1, 2, 3, 4, 5, 6, 7, 8, 9, 10, 12, 15, 18, 21, 24, 27 and/or 30 days or more after administration of the cell therapy, or a first administration or dose thereof, or after the initiation of any of the foregoing. In some embodiments, the parameter assessed is a relative change in levels, concentrations and/or activity of the biomarker or panel of biomarkers, such as relative change over a defined period of time or compared to a different condition (e.g., before or after administration of a particular therapeutic). In some embodiments, reference values are calculated or determined based on parameters that are determined, such as peak serum levels, levels at a specific time point, e.g., day 1 levels, AUC in a defined period of time, e.g., AUC0-28 days and/or changes in such parameters.

In some embodiments, the parameters assessed are peak or trough levels or measurements, e.g., serum levels or concentrations or measurements of a particular parameter, such as temperature or cell counts, within a defined period of time, e.g., the peak or trough levels or measurements within 1, 2, 3, 4, 5, 6, 7, 8, 9, 10, 12, 15, 18, 21, 24, 27 and/or 30 days or more after administration of the cell therapy, or a first administration or dose thereof, or after the initiation of any of the foregoing. In some embodiments, the peak level or measurement is the highest level or measurement within the defined period. In some embodiments, the trough level or measurement is the lowest level or measurement within the defined period. In some embodiments, the parameters assessed are peak or trough levels or measurements within a relatively short period of time following the administration of the cell therapy, e.g., the peak or trough levels or measurements within 4, 8, 12, 24, 36 or 48 hours after, administration of the cell therapy, or a first administration or dose thereof, or after the initiation of any of the foregoing.

In some embodiments, the parameters assessed are peak or trough levels or measurements at or around a defined time point, e.g., the level measured at a time point generally within 4 hours to 3 days of administration of the cell therapy, or a first administration or dose thereof, or after the initiation of any of the foregoing, such as generally within or about 1 day, 2 days or 3 days after administration of the cell therapy, or a first administration or dose thereof, or after the initiation of any of the foregoing. In some embodiments, the parameter assessed is an integral over time of particular levels or measurements of the biomarker or panel of biomarkers, such as those determined by area under the curve (AUC; defined integral) of a plot of levels or measurements over a defined period of time, e.g., over 1, 2, 3, 4, 5, 6, 7, 8, 9, 10, 12, 15, 18, 21, 24, 27 and/or 30 days or more after administration of the cell therapy, or a first administration or dose thereof, or after the initiation of any of the foregoing. In some embodiments, the parameter assessed is a relative change in level or measurements of the biomarker or panel of biomarkers, such as relative change over a defined period of time or compared to a different condition (e.g., before or after administration of a particular therapeutic). In some embodiments, reference values are calculated or determined based on parameters that are determined, such as peak levels or measurements, levels or measurements at a specific time point, e.g., day 1 levels, AUC in a defined period of time, e.g., AUC0-28 days and/or changes in such parameters.

In some embodiments, the reference value is based on a receiver operating characteristic (ROC) curve of the biomarker or each biomarker in the panel of biomarkers in a population of diseased subjects having a cancer treated with a cell therapy. In some aspects, the reference value is an amount, concentration or an activity of the biomarker, and generally is a reference value of the same parameter that is being assessed, detected or measured in the subject. In some cases, the reference value is determined by the Youden Index. Generally, the Youden-Index is the reference value in which sensitivity and specificity are maximal. In some embodiments, other methods known to a skilled artisan for determining a threshold or cut-off at which there is a good predictive value (e.g. accuracy, sensitivity, specificity and/or AUC) also can be used for determining or setting the reference value.

In some aspects, the reference value for a biomarker or, individually, for each biomarker in a panel, is selected based on sensitivity or net sensitivity and/or specificity or net specificity, such as determined by ROC analysis. In some embodiments, the reference value for a biomarker or, individually, for each biomarker in a panel is selected to provide a sensitivity or net sensitivity of greater than 0.50, greater than 0.60, greater than 0.70, greater than 0.80, greater than 0.90 or greater than 0.95. In some cases, the reference value for a biomarker or, individually, for each biomarker in a panel is selected to provide a specificity or net specificity of greater than 0.50, greater than 0.60, greater than 0.70, greater than 0.80, greater than 0.90 or greater than 0.95. In some instances, the reference value for a biomarker or, individually, for each biomarker in a panel is selected to provide an area under the curve (AUC) in a ROC analysis of greater than 0.80, greater than 0.85, greater than 0.90 or greater than 0.95.

In some embodiments, the reference value for a biomarker or, individually, for each biomarker in a panel, is selected to provide a sensitivity or net sensitivity of greater than 0.80, greater than 0.85, greater than 0.90 or greater than 0.95. In some instances, the reference value for a biomarker or, individually, for each biomarker in a panel is selected to provide a specificity or net specificity of greater than 0.60, greater than 0.70, greater than 0.80, greater than 0.90 or greater than 0.95. In some aspects, the reference value for a biomarker or, individually, for each biomarker in a panel is selected to provide an AUC in a ROC analysis of greater than 0.85, greater than 0.90 or greater than 0.95.

In some embodiments, for a given assay that indicates a positive or negative result for an outcome, true positive (TP) is a positive call (PC) in that assay in the case of an actual positive; false positive (FP) is a positive call in the case of an actual negative; true negative (TN) is a negative call (NC) in the case of an actual negative; false negative is a negative call in the case of an actual positive.

Positive predictive value (PPV) is calculated as number of true positives (TPs) divided by the total number of positive calls (i.e., the number of TP+FP) (PPV=TP/(TP+FP).

Negative predictive value (NPV) is calculated as number of true negatives (TNs) divided by the total number of negative calls (i.e., the number of TN+FN) (NPV=TN/(TN+FN).

For a given assay, Sensitivity may be calculated as TP divided by actual positives (TP/AP). Specificity may be calculated as TN/actual negatives (TN/AN).

In some embodiments, two or more simultaneous assays (e.g., Test 1, Test 2, and so forth) are used, each individually designed to give a positive or negative result for the same outcome. In some embodiments, the goal of a simultaneous two-stage assay approach is to maximize sensitivity, and thus to identify a higher number of positives, even if it means a reduced specificity or increase in false positives. In such embodiments of a simultaneous two-stage testing, for a given sample or subject, a positive call is only made if the sample or subject receives a positive call in each of the simultaneous tests. Simultaneous does not necessarily mean that the tests need to physically be run simultaneously; the term is merely used to indicate that to receive a positive call for the simultaneous tests, collectively, the subject or sample must receive a positive call on each of the individual simultaneous tests. Accordingly, simultaneous testing is generally designed to increase specificity but may decrease sensitivity.

In some embodiments, two or more assays (e.g., Test 1, Test 2, and so forth) are used, each individually designed to give a positive or negative result for the same outcome, in which the two-stage approach is designed to increase net sensitivity, e.g., to increase overall sensitivity even if specificity is decreased. In some embodiments, such net-sensitivity-increased design is used in simultaneous approaches. Generally, the goal of such a two-stage sequential assay approach is to maximize or increase specificity, even at the expense of sensitivity. Thus, such an approach increases net sensitivity. Thus, such an approach may be designed to avoid too many false positives, even if it means a reduced sensitivity or increase in false negatives. In such a sequential assay, for a given sample or subject, a negative call is only made if the sample or subject receives a negative call in each of the sequential tests; in other words, samples/subjects with negative calls on Test 1 or on Test 2 are called as negative. A sequential two-stage testing approach does not necessarily mean that the detection assays need to physically be run simultaneously. This language refers only to the approach that to receive a positive call for the sequential tests, collectively, the subject/sample need only must receive a positive call on one of the individual sequential tests, but that to receive a negative score, it must be negative on all sequential tests. Accordingly, sequential testing is generally designed to increase specificity but may decrease sensitivity.

With reference to an assay approach with two or more stages (e.g., test 1, test 2 . . . ), "Net Specificity" may be calculated as the total number of true positives calls (as made taking into account the overall specificity both tests, whichever approach is used) (total TP) divided by the number of actual positives in the population assessed (total TP/AP). Similarly, the "Net Sensitivity" may be calculated as the total number of true negatives (as made taking into account both tests, whichever approach is used). For two test-approach designed to increase sensitivity, the net specificity may be calculated as equal to the (specificity of test 1 (Sped))+(specificity of test 2 (Spec2))−(Spec 1×Spec 2). Thus in some embodiments, the net specificity may be calculated as Sen1×Sen2. For two test-approach designed to increase specificity, the net sensitivity may be calculated as equal to the (sensitivity of test 1 (Sen1))+(sensitivity of test 2 (Sen2))−(Sen1×Sen2). The net specificity may be calculated as Spec1×Spec2.

In many contexts of certain diagnostic methods, a so-called "sequential" approach is most often used in approaches involving an initial, often less-invasive, screening test, which is carried out on an often larger group, followed by an often more invasive diagnostic test, generally administered only to subjects identified as positive on the first (screening) test. In this respect, the net sensitivity is lower, but net specificity is higher. On the other hand, it is often the case that when different parameters are physically assessed at the same time or based on a single sample collection (e.g., based on a single sample obtained from a subject or single physical test), for many diagnostic approaches, an increased sensitivity is favored over specificity. In other words, there is often a desire to avoid false negatives, even at the expense of specificity (e.g., even if more false positives occur). For example, if two parameters are indicative of a cancer, but alone would risk too many false positives, a so-called "simultaneous" approach in many contexts may be used, in which a subject is deemed positive if positive for either individual test, but only deemed negative if negative for both.

On the other hand, in some embodiments of the provided methods and biomarkers, a so-called "sequential" approach is used, despite the fact that only a single sample often is collected and/or multiple samples are collected simultaneously, and the tests actually run at the same time. Whereas there is a desire to mitigate true risk of developing severe toxicities, certain interventions designed to mitigate such development may present their own challenges. For example, administration of certain agents to treat or prevent toxicities, such as neurotoxicity or CRS, such as steroids, may not be well-tolerated, particularly in subjects having just undergone a transplant and/or other cancer-related intervention. Thus, in some embodiments, the tests are designed to increase specificity, to avoid treating subjects falsely identified as positive for the risk. For example, a so-called "Sequential" test may be used in this case where a subject is only deemed positive if positive on two or more separate tests, even if run simultaneously. In other embodiments, a sequential approach may be used. In one such aspect, the provided methods, because they predict neurotoxicity and/or CRS at an earlier stage, allow for administration of a dosage of the agent that is reduced as compared to what would be given to a subject already exhibiting signs or symptoms of the toxicity.

Thus, in some embodiments of the provided assays and kits, there is a desire for increased specificity over sensitivity, even when testing is carried out simultaneously. Thus in some embodiments, a two-stage assay is used, and even when carried out simultaneously or from the same sample, specificity and NPV is increased as compared to the individual tests, and PPV and sensitivity is decreased, e.g., by applying a "sequential" approach (e.g., where a subject is only deemed positive if positive for both markers or tests, and otherwise is deemed negative). In some embodiments, a combination of sequential and simultaneous methods is used.

In other embodiments, however, by way of allowing reduced dosage and/or the frequency of administration of the agent to treat or prevent neurotoxicity and/or CRS as compared to that used in a subject already exhibiting signs or symptoms of neurotoxicity and/or CRS, e.g., already exhibiting signs of severe such toxicity. Thus, in some embodiments, because the methods allow administration of a reduced dose or frequency, a lower specificity is tolerable and a so-called "simultaneous" approach may be used to reduce the risk of false negatives, e.g., wherein the subject is only deemed negative if negative on both or all tests or markers, and otherwise deemed positive or at risk.

In some embodiments, parameters of one or more biomarkers are assessed from an assessment of the parameters in a biological sample. In some aspects, the biological sample is a bodily fluid or a tissue. In some such embodiments, the biological sample, e.g., bodily fluid, is or contains whole blood, serum or plasma.

In some embodiments, measuring the value of the one or more biomarkers comprises performing an in vitro assay. In some aspects, the in vitro assay is an immunoassay, an aptamer-based assay, a histological or cytological assay, or an mRNA expression level assay. In some embodiments, the values of the one or more biomarkers are measured by an enzyme-linked immunosorbent assay (ELISA), immunoblotting, immunoprecipitation, radioimmunoassay (RIA), immunostaining, a flow cytometry assay, surface plasmon resonance (SPR), a chemiluminescence assay, a lateral flow immunoassay, an inhibition assay or an avidity assay. In some cases, the value of at least one of the one or more biomarkers is determined using a binding reagent that specifically binds to at least one biomarker. In some aspects, the binding reagent is an antibody or antigen-binding fragment thereof, an aptamer or a nucleic acid probe.

In some embodiments, the accuracy of the identification or prediction is greater than 80%, greater than 85%, greater than 90%, or greater than 95%.

A. Exemplary Biomarkers Predictive of Neurotoxicity

In some aspects, the biomarkers or each of the biomarkers in a panel is a cytokine (e.g. IL-6, IL-15, IL-10, IFN-gamma or MCP-1), and the subject is identified or is predicted or diagnosed to be at risk for developing a toxicity (e.g. neurotoxicity, or severe neurotoxicity) if the detected parameters of at least two of the cytokines meet the classification. In some cases, the subject is identified or is predicted or diagnosed to be at risk for developing a toxicity (e.g. neurotoxicity, such as severe neurotoxicity) if the detected parameters of at least three of the cytokines meet the classification.

In some embodiments, the biomarker or panel of biomarkers or one or more biomarkers include(s) one or more cytokine or chemokine, such as a concentration or relative concentration thereof. In some such embodiments, the cytokine is or comprises transforming growth factor beta (TGF-beta), interleukin 6 (IL-6), interleukin 10 (IL-10), interleukin 15 (IL-15), interferon gamma (IFN-gamma), or monocyte chemoattractant protein-1 (MCP-1). In some embodiments, the biomarkers comprise IL-6 and IL-15; in some embodiments, they comprise IL-6.

In some cases, the one or more biomarkers include at least 2 cytokines or at least 3 cytokines. In some aspects the cytokine is transforming growth factor beta (TGF-beta), interleukin 6 (IL-6), interleukin 10 (IL-10), interleukin 15 (IL-15), interferon gamma (IFN-gamma), monocyte chemoattractant protein-1 (MCP-1).

In some embodiments, the parameter is a concentration such as a concentration of pg/mL. In some embodiments, the parameter is a concentration that is transformed, such as on a log scale, e.g., Log 2 scale. In some embodiments, reference to a Log 2 scale is a Log 2 transformation of a concentration in pg/mL, and can be displayed with or without the corresponding units.

In some embodiments, a panel of cytokine biomarkers is assessed, detected or measured that includes at least a first and second cytokine. In some embodiments, if the detected parameters of the first and second cytokines meet the classification, the subject is identified or is diagnosed or predicted to be at risk for developing toxicity (e.g. neurotoxicity, such as severe neurotoxicity). In some such aspects, if the detected parameters of both the first and second cytokines do not meet the classification, the subject is identified or is diagnosed or predicted not to be at risk for developing toxicity (e.g. neurotoxicity, such as severe neurotoxicity). In some cases, if the detected parameter of only one of the first and second cytokines does not meet the classification, the method can further include measuring a parameter of at least a third biomarker, e.g., cytokine, that alone or together with the other biomarkers in the panel is indicative of risk for developing a toxicity (e.g. neurotoxicity, such as severe neurotoxicity). In some embodiments, the third biomarker can be compared to a reference value for the biomarker, such as based on a classification scheme, to thereby determine whether the subject is at risk for developing a toxicity (e.g. neurotoxicity, such as severe neurotoxicity). In some embodiments, the third biomarker is a cytokine that is different from the first and second cytokines. In some such aspects, if the detected parameter of the third cytokine meets the classification, the subject is identified or is diagnosed or predicted to be at risk for developing toxicity (e.g. neurotoxicity, such as severe neurotoxicity). In some cases, if the detected parameter of the third cytokine does not meet the classification, the subject is identified or is diagnosed or predicted not to be at risk for developing toxicity (e.g. neurotoxicity, such as severe neurotoxicity).

In some cases, the classification, and whether the classification is met based on a higher or lower detected parameter of the biomarker or each of the biomarkers in a panel can depend on the particular biomarker being measured. For example, in some embodiments, such as where the disease or condition is NHL, prediction can be based on a panel of cytokines that can include TGF-beta, IL-6 and/or IL-15. In some embodiments, the subject is identified or is diagnosed or predicted to be at risk for developing toxicity (e.g. neurotoxicity, such as severe neurotoxicity) if the detected parameter of at least one of the cytokines meets a classification selected from: i) a detected parameter of TGF-beta that is less than the TGF-beta reference value; ii) a detected parameter of IL-6 that is greater than the IL-6 reference value; and/or iii) a detected parameter of IL-15 that is greater than the IL-15 reference value.

In some cases, such as where the disease or condition is NHL, prediction can be based on a panel of cytokines that can include all of the cytokines TGF-beta, IL-6 and IL-15, in which each is measured. In some embodiments, if the detected parameters of all three cytokines meet the classification, the subject is identified or is diagnosed or predicted to be at risk of toxicity (e.g. neurotoxicity, such as severe neurotoxicity). In some aspects, if the detected parameters of at least two of the cytokines, e.g., two of TGF-beta, IL-6 or IL-15, meet the classification, the subject is identified or is diagnosed or predicted to be at risk for toxicity (e.g. neurotoxicity, such as severe neurotoxicity). In some instances, if the detected parameter of only one of the cytokines meets the classification, the subject is identified or is diagnosed or predicted not to be at risk for toxicity (e.g. neurotoxicity, such as severe neurotoxicity).

In some embodiments, such as where the disease or condition is ALL, prediction can be based on a panel of cytokines that include IL-6, IL-15 and MCP-1. In some such cases, the subject is identified or is diagnosed or predicted to be at risk for developing toxicity (e.g. neurotoxicity, such as severe neurotoxicity) if the detected parameter of at least one of the cytokines (e.g., at least one of IL-6, IL-15 or MCP-1) meets a classification selected from: i) a detected parameter of IL-6 that is greater than the IL-6 reference value; ii) a detected parameter of IL-15 that is greater than the IL-15 reference value; and/or iii) a detected parameter of MCP-1 that is greater than the MCP-1 reference value.

Thus, in some cases, such as where the disease or condition is ALL, prediction can be based on a panel of cytokines that can include all of the cytokines IL-6, IL-15, and MCP-1, in which each is measured. In some embodiments, if the detected parameters of all three cytokines meet the classification, the subject is identified or is diagnosed or predicted to be at risk of toxicity (e.g. neurotoxicity, such as severe neurotoxicity). In some aspects, if the detected parameters of at least two of the cytokines, e.g., two of IL-6, IL-15, or MCP-1, meet the classification, the subject is identified or is diagnosed or predicted to be at risk for toxicity (e.g. neurotoxicity, such as severe neurotoxicity). In some instances, if the detected parameter of only one of the cytokines meets the classification, the subject is identified or is diagnosed or predicted not to be at risk for toxicity (e.g. neurotoxicity, such as severe neurotoxicity).

In some aspects of the methods, if the comparison indicates that the subject is identified as at risk for developing toxicity (e.g. meets a threshold level or cut-off in which classification predicts toxicity), the methods include treating the subject with an agent or therapy that treats neurotoxicity and/or an agent that prevents, delays, or attenuates the development of severe neurotoxicity, thereby ameliorating the development of neurotoxicity in the subject. Exemplary of such agents, including agents for ameliorating or treating neurotoxicity, are described in a section below.

In some embodiments, the one or more biomarkers include IL-15 and IL-6. In some aspects, the one or more biomarkers include IL-15 and TGF-beta. In some cases, the one or more biomarkers include IL-6 and TGF-beta. In some instances, the one or more biomarkers include IL-15 and MCP-1. In some cases, the one or more biomarkers include IL-6 and MCP-1.

In some embodiments, such as where the disease or condition is NHL, the cytokines include TGF-beta, IL-6 and/or IL-15. In some embodiments, the subject is identified or is diagnosed or predicted to be at risk for developing neurotoxicity, e.g. severe neurotoxicity, if the detected parameter of at least one of the cytokines meets a classification selected from: i) a detected parameter of TGF-beta that is less than the TGF-beta reference value; ii) a detected parameter of IL-6 that is greater than the IL-6 reference value; and/or iii) a detected parameter of IL-15 that is greater than the IL-15 reference value.

In some embodiments, the TGF-beta reference value is within a range from or from about 5.5 to 15.00 (log 2 scale) or from or from about 45 pg/mL to 33000 pg/mL. In some cases, the TGF-beta reference value is within a range from or from about 10.00 to 15.00 (log 2 scale) or from or from about 20000 to 33000 pg/mL. In some instances, the TGF-beta reference value is at least or at least about 10.00, 11.00, 12.00, 13.00, 14.00 or 15.00, each on a log 2 scale. In some embodiments, the TGF-beta reference value is at least or at least about 20000, 22000, 24000, 26000, 28000, 30000 or 32000 pg/mL. In some cases, the TGF-beta reference value is or is about 25000±100 pg/mL or is or is about 14.0±1.0 on a log 2 scale.

In some aspects, the IL-6 reference value is within a range from or from about 2.6 to 5.4 (log 2 scale) or from or from about 6.00 pg/mL to 41.0 pg/mL. In some cases, the IL-6 reference value is within a range from or from about 3.5 to 5.4 (log 2 scale) or from or from about 12 pg/mL to 41 pg/mL. In some aspects, the IL-6 reference value is at least or at least about 3.5, 4.0, 4.5, 4.8, 5.0, 5.2 or 5.4, each on log 2 scale. In some instances, the IL-6 reference value is at least or at least about 12 pg/mL, 18 pg/mL, 24 pg/mL, 30 pg/mL or 36 pg/mL. In some embodiments, the IL-6 reference value is or is about 15.2±1.0 pg/mL and/or is or is about 3.9±1.0 pg/mL.

In some cases, the IL-15 reference value is within a range from or from about 6.1 to 7.1 (log 2 scale) or from or from about 69.0 pg/mL to 135.0 pg/mL. In some embodiments, the IL-15 reference value is a within a range from or from about 6.0 to 7.1 (log 2 scale) or from or from about 74 pg/mL to 135 pg/mL. In some aspects, the IL-15 reference value is at least or at least about 6.0, 6.2, 6.4, 6.6, 6.8 or 7.0, each on log 2 scale. In some instances the IL-15 reference value is at least or at least about 74 pg/mL, 80 pg/mL, 90 pg/mL, 100 pg/mL, 110 pg/mL, 120 pg/mL or 130 pg/mL, or is or is about 6.2±1.0 on a log 2 scale or is or is about 76±4.0 pg/mL.

In some embodiments, such as where the disease or condition is ALL, the cytokines include IL-6, IL-15 and MCP-1. In some such cases, the subject is identified or is diagnosed or predicted to be at risk for developing severe neurotoxicity if the detected parameter of at least one of the cytokines (e.g., at least one of IL-6, IL-15 or MCP-1) meets a classification selected from: i) a detected parameter of IL-6 that is greater than the IL-6 reference value; ii) a detected parameter of IL-15 that is greater than the IL-15 reference value; and/or iii) a detected parameter of MCP-1 that is greater than the MCP-1 reference value.

In some aspects, such as in which a first and second cytokine, and optionally a third cytokine, are measured, the first cytokine is IL-15, the second cytokine is IL-6 and, optionally, the third cytokine is MCP-1. Thus, in some embodiments in which each of IL-15, IL-6 and MCP-1 are measured, if the detected parameters of all three cytokines meet the classification, the subject is identified or is diagnosed or predicted to be at risk for developing severe neurotoxicity. In some cases, if the detected parameters of at least two of the cytokines, e.g., IL-15 and IL-6 or IL-15 and MCP-1, meet the classification, the subject is identified or is diagnosed or predicted to be at risk for neurotoxicity. In some instances, if the detected parameter of only one of the cytokines meets the classification, the subject is not identified or diagnosed predicted to be at risk for developing neurotoxicity.

In some embodiments, such as where the disease or condition is ALL, the IL-6 reference value is within a range from or from about 2.0 to 4.0 (log 2 scale) or from or from about 6.00 pg/mL to 12.0 pg/mL. In some aspects, the IL-6 reference value is at least or at least about 3.0 or 4.0, each on a log 2 scale, or is at least or at least about 8.0, 9.0, 10.0, 11.0 or 12.0 pg/mL. In some cases, the IL-6 reference value is or is about 3.0±1.0 on a log 2 scale or is or is about 10.5±1.0 pg/mL.

In some aspects, the IL-15 reference value is within a range from or from about 5.0 to 6.5 (log 2 scale) or from or from about 40.0 pg/mL to 90.0 pg/mL. In some embodiments, the IL-15 reference value is within a range from or from about 6.0 to 6.5 (log 2 scale) or from or from about 70 pg/mL to 90 pg/mL. In some cases, the IL-15 reference value is at least or at least about 6.0, 6.1, 6.2, 6.3, 6.4 or 6.5, each on log 2 scale or is at least or at least about 70 pg/mL, 75 pg/mL, 80 pg/mL, 85 pg/mL or 90 pg/ml. In some instances, the IL-15 reference value is or is about 6.0±1.0 on a log 2 scale or is or is about 81±4 pg/mL.

In some embodiments, the MCP-1 reference value is within a range from or from about 7.00 to 12.0 (log 2 scale) or from or from about 700 pg/mL to 1400 pg/mL. In some aspects, the MCP-1 reference value is within a range from or from about 9.0 to 12.0 (log 2 scale) or from or from about 1000 pg/mL to 1400 pg/mL. In some cases, the MCP-1 reference value is at least or at least about 9.0, 10.0, 11.0 or 12.0, each on log 2 scale or is at least or at least about 1000 pg/mL, 1100 pg/mL, 1200 pg/mL, 1300 pg/mL or 1400 pg/mL. In some instances, the MCP-1 reference value is or is about 10.0±1.0 on a log 2 scale or is or is about 1200±100 pg/mL.

In some aspects, the one or more biomarkers include IL-10 and/or IFN-gamma. In some embodiments, the subject is identified as at risk of developing neurotoxicity if the detected parameter of IL-10 or IFN-gamma meets a classification selected from: iv) a value of IL-10 that is greater than the IL-10 reference value; or v) a value of IFN-gamma that is greater than the IFN-gamma reference value.

In some instances, the IL-10 reference value is a reference value that is at least or at least about 3.0 (log 2 scale) or is at least or at least about 10.0 pg/mL. In some embodiments, the IL-10 reference value is or is about 3.5±1.0 on log 2 scale or is or is about 11.0±1.0 pg/mL.

In some embodiments, the IFN-gamma reference value is a reference value that is at least or at least about 4.0 (log 2 scale) or is at least or at least about 18.0 pg/mL. In some aspects, the IFN-gamma reference value is or is about 4.2±1.0 on log 2 scale or is or is about 19.0±1.0 pg/mL.

In some embodiments, the method is for predicting the risk for developing neurotoxicity. In some embodiments, the method is for predicting severe neurotoxicity, which can generally be classified based on a grading scale. In some embodiments, neurotoxicity is graded based on severity (e.g., using a Grade 1-5 scale, as shown in Table 1 (see, e.g., Guido Cavaletti & Paola Marmiroli *Nature Reviews Neurology* 6, 657-666 (December 2010); National Cancer Institute-Common Toxicity Criteria version 4.03 (NCI-CTCAE v4.03). In some embodiments, the risk for developing neurotoxicity or severe neurotoxicity can be predicted prior to the development of any signs or symptoms of the neurotoxicity.

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus.

In some embodiments, the physical signs or symptoms associated with severe neurotoxicity and/or grade 3 or higher neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some cases, the physical signs or symptoms associated with severe neurotoxicity are associated with grade 3, grade 4 or grade 5 neurotoxicity. In some instances, the physical signs or symptoms associated with severe neurotoxicity manifest greater than or greater than about or about 5 days after cell therapy, 6 days after cell therapy or 7 days after cell therapy. In some embodiments, severe neurotoxicity includes neurotoxicity with a grade of 3 or greater, such as set forth in Table 1.

TABLE 1

Exemplary Grading Criteria for neurotoxicity

| Grade | Description of Symptoms |
|---|---|
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the methods reduce symptoms associated with neurotoxicity compared to other methods. For example, subjects treated according to the provided methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the provided methods may have reduced symptoms associated with peripheral motor neuropathy, peripheral sensory neuropathy, dysethesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, subjects administered the agent that treats, prevents, or reduces the risk of developing neurotoxicity have reduced symptoms, outcomes, or factors associated with neurotoxicity compared to subjects who are not administered the agent, and/or subjects who are administered the agent at a time at which the subject exhibits clinical signs or symptoms of neurotoxicity or severe neurotoxicity, e.g., neurotoxicity of grade 3 or higher. Thus, in some aspects, subjects treated according to the provided methods do not develop grade 3 or higher neurotoxicity or develop a grade of neurotoxicity that is less severe than if the subject had been identified or treated by other methods.

In some embodiments, the provided methods enable identification of subjects as at risk for developing neurotoxicity at a timepoint before other methods would diagnose or predict risk for developing neurotoxicity. For example, the provided methods, in some aspects, enable detection of risk for developing neurotoxicity before the subject has manifested physical signs or symptoms of neurotoxicity or severe neurotoxicity. For example, the provided methods, in some aspects, enable detection of risk for developing neurotoxicity before the subject has manifested certain physical signs or symptoms of neurotoxicity, such as those indicative of a current or imminent state of severe neurotoxicity, or before the subject has manifested certain signs or symptoms of severe neurotoxicity, or before he or she has developed signs and symptoms typically appearing or indicative of such toxicity later than a given time-point post-treatment, such as later than 1, 2, 3, or 4 days post-treatment. In some embodiments, diagnosis at an early timepoint may allow for a broader range of interventions to be used to ameliorate neurotoxicity in the subject as compared to those interventions available once diagnosis is made by other methods, such as after physical signs or symptoms of neurotoxicity have manifested in the subject. In some embodiments, the identification or prediction by the provided methods at an early timepoint, e.g., prior to the appearance of physical symptoms of neurotoxicity, may allow for administration of a reduced dose of the agent that treats, prevents, delays, or attenuates neurotoxicity or the risk of developing neurotoxicity. In some cases, this reduced dose results in fewer side effects than larger doses that are administered in other methods, such as at a time once symptoms of neurotoxicity have manifested. In some aspects, the reduced dose is advantageous in that it is less likely to interfere with or reduce the potency of cell therapy.

In some aspects, the method further includes, after administration of the agent or therapy for ameliorating or treating toxicity (e.g. neurotoxicity, such as severe neurotoxicity), monitoring the efficacy of the agent on the treatment, prevention, delay, or attenuation of the toxicity (e.g. neurotoxicity, such as severe neurotoxicity). In some cases, monitoring the efficacy includes determining a subsequent detected parameter of the one or more biomarkers (e.g. cytokines), in a subsequent biological sample from the subject that is or has been obtained following administration of the agent to the subject, thereby measuring a subsequent detected parameter for the one or more biomarkers, and optionally comparing the subsequent detected parameter of each biomarker to a detected parameter of the biomarker present in a prior sample or to a baseline sample prior to the administration of the agent. In some instances, the agent is considered to be efficacious if the subsequent detected parameter is not altered to a value that is more predictive of the development of toxicity (e.g. neurotoxicity, such as severe neurotoxicity) than the detected parameter present in the prior sample or baseline sample. For example, in some aspects, the biomarker is a cytokine such as IL-15, IL-6, IL-10, IFN-gamma and MCP-1, and treatment with the agent is considered to be efficacious if the subsequent detected parameter of the cytokine is about the same or is the same or is less than the detected parameter present in a prior sample or the baseline sample. In some cases, such as where the biomarker, e.g., cytokine, is TGF-beta, treatment with the agent is considered to be efficacious if the subsequent detected parameter of the cytokine is about the same or is the same or is greater than the detected parameter present in a prior sample or the baseline sample.

B. Exemplary Biomarkers Predictive of CRS

In some aspects, the biomarkers or each of the biomarkers in a panel is a cytokine or a serum protein such as any described above, and the subject is identified or is predicted or diagnosed to be at risk for developing a toxicity (e.g. CRS, or severe CRS) if the detected parameters of at one or more biomarkers meet the classification. In some embodiments, the biomarkers or each of the biomarkers in a panel is a cytokine or a serum protein (e.g. IFN-γ, IL-2, IL-6, IL-8, IL-10, IL-15, IL-2Ra, MCP-1, TNFRp55, TNFRp75, TIM3, BAFF, MIP-1β, CRP, IL-18, sIL-6R and/or ferritin), and the subject is identified or is predicted or diagnosed to be at risk for developing a toxicity (e.g. CRS, or severe CRS) if the detected parameters of at one or more biomarkers meet the classification. In some embodiments, the biomarker or each of the biomarkers in a panel is IL-15, IL-6, IL-2, IFN-gamma, CRP, ferritin, IL-8, IL-10 and/or sTNFR1. In some embodiments, the subject is treated with the recombinant receptor-expressing cells (e.g. CAR-T cells) for treating a disease or condition (e.g. cancer) and the methods identify a subject at risk for developing toxicity from the therapy. In some embodiments, the disease or condition is NHL, ALL or CLL.

In some aspects, the biomarker or biomarkers indicative of risk of developing toxicity, e.g., CRS or severe CRS, include clinical or laboratory parameters such as temperature, heart rate, ANC count, monocyte count, platelet count, albumin levels, ferritin levels, and/or CRP levels, and the subject is identified or is predicted or diagnosed to be at risk for developing a toxicity (e.g. CRS, or severe CRS) if the detected parameters of at one or more biomarkers meet the classification. In some cases, the subject is identified or is predicted or diagnosed to be at risk for developing a toxicity (e.g. CRS, such as severe CRS) if the detected parameters of at least two of the biomarkers, e.g., cytokines, serum factors or clinical or laboratory parameters, meet the classification. In some embodiments, the toxicity is cytokine release syndrome (CRS).

In some aspects, the biomarker or biomarkers indicative of risk of developing toxicity, e.g., CRS or severe CRS, include biomarker(s) that relate to vital signs, hemodynamics, coagulation, blood counts, hepatic function and/or renal function. For example, in some embodiments, the biomarker(s) include vital signs, hemodynamic parameters and/or biomarkers, such as one or more of absolute maximum temperature (° C.), heart rate (beats/min), systolic blood pressure (mm Hg), diastolic blood pressure (mm Hg), respiratory rate (breaths/min), total blood protein (g/dL), blood albumin levels (g/dL), and weight change from baseline (kg); coagulation factors and/or biomarkers, such as one or more of levels of D-dimer (μg/mL), fibrinogen (mg/dL), prothrombin time (PT; sec), activated partial thromboplastin time (aPTT; sec), platelet count (1000/μL), and transfusion requirements; blood counts, e.g., blood cell counts, such as one or more of neutrophil count (1000/μL), monocyte count (1000/μL), eosinophil count (1000/μL), hemoglobin (g/dL) and hematocrit percentage (%); and/or hepatic and renal factors and/or biomarkers, such as one or more of levels of aspartate transaminase (AST; units/L), alanine aminotransferase (ALT; units/L), alkaline phosphatase (ALP; units/L), total bilirubin (mg/dL) and blood urea nitrogen (BUN; mg/dL).

In some embodiments, the parameter(s) indicative of risk of developing toxicity, e.g., CRS or severe CRS, include vital signs, hemodynamic parameters and/or biomarkers, such as parameters that indicate hemodynamic instability or capillary leak, e.g., hypoalbumenia, such as temperature (° C.), heart rate (beats/min), respiratory rate (breaths/min), total blood protein (g/dL) and blood albumin levels (g/dL). In some embodiments, CRS or severe CRS is associated with higher temperature, higher heart rate, higher respiratory rate, lower total blood protein and lower total blood albumin (hypoalbumenia), within a relatively short period of time following the administration of the cell therapy, e.g., the peak or trough level within 4, 8, 12, 24, 36 or 48 hours after administration of the cell therapy.

In some embodiments, the parameter(s) indicative of risk of developing toxicity, e.g., CRS or severe CRS, include factors and/or biomarkers involved in coagulation, such as biomarkers associated with coagulopathy or requirement for transfusion, such as levels of D-dimer (μg/mL), prothrombin time (PT; sec), activated partial thromboplastin time (aPTT; sec), and platelet count (1000/μL). In some embodiments, CRS or severe CRS is associated with higher D-dimer, higher prothrombin time, higher activated partial thromboplastin time and lower platelet count, within a relatively short period of time following the administration of the cell therapy, e.g., the peak or trough level within 4, 8, 12, 24, 36 or 48 hours after administration of the cell therapy.

In some embodiments, the parameter(s) indicative of risk of developing toxicity, e.g., CRS or severe CRS, include blood counts, e.g., blood cell counts, such as measurements that indicate cytopenia, e.g., monocytopenia or low eosinophils. In some embodiments, the parameters include neutrophil count (1000/μL), monocyte count (1000/μL) and eosinophil count (1000/μL). In some embodiments, CRS or severe CRS is associated with lower neutrophil ount, lower monocyte count and lower eosinophil count, within a relatively short period of time following the administration of the cell therapy, e.g., the peak or trough level within 4, 8, 12, 24, 36 or 48 hours after administration of the cell therapy.

In some embodiments, the parameter(s) indicative of risk of developing toxicity, e.g., CRS or severe CRS, include hepatic and renal factors and/or biomarkers, such as factors or biomarkers that indicate hepatic and renal dysfunction, such as aspartate transaminase (AST; units/L) and total bilirubin (mg/dL). In some embodiments, CRS or severe CRS is associated with higher AST and higher bilirubin, within a relatively short period of time following the administration of the cell therapy, e.g., the peak or trough level within 4, 8, 12, 24, 36 or 48 hours after administration of the cell therapy.

In some embodiments, a panel of biomarkers is assessed, detected or measured that includes at least a first and second biomarker. In some embodiments, if the detected parameters of the first and second biomarkers meet the classification, the subject is identified or is diagnosed or predicted to be at risk for developing toxicity (e.g. CRS, such as severe CRS). In some such aspects, if the detected parameters of both the first and second biomarkers do not meet the classification, the subject is identified or is diagnosed or predicted not to be at risk for developing toxicity (e.g. CRS, such as severe CRS). In some cases, if the detected parameter of only one of the first and second biomarkers does not meet the classification, the method can further include measuring a parameter of at least a third biomarker, e.g., a third biomarker that is different from the first and second biomarkers, that alone or together with the other biomarkers in the panel is indicative of risk for developing a toxicity (e.g. CRS, such as severe CRS). In some such aspects, if the detected parameter of the third biomarker meets the classification, the subject is identified or is diagnosed or predicted to be at risk for developing toxicity (e.g. CRS, such as severe CRS). In some cases, if the detected parameter of the third biomarker does not meet the classification, the subject is identified or is diagnosed or predicted not to be at risk for developing toxicity (e.g. CRS, such as severe CRS).

In some cases, the classification, and whether the classification is met based on a higher or lower detected parameter of the biomarker or each of the biomarkers in a panel can depend on the particular biomarker being measured. In some embodiments, the classification includes assessing parameters of a biomarker or a panel of biomarkers such as peak or trough levels, measurements, concentrations and/or activity over or within a defined period of time, or the levels, measurements, concentrations and/or activity of a biomarker or a panel of biomarkers at a specific time point. In some embodiments, the specific time point is an early time point after administration of the cell therapy, or a first administration or dose thereof, or after the initiation of any of the foregoing, e.g., before the subject has manifested physical signs or symptoms of toxicity, e.g., CRS or severe CRS. In some embodiments, the parameter assessed for classification is the peak or trough level of a biomarker or a panel of biomarkers, within 1, 2, 3, 4, 5, 6, 7, 8, 9, 10, 12, 15, 18, 21, 24, 27 and/or 30 days or more after administration of the cell therapy. In some embodiments, the parameter assessed for classification is the level of a biomarker or a panel of biomarkers at a defined time point, e.g., a time point generally within 4 hours to 3 days of administration of the cell therapy, such as generally within or about 1 day, 2 days or 3 days after administration of the cell therapy. In some embodiments, the parameter assessed for classification is the level of a biomarker or a panel of biomarkers, e.g., cytokines, at or about day 1 after administration of the cell therapy. In some embodiments, the parameters assessed are peak or trough levels, measurements, concentrations and/or activity of the biomarker or a panel of biomarkers, e.g., cytokines, within a relatively short period of time following the administration of the cell therapy, e.g., the peak or trough level within 4, 8, 12, 24, 36 or 48 hours after, administration of the cell therapy, or a first administration or dose thereof, or after the initiation of any of the foregoing.

In some embodiments, the biomarker or biomarkers indicative of risk of developing toxicity, e.g., CRS or severe CRS, comprise one or more of temperature, heart rate, ANC count, monocyte count, platelet count, albumin levels, ferritin levels, and/or CRP levels, such as at or above (or at or below) a reference or threshold level. In some embodiments, the biomarker or biomarkers indicative of risk of developing toxicity, e.g., CRS or severe CRS, comprise one or more of temperature, heart rate, respiratory rate, total blood protein, blood albumin levels, levels of D-dimer, prothrombin time (PT), activated partial thromboplastin time (aPTT), platelet count, neutrophil count, monocyte count, and eosinophil count, aspartate transaminase (AST) and total bilirubin, such as at or above (or at or below) a reference or threshold level. In one aspect, the subject is deemed at risk of developing severe CRS (e.g., grade≥3 CRS or grade≥4 CRS), and in some aspects treated with one or more interventions therefor, if the subject exhibits a temperature, heart rate, level of ferritin, and/or level of C-reactive protein at or above a reference or threshold level, or exhibits a combination of one, two, three or each of such factors. In each case, such level in some aspects is at a point in time that may be individually specified and/or is a peak or trough level. In some embodiments, the level is peak or trough level within a relatively short period of time following the administration of the cell therapy, e.g., the peak or trough level within 4, 8, 12, 24, 36 or 48 hours after, administration of the cell therapy. In some aspects, it is the level at day 1 or at day 2 post-administration of the cells, and in some aspects at day 3, 4, 5, 6, 7, 8, 9, 10, 11, 12, 13, 14, or 15. For example, in some aspects, the subject exhibits the relatively high level of ferritin (e.g., in a blood sample) at day 1 or 2 post-CAR+ T cell administration.

In one aspect, the subject is deemed at risk of developing severe CRS (e.g., grade≥3 CRS or grade>4 CRS), and in some aspects treated with one or more interventions therefor, if the subject exhibits a platelet count, ANC count, or monocyte count, that is at or below a reference or threshold level, or a combination of two or more of the foregoing. In each case, such level in some aspects is at a point in time that may be individually specified and/or is a peak level. In some aspects, the level is the level of the individual marker at day 1 or at day 2 post-administration of the cells, and in some aspects at day 3, 4, 5, 6, 7, 8, 9, 10, 11, 12, 13, 14, or 15. For example, in some aspects, the subject exhibits the relatively high level of ferritin (e.g., in a blood sample) at day 1 or 2 post-CAR+ T cell administration. In some aspects, the reference level is an average level of a group of subjects receiving the same treatment, e.g., for the same indication, and/or such subjects that do not develop the toxicity outcome, such as do not develop grade 3 or higher CRS or do not develop severe neurotoxicity. In some embodiments, the subject is deemed to be at risk if he or she exhibits a level of ferritin that is at or above a threshold or reference level and a platelet count that is at or below a reference level, at a time-point following administration, such as at day 1 or 2 following T cell administration.

In some embodiments, such as where the disease or condition is NHL or ALL, prediction can be based on a panel of biomarkers that can include one or more of temperature, heart rate, ANC count, monocyte count, platelet count, albumin levels, ferritin levels and/or CRP levels, of a subject or a biological sample derived from a subject. In some embodiments, the detecting comprises detection of the concentration or relative concentration directly in the biological sample or indirectly, by detection in a test sample obtained from said biological sample, wherein the detection is carried out no more than 1, 2, 3, 4, 5, 6, 7, 8, 9, 10, 12, 15, 18, 21, 24, 27 and/or 30 days after administration of the cell therapy, or a first administration or dose thereof, or after initiation of any of the foregoing. In some embodiments, the methods include comparing the levels of each of the biomarkers in the panel to a reference value for each respective biomarker, wherein, if the detected value or relative value of the one or more of the biomarkers individually meet a classification, the subject is identified or is diagnosed or predicted to be at risk for developing neurotoxicity, which optionally is severe neurotoxicity, wherein the classification is selected from: i) for temperature, greater than the temperature reference value; ii) for ANC count, less than the ANC count reference value; iii) for monocyte count, less than the reference monocyte count value; iv) for heart rate, greater than the reference heart rate value; v) for platelet count, less than the reference platelet count value; vi) for ferritin levels, greater than the reference ferritin value; vii) for albumin levels, lower than the reference albumin value; and/or viii) for CRP levels, greater than the reference CRP value.

In some embodiments, prediction can be based on a panel of biomarkers that can include one or more of one or more of temperature, heart rate, respiratory rate, total blood protein, blood albumin levels, levels of D-dimer, prothrombin time (PT), activated partial thromboplastin time (aPTT), platelet count, neutrophil count, monocyte count, and eosinophil count, aspartate transaminase (AST) and total bilirubin, such as at or above (or at or below) a reference or threshold level. In some emodiments, the level is peak or trough level within 4, 8, 12, 24, 36 or 48 hours after, administration of the cell therapy. In some embodiments, the methods include comparing the levels of each of the biomarkers in the panel to a reference value for each respective biomarker, wherein, if the detected value or relative value of the one or more of the biomarkers individually meet a classification, the subject is identified or is diagnosed or predicted to be at risk for developing neurotoxicity, which optionally is severe neurotoxicity, wherein the classification is selected from: i) for temperature, greater than the temperature reference value; ii) for heart rate, greater than the heart rate reference value; iii) for respiratory rate, greater than the respiratory rate reference value; iv) for total blood protein levels, lower than the reference total blood protein value; v) for albumin levels, lower than the reference albumin value; vi) for D-dimer level, greater than the D-dimer level reference value; vii) for PT, greater than the PT reference value; viii) for aPTT, greater than the aPTT reference value; ix) for platelet count, less than the reference platelet count value; x) for neutrophil count, less than the neutrophil count reference value; xi) for monocyte count, less than the reference monocyte count value; xii) for eosinophil count, less than the reference eosinophil count value; xiii) for AST, greater than the reference AST value; and/or xivi) for bilirubin levels, greater than the reference bilirubin value.

In some embodiments, the subject is deemed to be at risk for the toxic outcome (such as grade≥3 CRS and/or severe neurotoxicity) if he or she exhibits a peak level of one or of or a combination of two or more (e.g., each of) IL-15, IL-6, IL-2, IFN-γ, C-reactive protein and ferritin in a sample, such as in a blood or blood-derived sample, following the treatment, that is at or above a reference or threshold level. In some embodiments, the subject is deemed to be at risk for the toxic outcome (such as grade≥3 CRS and/or severe neurotoxicity) if he or she exhibits a level of one or of, or a combination of two or more of (e.g., each of), IL-15, IL-6, IL-8, IL-10, soluble TNF receptor type 1 (sTNFR1), and IFN-γ in a sample from the subject, e.g., a blood sample, on or about day 1 or day 2 following administration of the therapy, such as of the cells.

In some embodiments, the subject has NHL or ALL, and the biomarker and biomarkers in a panel can be interleukin-15 (IL-15), interleukin-6 (IL-6), interleukin-2 (IL-2), interferon gamma (IFN-gamma), C-reactive protein (CRP) and/or ferritin, such as generally at least one, two or three of IL-15, IL-6, IL-2, IFN-gamma, CRP and/or ferritin. In some embodiments, the subject has NHL or ALL, and the biomarker and biomarkers in a panel can be interleukin-15 (IL-15), interleukin-6 (IL-6), interleukin-8 (IL-8), interleukin-10 (IL-10), soluble TNF receptor type 1 (sTNFR1) and/or interferon gamma (IFN-gamma), such as generally at least one, two or three of IL-15, IL-6, IL-8, IL-10, sTNFR1 and/or IFN-gamma. In some embodiments, the subject has NHL, ALL or NHL, and the biomarker and biomarkers in a panel is one or more IFN-γ, IL-2, IL-6, IL-8, IL-10, IL-15, IL-2Ra, MCP-1, TNFRp55, TNFRp75, TIM3, BAFF, MIP-1β, CRP, IL-18, sIL-6R and/or ferritin, such as generally at least two or three or four of IL-6, MCP-1, IL-10 and IL-15. In some embodiments, the one or more biomarkers include a cytokine, such as IL-15, IL-6, IL-8, IL-18 and/or IL-2. In some embodiments, the biomarker or biomarkers can be ferritin, C-reactive protein (CRP) and/or soluble TNF receptor type 1 (sTNFR1).

In some embodiments, the parameter is a concentration such as a concentration of pg/mL. In some embodiments, the parameter is a concentration that is transformed, such as on a log scale, e.g., Log 2 scale. In some embodiments, reference to a Log 2 scale is a Log 2 transformation of a concentration in pg/mL, and can be displayed with or without the corresponding units.

In some embodiments, such as where the disease or condition is NHL or ALL, prediction can be based on a panel of biomarkers that can include IL-15, IL-6, IL-2, IFN-gamma, CRP and/or ferritin. In some embodiments, the parameter assessed is the peak serum levels of one or more of IL-15, IL-6, IL-2, IFN-gamma, CRP and/or ferritin, within 1, 2, 3, 4, 5, 6, 7, 8, 9, 10, 12, 15, 18, 21, 24, 27 and/or 30 days or more after administration of the cell therapy, such as the peak serum level within 10 days after administration of one or more doses of the cell therapy. In some embodiments, the subject is identified or is diagnosed or predicted to be at risk for developing toxicity (e.g. CRS, such as severe CRS) if the detected parameter of at least one of the cytokines meets a classification selected from: i) a detected parameter of IL-15 that is greater than the IL-15 reference value; ii) a detected parameter of IL-6 that is greater than the IL-6 reference value; iii) a detected parameter of IL-2 that is greater than the IL-2 reference value; iv) a detected parameter of IFN-gamma that is greater than the IFN-gamma reference value; v) a detected parameter of CRP that is greater than the CRP reference value; and/or vi) a detected parameter of ferritin that is greater than the ferritin reference value.

In some embodiments, such as where the disease or condition is NHL or ALL, prediction can be based on a panel of biomarkers that can include IL-15, IL-6, IL-8, IL-10, sTNFR1 and/or IFN-gamma. In some embodiments, the parameter assessed is the serum levels of one or more of IL-15, IL-6, IL-2, IFN-gamma, CRP and/or ferritin, measured within 4 hours to 3 days after administration of the cell therapy, such as the serum level at or about 1 day after administration of one or more doses of the cell therapy. In some embodiments, the subject is identified or is diagnosed or predicted to be at risk for developing toxicity (e.g. CRS, such as severe CRS) if the detected parameter of at least one of the cytokines meets a classification selected from: i) a detected parameter of IL-15 that is greater than the IL-15 reference value; ii) a detected parameter of IL-6 that is greater than the IL-6 reference value; iii) a detected parameter of IL-8 that is greater than the IL-8 reference value; iv) a detected parameter of IL-10 that is greater than the IL-10 reference value; v) a detected parameter of sTNFR1 that is greater than the sTNFR1 reference value; and/or vi) a detected parameter of IFN-gamma that is greater than the IFN-gamma reference value.

In some embodiments, such as where the disease or condition is NHL, ALL or NHL, prediction can be based on a panel of biomarkers that can include IFN-γ, IL-2, IL-6, IL-8, IL-10, IL-15, IL-2Ra, MCP-1, TNFRp55, TNFRp75, TIM3, BAFF, MIP-1β, CRP, IL-18, sIL-6R and/or ferritin. In some embodiments, the level is peak or trough level within 4, 8, 12, 24, 36 or 48 hours after, administration of the cell therapy. In some embodiments, the subject is identified or is diagnosed or predicted to be at risk for developing toxicity (e.g. CRS, such as severe CRS, e.g., grade 4 or higher CRS) if the detected parameter of at least one of the cytokines meets a classification selected from: i) a detected parameter of IFN-γ that is greater than the IFN-γ reference value; ii) a detected parameter of IL-2 that is greater than the IL-2 reference value; iii) a detected parameter of IL-6 that is greater than the IL-6 reference value; iv) a detected parameter of IL-8 that is greater than the IL-8 reference value; v) a detected parameter of IL-10 that is greater than the IL-10 reference value; vi) a detected parameter of IL-15 that is greater than the IL-15 reference value; vii) a detected parameter of IL-2Ra that is greater than the IL-2Ra reference value; viii) a detected parameter of MCP-1 that is greater than the MCP-1 reference value; ix) a detected parameter of TNFRp55 that is greater than the TNFRp55 reference value; x) a detected parameter of TNFRp75 that is greater than the TNFRp75 reference value; xi) a detected parameter of TIM3 that is greater than the TIM3 reference value; xii) a detected parameter of BAFF that is greater than the BAFF reference value; xiii) a detected parameter of MIP-1β that is greater than the MIP-1β reference value; xiv) a detected parameter of CRP that is greater than the CRP reference value; xv) a detected parameter of IL-18 that is greater than the IL-18 reference value; xvi) a detected parameter of sIL-6R that is greater than the sIL-6R reference value; and/or xvii) a detected parameter of ferritin that is greater than the ferritin reference value.

In some embodiments, prediction can be based on a panel of cytokines that can include one or more of the biomarkers IL-15, IL-6, IL-2, IFN-gamma, CRP and/or ferritin; or one or more of the biomarkers IL-15, IL-6, IL-8, IL-10, sTNFR1 and/or IFN-gamma; or one or more of the biomarkers IL-6, MCP-1, IL-10 and/or IL-15, in which each is measured. In some embodiments, if the detected parameters of one, two, three, four, five or six biomarkers meet the classification, the subject is identified or is diagnosed or predicted to be at risk of toxicity (e.g. CRS, such as severe CRS). In some aspects, if the detected parameters of at least two of the biomarkers meet the classification, the subject is identified or is diagnosed or predicted to be at risk for toxicity (e.g. CRS, such as severe CRS). In some aspects, if the detected parameters of at least three of the biomarkers meet the classification, the subject is identified or is diagnosed or predicted to be at risk for toxicity (e.g. CRS, such as severe CRS). In some instances, if the detected parameters of only one of the biomarkers meet the classification, the subject is identified or is diagnosed or predicted not to be at risk for toxicity (e.g. CRS, such as severe CRS).

In some embodiments, such as where the disease or condition is CLL, NHL or ALL, the panel of biomarkers can include one or more of IL-6, MCP-1, IL-10 and/or IL-15. In some embodiments, if the parameter for the cytokine or, in the case of the combination, for at least one, at least two, or at least three of the cytokines selected from among IL-6, MCP-1, IL-10 and IL-15, individually, meet a classification selected from: i) for IL-6, greater than the IL-6 reference value; ii) for MCP-1, greater than the MCP-1 reference value; iii) for IL-10, greater than the IL-10 reference value; and/or iv) for IL-15, greater than the IL-15 reference value, then the comparison indicates that the subject is at risk for the toxicity and/or that the risk is above the threshold level of risk. In some embodiments, the IL-6 reference value is a reference value that is at least or at least about 26.0 pg/mL is or is about 27.0±1.0 pg/mL; and/or the MCP-1 reference value is a reference value that is at least or at least about 1343.0 pg/mL is or is about 1344.0±1.0 pg/mL; and/or the IL-10 reference value is a reference value that is at least or at least about 30.0 pg/mL is or is about 31.0±1.0 pg/mL; and/or the IL-15 reference value is a reference value that is at least or at least about 89.0 pg/mL is or is about 90.0±1.0 pg/mL.

In some embodiments, the reference value for the parameter, or the combination of the reference values for the parameter for each of the panel of biomarkers, is selected to provide a sensitivity or net sensitivity of greater than 0.80, greater than 0.85, greater than 0.90 or greater than 0.95; and/or the reference value for the parameter, or the combination of the reference values for the parameter for each of the panel of biomarkers, is selected to provide a specificity or net specificity of greater than 0.60, greater than 0.70, greater than 0.80, greater than 0.90 or greater than 0.95; and/or the reference value for the parameter, or the combination of the reference values for the parameter for each of the panel of biomarkers, is selected to provide an AUC in a ROC analysis of greater than 0.85, greater than 0.90 or greater than 0.95.

In some aspects of the methods, if the comparison indicates that the subject is identified as at risk for developing toxicity (e.g. meets a threshold level or cut-off in which classification predicts toxicity), the methods include treating the subject with an agent or therapy that treats CRS and/or an agent that prevents, delays, or attenuates the development of severe CRS, thereby ameliorating the development of CRS in the subject. Exemplary of such agents, including agents for ameliorating or treating CRS, are described below.

In some aspects, the toxic outcome is or is associated with or indicative of cytokine release syndrome (CRS) or severe CRS (sCRS). CRS, e.g., sCRS, can occur in some cases following adoptive T cell therapy and/or following administration of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78. In some embodiments, the toxicity is related to or is cytokine release syndrome (CRS), such as severe CRS (sCRS). In some embodiments, the provided methods can predict the risk of developing toxicity, such as CRS or sCRS. In some embodiments, toxicity or toxic effects or outcomes of administration of T cell therapy parallel high levels of circulating cytokines, which may underlie the observed toxicity.

In some cases, without wishing to be bound by theory, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity such as neurotoxicity and/or hepatic failure.

CRS in some aspects is treated or ameliorated using anti-inflammatory therapy such as an anti-IL-6 therapy, e.g., anti-IL-6R antibody, e.g., tocilizumab. Outcomes, signs and symptoms of CRS are known and include those described herein.

In the context of administering CAR-expressing cells, CRS, if applicable, typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1(3, IL-6, IL-8, and IL-10.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

In some embodiments, outcomes associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures).

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

In some embodiments, the CRS-associated serum factors or CRS-related outcomes include inflammatory cytokines and/or chemokines, including interferon gamma (IFN-γ), TNF-a, IL-1β, IL-2, IL-6, IL-7, IL-8, IL-10, IL-12, sIL-2Ra, granulocyte macrophage colony stimulating factor (GM-CSF), macrophage inflammatory protein (MIP)-1, tumor necrosis factor alpha (TNFα), IL-6, and IL-10, IL-1(3, IL-8, IL-2, MIP-1, Flt-3L, fracktalkine, and/or IL-5. In some embodiments, the factor or outcome includes C reactive protein (CRP). In addition to being an early and easily measurable risk factor for CRS, CRP also is a marker for cell expansion. In some embodiments, subjects that are measured to have high levels of CRP, such as ≥15 mg/dL, have CRS. In some embodiments, subjects that are measured to have high levels of CRP do not have CRS. In some embodiments, a measure of CRS includes a measure of CRP and another factor indicative of CRS.

In some embodiments, one or more inflammatory cytokines or chemokines are monitored before, during, or after CAR treatment. In some aspects, the one or more cytokines or chemokines include IFN-γ, TNF-α, IL-2, IL-1(3, IL-6, IL-7, IL-8, IL-10, IL-12, sIL-2Ra, granulocyte macrophage colony stimulating factor (GM-CSF), or macrophage inflammatory protein (MIP). In some embodiments, IFN-γ, TNF-α, and IL-6 are monitored.

CRS criteria that appear to correlate with the onset of CRS have been developed (see Davilla et al. Science translational medicine. 2014; 6(224):224ra25). Factors can include fevers, hypoxia, hypotension, neurologic changes, elevated serum levels of inflammatory cytokines, such as a set of seven cytokines (IFNγ, IL-5, IL-6, IL-10, Flt-3L, fracktalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, exemplary criteria reflective of CRS grade are those detailed in Table 2 below.

TABLE 2

Exemplary Grading Criteria for CRS

| Grade | Description of Symptoms |
|---|---|
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention:<br>Oxygen requirement < 40%, or<br>Hypotension responsive to fluids or low dose of a single vasopressor, or<br>Grade 2 organ toxicity (by CTCAE v4.0) |
| 3<br>Severe | Require and respond to aggressive intervention:<br>Oxygen requirement ≥ 40%, or<br>Hypotension requiring high dose of a single vasopressor (e.g.,<br>norepinephrine ≥ 20 μg/kg/min, dopamine > 10 μg/kg/min, phenylephrine<br>≥200 μg/kg/min, or epinephrine ≥ 10 μg/kg/min), or<br>Hypotension requiring multiple vasopressors (e.g., vasopressin + one of<br>the above agents, or combination vasopressors equivalent to ≥ 20 μg/kg/min<br>norepinephrine), or<br>Grade 3 organ toxicity or Grade 4 transaminitis (by CTCAE v4.0) |
| 4<br>Life-threatening | Life-threatening:<br>Requirement for ventilator support, or<br>Grade 4 organ toxicity (excluding transaminitis) |
| 5<br>Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater, such as grade of 4 or greater, such as set forth in Table 2. In some embodiments, severe CRS includes CRS that requires management or care in the intensive care unit (ICU).

In some embodiments, the toxicity includes macrophage activation syndrome, tumor lysis syndrome, fever of at least at or about 38 degrees Celsius for three or more days and/or a plasma level of CRP of at least at or about 20 mg/dL. In some embodiments, the CRS encompasses a combination of (1) persistent fever (fever of at least 38 degrees Celsius for at least three days) and (2) a serum level of CRP of at least at or about 20 mg/dL.

In some embodiments, the CRS encompasses hypotension requiring the use of two or more vasopressors or respiratory failure requiring mechanical ventilation.

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, subjects treated according to the provided methods may have reduced symptoms associated with CRS compared to other methods. For example, subjects treated according to the provided methods may have reduced symptoms of CRS, such as acute inflammatory response and/or endothelial organ damage, fever, rigors, chills, hypotension, dyspnea, acute respiratory distress syndrome (ARDS), encephalopathy, ALT/AST elevation, renal failure, cardiac disorders, hypoxia, neurologic disturbances, and death, neurological complications such as delirium, seizure-like activity, confusion, word-finding difficulty, aphasia, and/or becoming obtunded, or fatigue, nausea, headache, seizure, tachycardia, myalgias, rash, acute vascular leak syndrome, liver function impairment, and renal failure, compared to subjects treated by other methods. In some embodiments, a fever is one of the earliest symptoms of CRS, such as severe CRS.

In some embodiments, the methods reduce outcomes associated with CRS, including endothelial organ damage. In some aspects, the methods reduce the level of factors associated with CRS such as serum-ferritin, d-dimer, aminotransferases, lactate dehydrogenase and triglycerides, or with hypofibrinogenemia or hepatosplenomegaly.

In some embodiments, the provided methods enable identification of subjects as at risk for developing CRS at a timepoint before other methods would diagnose or predict risk for developing CRS. For example, the provided methods, in some aspects, enable detection of risk for developing CRS before the subject has manifested certain physical signs or symptoms of CRS, such as those indicative of a current or imminent state of severe CRS, or before the subject has manifested certain signs or symptoms of severe CRS, or before he or she has developed signs and symptoms typically appearing or indicative of such toxicity later than a given time-point post-treatment, such as later than 1, 2, 3, or 4 days post-treatment. In some embodiments, diagnosis at an early timepoint may allow for a broader range of interventions to be used to ameliorate CRS in the subject as compared to those interventions available once diagnosis is made by other methods, such as after physical signs or symptoms of CRS have manifested in the subject. In some embodiments, the identification or prediction by the provided methods at an early timepoint, e.g., prior to the appearance of physical symptoms of CRS, may allow for administration of a reduced dose of the agent that treats, prevents, delays, or attenuates CRS or the risk of developing CRS. In some cases, this reduced dose results in fewer side effects than larger doses that are administered in other methods, such as at a time once symptoms of CRS have manifested. In some aspects, the reduced dose is advantageous in that it is less likely to interfere with or reduce the potency of cell therapy.

In some aspects, the method further includes, after administration of the agent or therapy for ameliorating or treating toxicity (e.g. CRS, such as severe CRS), monitoring the efficacy of the agent on the treatment, prevention, delay, or attenuation of the toxicity (e.g. CRS, such as severe CRS). In some cases, monitoring the efficacy includes determining a subsequent detected parameter of the biomarker or each biomarker in a panel of biomarkers, in a subsequent biological sample from the subject that is or has been obtained following administration of the agent to the subject, thereby measuring a subsequent detected parameter for the biomarker or for each of the biomarkers in a panel, and optionally comparing the subsequent detected parameter of each biomarker to a detected parameter of the biomarker present in a prior sample or to a baseline sample prior to the administration of the agent. In some instances, the agent is considered to be efficacious if the subsequent detected parameter is not altered to a value that is more predictive of the development of toxicity (e.g. CRS, such as severe CRS) than the detected parameter present in the prior sample or baseline sample.

III. ADMINISTRATION OF CELLS IN ADOPTIVE CELL THERAPY

In some embodiments, the methods for predicting toxicity in a subject are associated with the administration of a cell therapy, such as for the treatment of diseases or conditions including various tumors. The methods involve administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

A. Recombinant Receptors Expressed by the Cells

In some embodiments, the cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or $CD8^+$ or $CD4^+$ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the subject to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

a. Chimeric Antigen Receptors (CARs)

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 March 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7. An exemplary T2A linker sequence comprises the sequence of amino acids set forth in SEQ ID NO: 6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802, 374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

b. TCRs

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

c. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

1. Vectors and Methods for Genetic Engineering

Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

2. Cells and Preparation of Cells for Genetic Engineering

Provided are methods, nucleic acids, compositions, and kits for producing the genetically engineered cells. Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of $CD4^+$ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg)

cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive CD4+T lymphocytes are $CD45RO^-$, $CD45RA^+$, $CD62L^+$, $CD4^+$ T cells. In some embodiments, central memory $CD4^+$ cells are $CD62L^+$ and CD45R0+. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotech, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4$^+$ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

B. Treatments and Methods

In some embodiments, a dose of cells expressing a recombinant receptor are administered to a subject to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), acute-lymphoblastic leukemia (ALL), non-Hodgkin's lymphoma (NHL), acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma. In some embodiments, the subject has acute-lymphoblastic leukemia (ALL). In some embodiments, the subject has non-Hodgkin's lymphoma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

Thus, the methods and uses can be for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. In some embodiments, the cells, or individual populations of sub-types of cells, are administered to the subject at a range of about $1\times10^5$ cells/kg of body weight to about $5\times10^7$ cells/kg of body weight, such as between about $1\times10^5$ cells/kg and $5\times10^7$ cells/kg, $2\times10^5$ cells/kg and $2\times10^7$ cells/kg, $2\times10^5$ cells/kg and $1\times10^7$ cells/kg, $2\times10^5$ cells/kg and $5\times10^6$ cells/kg, $2\times10^5$ cells/kg and $2\times10^6$ cells/kg, $2\times10^5$ cells/kg and $1\times10^6$ cells/kg, such as at or about $2\times10^5$ cells/kg, $2\times10^6$ cells/kg or $2\times10^7$ cells/kg. Again, dosages may vary depending on attributes particular to the disease or disorder and/or patient and/or other treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

IV. AGENTS THAT TREAT OR AMELIORATE SYMPTOMS OF TOXICITY

In some embodiments, the methods include an intervention or interventions, including by administration of agents or therapies that treat the toxicity (e.g. neurotoxicity, such as severe neurotoxicity and/or CRS, such as severe CRS) and/or that prevent, delay, or attenuate the development of or risk for developing neurotoxicity, e.g., severe neurotoxicity and/or CRS, such as severe CRS. Also provided are compositions and formulations, e.g., pharmaceutical formulations, comprising one or more of the agents.

In some embodiments, the agent is a steroid, is an antagonist or inhibitor of a cytokine receptor, such as IL-6 receptor, CD122 receptor (IL-2R/IL-15Rbeta receptor), or CCR2, or is an inhibitor of a cytokine, such as IL-6, IL-15, MCP-1, IL-10, IFN-γ, IL-8, or IL-18. In some embodiments, the agent is an agonist of a cytokine receptor and/or cytokine, such as TGF-β. In some embodiments, the agent, e.g., agonist, antagonist or inhibitor, is an antibody or antigen-binding fragment, a small molecule, a protein or peptide, or a nucleic acid. In some embodiments, the agent is an anti-histamine.

In some embodiments, the intervention includes the use of absorbent resin technology with blood or plasma filtration. In some cases, the intervention includes dialysis, plasmapheresis, or similar technologies.

In some embodiments, the agent can be administered sequentially, intermittently, or at the same time as or in the same composition as cells for adoptive cell therapy. For example, the agent can be administered before, during, simultaneously with, or after administration of the cell therapy.

In some embodiments, the agent is administered at a time following administration of cell therapy when the subject has been identified or predicted to be at risk for developing neurotoxicity and/or CRS, such as severe CRS. In some embodiments, the agent is administered at a time following administration of cell therapy when the subject has been identified or predicted to be at risk for developing neurotoxicity and/or CRS, but before physical symptoms of severe neurotoxicity, such as neurotoxicity of grade 3 or above and/or severe CRS, such as a CRS of grade 3 or above, manifest.

In some embodiments, the agent is administered at a time at which a clinical risk for neurotoxicity and/or CRS is detected to be present following the administration of cell therapy. In some embodiments, the agent is administered at a time at which a biochemical readout evidencing neurotoxicity and/or CRS is detected following administration of cell therapy. In some embodiments, the agent is administered at a time at which a serum level of a factor indicative of neurotoxicity and/or CRS in the subject indicates a higher risk for the development of neurotoxicity and/or CRS as compared to the serum level of the indicator in the subject immediately prior to said administration of the cells. In some embodiments, the agent is administered at a time at which the subject does not exhibit neurotoxicity and/or CRS, does not exhibit severe neurotoxicity and/or CRS, or does not exhibit neurotoxicity and/or CRS above grade 3 following administration of cell therapy.

In some embodiments, administration of the agent reduces symptoms associated with neurotoxicity and/or CRS compared to other methods. For example, subjects treated with the agent may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects who do not receive the agent, or receive the agent at a time when physical symptoms of neurotoxicity have manifested in the subject. In some embodiments, subjects treated with the agent according to the provided methods may have reduced symptoms associated with peripheral motor neuropathy, peripheral sensory neuropathy, dysethesia, neuralgia or paresthesia.

In some embodiments, the administration of the agent according to the provided methods reduces outcomes associated with neurotoxicity including damages to the nervous system and/or brain, such as the death of neurons. In some aspects, the administration of the agent reduces the level of factors associated with neurotoxicity such as beta amyloid (Aβ), glutamate, and oxygen radicals.

In some embodiments, the administration of the agent according to the provided methods reduces outcomes associated with CRS including fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. In some embodiments, the administration of the agent according to the provided methods reduces outcomes associated with CRS including such as fatigue, nausea, headache, seizure, tachycardia, myalgias, rash, acute vascular leak syndrome, liver function impairment, and renal failure. In some embodiments, the administration of the agent according to the provided methods reduces outcomes associated with CRS including such as an increase in one or more factors such as serum-ferritin, d-dimer, aminotransferases, lactate dehydrogenase and triglycerides, or with hypofibrinogenemia or hepatosplenomegaly.

Thus, in some embodiments, subjects administered the agent that treats, prevents, or reduces the risk of developing neurotoxicity and/or CRS have reduced symptoms, outcomes, or factors associated with neurotoxicity and/or CRS compared to subjects who are not administered the agent, and/or subjects who are administered the agent at a time at which the subject exhibits clinical signs or symptoms of neurotoxicity or severe neurotoxicity, e.g., neurotoxicity of grade 3 or higher and/or severe CRS, such as a CRS of grade 3 or above.

In some embodiments, the agent can be administered greater than 4 hours, 5 hours, 6 hours, 7 hours, 8 hours, 9 hours, 10 hours, 11 hours, 12 hours, 18 hours, 24 hours, 36 hours, 2 days, 3 days, 4 days, or 5 days or more following administration of the cell therapy. In some of such embodiments, the agent may be administered no later than 5 hours, 6 hours, 7 hours, 8 hours, 9 hours, 10 hours, 11 hours, 12 hours, 18 hours, 24 hours, 36 hours, 2 days, 3 days, 4 days, or 5 days or more following administration of the cell therapy.

In some aspects, the agent can be administered between or between about 4 hours and 5 days following administration of cell therapy, such as between or between about 4 hours and 4 days, 8 hours and 3 days, 1 day and 3 days, 2 days and 3 days, or 1 day and 2 days following administration of cell therapy. In some such cases, the agent is administered at or about 1 day, at or about 2 days, or at or about 3 days following the administration of cell therapy. In some instances, the subject is treated with the agent within 3 days, within 2 days or within 1 day after administration of the cell therapy.

In some cases, the agent is administered alone or is administered as part of a composition or formulation, such as a pharmaceutical composition or formulation, as described herein. Thus, the agent alone or as part of a pharmaceutical composition can be administered intravenously or orally, or by any other acceptable known route of administration or as described herein.

In some embodiments, the dosage of agent or the frequency of administration of the agent in a dosage regimen is reduced compared to the dosage of the agent or its frequency in a method in which a subject is treated with the agent after severe, e.g., grade 3 or higher, neurotoxicity has developed or been diagnosed (e.g. after physical signs or symptoms of grade 3 or higher neurotoxicity has manifested). In some embodiments, the dosage of agent or the frequency of administration of the agent in a dosage regimen is reduced compared to the dosage of the agent or its frequency in a method in which a subject is treated for neurotoxicity greater than 3 days, 4 days, 5 days, 6 days, 1 week 2 weeks, three weeks, or more after administration of the cell therapy. In some embodiments, the dosage is reduced by greater than or about 10%, 20%, 30%, 40%, 50%, 60%, 70%, 80%, 90%, or more. In some embodiments, the frequency of dosing is reduced, such as the number of daily doses is reduced or the number of days of dosing is reduced.

A. Steroid

In some embodiments, the agent that treats neurotoxicity and/or CRS, and/or that prevents, delays, or attenuates the development of or risk for developing severe neurotoxicity is a steroid, e.g., corticosteroid. Corticosteroids typically include glucocorticoids and mineralocorticoids.

Generally, any corticosteroid, e.g., glucocorticoid, can be used in the methods or compositions provided herein. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemisuccinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980).

In some examples, the glucocorticoid is selected from among cortisones, dexamethasones, hydrocortisones, methylprednisolones, prednisolones and prednisones. In a particular example, the glucocorticoid is dexamethasone.

In some embodiments, the agent is a corticosteroid and is administered in an amount that is therapeutically effective to treat, ameliorate or reduce one or more symptoms of neurotoxicity and/or CRS. In some embodiments, indicators of improvement or successful pretreatment include determination of the failure to manifest a relevant score on neurotoxicity and/or CRS grading scale, such as a score of less than 3, or a change in grading or severity on the neurotoxicity and/or CRS grading scale as discussed herein, such as a change from a score of 4 to a score of 3.

In some aspects, the corticosteroid is provided in a therapeutically effective dose. Therapeutically effective concentration can be determined empirically by testing in known in vitro or in vivo (e.g. animal model) systems. For example, the amount of a selected corticosteroid to be administered to ameliorate symptoms or adverse effects of neurotoxicity and/or CRS can be determined by standard clinical techniques. In addition, animal models can be employed to help identify optimal dosage ranges. The precise dosage, which can be determined empirically, can depend on the particular therapeutic preparation, the regime and dosing schedule, the route of administration and the seriousness of the disease.

The corticosteroid can be administered in any amount that is effective to ameliorate one or more symptoms associated with neurotoxicity and/or CRS. Thus, the corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid can be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

The corticosteroid, or glucocorticoid, for example dexamethasone, can be administered orally (tablets, liquid or liquid concentrate), PO, intravenously (IV), intramuscularly or by any other known route or route described herein (e.g., with respect to pharmaceutical formulations). In some aspects, the corticosteroid is administered as a bolus, and in other aspects it may be administered over a period of time.

In some aspects, the glucocorticoid can be administered over a period of more than one day, such as over two days, over 3 days, or over 4 or more days. In some embodiments, the corticosteroid can be administered one per day, twice per day, or three times or more per day. For example, the corticosteroid, e.g., dexamethasone, may in some examples be administered at 10 mg (or equivalent) IV twice a day for three days.

In some embodiments, the dosage of corticosteroid, e.g., glucocorticoid, is administered in successively lower dosages per treatment. Hence, in some such treatment regimes, the dose of corticosteroid is tapered. For example, the corticosteroid may be administered at an initial dose (or equivalent dose, such as with reference to dexamethasone) of 4 mg, and upon each successive administration the dose may be lowered, such that the dose is 3 mg for the next administration, 2 mg for the next administration, and 1 mg for the next administration Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Table 3 shows equivalence in terms of potency for various glucocorticoids and routes of administration. Equivalent potency in clinical dosing is well known. Information relating to equivalent steroid dosing (in a non-chronotherapeutic manner) may be found in the British National Formulary (BNF), 37 Mar. 1999.

TABLE 3

| Glucocorticoid administration | |
|---|---|
| Glucocorticoid (Route) | Equivalency Potency |
| Hydrocortisone (IV or PO) | 20 |
| Prednisone | 5 |
| Prednisolone (IV or PO) | 5 |
| Methylprednisolone sodium succinate (IV) | 4 |
| Dexamethasone (IV or PO) | 0.5-0.75 |

Thus, in some embodiments, the steroid is administered in an equivalent dosage amount of from or from about 1.0 mg to 20 mg dexamethasone per day, such as 1.0 mg to 15 mg dexamethasone per day, 1.0 mg to 10 mg dexamethasone per day, 2.0 mg to 8 mg dexamethasone per day, or 2.0 mg to 6.0 mg dexamethasone per day, each inclusive. In some cases, the steroid is administered in an equivalent dose of at or about 4 mg or at or about 8 mg dexamethasone per day.

B. Other Agents

In some embodiments, the agent that treats or ameliorates symptoms of neurotoxicity and/or CRS toxicity is one that targets a cytokine, e.g., is an antagonist or inhibitor of a cytokine, such as transforming growth factor beta (TGF-beta), interleukin 6 (IL-6), interleukin 10 (IL-10), interleukin 15 (IL-15), interferon gamma (IFN-gamma), or monocyte chemoattractant protein-1 (MCP-1). In some embodiments, the agent that treats or ameliorates symptoms of neurotoxicity and/or CRS toxicity is one that targets (e.g. inhibits or is an antagonist of) a cytokine receptor, such as IL-6 receptor (IL-6R), CD122 receptor (IL-2R/IL-15Rbeta), MCP-1 (CCL2) receptor (CCR2 or CCR4), a TGF-beta receptor (TGF-beta I, II, or II), IFN-gamma receptor (IFNGR), IL-1 receptor (IL-1R) or IL-10 receptor (IL-10R). In some embodiments, the agent is a blocker or inhibitor of a tumor necrosis factor. In some embodiments, the agent is a JAK/STAT inhibitor. In some embodiments, the agent is a kinase inhibitor, e.g., an inhibitor of Bruton's tyrosine kinase (BTK). In some embodiments, the agent is a device used to reduce cytokines, such as a physical cytokine absorber.

In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive. In some aspects, the agent is administered in a dosage amount of at least or at least about or about 2 mg/kg, 4 mg/kg, 6 mg/kg or 8 mg/kg. In some embodiments, the agent is administered at a dose of 4 mg or 8 mg. In some embodiments, the agent is administered from or from about 0.5 mg/kg to 100 mg/kg, such as from or from about 1 mg/kg to 50 mg/kg, 1 mg/kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount of from or from about 1 mg/kg to 20 mg/kg, 2 mg/kg to 19 mg/kg, 4 mg/kg to 16 mg/kg, 6 mg/kg to 14 mg/kg or 8 mg/kg to 12 mg/kg, each inclusive. In some aspects, the agent is administered in a dosage amount of at least or at least about or about 1 mg/kg, 2 mg/kg, 4 mg/kg, 6 mg/kg, 8 mg/kg, 10 mg/kg, 12 mg/kg, 14 mg/kg, 16 mg/kg, 18 mg/kg, 20 mg/kg or more. In some embodiments, the agent is administered at a dose of 8 mg/kg or 12 mg/kg, such as about 8 mg/kg, 9 mg/kg, 10 mg/kg, 11 mg/kg or 12 mg/kg. In some embodiments, the agent is administered as part of a composition or formulation, such as a pharmaceutical composition or formulation as described below. Thus, in some cases, the composition comprising the agent is administered as described below. In other aspects, the agent is administered alone and may be administered by any known acceptable route of administration or by one described herein, such as with respect to compositions and pharmaceutical formulations.

In some embodiments, the agent that treats or ameliorates symptoms of neurotoxicity and/or CRS is an antibody or antigen binding fragment. In some embodiments, the agent is tocilizumab, siltuximab, sarilumab, clazakizumab, olokizumab (CDP6038), elsilimomab, ALD518/BMS-945429, sirukumab (CNTO 136), CPSI-2634, ARGX-109, FE301, FM101, Hu-Mik-β-1, tofacitinib, ruxolitinib, CCX140-B, RO523444, BMS CCR2 22, INCB 3284 dimesylate, JNJ27141491, RS 504393, adalimumab, certolizumab pegol or golimumab. In some embodiments, the agent is infliximab, etanercept, or anakinra. In some embodiments, the agent is siltuximab.

In some embodiments, the agent that treats or ameliorates symptoms of neurotoxicity and/or CRS is a small molecule. In some embodiments, the agent is ibrutinib or ruxolitinib.

In some embodiments, the agent is an antagonist or inhibitor of IL-6 or the IL-6 receptor (IL-6R). In some aspects, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-IL-6 antibody, such as siltuximab, sarilumab, clazakizumab, elsilimomab, ALD518/BMS-945429, sirukumab (CNTO 136), CPSI-2634, ARGX-109, FE301, FM101, or olokizumab (CDP6038). In some aspects, the agent may neutralize IL-6 activity by inhibiting the ligand-receptor interactions. The feasibility of this general type of approach has been demonstrated with a natural occurring receptor antagonist for interleukin-1. See Harmurn, C. H. et al., Nature (1990) 343:336-340. In some aspects, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, the agent is an antagonist or inhibitor of IL-15 or the IL-15 receptor (CD122). In some aspects, the agent is an antibody that neutralizes IL-15 activity, such as an antibody or antigen-binding fragment that binds to IL-15 or its receptor CD122. For example, in some instances, the agent is Hu-Mik-β-1, a humanized monoclonal antibody directed to the IL-2/IL-15R-β subunit (CD122) that blocks IL-15 action. In some aspects, the IL-15 antagonist or inhibitor is an IL-15 mutein, such as one described in U.S. Pat. No. 7,235,240. In some embodiments, the agent that is an antagonist or inhibitor of IL-15/CD122 is a small molecule, a protein or peptide, or a nucleic acid.

In some embodiments, the agent is an agonist or stimulator of TGF-β or a TGF-β receptor (e.g., TGF-β receptor I, II, or III). In some aspects, the agent is an antibody that increases TGF-β activity, such as an antibody or antigen-binding fragment that binds to TGF-β or one of its receptors. In some embodiments, the agent that is an agonist or stimulator of TGF-β and/or its receptor is a small molecule, a protein or peptide, or a nucleic acid.

In some embodiments, the agent is an antagonist or inhibitor of MCP-1 (CCL2) or a MCP-1 receptor (e.g., MCP-1 receptor CCR2 or CCR4). In some aspects, the agent is an antibody that neutralizes MCP-1 activity, such as an antibody or antigen-binding fragment that binds to MCP-1 or one of its receptors (CCR2 or CCR4). In some embodiments, the MCP-1 antagonist or inhibitor is any described in Gong et al. J Exp Med. 1997 Jul. 7; 186(1): 131-137 or Shahrara et al. J Immunol 2008; 180:3447-3456. In some embodiments, the agent that is an antagonist or inhibitor of MCP-1 and/or its receptor (CCR2 or CCR4) is a small molecule, a protein or peptide, or a nucleic acid.

In some embodiments, the agent is an antagonist or inhibitor of IFN-γ or an IFN-γ receptor (IFNGR). In some aspects, the agent is an antibody that neutralizes IFN-γ activity, such as an antibody or antigen-binding fragment that binds to IFN-γ or its receptor (IFNGR). In some aspects, the IFN-gamma neutralizing antibody is any described in Dobber et al. Cell Immunol. 1995 February; 160(2):185-92 or Ozmen et al. J Immunol. 1993 Apr. 1; 150(7):2698-705. In some embodiments, the agent that is an antagonist or inhibitor of IFN-γ/IFNGR is a small molecule, a protein or peptide, or a nucleic acid.

In some embodiments, the agent is an antagonist or inhibitor of IL-10 or the IL-10 receptor (IL-10R). In some aspects, the agent is an antibody that neutralizes IL-10 activity, such as an antibody or antigen-binding fragment that binds to IL-10 or IL-10R. In some aspects, the IL-10 neutralizing antibody is any described in Dobber et al. Cell Immunol. 1995 February; 160(2):185-92 or Hunter et al. J Immunol. 2005 Jun. 1; 174(11):7368-75. In some embodiments, the agent that is an antagonist or inhibitor of IL-10/IL-10R is a small molecule, a protein or peptide, or a nucleic acid.

In some embodiments, the agent is an antagonist or inhibitor of IL-1 or the IL-1 receptor (IL-1R). In some aspects, the agent is an IL-1 receptor antagonist, which is a modified form of IL-1R, such as anakinra (see, e.g., Fleischmann et al., (2006) Annals of the rheumatic diseases. 65(8):1006-12). In some aspects, the agent is an antibody that neutralizes IL-1 activity, such as an antibody or antigen-binding fragment that binds to IL-1 or IL-1R, such as canakinumab (see also EP 2277543). In some embodiments, the agent that is an antagonist or inhibitor of IL-1/IL-1R is a small molecule, a protein or peptide, or a nucleic acid.

In some embodiments, the agent is an antagonist or inhibitor of a tumor necrosis factor (TNF) or a tumor necrosis factor receptor (TNFR). In some aspects, the agent is an antibody that blocks TNF activity, such as an antibody or antigen-binding fragment that binds to a TNF, such as TNFα, or its receptor (TNFR, e.g., TNFRp55 or TNFRp75). In some aspects, the agent is selected from among infliximab, adalimumab, certolizumab pegol, golimumab and etanercept. In some embodiments, the agent that is an antagonist or inhibitor of TNF/TNFR is a small molecule, a protein or peptide, or a nucleic acid. In some embodiments, the agent is a small molecule that affects TNF, such as lenalidomide (see, e.g., Muller et al. (1999) Bioorganic & Medicinal Chemistry Letters. 9 (11):1625).

In some embodiments, the agent is an antagonist or inhibitor of signaling through the Janus kinase (JAK) and two Signal Transducer and Activator of Transcription (STAT) signaling cascade. JAK/STAT proteins are common components of cytokine and cytokine receptor signaling. In some embodiments, the agent that is an antagonist or inhibitor of JAK/STAT, such as ruxolitinib (see, e.g., Mesa et al. (2012) Nature Reviews Drug Discovery. 11(2):103-104), tofacitinib (also known as Xeljanz, Jakvinus tasocitinib and CP-690550), Baricitinib (also known as LY-3009104, INCB-28050), Filgotinib (G-146034, GLPG-0634), Gandotinib (LY-2784544), Lestaurtinib (CEP-701), Momelotinib (GS-0387, CYT-387), Pacritinib (SB1518), and Upadacitinib (ABT-494). In some embodiments, the agent is a small molecule, a protein or peptide, or a nucleic acid.

In some embodiments, the agent is a kinase inhibitor. In some embodiments, the agent is an inhibitor of Bruton's tyrosine kinase (BTK). In some embodiments, the inhibitor is or comprises ibrutinib or acalabrutinib (see, e.g., Barrett et al., ASH 58$^{th}$ Annual Meeting San Diego, CA Dec. 3-6, 2016, Abstract 654; Ruella et al., ASH 58$^{th}$ Annual Meeting San Diego, CA Dec. 3-6, 2016, Abstract 2159). In some embodiments, the agent is an inhibitor as described in U.S. Pat. Nos. 7,514,444; 8,008,309; 8,476,284; 8,497,277; 8,697,711; 8,703,780; 8,735,403; 8,754,090; 8,754,091; 8,957,079; 8,999,999; 9,125,889; 9,181,257; or 9,296,753.

In some embodiments, a device, such as absorbent resin technology with blood or plasma filtration, can be used to reduce cytokine levels. In some embodiments, the device used to reduce cytokine levels is a physical cytokine absorber, such as an extracorporeal cytokine absorber. In some embodiments, a physical cytokine absorber can be used to eliminate cytokines from the bloodstream in an ex vivo, extracorporeal manner. In some embodiments, the agent is a porous polymer. In some embodiments, the agent is CytoSorb (see, e.g., Basu et al. Indian J Crit Care Med. (2014) 18(12): 822-824).

V. COMPOSITIONS AND FORMULATIONS

Also provided are compositions containing the engineered receptor (e.g., engineered antigen receptor), such as CAR or TCR, and compositions containing the agents that treat or ameliorate symptoms of neurotoxicity and/or CRS, including pharmaceutical compositions and formulations. Also provided are methods of using and uses of the compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the agent or host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity and/or CRS), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

VI. KITS AND ARTICLES OF MANUFACTURE

Also provided are kits, such as those containing reagents for measuring the level at least two biomarkers, e.g., cytokines. In some embodiments, the kit comprises reagents for measuring only two biomarkers, e.g., cytokines. In some aspects, the kit comprises reagents for measuring at least three biomarkers, e.g., cytokines. In some instances, the kit includes instructions for measuring the at least two cytokines. In some embodiments, the reagents include components for performing an in vitro assay to measure the at least two biomarkers, e.g., cytokines. In some cases, the in vitro assay is an immunoassay, an aptamer-based assay, a histological or cytological assay, or an mRNA expression level assay. In some embodiments, the in vitro assay is selected from among an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay. In some aspects, the reagent is a binding reagent that specifically binds the biomarkers, e.g., cytokines. In some cases, the binding reagent is an antibody or antigen-binding fragment thereof, an aptamer or a nucleic acid probe.

In some instances, the two or at least three cytokines for which the kit contains reagents for measuring include transforming growth factor beta (TGF-beta), interleukin 6 (IL-6), interleukin 10 (IL-10), interleukin 15 (IL-15), interferon gamma (IFN-gamma) or monocyte chemoattractant protein-1 (MCP-1). In some cases, the at least two cytokines are IL-6 and IL-15, TGF-beta and IL-6, TGF-beta and IL-15, IL-6 and IL-15 or IL-15 and MCP-1. In some embodiments, the three cytokines are TGF-beta, IL-6 and IL-15 or are IL-6, IL-15 and MCP-1.

In some instances, the kit contains reagents for detecting a parameter for at least two biomarkers selected from among interleukin 15 (IL-15), interleukin 6 (IL-6), interleukin 10 (IL-10), interleukin 8 (IL-8), interferon gamma (IFN-gamma), ferritin and soluble TNF receptor type 1 (sTNFR1). In some instances, the kit contains reagents for detecting a parameter for at least two biomarkers selected from among FN-γ, IL-2, IL-6, IL-8, IL-10, IL-15, IL-2Ra, MCP-1, TNFRp55, TNFRp75, TIM3, BAFF, MIP-1β, CRP, IL-18, sIL-6R and/or ferritin.

VII. EXEMPLARY EMBODIMENTS

The following examples are included for illustrative purposes only and are not intended to limit the scope of the invention.

1. A method of ameliorating the development of toxicity in a subject, the method comprising:
   (a) detecting a parameter for a biomarker or, individually, for of each biomarker in a panel of biomarkers in a biological sample, which is derived from a subject at a time at which the subject does or did not exhibit a physical sign or symptom of toxicity, neurotoxicity, and/or severe neurotoxicity, the detecting of the parameter or the detecting of each parameter, individually, comprising detection of the parameter directly in the biological sample or detection of the parameter indirectly, in a test sample obtained from said biological sample;
   (b) comparing the parameter detected for the biomarker, or the parameter detected for each of the biomarkers in the panel, individually, to a reference value for said parameter, wherein the comparison indicates whether the subject is or is not at risk for developing toxicity, which optionally is neurotoxicity or CRS, optionally is severe neurotoxicity or severe CRS, and/or indicates a degree of risk for developing said toxicity; and
   (c) if the comparison indicates that the subject is at risk for developing the toxicity, and/or indicates that the risk is above a threshold level, administering to the subject an agent or therapy that is capable of treating, preventing, delaying, or attenuating the development of the toxicity.
2. The method of embodiment 1, wherein, at the time of the detecting, comparison or administration, the subject has received or is receiving a cell therapy for treating a disease or condition in the subject, which cell therapy is associated with or is capable of inducing toxicity, wherein the cell therapy optionally is adoptive cell therapy and/or wherein the cell therapy comprises administration of a dose of cells to treat a disease or condition in the subject, which cells comprise cells expressing a recombinant receptor.
3. A method of treatment, comprising:
   (a) administering to a subject having a disease or condition a cell therapy comprising a dose of cells expressing a recombinant receptor;
   (b) detecting a parameter for a biomarker or, individually, for of each biomarker in a panel of biomarkers, in a biological sample derived from a subject, the detecting of the parameter or the detecting of each parameter, individually, comprising detection of the parameter directly in the biological sample or detection of the parameter indirectly, in a test sample obtained from said biological sample;
   (c) comparing detected parameter for the biomarker, or the parameter detected for each of the biomarkers in the panel, individually, to a reference value for said parameter, wherein the comparison indicates whether the subject is or is not at risk for developing a toxicity, which optionally is neurotoxicity or CRS, optionally severe neurotoxicity or severe CRS, and/or indicates a degree of risk for developing said toxicity; and
   (d) if the comparison indicates that the subject is at risk for developing the toxicity, and/or indicates that the risk is above a threshold level, administering to the subject an agent or therapy that is capable of treating, preventing, delaying, or attenuating the development of the toxicity.
4. The method of any of embodiments 1-3, wherein the subject does not exhibit a physical sign or symptom of the toxicity, does not exhibit a physical sign or symptom of toxicity, or of neurotoxicity, and/or does not exhibit a physical sign or symptom of severe neurotoxicity, at the time of the detection, the comparison or the administering of the agent or therapy.
5. A method of diagnosing or predicting a risk for developing toxicity associated with cell therapy in a subject, the method comprising:
   (a) detecting a parameter for a biomarker, or, individually, for each biomarker in a panel of biomarkers, in a biological sample derived from a subject that has been administered a cell therapy for treatment of a disease or condition in the subject, the detecting of the parameter or the detecting of each parameter, individually, comprising direct detection of the parameter in the biological sample, or detection of the parameter indirectly, in a test sample obtained from said biological sample, wherein the biological sample is or has been derived from the subject no more than fourteen, no more than ten, no more than five, or no more than three days after the administration of the cells; and (b) comparing the parameter detected for the biomarker, or the parameter detected for each biomarker of the panel, individually, to a reference value for said parameter, wherein the comparison indicates whether the subject is at risk for developing toxicity, which optionally is neurotoxicity or CRS, which optionally is severe neurotoxicity or severe CRS, and/or a degree of risk for developing said toxicity.

6. The method of any of embodiments 1-5, wherein the parameter for the biomarker or the parameter for one or more or each of the panel of biomarkers, individually, is or comprises a concentration of the biomarker, an amount of the biomarker, a level of the biomarker, a relative concentration of the biomarker, a relative amount of the biomarker, or an activity of or associated with the biomarker.

7. The method of embodiment 6, wherein the parameter for the biomarker or the parameter for one or more or each of the panel of biomarkers, individually, is or comprises a concentration of the biomarker, an amount of the biomarker, a level of the biomarker, a relative concentration of the biomarker, or a relative amount of the biomarker.

8. The method of any of embodiments 1-7, wherein the parameter for the biomarker or the parameter for one or more or each of the panel of biomarkers, individually, is a peak serum level of the biomarker within a defined period of time, which optionally is within 1, 2, 3, 4, 5, 6, 7, 8, 9, 10, 12, 15, 18, 21, 24, 27 and/or 30 days after administration of the cell therapy, or a first administration or dose thereof, or after the initiation of any of the foregoing, wherein the peak serum level is the highest serum level of the biomarker within the defined period.

9. The method of any of embodiments 1-8, wherein the comparison to the reference value, or each of the comparisons to each of the reference values, individually, comprises thereby determining a relative value for the parameter, as compared to the reference value, whereby the relative value, or combination thereof, indicates whether the subject is at risk for the for developing the toxicity or whether the risk is above the level, or the level of the risk.

10. The method of embodiment 9, wherein the relative value is a percentage or fold increase or percentage or fold decrease, compared to the reference value, or is an indication that the parameter is at, within, above, or below the reference value.

11. The method of any of embodiments 1-10, wherein the reference value comprises a range of values and optionally wherein the relative value is an indication that the detected parameter is within the range or is not within the range.

12. The method of embodiment any of embodiments 1-11, wherein the comparison indicates that the subject is at risk for developing the toxicity, wherein the method thereby diagnoses or predicts a risk for the toxicity and/or a level of risk thereof 13. The method of any of embodiments 5-12, wherein the subject does not exhibit a physical sign or symptom of the toxicity or of neurotoxicity or CRS or does not exhibit a physical sign or symptom of severe neurotoxicity or severe CRS at the time of the detection, comparison, diagnosing or predicting.

14. The method of any of embodiments 2-13, wherein the biological sample is obtained or has been obtained from the subject:
no more than 3 days after administration of the cell therapy, or a first administration of the cell therapy, or a first administration or dose thereof or after the initiation of any of the foregoing;
no more than 2 days after administration of the cell therapy, or a first administration or dose thereof, or after the initiation of any of the foregoing; or no more than 1 day after administration of the cell therapy or a first administration or dose thereof to the subject, or after the initiation of any of the foregoing.

15. The method of any of embodiments 2-14, wherein the biological sample is obtained or has been obtained from the subject greater than 4 hours after administration of the cell therapy or greater than 4 hours after the first administration or dose thereof to the subject, or greater than 4 hours after the initiation of any of the foregoing.

16. The method of any of embodiments 5-15, wherein the cell therapy comprises administration of a dose of cells expressing a recombinant receptor.

17. The method of any of embodiments 2-16, wherein the dose of cells comprises a number of cells between about $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive.

18. The method of any of embodiments 2-16, wherein the dose of cells comprises a number of cells between about such as between about $1 \times 10^5$ cells/kg and $5 \times 10^7$ cells/kg, $2 \times 10^5$ cells/kg and $2 \times 10^7$ cells/kg, $2 \times 10^5$ cells/kg and $1 \times 10^7$ cells/kg, $2 \times 10^5$ cells/kg and $5 \times 10^6$ cells/kg, $2 \times 10^5$ cells/kg and $2 \times 10^6$ cells/kg or $2 \times 10^5$ cells/kg and $1 \times 10^6$ cells/kg, each inclusive.

19. The method of any of embodiments 5-18, further comprising, if the subject is predicted to be at a risk for or diagnosed with the toxicity, altering the treatment of the cell therapy.

20. The method of embodiment 19, wherein the altering the treatment comprises discontinuing the treatment of the cell therapy, administering a different cell therapy for treating the disease or condition, administering a treatment for treating the disease or condition other than the cell therapy, administering subsequent dose of cells in combination with a second therapeutic agent or treatment for the treatment of the disease or condition, administering a subsequent dose of cells that is decreased compared to the prior dose of cells, or decreasing the frequency of administration of the cell therapy.

21. The method of any of embodiments 7-19, further comprising, if the subject is diagnosed with or predicted to be at a risk for, or predicted to be at risk for above the threshold level, developing the toxicity, administering an agent that treats toxicity, optionally neurotoxicity and/or CRS, and/or an agent that prevents, delays, or attenuates the development of or risk for developing toxicity, optionally neurotoxicity and/or CRS.

22. The method of any of embodiments 1-21, wherein the biomarker or one or more or all of the panel of biomarkers comprises a cytokine or a plurality of cytokines.

23. The method of any of embodiments 1-22, wherein the toxicity is neurotoxicity, and/or the toxicity is severe neurotoxicity and/or the severe neurotoxicity is a grade 3 or higher neurotoxicity.

24. The method of embodiment 22 or embodiment 23, wherein the cytokine or the plurality of cytokines is selected from among transforming growth factor beta (TGF-beta), interleukin 6 (IL-6), interleukin 10 (IL-10), interleukin 15 (IL-15), interferon gamma (IFN-gamma) and monocyte chemoattractant protein-1 (MCP-1).

25. The method of any of embodiments 1-24, wherein the biomarker or panel of biomarkers comprises the panel of biomarkers, said panel of biomarkers comprising at least 2 cytokines or at least 3 cytokines.

26. The method of embodiment 25, wherein the at least two biomarkers comprise IL-15 and IL-6.

27. The method of any of embodiments 1-26, wherein the biomarker or panel of biomarkers comprises IL-6.

28. The method of any of embodiments 1-27, wherein the biomarker or biomarkers comprises the panel and the parameter for each of the biomarkers in the panel is detected simultaneously or sequentially, in the same biological sample or test sample, or in different test samples obtained from the subject or the biological sample.

29. The method of any of embodiments 1-28, wherein the reference value is based on, or has been predetermined using information obtained from assessment of a ROC curve of the one or more biomarkers in a population of diseased subjects having a cancer treated with a cell therapy.

30. The method of any of embodiments 1-29, wherein the reference value is a value, optionally a threshold value, and/or optionally a value of optimal sensitivity and/or specificity, which optionally is established based on the Youden Index.

31. The method of any of embodiments 1-30, wherein:
the reference value for the parameter, or the combination of the reference values for the parameter for each of the panel of biomarkers, has been selected to or does provide a sensitivity or net sensitivity of greater than 0.50, greater than 0.60, greater than 0.70, greater than 0.80, greater than 0.90 or greater than 0.95; and/or
the reference value for the parameter, or the combination of the reference values for the parameter for each of the panel of biomarkers, has been selected to or does provide a specificity or net specificity of greater than 0.50, greater than 0.60, greater than 0.70, greater than 0.80, greater than 0.90 or greater than 0.95; and/or
the reference value for the parameter, or the combination of the reference values for the parameter for each of the panel of biomarkers, has been selected to or does provide an area under the curve (AUC) in a ROC analysis for the biomarker or panel of biomarkers of greater than 0.80, greater than 0.85, greater than 0.90 or greater than 0.95.

32. The method of any of embodiments 1-31, wherein:
the reference value for the parameter, or the combination of the reference values for the parameter for each of the panel of biomarkers, is selected to provide a sensitivity or net sensitivity of greater than 0.80, greater than 0.85, greater than 0.90 or greater than 0.95; and/or
the reference value for the parameter, or the combination of the reference values for the parameter for each of the panel of biomarkers, is selected to provide a specificity or net specificity of greater than 0.60, greater than 0.70, greater than 0.80, greater than 0.90 or greater than 0.95; and/or
the reference value for the parameter, or the combination of the reference values for the parameter for each of the panel of biomarkers, is selected to provide an AUC in a ROC analysis of greater than 0.85, greater than 0.90 or greater than 0.95.

33. The method of any of embodiments 2-32, wherein the disease or condition is a cancer; and/or
the disease or condition is a leukemia or lymphoma; and/or the disease or condition is a non-Hodgkin lymphoma (NHL).

34. The method of any of embodiments 1-33, wherein:
the biomarker or panel of biomarkers comprise one or a combination of cytokines, comprising at least one cytokine selected from among TGF-beta, IL-6 and IL-15; and
if the parameter for the cytokine or, in the case of the combination, for at least one, at least two, or at least three of the cytokines selected from among TGF-beta, IL-6 and IL-15, individually, meet a classification selected from: i) for TGF-beta, less than the TGF-beta reference value; ii) for IL-6, greater than the IL-6 reference value; and/or iii) for IL-15, greater than the IL-15 reference value, then the comparison indicates that the subject is at risk for the toxicity and/or that the risk is above the threshold level of risk.

35. The method of embodiment 34, wherein:
the at least one, at least two, or at least three of the cytokines is at least two of the cytokines; or
the at least one, at least two, or at least three of the cytokines is at least three of the cytokines.

36. The method of embodiment 34 or embodiment 35, wherein the biomarker or panel of biomarkers comprise the panel of biomarkers, said panel of biomarkers comprising a first and second cytokine, the first and second cytokine being: TGF-beta and IL-6, TGF-beta and IL-15, or IL-6 and IL-15, and wherein:
if the detected parameter for each of the first and second cytokines, individually, meets the classification, then the comparison indicates that the subject is at risk for the toxicity and/or that the risk is above the threshold level of risk; or
if the detected parameters for both the first and second cytokines do not meet the classification, then the comparison indicates that the subject is at risk for the toxicity and/or that the risk is above the threshold level of risk; or
if the detected parameter for only one of the first and second cytokines does not meet the classification, optionally, the method further comprises:
i) detecting a parameter for at least a third biomarker in a biological sample derived from the subject, wherein the biological sample is or has been derived from the subject no more than three days after the administration of the cells; and
ii) comparing the detected parameter for the third biomarker to a third reference value, thereby indicating whether the subject is at risk for developing severe neurotoxicity and/or a degree of risk for developing severe neurotoxicity.

37. The method of embodiment 36, wherein the third biomarker is a cytokine selected from among TGF-beta, IL-6 and IL-15 and is different from the first and second cytokines, and wherein:

if the detected parameter for the third cytokine meets the classification, the subject is identified or is diagnosed or predicted to be at risk for developing the toxicity, which is optionally neurotoxicity, which optionally is severe neurotoxicity; or if the detected parameter for the third cytokine does not meet the classification, the subject is identified or is diagnosed or predicted not to be at risk for developing the toxicity, which is optionally neurotoxicity or severe neurotoxicity.

38. The method of any of embodiments 34-37, wherein a parameter of each of TGF-beta, IL-6 and IL-15 are detected, and wherein:

if the detected parameter for all three cytokines meet the classification, the subject is identified or is diagnosed or predicted to be at risk of the toxicity, which optionally is neurotoxicity; or if the detected parameter for at least two of the cytokines meet the classification, the subject is identified or is diagnosed or predicted to be at risk for the toxicity, which optionally is neurotoxicity; or if the detected parameter for only one of the cytokines meets the classification, the subject is identified or is diagnosed or predicted not to be at risk for the toxicity, which optionally is neurotoxicity.

39. The method of any of embodiments 1-38, wherein the parameter, or the parameter for each of the biomarkers in the panel, individually, is a concentration of the biomarker, or relative concentration of the biomarker, and the reference value for said parameter is a reference concentration.

40. A method of ameliorating the development of toxicity in a subject, comprising:

(a) detecting a concentration or relative concentration of each of a panel of cytokines, the panel comprising one, two, or three of TGF-beta, IL-6 and IL-15, in a biological sample derived from a subject, the detecting comprising detection of the concentration or relative concentration directly in the biological sample or indirectly, by detection in a test sample obtained from said biological sample, wherein the biological sample is obtained or has been obtained from the subject no more than 1 day, 2 days or 3 days after administration of the cell therapy, or a first administration or dose thereof, or after initiation of any of the foregoing;

(b) comparing the concentration or relative concentration of each of the cytokines in the panel to a reference value for each respective concentration of cytokine, wherein:

if the detected concentration or relative concentration of the two or three of the cytokines individually meet a classification, the subject is identified or is diagnosed or predicted to be at risk for developing neurotoxicity, which optionally is severe neurotoxicity, wherein the classification is selected from: i) for TGF-beta, less than the TGF-beta reference value; ii) for IL-6, greater than the IL-6 reference value; and/or iii) for IL-15, greater than the IL-15 reference value; and if the concentration or relative concentrations of at least two of the cytokines do not meet the classification, the subject is identified or is diagnosed or predicted not to be at risk for developing toxicity, optionally neurotoxicity.

41. The method of embodiment 40, wherein the disease or condition is a non-Hodgkin lymphoma (NHL).

42. A method of ameliorating the development of toxicity in a subject, comprising:

(a) detecting a concentration or relative concentration of each of a panel of cytokines, the panel comprising one, two, or three of IL-6, IL-15 and MCP-1, in a biological sample derived from a subject, the detecting comprising detection of the concentration or relative concentration directly in the biological sample or indirectly, by detection in a test sample obtained from said biological sample, wherein the biological sample is obtained or has been obtained from the subject no more than 1 day, 2 days or 3 days after administration of the cell therapy, or a first administration or dose thereof, or after initiation of any of the foregoing;

(b) comparing the concentration or relative concentration of each of the cytokines in the panel to a reference value for each respective concentration of cytokine, wherein:

if the detected concentration or relative concentration of the two or three of the cytokines individually meet a classification, the subject is identified or is diagnosed or predicted to be at risk for developing neurotoxicity, which optionally is severe neurotoxicity, wherein the classification is selected from: i) for MCP-1, greater than the MCP-1 reference value; ii) for IL-6, greater than the IL-6 reference value; and/or iii) for IL-15, greater than the IL-15 reference value; and if the concentration or relative concentrations of at least two of the cytokines do not meet the classification, the subject is identified or is diagnosed or predicted not to be at risk for developing toxicity, optionally neurotoxicity.

43. The method of any of embodiments 40-42, further comprising, if the comparison indicates that the subject is at risk for developing toxicity, optionally neurotoxicity, which optionally is severe neurotoxicity and/or indicates that the risk is above a threshold level, administering to the subject an agent or therapy that is capable of treating, preventing, delaying, or attenuating the development of toxicity, optionally neurotoxicity.

44. The method of embodiment 42 or embodiment 43, wherein the disease or condition is acute lymphoblastic leukemia (ALL).

45. The method of any of embodiments 34-44, wherein:

the TGF-beta reference value is within a range from or from about 5.5 pg/mL to about 15.00 pg/mL (log 2 scale) or from or from about 45 pg/mL to about 33000 pg/mL;

the IL-6 reference value is within a range from or from about 2.6 pg/mL to 5.4 pg/mL (log 2 scale) or from or from about 6.00 pg/mL to about 41.0 pg/mL; and/or the IL-15 reference value is within a range from or from about 6.1 pg/mL to about 7.1 pg/mL (log 2 scale) or from or from about 69.0 pg/mL to about 135.0 pg/mL.

46. The method of any of embodiments 34-45, wherein:

the TGF-beta reference value is within a range from or from about 10.00 pg/mL to about 15.00 pg/mL (log 2 scale) or from or from about 20000 pg/mL to about 33000 pg/mL; or is at least or at least about 10.00 pg/mL, 11.00 pg/mL, 12.00 pg/mL, 13.00 pg/mL, 14.00 pg/mL or 15.00 pg/mL, each on a log 2 scale; or is at least or at least about 20000 pg/mL, 22000 pg/mL, 24000 pg/mL, 26000 pg/mL, 28000 pg/mL, 30000 pg/mL or 32000 pg/mL; or is or is about 25000±100 pg/mL or is or is about 14.0±1.0 pg/mL on a log 2 scale;

the IL-6 reference value is within a range from or from about 3.5 pg/mL to 5.4 pg/mL (log 2 scale) or from or from about 12 pg/mL to 41 pg/mL; or is at least or at least about 3.5 pg/mL, 4.0 pg/mL, 4.5 pg/mL, 4.8 pg/mL, 5.0 pg/mL, 5.2 pg/mL or 5.4 pg/mL, each on log 2 scale; or is at least or at least about 12 pg/mL, 18 pg/mL, 24 pg/mL, 30 pg/mL or 36 pg/mL; or is or is about 15.2±1.0 pg/mL and/or is or is about 3.9±1.0 pg/mL;

the IL-15 reference value is a within a range from or from about 6.0 pg/mL to 7.1 pg/mL (log 2 scale) or from or from about 74 pg/mL to 135 pg/mL; or is at least or at least about 6.0 pg/mL, 6.2 pg/mL, 6.4 pg/mL, 6.6 pg/mL, 6.8 pg/mL or 7.0 pg/mL, each on log 2 scale; or is at least or at least about 74 pg/mL, 80 pg/mL, 90 pg/mL, 100 pg/mL, 110 pg/mL, 120 pg/mL or 130 pg/mL, or is or is about 6.2±1.0 on a log 2 scale or is or is about 76±4.0 pg/mL.

47. The method of any of embodiments 34-46, further comprising:
detecting a parameter for IL-10 or IFN-gamma in a sample from the subject, wherein the biological sample is or has been derived from the subject no more than three days after the administration of the cells; and
identifying the subject as at risk of developing neurotoxicity if the detected parameter of IL-10 and/or IFN-gamma meets a classification selected from: iv) for IL-10, greater than a IL-10 reference value; or v) a for IFN-gamma, greater than a IFN-gamma reference value.

48. The method of embodiment 47, wherein:
the IL-10 reference value is a reference value that is at least or at least about 3.0 pg/mL (log 2 scale) or is at least or at least about 10.0 pg/mL; or is or is about 3.5±1.0 pg/mL on log 2 scale or is or is about 11.0±1.0 pg/mL; and/or
the IFN-gamma reference value is a reference value that is at least or at least about 4.0 pg/mL (log 2 scale) or is at least or at least about 18.0 pg/mL; or is or is about 4.2±1.0 pg/mL on log 2 scale or is or is about 19.0±1.0 pg/mL.

49. The method of any of embodiments 2-40 and 42-48, wherein the disease or condition is acute lymphoblastic leukemia (ALL).

50. The method of any of embodiments 2-40 and 42-49, wherein:
the one or more biomarkers comprise a cytokine selected from among IL-6, IL-15 and MCP-1; and
the subject is identified or is diagnosed or predicted to be at risk for developing the toxicity if the detected parameter of at least one of the cytokines meets a classification selected from: i) for IL-6, greater than the IL-6 reference value; ii) a for IL-15, greater than the IL-15 reference value; and/or iii) a for MCP-1, greater than the MCP-1 reference value.

51. The method of embodiment 50, wherein the subject is identified or is diagnosed or predicted to be at risk for developing severe neurotoxicity if the parameter detected for at least two of the cytokines meet the classification or if the parameter detected for at least three of the cytokines meet the classification.

52. The method of embodiment 42 or embodiment 43, wherein the one or more biomarkers comprise a first and second cytokine selected from among IL-15 and IL-6, IL-15 and MCP-1 and IL-6 and MCP-1 and wherein:
if the parameter detected for the first and second cytokines meet the classification, the subject is identified or is diagnosed or predicted to be at risk for developing severe neurotoxicity; or
if the parameter detected for both the first and second cytokines do not meet the classification, the subject is identified or predicted not to be at risk for developing severe neurotoxicity; or
if the parameter detected for only one of the first and second cytokines does not meet the classification, optionally, the method further comprises:
  i) detecting parameter for at least a third biomarker in a biological sample derived from the subject wherein the biological sample is or has been derived from the subject no more than three days after the administration of the cells; and
(c) comparing the detected parameter for the third biomarker to a reference value, wherein the comparison or the method thereby indicates whether the subject is at risk for developing severe neurotoxicity and/or a degree of risk for developing severe neurotoxicity.

53. The method of embodiment 52, wherein the third biomarker is a cytokine selected from MCP-1, IL-6 or IL-15 and is different from the first and second cytokines, and wherein:
if the detected parameter for the third cytokine meets the classification, the subject is identified or predicted to be at risk for developing severe neurotoxicity; or
if the detected parameter for the third cytokine does not meet the classification, the subject is identified or predicted not to be at risk for developing neurotoxicity.

54. The method of embodiment 52 or embodiment 53, wherein the first cytokine is IL-15, the second cytokine is IL-6 and, optionally, the third cytokine is MCP-1.

55. The method of any of embodiments 50-54, wherein each of IL-15, IL-6 and MCP-1 are detected, and wherein:
if the detected parameter for all three cytokines meet the classification, the subject is identified or is diagnosed or predicted to be at risk for developing severe neurotoxicity; or
if the detected parameter for at least two of the cytokines meet the classification, the subject is identified or is diagnosed or predicted to be at risk for neurotoxicity, which two cytokines optionally are IL-15 and IL-6 or IL-15 and MCP-1; or
if the parameter for only one of the cytokines meets the classification, the subject is not identified or is diagnosed predicted to be at risk for developing neurotoxicity.

56. The method of any of embodiments 50-55, wherein:
the IL-6 reference value is within a range, or is a range, from or from about 2.0 pg/mL to 4.0 pg/mL (log 2 scale) or from or from about 6.00 pg/mL to 12.0 pg/mL; and/or
the IL-15 reference value is within a range, or is a range, from or from about 5.0 pg/mL to 6.5 pg/mL (log 2 scale) or from or from about 40.0 pg/mL to 90.0 pg/mL; and/or
the MCP-1 reference value is within a range, or is a range, from or from about 7.00 pg/mL to 12.0 pg/mL (log 2 scale) or from or from about 700 pg/mL to 1400 pg/mL.

57. The method of any of embodiments 50-56, wherein:
the IL-6 reference value is at least or at least about 3.0 pg/mL or 4.0 pg/mL, each on a log 2 scale; or is at least or at least about 8.0 pg/mL, 9.0 pg/mL, 10.0 pg/mL, 11.0 pg/mL or 12.0 pg/mL; or is or is about 3.0±1.0 pg/mL on a log 2 scale or is or is about 10.5±1.0 pg/mL;
the IL-15 reference value is within a range from or from about 6.0 pg/mL to 6.5 pg/mL (log 2 scale) or from or from about 70 pg/mL to 90 pg/mL; or is at least or at least about 6.0 pg/mL, 6.1 pg/mL, 6.2 pg/mL, 6.3 pg/mL, 6.4 pg/mL or 6.5 pg/mL, each on log 2 scale; or is at least or at least about 70 pg/mL, 75 pg/mL, 80 pg/mL, 85 pg/mL or 90 pg/ml; or is or is about 6.0±1.0 pg/mL on a log 2 scale or is or is about 81±4 pg/mL; and/or
the MCP-1 reference value is within a range from or from about 9.0 pg/mL to 12.0 pg/mL (log 2 scale) or from or from about 1000 pg/mL to 1400 pg/mL; or is at least or at least about 9.0 pg/mL, 10.0 pg/mL, 11.0 pg/mL or 12.0 pg/mL, each on log 2 scale; or is at least or at least about 1000 pg/mL, 1100 pg/mL, 1200 pg/mL, 1300 pg/mL or 1400 pg/mL; or is or is about 10.0±1.0 pg/mL on a log 2 scale or is or is about 1200±100 pg/mL.

58. The method of any of embodiments 1-22, wherein the toxicity is CRS, and/or the toxicity is severe CRS and/or the severe CRS is a grade 3 or higher CRS.

59. The method of any of embodiments 1-22 and 58, wherein the biomarker or one or more or each of the panel of biomarkers, individually, is or comprises IL-15, IL-6, IL-8, IL-10, IFN-gamma, soluble TNF receptor type I (sTNFR1) or ferritin.

60. A method of ameliorating the development of toxicity in a subject, comprising:
(a) detecting a concentration or relative concentration of each of a panel of biomarkers, the panel comprising one or more of IL-15, IL-6, IL-8, IL-10, soluble TNF receptor type 1 (sTNFR1), IFN-gamma and ferritin, in a biological sample derived from a subject, the detecting comprising detection of the concentration or relative concentration directly in the biological sample or indirectly, by detection in a test sample obtained from said biological sample, wherein the biological sample is obtained or has been obtained from the subject no more than 1 day, 2 days or 3 days after administration of the cell therapy, or a first administration or dose thereof, or after initiation of any of the foregoing;
(b) comparing the concentration or relative concentration of each of the biomarkers in the panel to a reference value for each respective concentration of biomarker, wherein:
if the detected concentration or relative concentration of the one or more of the biomarkers individually is higher than the reference value, the subject is identified or is diagnosed or predicted to be at risk for developing CRS, which optionally is severe CRS.

61. The method of any of embodiments 58-60, wherein the biological sample is obtained or has been obtained from the subject at or about 1 day after administration of the cell therapy, or a first administration or dose thereof, or after initiation of any of the foregoing.

62. The method of embodiment 60 or embodiment 61, wherein the reference level is an average level of a group of subjects receiving the same treatment for the same indication, and/or such subjects that do not develop the toxicity, which optionally is severe CRS or grade 3 or higher CRS.

63. The method of any of embodiments 58-62, wherein the disease or condition is a non-Hodgkin lymphoma (NHL) or acute lymphoblastic leukemia (ALL).

64. The method of any of embodiments 1-63, wherein the accuracy of the identification or prediction is greater than 80%, greater than 85%, greater than 90%, or greater than 95%.

65. The method of any of embodiments 1-64, wherein the agent that treats toxicity, optionally neurotoxicity and/or CRS, or prevents, delays, or attenuates the development of or risk for developing the toxicity, is a steroid, is an antagonist or inhibitor of a cytokine receptor selected from among IL-6 receptor, CD122 receptor (IL-2R/IL-15Rbeta) and CCR2, or is an inhibitor of a cytokine selected from among IL-6, IL-15 and MCP-1.

66. The method of embodiment 65, wherein the antagonist or inhibitor is selected from among an antibody or antigen-binding fragment, a small molecule, a protein or peptide and a nucleic acid.

67. The method of embodiment 65 or embodiment 66, wherein:
the agent is selected from among tocilizumab, siltuximab, sarilumab, olokizumab (CDP6038), elsilimomab, ALD518/BMS-945429, sirukumab (CNTO 136), CPSI-2634, ARGX-109, FE301, FM101, Hu-Mik-β-1, tofacitinib, ruxolitinib, CCX140-B, R0523444, BMS CCR2 22, INCB 3284 dimesylate, JNJ27141491 and RS 504393;
the agent is tocilizumab, optionally wherein the tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg.

68. The method of embodiment 65, wherein: the agent is a steroid that is a corticosteroid; which optionally is a glucocorticoid.

69. The method of embodiment 68, wherein the corticosteroid is dexamethasone or prednisone.

70. The method of any of embodiments 65-69, wherein the agent is or comprises a steroid that is administered in an equivalent dosage amount of from or from about 1.0 mg to 20 mg dexamethasone per day, 1 mg to 10 mg dexamethasone per day, or 2.0 mg to 6.0 mg dexamethasone per day, each inclusive.

71. The method of any of embodiments 65-70, wherein the agent is or comprises a steroid that is administered intravenously or orally.

72. The method of any of embodiments 1-71, wherein the subject is treated with the agent within 3 days, within 2 days or within 1 day after administration of the cell therapy.

73. The method of any of embodiments 1-72, wherein, when the method comprises administering the agent, the method further comprises, after administration of the agent, monitoring the efficacy of the agent on the treatment, prevention, delay, or attenuation of toxicity, optionally of neurotoxicity and/or CRS.

74. The method of embodiment 73, wherein monitoring the efficacy comprises:
detecting a parameter for the biomarker or for one or more of the panel of biomarkers, individually, which optionally are the one or more cytokines, in a subsequent biological sample obtained from the subject following administration of the agent to the subject, the detecting of the parameter for the biomarker or individually for each of the panel of biomarkers comprising detection directly in the biological sample or detection indirectly, in a test sample obtained from said subsequent biological sample; and comparing the subsequent parameter for the biomarker, or parameter of one or more or each of the biomarkers, individually, to a reference value, which optionally is a value for the parameter present in a prior sample from the subject or to a baseline sample prior to the administration of the agent, wherein optionally, the agent is deemed or considered to have been or be efficacious if the subsequent parameter based on the comparison, and optionally if the parameter is not deemed to be altered to a value that is more predictive of the development of neurotoxicity and/or CRS than the level, amount, relative amount, concentration, or relative concentration present in the prior sample or baseline sample.

75. The method of embodiment 73 or embodiment 74, wherein the method comprises monitoring the efficacy on the treatment, prevention, delay, or attenuation of severe neurotoxicity or grade 3 or higher neurotoxicity and the parameter is predictive of the development of severe neurotoxicity or grade 3 or higher neurotoxicity.

76. The method of embodiment 75, wherein:
the biomarker is a cytokine that is selected from among IL-15, IL-6, IL-10, IFN-gamma and MCP-1, and treatment with the agent is considered to be efficacious if the subsequent parameter of the cytokine is about the same or is the same or is less than the parameter present in a prior sample or the baseline sample; and/or
the biomarker is a cytokine that is TGF-beta, and treatment with the agent is considered to be efficacious if the subsequent parameter for the cytokine is about the same or is the same or is greater than the parameter detected in a prior sample or the baseline sample.

77. The method of embodiment 73 or embodiment 74, wherein the method comprises monitoring the efficacy on the treatment, prevention, delay, or attenuation of severe CRS or grade 3 or higher CRS and the parameter is predictive of the development of severe CRS or grade 3 or higher CRS.

78. The method of embodiment 77, wherein the biomarker or one or more or each of the panel of biomarkers, individually, is or comprises IL-15, IL-6, IL-8, IL-10, IFN-gamma, soluble TNF receptor type 1 (sTNFR1) or ferritin, and treatment with the agent is considered to be efficacious if the subsequent parameter of the cytokine is about the same or is the same or is less than the parameter present in a prior sample or the baseline sample.

79. The method of any of embodiments 73-78, wherein if the treatment is not deemed to be efficacious, the method further comprises continuing treatment with the agent, increasing the dosage of the agent, increasing the frequency of administration of the agent or administering a different agent for treating, preventing, delaying, or attenuating the risk for developing neurotoxicity and/or CRS.

80. The method of any of embodiments 1-79, wherein:
the physical signs or symptoms associated with toxicity, optionally severe neurotoxicity are selected from among confusion, delirium, expressive aphasia, obtundation, myoclonus, lethargy, altered mental status, convulsions, seizure-like activity, seizures (optionally as confirmed by electroencephalogram [EEG]), encephalopathy, dysphasia, tremor, choreoathetosis, symptoms that limit self-care, symptoms of peripheral motor neuropathy, symptoms of peripheral sensory neuropathy and combinations thereof; and/or
the physical signs or symptoms associated with toxicity, optionally severe neurotoxicity, are associated with grade 3, grade 4 or grade 5 neurotoxicity; and/or
the physical signs or symptoms associated with toxicity, optionally severe neurotoxicity, manifest greater than or greater than about or about 5 days after cell therapy, 6 days after cell therapy or 7 days after cell therapy.

81. The method of any of embodiments 1-79, wherein:
the physical signs or symptoms associated with toxicity, optionally severe CRS, are selected from among acute inflammatory response and/or endothelial organ damage, fever, rigors, chills, hypotension, dyspnea, acute respiratory distress syndrome (ARDS), encephalopathy, ALT/AST elevation, renal failure, cardiac disorders, hypoxia, neurologic disturbances, and death, neurological complications such as delirium, seizure-like activity, confusion, word-finding difficulty, aphasia, and/or becoming obtunded, or fatigue, nausea, headache, seizure, tachycardia, myalgias, rash, acute vascular leak syndrome, liver function impairment, and renal failure and combinations thereof; and/or
the physical signs or symptoms associated with toxicity, optionally severe CRS, are associated with grade 3, grade 4 or grade 5 CRS; and/or
the physical signs or symptoms associated with toxicity, optionally severe CRS, manifest greater than or greater than about or about 5 days after cell therapy, 6 days after cell therapy or 7 days after cell therapy.

82. The method of any of embodiments 1-81, wherein:
the method ameliorates toxicity, optionally the neurotoxicity, optionally severe neurotoxicity and/or optionally CRS, optionally severe CRS, and/or reduces the physical signs or symptoms of severe neurotoxicity and/or severe CRS compared to a subject in which severe neurotoxicity and/or severe CRS is treated after the subject exhibits a physical sign or symptom of neurotoxicity and/or compared to a subject in which severe neurotoxicity and/or severe CRS is treated greater than 5 days, greater than 6 days or greater than 7 days after administration of the cell therapy; and/or
the treated subject does not exhibit grade 3 or higher neurotoxicity and/or CRS or a majority of treated subjects do not exhibit grade 3 or higher neurotoxicity and/or CRS.

83. The method of any of embodiments 1-82, wherein:
the recombinant receptor binds to, recognizes or targets an antigen associated with the disease or condition; and/or
the recombinant receptor is a T cell receptor or a functional non-T cell receptor; and/or
the recombinant receptor is a chimeric antigen receptor (CAR).

84. The method of embodiment 83, wherein:
the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

85. The method of any of embodiments 1-84, wherein the dose of cells comprises T cells.

86. The method of embodiment 85, wherein the T cells are CD4+ or CD8+.

87. The method of any of embodiments 1-86, wherein the biological sample is a bodily fluid or a tissue.
88. The method of embodiment 87, wherein the bodily fluid comprises whole blood, serum or plasma.
89. The method of any of embodiments 1-88, wherein detecting the parameter for the biomarker or individually for one or more of each of the panel of biomarkers comprises performing an in vitro assay.
90. The method of embodiment 89, wherein the in vitro assay is an immunoassay, an aptamer-based assay, a histological or cytological assay, or an mRNA expression level assay.
91. The method of any of embodiments 1-90, wherein the parameter or parameters for one or more of each of the one or more biomarkers are detected by a format selected from among an enzyme-linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay.
92. The method of any of embodiments 1-91, wherein the parameter for at least one of the one or more biomarkers is determined using a binding reagent that specifically binds to at least one biomarker.
93. The method of embodiment 92, wherein the binding reagent is an antibody or antigen-binding fragment thereof, an aptamer or a nucleic acid probe.
94. A kit, comprising reagents for detecting a parameter for at least two cytokines selected from among transforming growth factor beta (TGF-beta), interleukin 6 (IL-6), interleukin 10 (IL-10), interleukin 15 (IL-15), interferon gamma (IFN-gamma) and monocyte chemoattractant protein-1 (MCP-1), and, optionally, instructions for detecting the parameter for at least two cytokines, wherein the parameter is optionally a concentration or relative concentration.
95. The kit of embodiment 94, wherein the at least two cytokines are or comprise one or more of IL-6 and IL-15, TGF-beta and IL-6, TGF-beta and IL-15, IL-6 and IL-15 or IL-15 and MCP-1.
96. The kit of embodiment 94 or embodiment 95, wherein the kit comprises reagents for detecting a parameter for only two cytokines.
97. The kit of embodiment 94 or embodiment 95, wherein the kit comprises reagents for detecting a parameter for at least three cytokines.
98. The kit of embodiment 97, wherein the at least three cytokines comprise or are TGF-beta, IL-6 and IL-15 or are IL-6, IL-15 and MCP-1.
99. A kit, comprising reagents for detecting a parameter for at least two biomarkers selected from among interleukin 15 (IL-15), interleukin 6 (IL-6), interleukin 10 (IL-10), interleukin 8 (IL-8), interferon gamma (IFN-gamma), ferritin and soluble TNF receptor type 1 (sTNFR1); and, optionally, instructions for detecting the parameter for at least two biomarkers, wherein the parameter is optionally a concentration or relative concentration.
100. The kit of any of embodiments 94-99, wherein the reagents comprise components for performing an in vitro assay to detect the parameters for or the at least two cytokines.
101. The kit of embodiment 100, wherein the in vitro assay is an immunoassay, an aptamer-based assay, a histological or cytological assay, or an mRNA expression level assay.
102. The kit of embodiment 100 or embodiment 101, wherein the in vitro assay is selected from among an enzyme-linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay.
103. The kit of any of embodiments 94-99, wherein the reagents comprise a binding reagent that specifically binds the cytokine.
104. The kit of embodiment 103, wherein the binding reagent is an antibody or antigen-binding fragment thereof, an aptamer or a nucleic acid probe.
105. A combination, comprising:
reagents for detecting a parameter, optionally a level or concentration, of at least two cytokines selected from among transforming growth factor beta (TGF-beta), interleukin 6 (IL-6), interleukin 10 (IL-10), interleukin 15 (IL-15), interferon gamma (IFN-gamma) and monocyte chemoattractant protein-1 (MCP-1); and
an agent that treats, prevents, delays, or attenuates the development of severe neurotoxicity.
106. The combination of embodiment 105, wherein the at least two cytokines are or comprise one, two or three of or are IL-6 and IL-15, TGF-beta and IL-6, TGF-beta and IL-15, IL-6 and IL-15 or IL-15 and MCP-1.
107. The combination of embodiment 105 or embodiment 106, wherein the kit comprises reagents for detecting only two cytokines.
108. The combination of embodiment 105 or embodiment 106, wherein the kit comprises reagents for detecting at least three cytokines.
109. The combination of embodiment 108, wherein the three cytokines are or comprise one two or three of or are TGF-beta, IL-6 and IL-15 or comprise one two or three of or are IL-6, IL-15 and MCP-1.
110. A combination, comprising:
reagents for detecting a parameter, optionally a level or concentration, of at least two biomarkers selected from among interleukin 15 (IL-15), interleukin 6 (IL-6), interleukin 10 (IL-10), interleukin 8 (IL-8), interferon gamma (IFN-gamma), ferritin and soluble TNF receptor type 1 (sTNFR1); and
an agent that treats, prevents, delays, or attenuates the development of severe CRS.
111. The combination of any of embodiments 105-110, wherein the reagents comprise components for performing an in vitro assay to detect the at least two cytokines.
112. The combination of embodiment 96, wherein the in vitro assay is an immunoassay, an aptamer-based assay, a histological or cytological assay, or an mRNA expression level assay.
113. The combination of embodiment 111 or embodiment 112, wherein the in vitro assay is selected from among an enzyme-linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay.
114. The combination of any of embodiments 105-113, wherein reagent comprises a binding reagent that specifically binds the cytokine.

115. The combination of embodiment 114, wherein the binding reagent is an antibody or antigen-binding fragment thereof, an aptamer or a nucleic acid probe.
116. The combination of any of embodiments 105-115, wherein the agent that treats, prevents, delays, or attenuates the development of or risk for developing severe neurotoxicity and/or severe CRS is a steroid, is an antagonist or inhibitor of a cytokine receptor selected from among IL-6 receptor, CD122 receptor (IL-2R/IL-15Rbeta) and CCR2, or is an inhibitor of a cytokine selected from among IL-6, IL-15 and MCP-1.
117. The combination of embodiment 116, wherein the antagonist or inhibitor is selected from among an antibody or antigen-binding fragment, a small molecule, a protein or peptide and a nucleic acid.
118. The combination of embodiment 116 or embodiment 117, wherein the agent is selected from among tocilizumab, siltuximab, sarilumab, olokizumab (CDP6038), elsilimomab, ALD518/BMS-945429, sirukumab (CNTO 136), CPSI-2634, ARGX-109, FE301, FM101, Hu-Mik-β-1, tofacitinib, ruxolitinib, CCX140-B, R0523444, BMS CCR2 22, INCB 3284 dimesylate, JNJ27141491 and RS 504393.
119. The combination of any of embodiments 116-118, wherein the agent is tocilizumab.
120 The combination of embodiment 119 that is formulated for single dosage administration of an amount from or from about 75 mg to 750 mg, 150 mg to 600 mg, 200 mg to 400 mg or 300 mg to 700 mg or in an amount that is at least or at least about 75 mg, 100 mg, 200 mg, 300 mg, 400 mg, 500 mg, 600 mg or 700 mg.
121. The combination of embodiment 116, wherein the agent is a steroid that is a corticosteroid.
122. The combination of embodiment 121, wherein the corticosteroid is a glucocorticoid.
123. The combination of embodiment 121 or embodiment 122, wherein the corticosteroid is selected from among cortisones, dexamethasones, hydrocortisones, methylprednisolones, prednisolones and prednisones.
124. The combination of any of embodiments 116 and 121-123 that is formulated for single dosage administration or multiple dosage administration.
125. The combination of any of embodiments 116 and 121-124 that is formulated for administration of an equivalent dosage amount of from or from about 1.0 mg to 20 mg dexamethasone per day, 1 mg to 10 mg dexamethasone per day, or 2.0 mg to 6.0 mg dexamethasone per day, each inclusive.
126. The combination of any of embodiments 116 and 121-125, wherein the steroid is formulated for intravenous or oral administration.

VIII. DEFINITIONS

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided agents, cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, agent, cells, or composition, in the context of administration, refers to an amount effective, at dosages/amounts and for periods of time necessary, to achieve a desired result, such as a therapeutic or prophylactic result.

A "therapeutically effective amount" of an composition, e.g., a pharmaceutical formulation comprising agents or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the agents or populations of cells administered. In some embodiments, the provided methods involve administering the agents, cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

IX. EXAMPLES

The following examples are included for illustrative purposes only and are not intended to limit the scope of the invention.

Example 1: Assessment of Cytokine Levels Predictive of Neurotoxicity in Subjects with NHL Administered CAR-Expressing Autologous T Cells Subjects (n=32) with Non-Hodgkin Lymphoma (NHL) (including DLBCL/de novo (N=7); Burkitt's (N=1); TCRBCL (N=1); PMBCL (N=2); DLBCL/transformed (N=11); Low grade NHL (N=6); MCL (N=4)) were administered autologous T cells expressing an anti-CD19 chimeric antigen receptor (CAR).

The construct encoding the CAR included a nucleotide encoding the CAR, which had an anti-CD19 scFv derived from a murine antibody, a hinge domain, a CD28 transmembrane domain, a 4-1BB intracellular signaling domain, and a CD3-zeta intracellular signaling domain; the construct further included a nucleic acid encoding a truncated EGFR (EGFRt), separated from the CAR-encoding nucleic acid by a T2A ribosome skip sequence. To generate the autologous CAR-expressing T cells, T cells were isolated by immunoaffinity-based enrichment from leukapheresis samples from individual subjects, activated and transduced with a viral vector encoding the anti-CD19 CAR. The cells were expanded, frozen, and thawed at bedside prior to administration.

CAR-expressing T cells were administered to subjects by single intravenous (IV) continuous infusion, over approximately 15-30 minutes, at a dose of either $2 \times 10^5$ cells/kg (N=5), $2 \times 10^6$ cells/kg (N=18) or $2 \times 10^7$ cells/kg (N=9). Prior to administration of the cells, a preconditioning chemotherapeutic treatment of cyclophosphamide (about 2-4 g/m$^2$), cyclophosphamide (2-4 g/m$^2$) and etoposide (100-200 mg/m$^2$, administered three times daily) or cyclophosphamide (30-60 mg/kg) and fludarabine (25 mg/m$^2$, administered three to five times daily) was administered to subjects prior to infusion.

Following treatment, subjects were assessed and monitored for neurotoxicity (neurological complications including symptoms of confusion, aphasia, seizures, convulsions, lethargy, and/or altered mental status), graded based on severity using a Grade 1-5 scale (see, e.g., Guido Cavaletti & Paola Marmiroli *Nature Reviews Neurology* 6, 657-666 (December 2010). Grade 3 (severe symptoms), 4 (life-threatening symptoms) or 5 (death) indicated severe neurotoxicity. Cytokine release syndrome (CRS) also was determined and monitored, graded based on severity.

In the 12/32 subjects who had received cyclophosphamide (Cy) or Cy/etoposide (Cy/E) lymphodepletion, there was observed an overall response rate (ORR) of 50% and a complete response (CR) rate of 8% CR. CAR-T cell persistence in these 12 subjects was limited, and the subjects developed immunogenicity. The 20 subjects having received fludarabine (Flu) and Cy lymphodepletion, who were observed to have increased CAR-T cell expansion and persistence, and decreased frequency of anti-CAR immune responses. These 20 subjects were observed to have an ORR of 72% and a complete response rate of 50%.

Some subjects developed toxicities expected with cytotoxic chemotherapy. CRS was deemed mild or moderate in 16/32 subjects and severe in 4/32 subjects. Twenty of 32 patients developed cytokine release syndrome (CRS), characterized by fever and/or hypotension, and the clinical symptoms were sufficiently severe in 4 of these patients to require management in the intensive care unit (ICU), and treatment with tocilizumab (n=3) and/or corticosteroids (n=4).

Severe cytokine release syndrome (sCRS) and grade≥3 neurotoxicity were observed in 13% and 25% of patients in the two groups having received pre-conditioning without fludarabine and those receiving cy/flu, respectively.

As shown in Table 4, 9 of the 32 subjects exhibited severe neurotoxicity, and 23 of the subjects exhibited grade 0-2 neurotoxicity. For the subjects that exhibited severe neurotoxicity, the following physical symptoms of the neurotoxicity were identified: encephalopathy (n=5), encephalopathy and pontine hemorrhage (n=1), encephalopathy and dysphasia (n=1), encephalopathy and tremor (n=1), and choreoathetosis alone (n=1).

TABLE 4

| | Incidence of Severe CRS or NT | | | | |
|---|---|---|---|---|---|
| Lymphodepletion | Non-Cy/Flu | Cy/Flu | Cy/Flu | | |
| Dose Level | All Doses | All Doses | $2 \times 10^5$/kg | $2 \times 10^6$/kg | $2 \times 10^7$/kg |
| Toxicity | | | | | |
| Severe CRS (ICU) | 0/12 (0%) | 4/20 (20%) | 0/3 (0%) | 1/11 (9%) | 3/6 (50%) |
| Neurotoxicity (Grade 3-5) | 2/12 (17%) | 7/20 (35%) | 1/3 (33%) | 2/11 (18%) | 4/6 (67%) |

The concentration (pg/mL) of the cytokines IL-15, TGF-β, IL-6, IL-10, IL-18, IL-8 and IFN-γ were measured (detected) at various timepoints in the serum of the subjects by Luminex® assay. Peak concentrations of these cytokines were measured and compared using statistical analysis to the development of toxicities.

Comparisons of continuous variables between two categories were made using Wilcoxon rank-sum test. Relationships between continuous variables were analyzed using a Spearman correlation. Univariate (with Firth correction) and stepwise multivariate logistic regression were performed to assess predictors for the occurrence of severe neurotoxicity, where Log 10 values were used to transform data as appropriate, with 0.01 substituting for values of 0. All p-values reported were two-sided, and no adjustments were made for multiple comparisons.

Figure 5A:
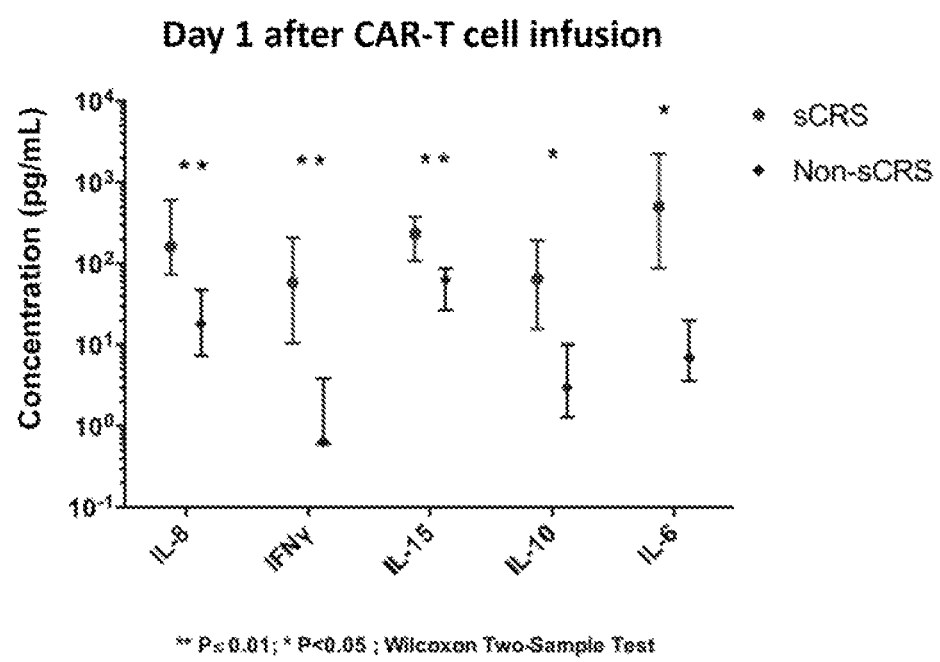
FIG. 5A shows values of various biomarkers as measured at day 1 following administration of cell therapy.
Figure 5B:
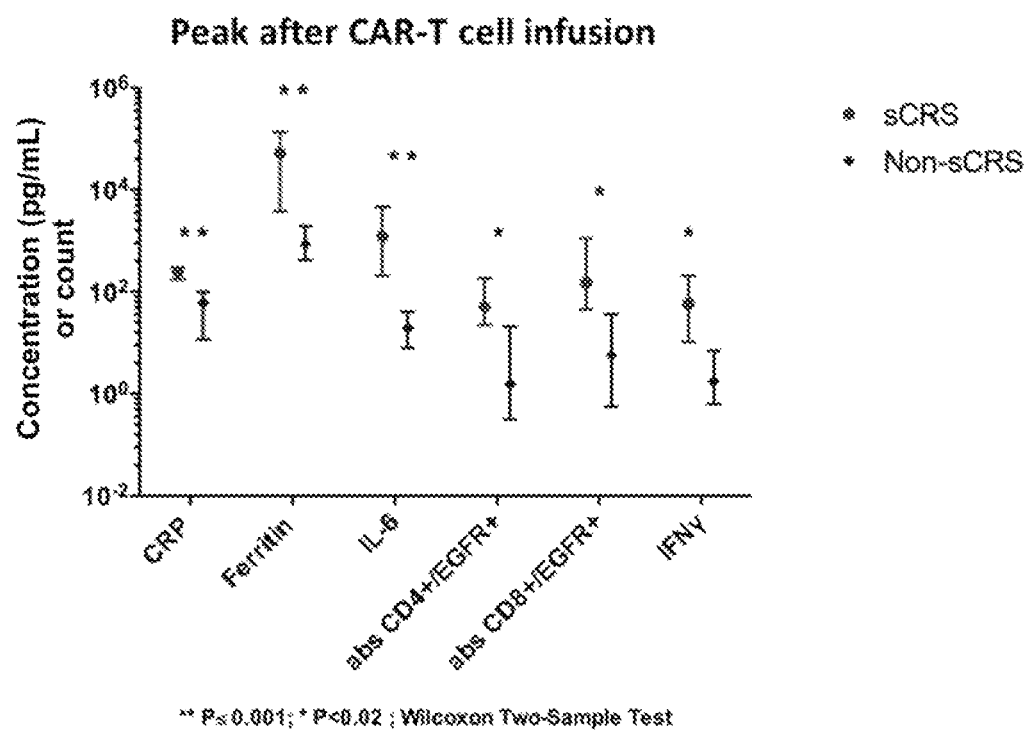
FIG. 5B shows peak values of various biomarkers following administration of cell therapy. Subjects were separated into two groups based on severe CRS (sCRS) and non-sCRS, respectively.

As shown in FIGS. 5A-5B, CART cell exposure, as well as peak serum concentrations of IL-6, IFN-γ, ferritin and C-reactive protein (CRP) after CAR-T cell infusion correlated with the occurrence of sCRS. Peak serum concentrations of IL-6, ferritin and C-reactive protein (CRP) correlated with the severity of CRS (see FIG. 5B).

Figure 1B:
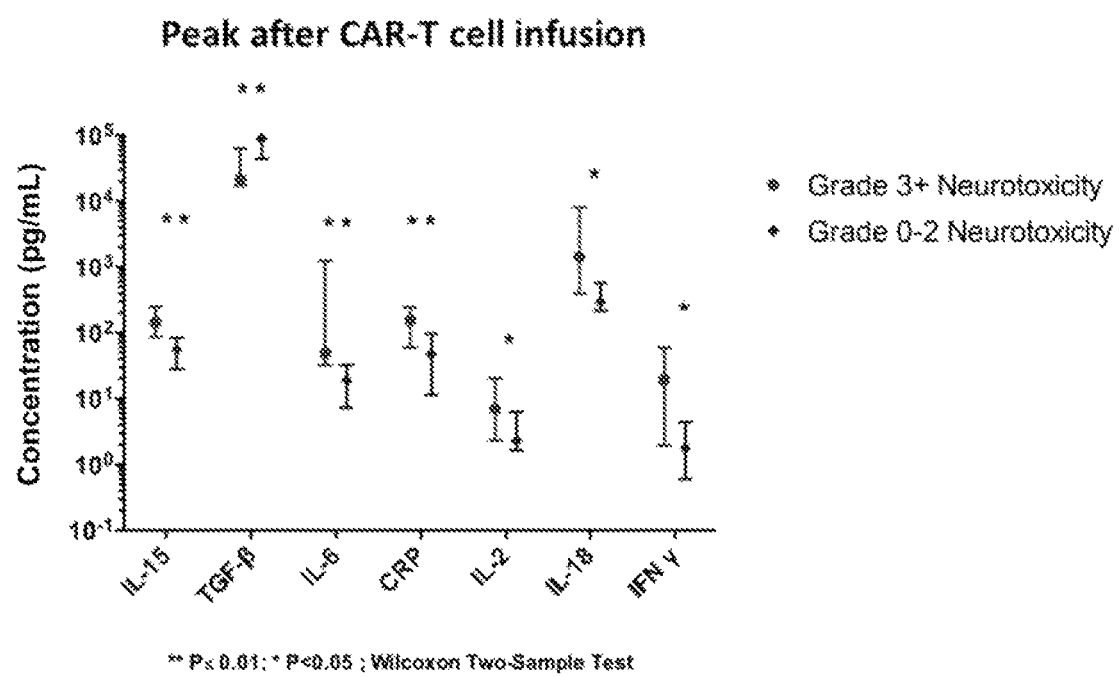
FIG. 1B shows peak values of various biomarkers following administration of cell therapy. Subjects were separated into two groups based on neurotoxicity grades of 0-2 and 3+, respectively.
Figure 2A:
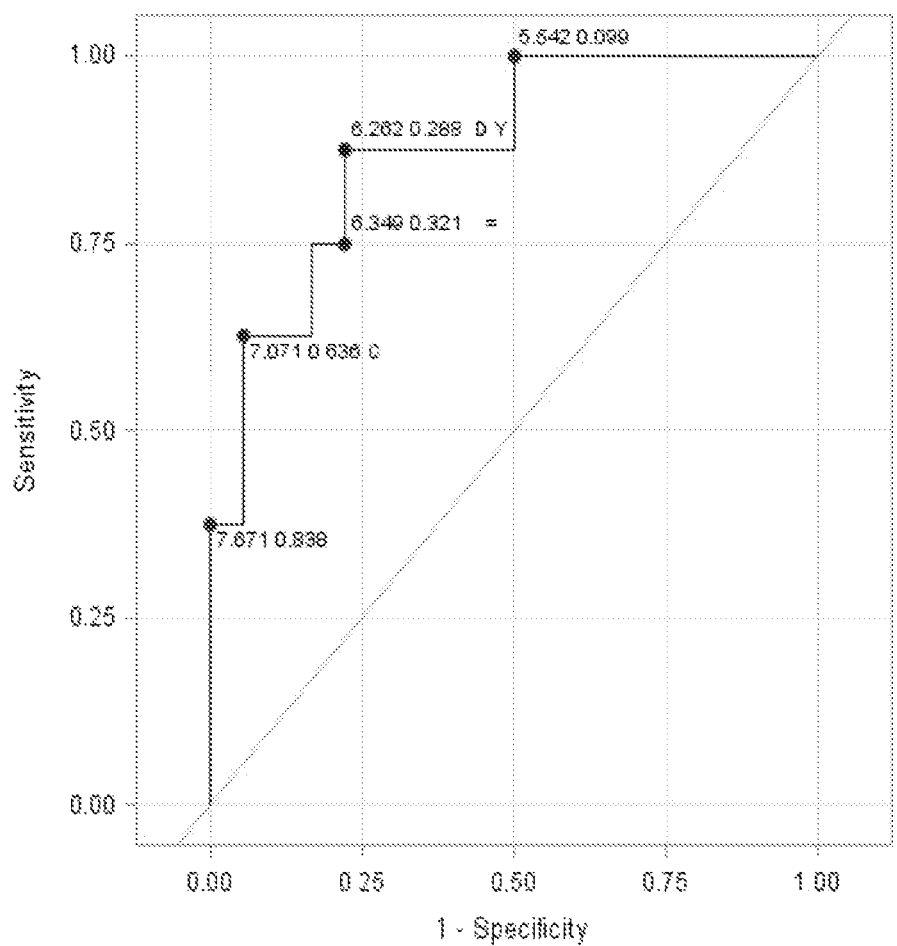
FIGS. 2A-2E show receiver operating characteristic (ROC) curves of the sensitivity and specificity of various cytokine markers as predictors of neurotoxicity in subjects with NHL treated with CAR T cells.
Figure 2B:
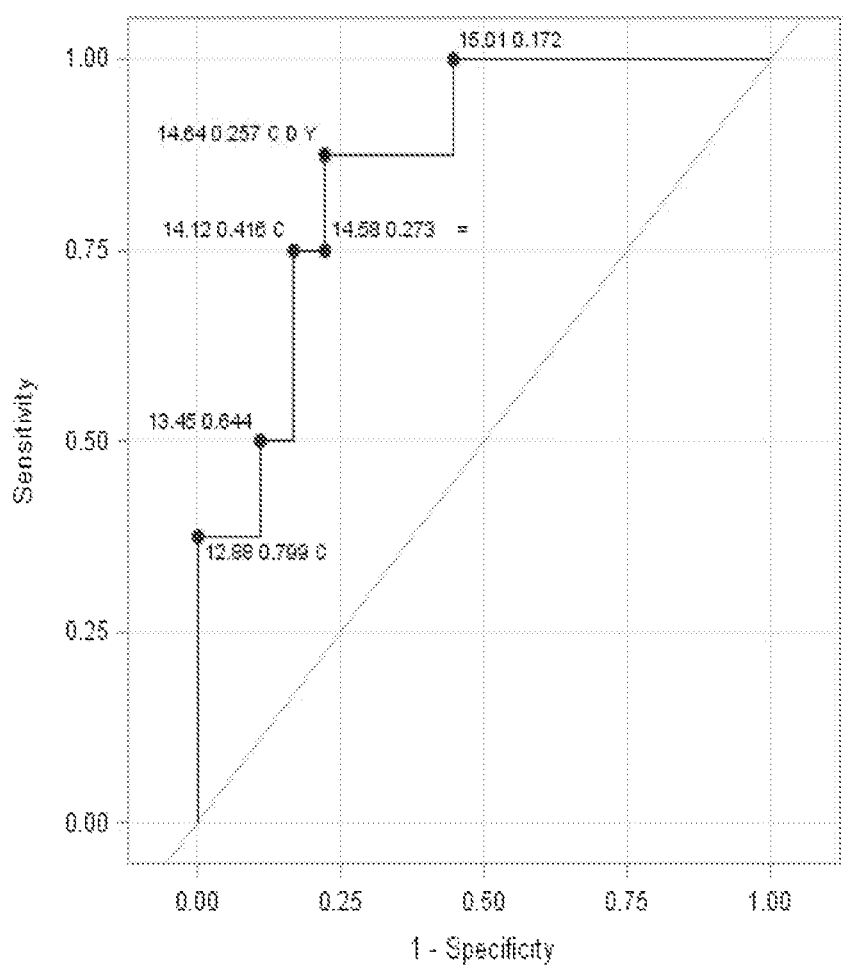
Figure 2C:
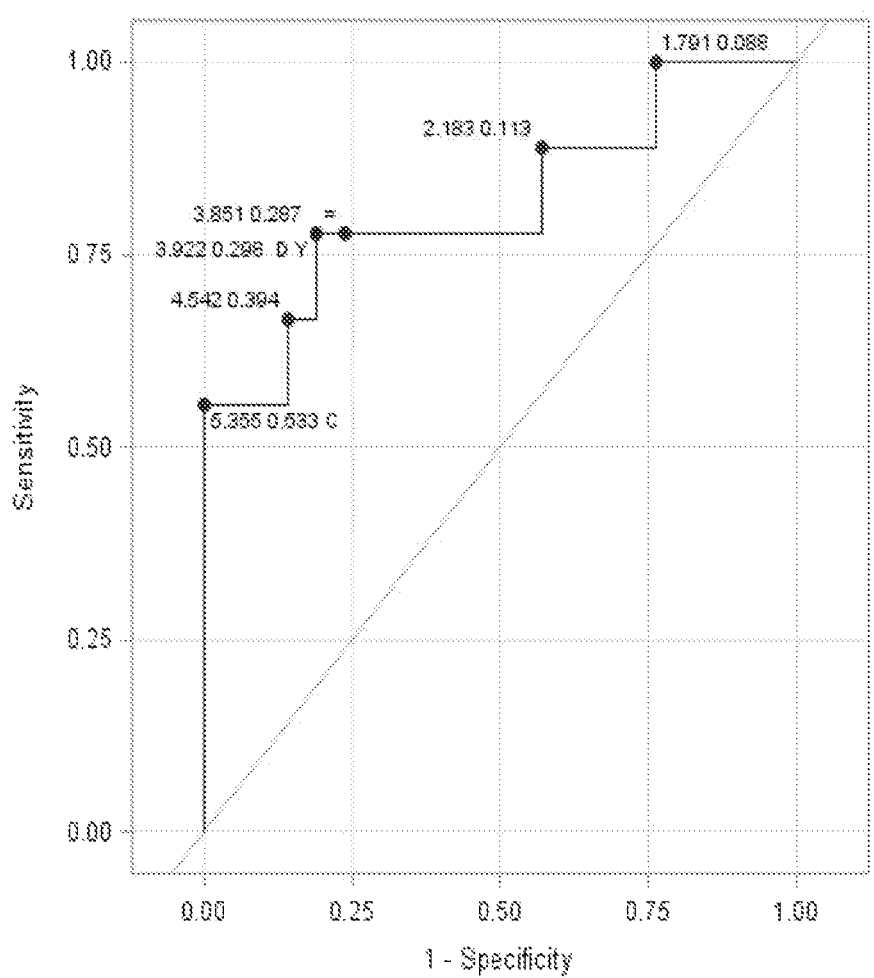
Figure 2D:
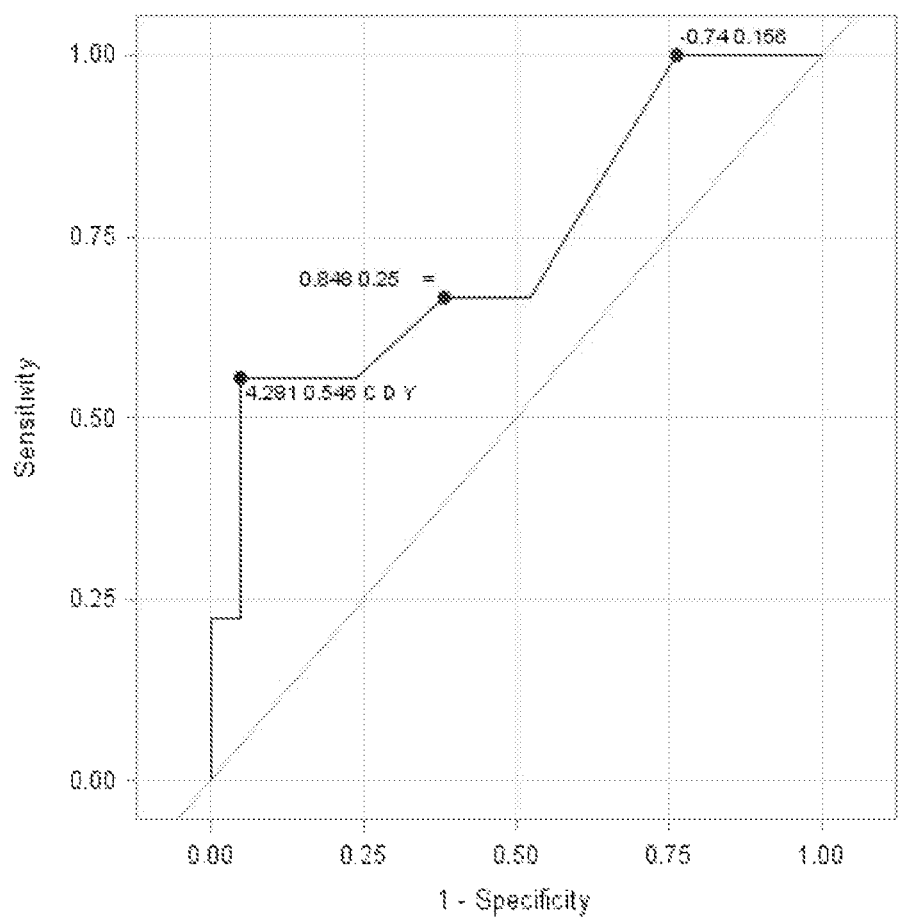
Figure 2E:
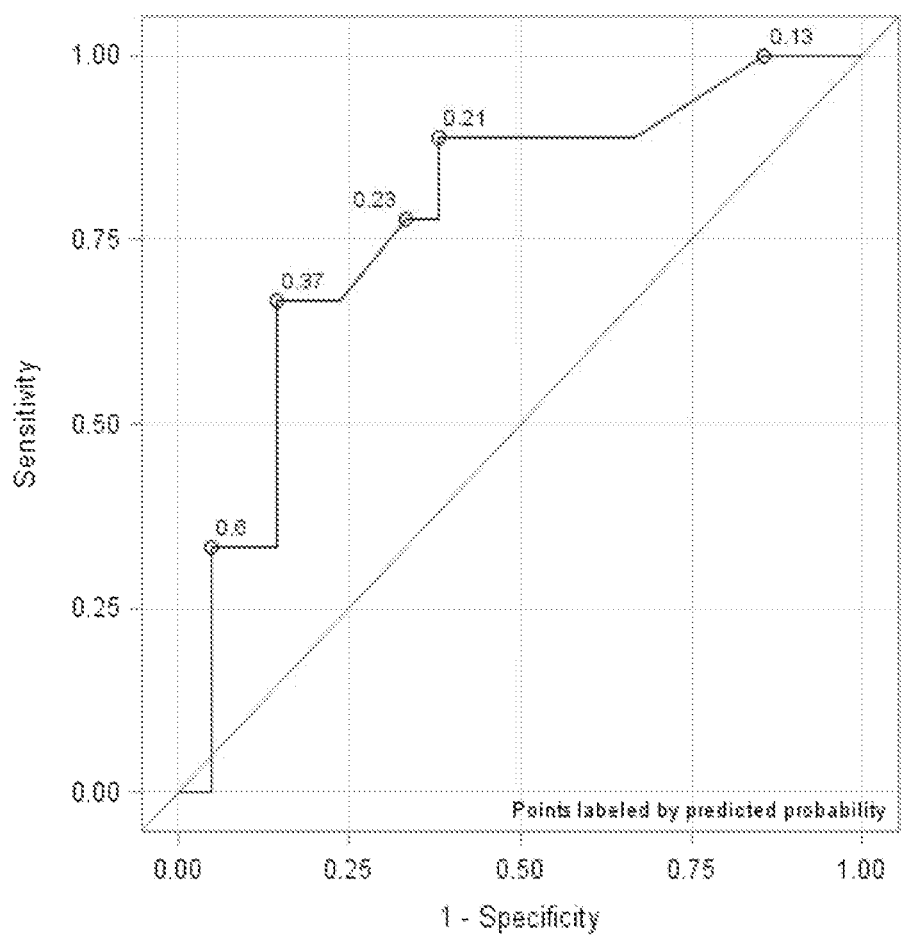

As shown in FIG. 1B, subjects who developed grade≥3 neurotoxicity had higher CART cell exposure and peak levels, and peak CD8+/EGFRt+ cells in blood, higher peak serum IL-6, IFN-γ, IL-15, IL-2, IL-18, ferritin and CRP levels, and lower serum TGF-beta compared to those without neurotoxicity (see FIG. 1B). In multivariate analyses, peak numbers of CD4+/EGFRt+ and CD8+/EGFRt+ cells, serum ferritin, and IL-6 had the strongest associations with severe neurotoxicity.

Serum biomarker concentrations were detected on the first day after CAR-T cell infusion.

Multivariate analysis (univariate pairwise comparison using a Wilcoxon two-sample test). was performed to determine which cytokine markers were able to predict sCRS or neurotoxicity, e.g., whether differences in biomarkers among the groups of subjects that ultimately exhibited severe CRS or neurotoxicity versus the respective groups of subjects that did not ultimately exhibit severe CRS or neurotoxicity.

Higher IL-6, IFN γ, IL-15, IL-8 and IL-10 concentrations were observed on day 1 after CAR-T cell infusion in subjects who subsequently developed severe CRS compared to those who did not (see FIG. 5A).

Higher IL-6, IFN-γ and IL-15 and lower TGF-13 levels were found in patients who subsequently developed severe neurotoxicity compared to those who did not develop severe neurotoxicity (FIG. 1A). As shown in FIG. 1A, the results showed that the concentration of cytokine markers IL-15, TGF-β and IL-6 in serum exhibited the greatest statistical difference between the groups. The concentration of the cytokine markers IL-10, IL-8 and IFN-γ also were statistically different between the two groups of subjects. In this study, statistically significant differences in cytokine levels were not observed in the two groups at 1 hour or 4 hours post-CAR T cell administration.

The strongest associations in univariate analyses were identified in patients with higher IL-6 and IL-15. To further assess the accuracy of measuring a cytokine as a marker predictive of neurotoxicity, receiver operating characteristic (ROC) analysis was performed for each of the respective cytokine biomarkers in blood at day 1. FIGS. 2A-2E show the ROC curves for IL-15, IL-6, TGF-β, IFN-γ and IL-10, respectively, with plot sensitivity on the vertical axis and 1—specificity on the horizontal axis for all possible thresholds in the study data set.

For each cytokine, the ROC curves were constructed using the empirical method and the optimal threshold of sensitivity and specificity is established based on the Youden index. Table 5 sets forth the Youden Index reference value and the calculated area under the curve (AUC), sensitivity, and 1-specificity associated with each cut-off reference value. The results showed that a reference value or cut-off for IL-15 of greater than 76.7 pg/mL (greater than 6.262 on Log 2 scale), for TGF-β of less than 25532 pg/mL (less than 14.64 on Log 2 scale) or for IL-6 of greater than 12.2 pg/mL (greater than 3.922 on Log 2 scale) each individually resulted in a good accuracy of prediction with an AUC of greater than 0.80. Analysis of receiver operating characteristic (ROC) curves identified serum concentrations of IL-6>15.2 pg/mL, IL-15>76.7 pg/mL and TGF-β<25532 pg/mL on day 1 as discriminators (threshold reference values) in this study for the risk of developing severe neurotoxicity.

The individual positive predictive value (PPV) and negative predictive value (NPV) of an assay detecting each of the cytokines IL-15, TGF-β and IL-6 and using the respective discriminator values also are set forth in Table 5.

TABLE 5

Summary of Accuracy and Performance of Cytokine Biomarkers for Predicting Severe Neurotoxicity in NHL Patients

| | IL-15 | TGF-β | IL-6 | IFN-γ | IL-10 |
|---|---|---|---|---|---|
| Reference value (Log2) | 6.262 | 14.64 | 3.922 | 4.281 | 3.529 |
| Reference value (pg/mL) | 76.7 | 25532 | 12.2 | 19.4 | 11.5 |
| AUC | 0.88 | 0.86 | 0.81 | 0.74 | 0.79 |
| Sensitivity | 0.88 | 0.88 | 0.78 | 0.56 | 0.68 |
| 1-Specificity | 0.22 | 0.22 | 0.19 | 0.04 | 0.14 |
| PPV | 0.64 | 0.64 | 0.64 | — | — |
| NPV | 0.93 | 0.93 | 0.89 | — | — |

Based on the ROC analysis, ranges of discriminators or reference concentration values of the cytokine in blood at day 1 for the individual cytokine biomarkers IL-15, TGF-β and IL-6 were determined (Table 6). In some embodiments, a value within the indicated range predicts severe neurotoxicity, e.g., with a sensitivity and/or specificity of greater than 0.50 (see Table 6).

TABLE 6

Exemplary Range of Reference Cut-off Values (for Concentration), NHL Subjects

| | IL-15 | TGF-β | IL-6 |
|---|---|---|---|
| Reference value (Log2) | 6.122-7.071 | 5.542-15.007 | 2.568-5.354 |
| Reference value (pg/mL) | 69.6-134.5 | 46-32921 | 6.00-40.9 |
| Sensitivity | 0.63-0.88 | 0.63-1.00 | 0.56-0.78 |
| 1-Specificity | 0.06-0.44 | 0.17-0.44 | 0.00-0.48 |
| PPV | 0.83-0.47 | 0.67-0.47 | 1.00-0.42 |
| NPV | 0.83-0.93 | 0.83-1.00 | 0.83-0.88 |

To assess whether a combined assessment of two or more of the above cytokine markers could increase accuracy, specificity and/or sensitivity of the prediction, ROC curves were generated, based on modeling of simultaneous assessment of a combination of the respective cytokine biomarkers IL-15, TGF-β, and/or IL-6 in blood at day 1 as predictors of severe neurotoxicity.

Figure 3A:
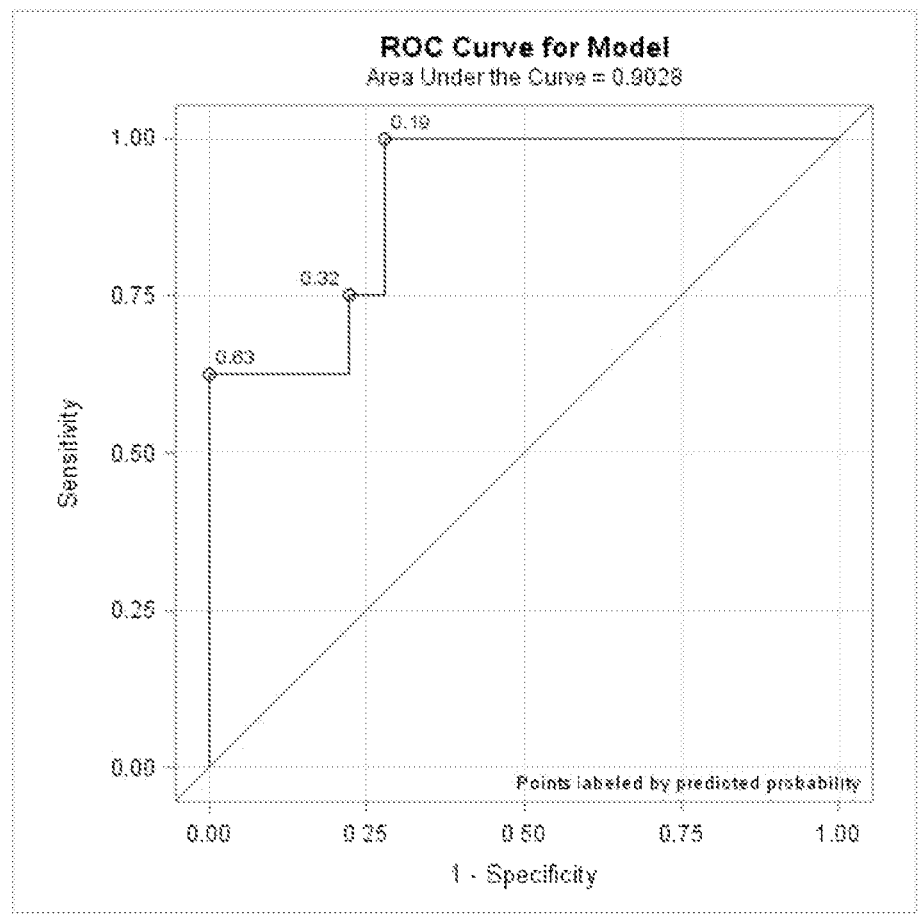
FIGS. 3A-3C show receiver operating characteristic (ROC) curves of the sensitivity and specificity of various combinations of cytokine markers as predictors of neurotoxicity in subjects with NHL treated with CAR T cells.
Figure 3B:
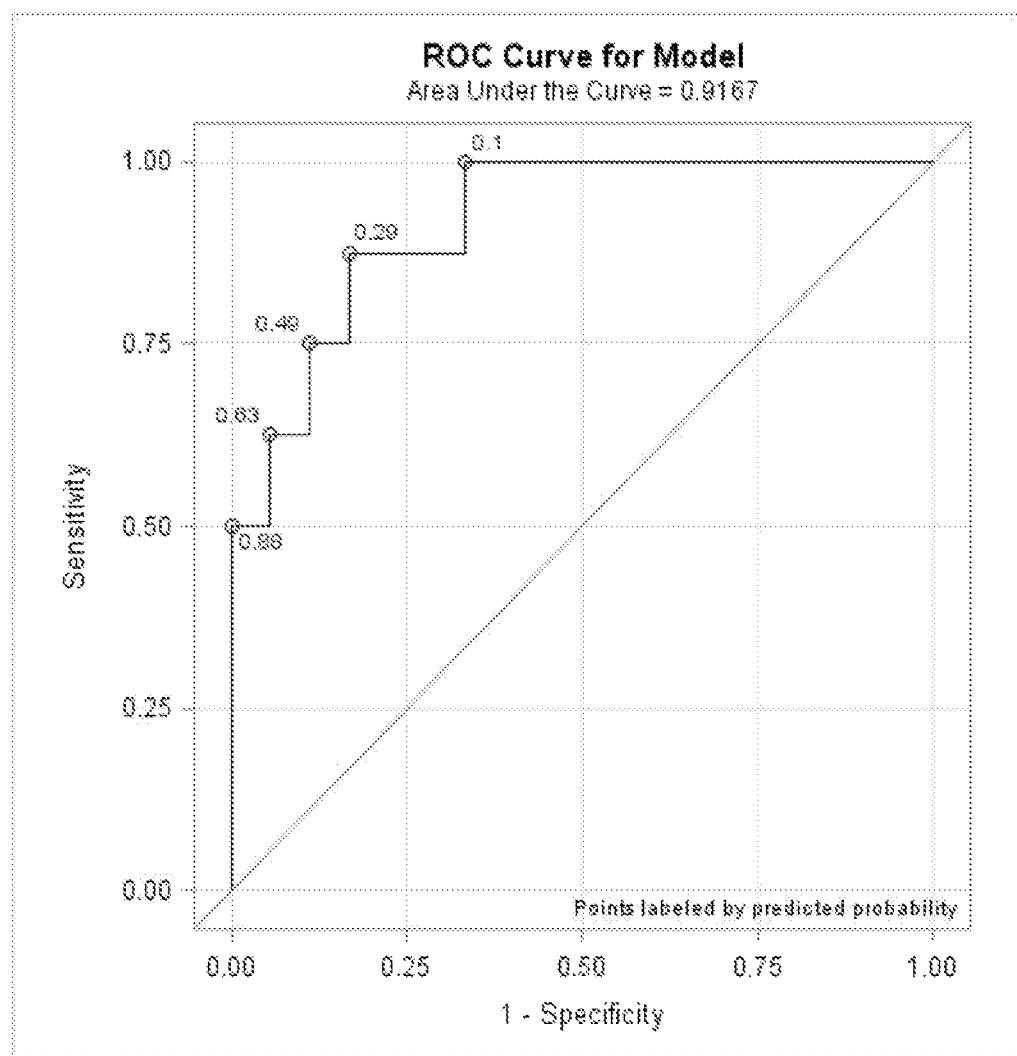
Figure 3C:
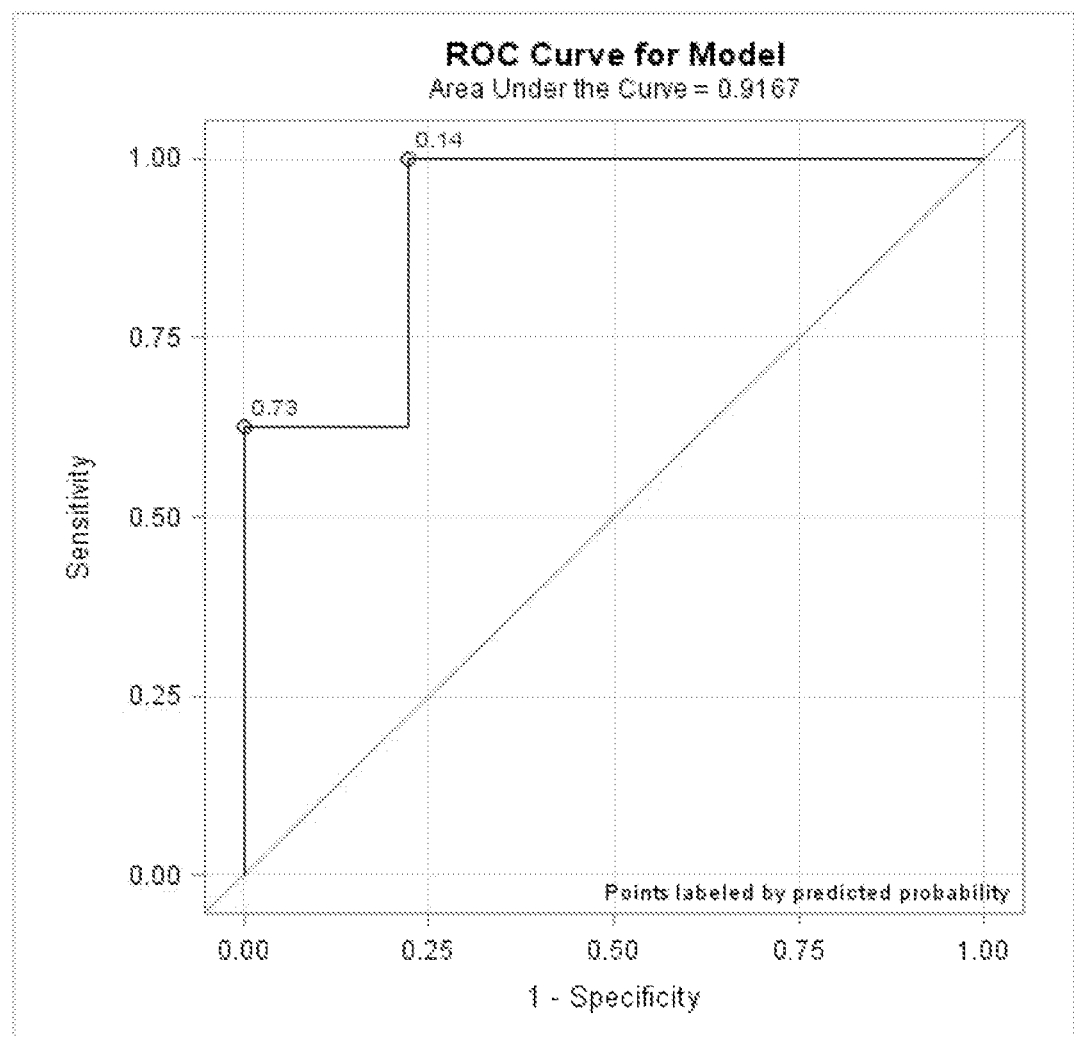

A multivariate regression analysis was performed by including two or three cytokines together to estimate the specificity and sensitivity of a combined test (indicated in grey highlighting in Table 7A), which was then used to build the ROC curve. FIG. 3A shows a ROC curve for the combination of IL-15 and TGF-β as a predictor of neurotoxicity. FIG. 3B shows a ROC curve for the combination of IL-6 and TGF-β as a predictor of neurotoxicity. FIG. 3C shows a ROC curve for the combination of IL-15, IL-6, and TGF-β as a predictor of neurotoxicity. The net specificity, net sensitivity, PPV and NPV based on simultaneous testing of IL-15 and TGF-β, IL-15 and IL-6, IL-6 and TGF-β or IL-15, IL-6, and TGF-β also were determined. The results of the analysis are summarized in Table 7A. The results showed that the accuracy of the combined test is predicted to result in an excellent test with an AUC of greater than 0.90 for each combination of cytokine.

TABLE 7

Summary of Accuracy and Performance of Simultaneous Assessment of Cytokine Biomarkers for Predicting Severe Neurotoxicity in NHL Patients

|  | IL-15 & TGF-β | IL-15 & IL-6 | TGF-β & IL-6 | IL-15, TGF-β & IL-6 |
|---|---|---|---|---|
| AUC | 0.9 | 0.88 | 0.92 | 0.92 |
| Sensitivity | 0.88 | 0.75 | 0.88 | 0.88 |
| 1-Specificity | 0.28 | 0.17 | 0.17 | 0.22 |
| PPV | 0.58 | 0.67 | 0.70 | 0.64 |
| NPV | 0.93 | 0.88 | 0.94 | 0.93 |
| Net sensitivity | 0.98 | 0.97 | 0.97 | 1.00 |
| Net specificity | 0.61 | 0.63 | 0.63 | 0.49 |

From the above analysis, an exemplary method for prediction of severe neurotoxicity in NHL patients was proposed as follows:

First, subjects are assessed or measured for the concentration, level, or amount of each of IL-15, TGF-β and IL-6 in serum at or about day 1 after administration of adoptive cell therapy, and if the value of all three cytokines in the blood individually meet the corresponding reference value cutoffs in Table 5 (or, optionally, are all within the range of corresponding reference values in Table 6) the subject is predicted to have severe neurotoxicity. For example, with reference to values in Table 5, if the measured value of TGF-beta is less than the TGF-beta reference value of 25532 pg/mL; the measured value of IL-6 is greater than the IL-6 reference value of 15.2 pg/mL; and the measured value of IL-15 is greater than the IL-15 reference value of 76.7 pg/mL, the subject is predicted to have severe neurotoxicity. In contrast, if the concentrations, amounts, or levels for each of all three cytokines in the serum, individually, does not meet the corresponding reference values in Table 5 (or, optionally, is not within the range of reference values in Table 6) the subject is predicted not to have severe neurotoxicity;

Second, if neither set of the criteria above is met (i.e., if the subject is not deemed positive or negative by the assessment in step 1), then if the value of TGF-beta and IL-15 or the value of IL-5 and IL-6 each individually meet the reference value in Table 5 (or, optionally, within the range of reference values in Table 6) the subject is predicted to have severe neurotoxicity; and Finally, if neither of the criteria above are met, then the subject is predicted not to have severe neurotoxicity.

Using the reference or cut-off values in Table 5, the above exemplary method was applied to retroactively predict neurotoxicity in 26 of the NHL patients treated as described above from cytokines measured in blood obtained at day 1 after administration of the CAR-T cells. The results showed that 15 subjects met the first classification with a correct prediction of 14/15 (93%), whereby 4 out of 4 subjects predicted at risk for severe neurotoxicity actually developed severe neurotoxicity, 10 out of 10 cases predicted not to be at risk for neurotoxicity did not develop severe neurotoxicity and 1 subject was falsely predicted to develop severe neurotoxicity, but did not actually develop severe neurotoxicity. For the remaining 11 subjects, 6 of the subjects met the second classification with a correction prediction of 5/6 (83%), whereby 5 out of 5 subjects predicted at risk for severe neurotoxicity actually developed severe neurotoxicity and 1 subject was falsely predicted to develop severe neurotoxicity, but did not actually develop severe neurotoxicity. For the remaining 5 subjects, all were defaulted as not predicted to develop severe neurotoxicity, which resulted in a correct prediction of 4/5 subjects (80%), since one subject actually did develop severe neurotoxicity. Overall, it was possible to correctly identify 23/26 (88%) events with a sensitivity of 0.86 and a specificity of 0.89.

The results showed that cytokine biomarkers in blood could accurately predict severe neurotoxicity in NHL patients treated with CAR-T cells as early as day 1 after CAR-T cell administration, which is generally before normal physical signs and symptoms of neurotoxicity develop. The ability to predict severe neurotoxicity early (e.g., soon after treatment is initiated) permits means that subjects may be treated with an intervention, e.g. an agent that treats neurotoxicity, to prevent or reduce the severity of neurotoxicity. Further, the subjects can optionally be tested again at one or more time points following the intervention to reevaluate the prediction based on the additional measured values or to determine whether the intervention has reduced or ameliorated the risk or development of neurotoxicity.

Example 2: Cytokine Levels Predictive of Neurotoxicity in Subjects with ALL Administered CAR-Expressing Autologous T Cells Subjects (n=21) with $CD19^+$ B cell acute lymphoblastic leukemia (ALL) were administered autologous T cells expressing an anti-CD19 chimeric antigen receptor (CAR). The CAR and autologous CAR-expressing cells were generated substantially as described in Example 1.

CAR-expressing T cells were administered to subjects by single intravenous (IV) continuous infusion, over approximately 15-30 minutes, at a dose of either $2 \times 10^5$ cells/kg, $2 \times 10^6$ cells/kg or $2 \times 10^7$ cells/kg. Prior to administration of the cells, a preconditioning chemotherapeutic treatment of cyclophosphamide (about 2 $g/m^2$), cyclophosphamide (2 $g/m^2$) and etoposide (100 $mg/m^2$, administered three times daily) or cyclophosphamide (60 mg/kg) and fludarabine (25 $mg/m^2$, administered three to five times daily) was administered to subjects prior to infusion.

Following treatment, subjects were assessed and monitored for neurotoxicity as described in Example 1. Cytokine release syndrome (CRS) also was determined and monitored, graded based on severity. Twenty of 32 patients developed cytokine release syndrome (CRS), characterized by fever and/or hypotension, and the clinical symptoms were sufficiently severe in 4 of these patients to require management in the intensive care unit (ICU), and treatment with tocilizumab (n=3) and/or corticosteroids (n=4). Severe neurotoxicity (NCI CTCAE v4.03 grade≥3) was observed in 9 of 32 patients, all of whom had CRS. Neurotoxicity presented as reversible encephalopathy alone (n=5), or with tremor (n=1) or speech disturbance (n=1). Choreoathetosis and fatal intracranial hemorrhage were observed in one patient each. Of 6 patients treated with CAR-T cells at $2 \times 10^7$/kg following Cy/Flu lymphodepletion, severe CRS (sCRS) developed in 3 (50%) and grade≥3 neurotoxicity developed in 4 (67%), and infusion of CAR-T cells at an initial dose of $2 \times 10^7$/kg after Cy/Flu lymphodepletion was not used going forward.

To assess if the presence of one or more serum biomarkers correlated to the presence of severe neurotoxicity or CRS in ALL patients, the concentration (pg/mL) of selected cytokines from among IL-15, IL-6, TGF-β, and MCP-1 were measured by ELISA in the blood of the subjects one day after administration of the cells.

Figure 6A:
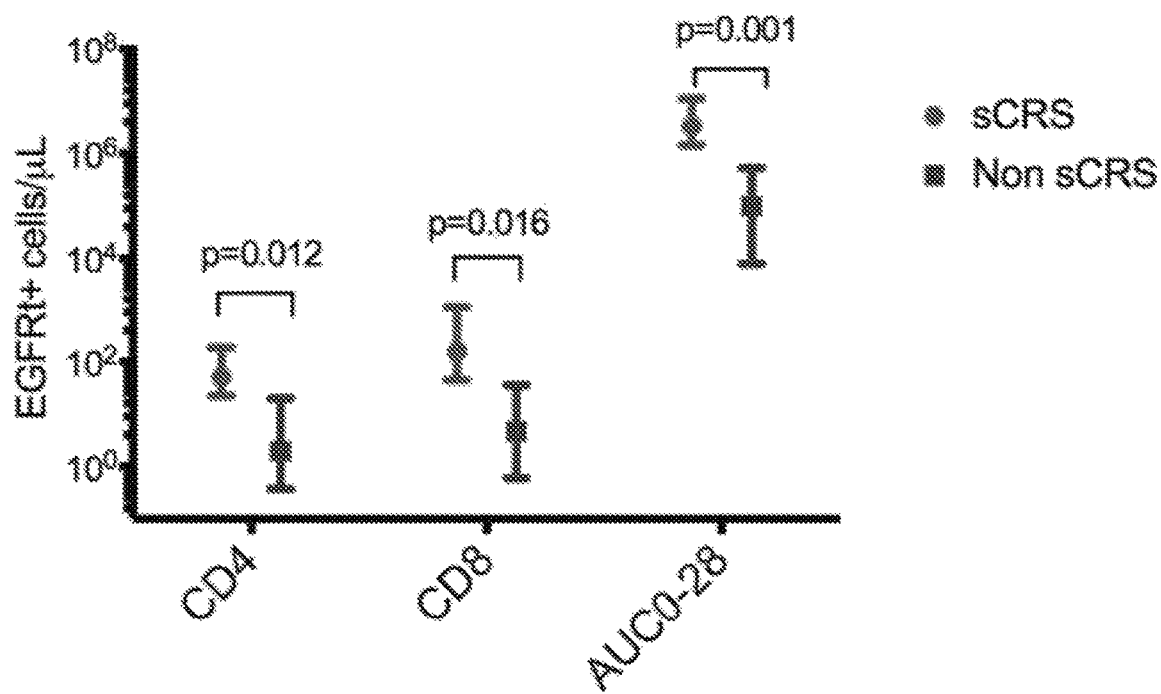
FIG. 6A shows the peak number of CD4+/EGFRt+ and CD8+/EGFRt+ CAR-T cells in blood following cell therapy.
Figure 6B:
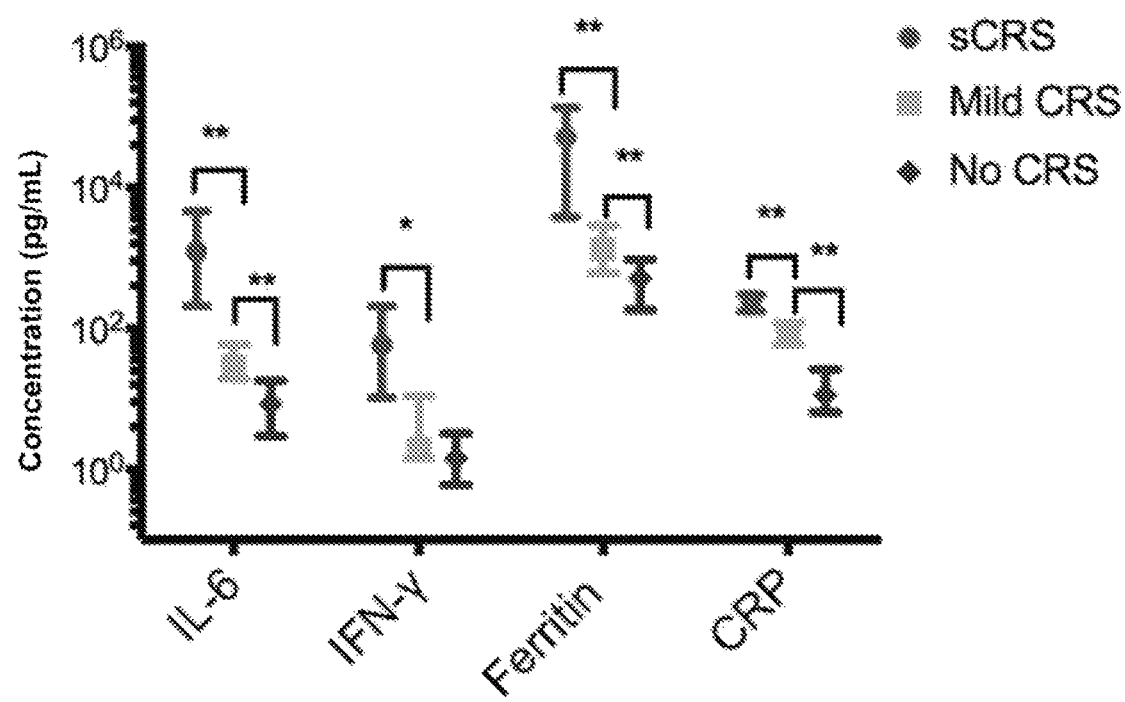
FIG. 6B shows peak serum concentrations of IL-6, IFN-γ, ferritin and C-reactive protein (CRP) after CAR-T cell infusion. Subjects were separated into three groups based on severe CRS (sCRS), mild CRS, and no CRS, respectively.
Figure 7A:
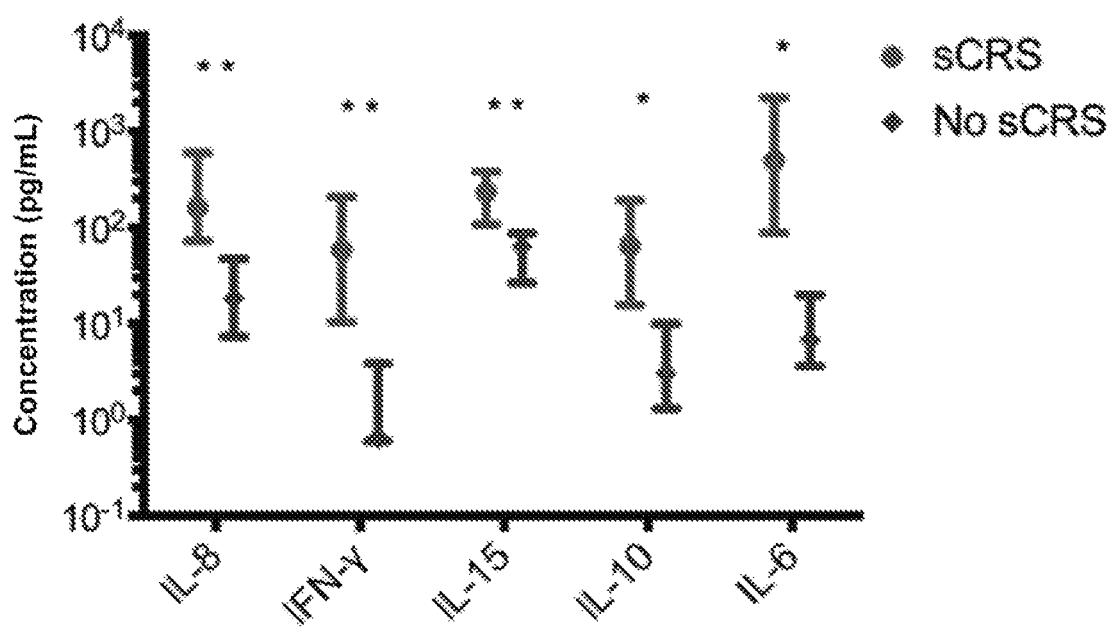
FIG. 7A shows IL-6, IFN-γ, IL-15, IL-8 and IL-10 concentrations on day 1 after CAR-T cell infusion. Subjects were separated into two groups based on severe CRS (sCRS) and non-sCRS, respectively.

The peak number of CD4+/EGFRt+ and CD8+/EGFRt+ CAR-T cells in blood, and AUC0-28 were associated with the occurrence of sCRS (FIG. 6A). Peak serum concentrations of IL-6, IFN-γ, ferritin and C-reactive protein (CRP) after CAR-T cell infusion correlated with the occurrence of sCRS and, with the exception of IFN-γ, the severity of CRS (FIG. 6B). Higher IL-6, IFN-γ, IL-15, IL-8 and IL-10 concentrations were observed on day 1 after CAR-T cell infusion in patients who subsequently developed sCRS (FIG. 7A).

Figure 6C:
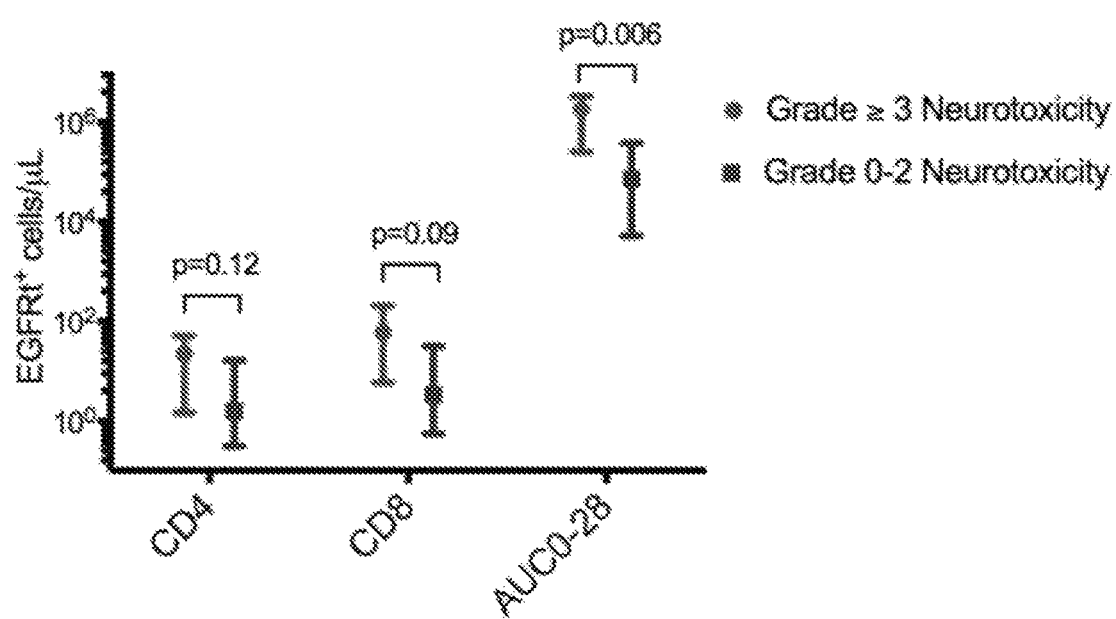
FIGS. 6C-6D show peak CD4+/EGFRt+ cells in blood, peak CD8+/EGFRt+ cells in blood and the area under the curve for 0-28 days (AUC 0-28) (FIG. 6C) and peak serum IL-6, IFN-γ, IL-15, IL-2, IL-18, TIM3, ferritin, CRP levels and TGF-β levels (FIG. 6D). Subjects were separated into two groups based on neurotoxicity grades of 0-2 and 3+, respectively.
Figure 6D:
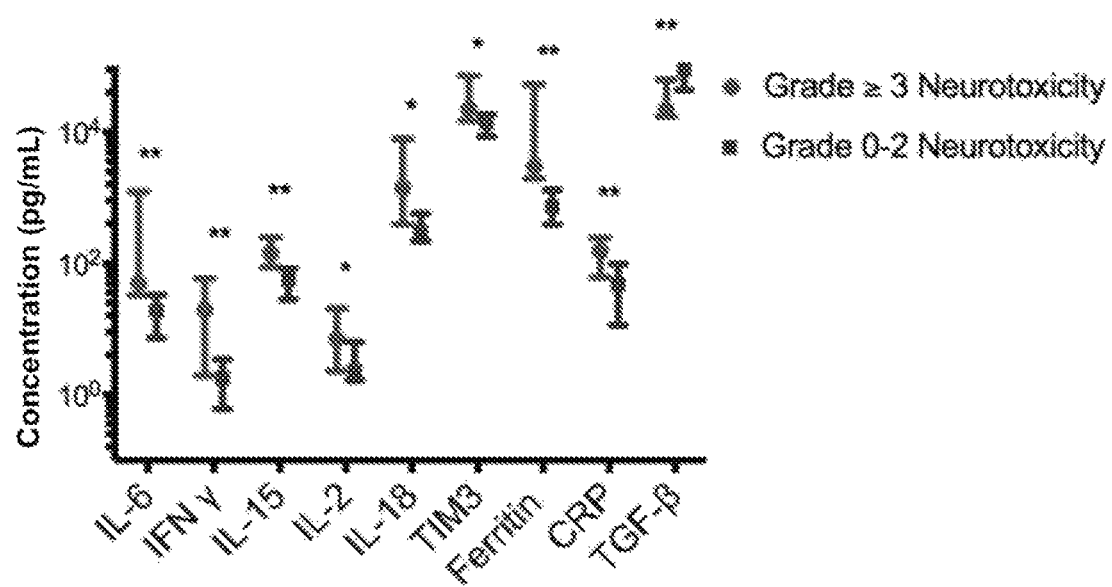
Figure 7B:
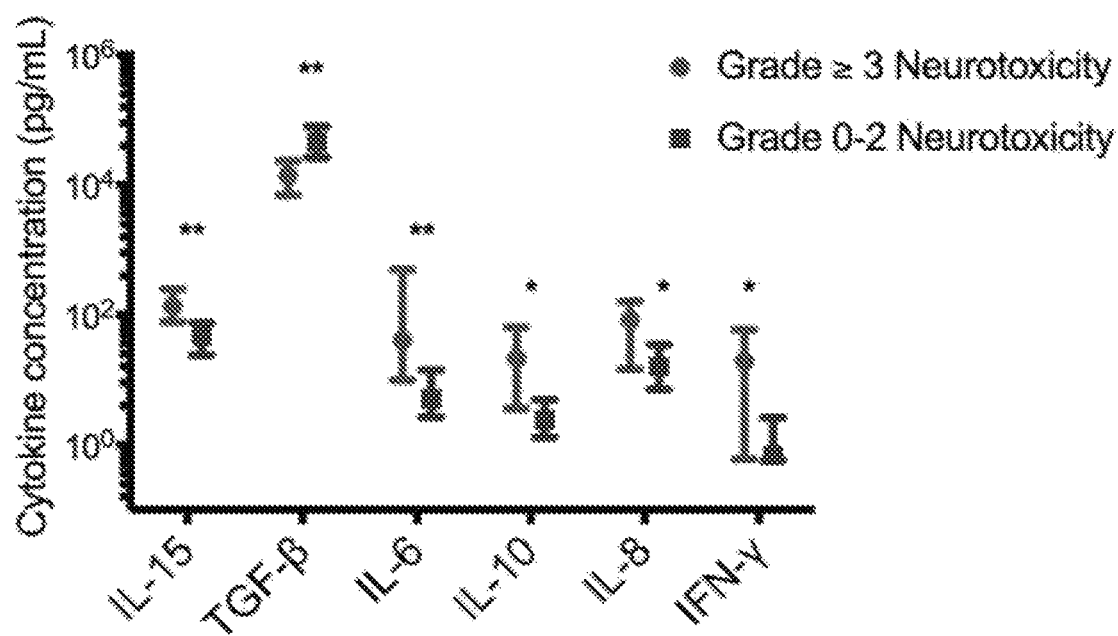
FIG. 7B shows IL-6, IFN-γ, IL-15, IL-8 and IL-10 and TGF-β levels at day 1 after CAR-T cell infusion. Subjects were separated into two groups based on neurotoxicity grades of 0-2 and 3+, respectively.
Figure 8A:
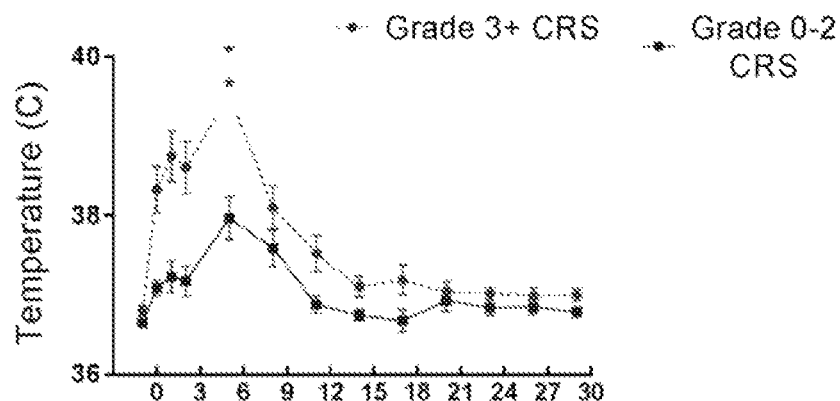
FIGS. 8A-8I show results for various clinical and laboratory parameters, measured over time in subjects with ALL or NHL, following lymphodepleting preconditioning with a combination of cyclophosphamide and fludarabine (cy/flu) and treatment with anti-CD19 CAR T cell infusion. Results are shown for groups of subjects who were observed to exhibit ("Grade 3+ CRS") and who were not observed to exhibit ("Grade 0-2 CRS") grade 3 or higher CRS following the treatment. The parameters included body temperature (° C.
Figure 8B:
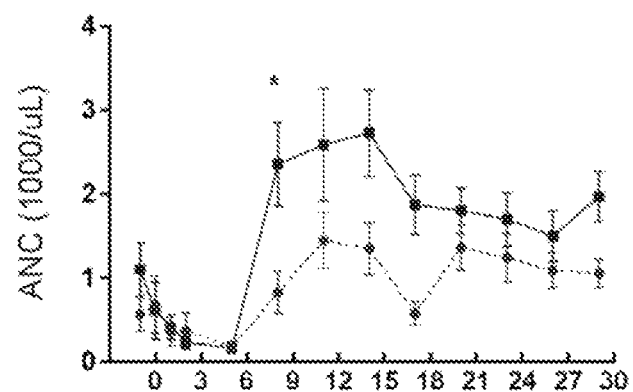
Figure 8C:
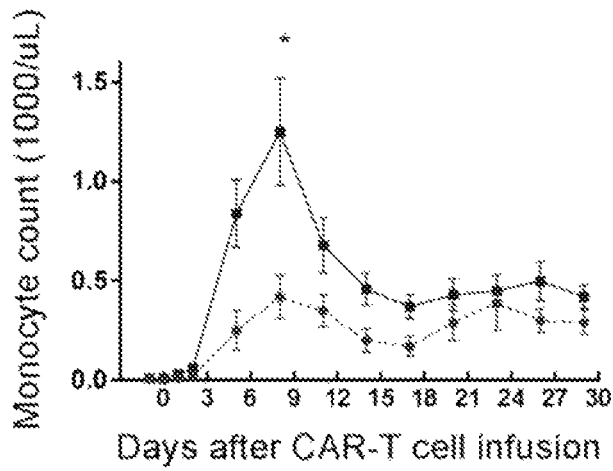
Figure 8D:
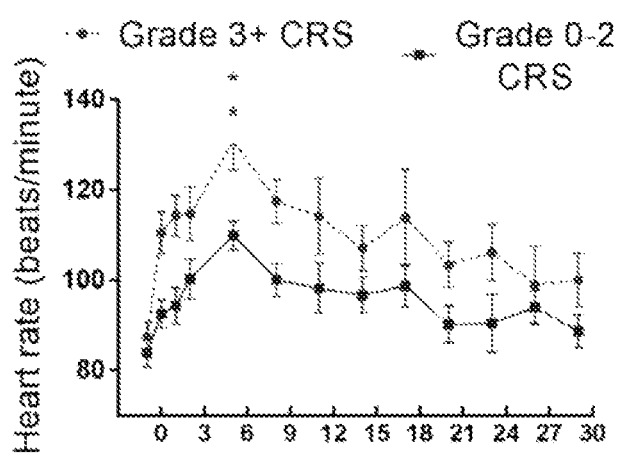
Figure 8E:
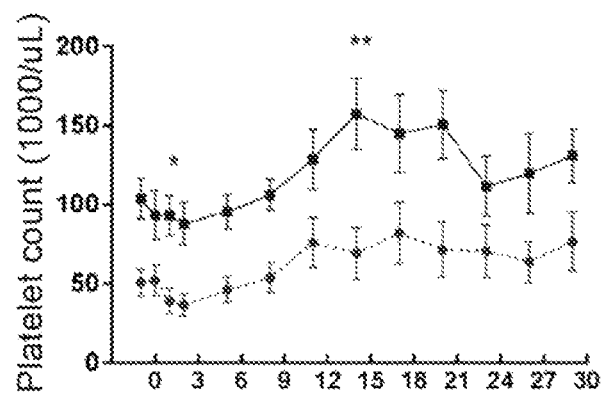
Figure 8F:
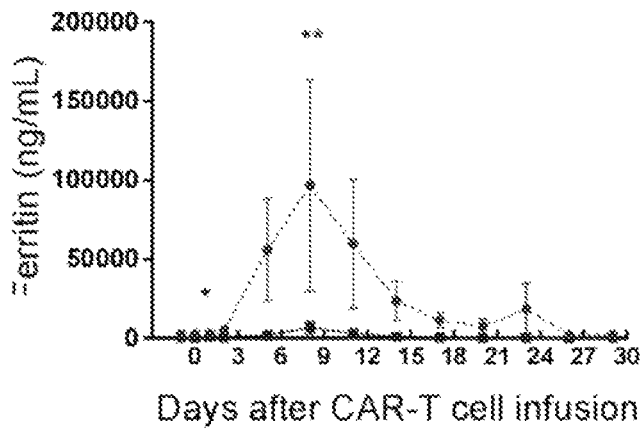
Figure 8G:
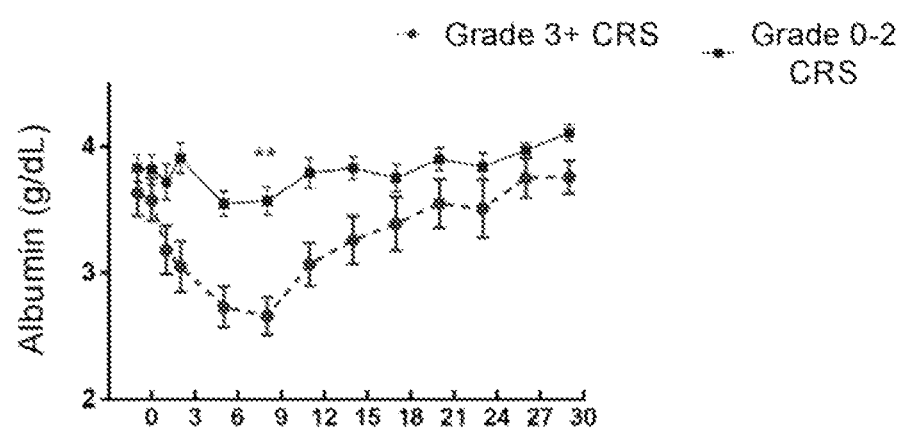
Figure 8H:
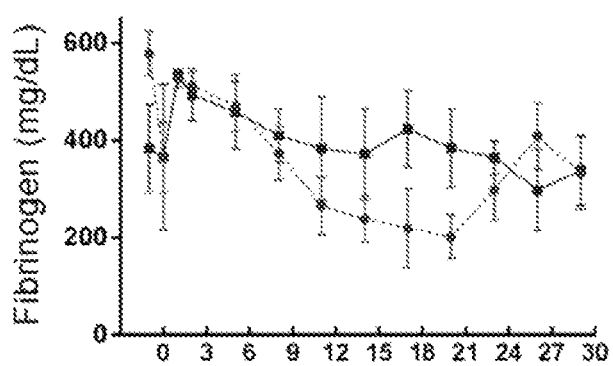
Figure 8I:
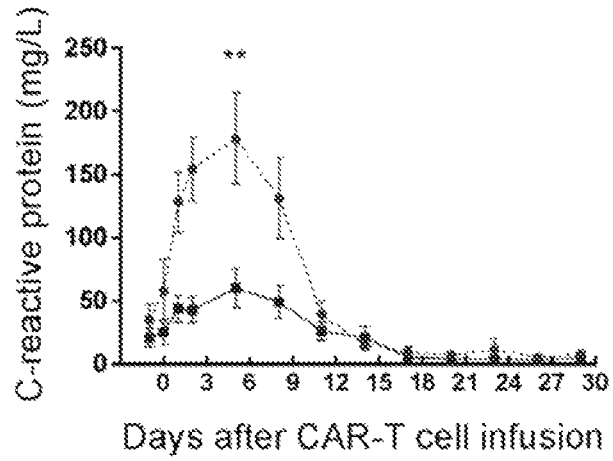

Patients who developed grade≥3 neurotoxicity had higher AUC0-28, peak CD4+/EGFRt+ and peak CD8+/EGFRt+ cells in blood, higher peak serum IL-6, IFN-γ, IL-15, IL-2, IL-18, TIM3, ferritin and CRP levels, and lower serum TGF-β compared to those without neurotoxicity (FIGS. 6C-6D). In multivariate analyses, peak numbers of CD4+/EGFRt+ and CD8+/EGFRt+ cells, serum ferritin, and IL-6 had the strongest associations with severe neurotoxicity. Higher IL-6, IFN-γ and IL-15 and lower TGF-β levels were found at day 1 in patients who subsequently developed severe neurotoxicity compared to those who did not develop severe neurotoxicity (FIG. 7B), with the strongest associations in multivariate analyses identified in patients with higher IL-6 and IL-15.

Subjects with severe CRS (sCRS) or neurotoxicity had higher peak serum levels of IL-6, IFN-γ, ferritin and C-reactive protein compared to those without serious toxicity. IL-6, IFN-γ and TNF-α levels in serum collected on day 1 after CAR-T cell infusion from those who subsequently developed grade≥3 neurotoxicity were higher than those collected from their counterparts who did not develop neurotoxicity (IL-6, p<0.01; IFN-γ, p=0.05; TNF-α, p=0.04). The risks of sCRS and neurotoxicity correlated with higher leukemic marrow infiltration and increasing CAR-T cell dose. IL-6, IFN-γ and TNF-α levels on the first day after CAR-T cell infusion were higher in patients with neurotoxicity and sCRS. Serum IL-6 concentration early after infusion could be used to evaluate the toxicity risk.

Figure 4A:
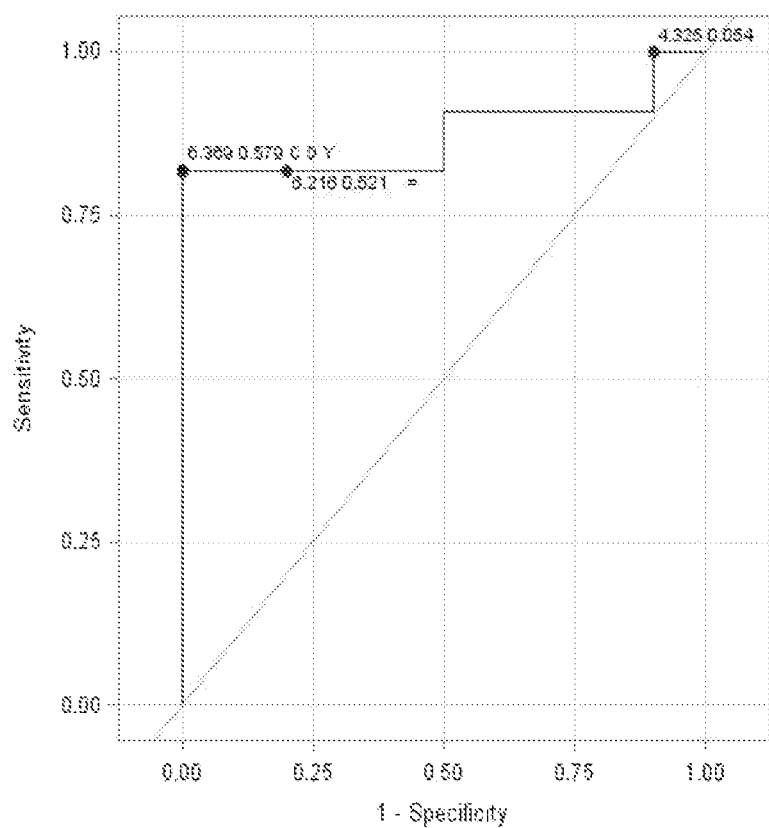
FIGS. 4A-4C shows receiver operating characteristic (ROC) curves of the sensitivity and specificity of various cytokine markers as predictors of neurotoxicity in subjects with ALL treated with CAR T cells.
Figure 4B:
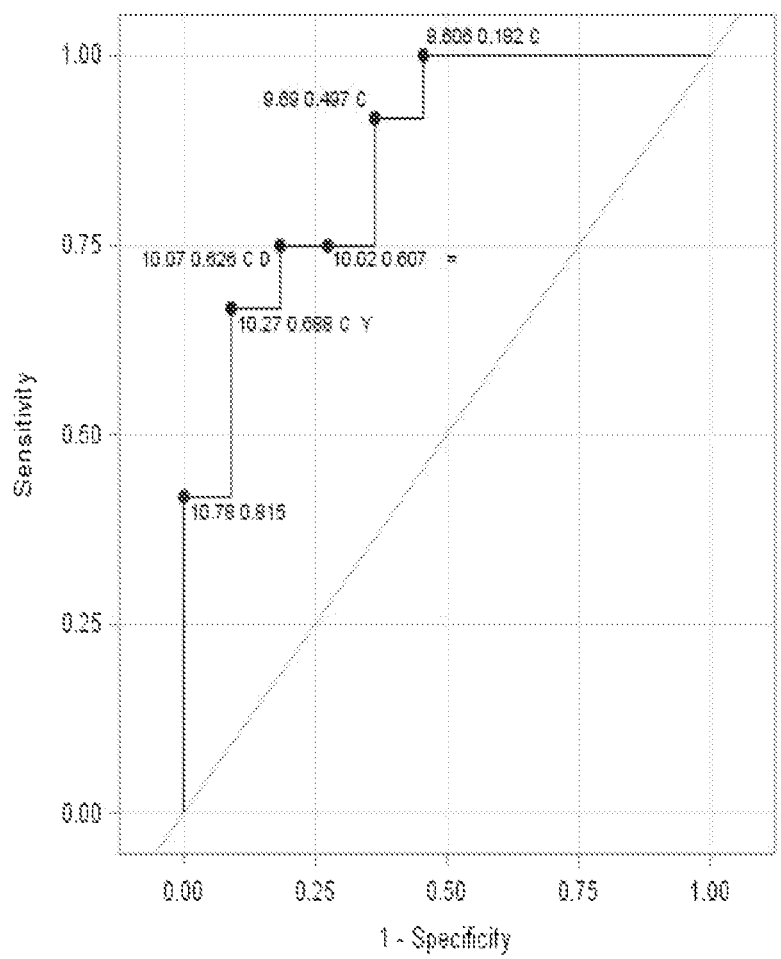
Figure 4C:
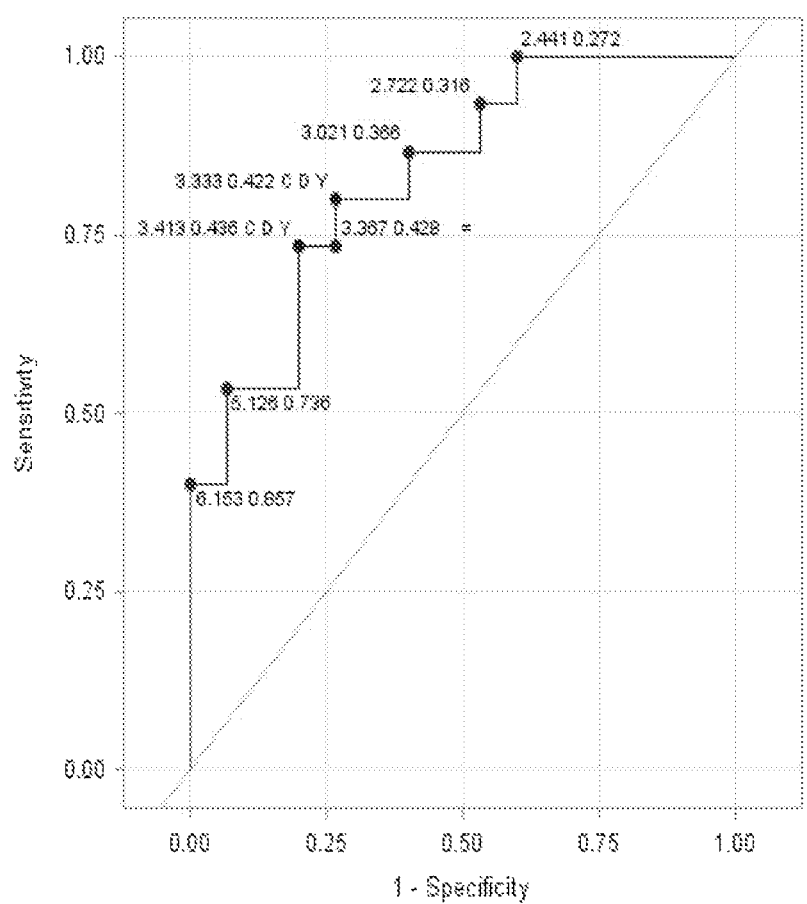

Receiver operating characteristic (ROC) analysis was performed for each of the respective cytokine biomarkers in blood at day 1 to assess the accuracy of each as a predictor of severe neurotoxicity. FIGS. 4A-4C set forth the ROC curves for IL-15, MCP-1 and IL-6, respectively.

For each cytokine, ROC curves were used to calculate the Youden Index (i.e. reference or cut-off value associated with maximal specificity and sensitivity) and the AUC sensitivity and 1-specificity associated with each cut-off reference value as described in Example 1. Table 7B summarizes the results. The results showed that a reference value or cut-off for IL-15 of greater than 83.0 pg/mL (greater than 6.369 on Log 2 scale), for MCP-1 of greater than 1235 pg/mL (greater than 10.27 on Log 2 scale) or for IL-6 of greater than 10.7 pg/mL (greater than 3.413 on Log 2 scale) each individually resulted in a good accuracy of prediction with an AUC of greater than 0.80.

TABLE 7

Summary of Accuracy and Performance of Cytokine Biomarkers for Predicting Severe Neurotoxicity in ALL Patients

|  | IL-15 | MCP-1 | IL-6 |
| --- | --- | --- | --- |
| Reference value (Log2) | 6.369 | 10.27 | 3.413 |
| Reference value (pg/mL) | 83 | 1235 | 10.7 |
| AUC | 0.87 | 0.86 | 0.83 |

TABLE 7-continued

Summary of Accuracy and Performance of Cytokine Biomarkers for Predicting Severe Neurotoxicity in ALL Patients

|  | IL-15 | MCP-1 | IL-6 |
| --- | --- | --- | --- |
| Sensitivity | 0.82 | 0.67 | 0.73 |
| 1-Specificity | 0.0 | 0.09 | 0.2 |

From the above analysis, an exemplary method for prediction of severe neurotoxicity in ALL patients was proposed as follows:

First, subjects are assessed or measured for the value of IL-15 and IL-6 in blood at or about day 1 after administration of the adoptive cell therapy, and if the value of both IL-15 and IL-6 cytokines in the blood individually meets the corresponding reference value in Table 7B, the subject is predicted to have severe neurotoxicity. For example, if the measured value of IL-15 is greater than 83.0 pg/mL and the measured value of IL-6 is greater than 10.7 pg/mL, the subject is predicted to have severe neurotoxicity. In contrast, if the value of both cytokines in the blood individually does not meet the reference value in Table 7B, the subject is not predicted to have severe neurotoxicity.

If neither of the criteria above are met (i.e., if the subject is not deemed by step 1 to be positive or negative), then the subject is assessed or measured for the value of MCP-1 and IL-15 in blood at or about day 1 after administration of the adoptive cell therapy, and if the value of both IL-15 and MCP-1 cytokines meets the reference value in Table 7B, the subject is predicted to have severe neurotoxicity. For example, if the measured value of MCP-1 is greater than 1235 pg/mL and the measured value of IL-15 is greater than 83.0 pg/mL, the subject is predicted to have severe neurotoxicity. In contrast, if the value of both cytokines in step 2 in the blood individually does not meet the reference value in Table 7B, the subject is not predicted to have severe neurotoxicity.

The above exemplary method was applied to retroactively predict neurotoxicity in the ALL patients treated as described above from cytokines measured in blood obtained at day 1 after administration of the CAR-T cells. The results showed that 15 out of 15 subjects met the first classification with a correct prediction of 100%, whereby 8 out of 8 subjects predicted at risk for severe neurotoxicity actually developed severe neurotoxicity and 7 out of 7 cases predicted not to be at risk for neurotoxicity did not develop severe neurotoxicity. For the remaining 6 subjects, 4 of the 6 subjects met the second classification with a correct prediction of 67%. Overall, it was possible to correctly identify 19/21 (90.5%) of events with a sensitivity of 0.91 and specificity of 0.90.

Thus, the results showed that cytokine biomarkers in blood could accurately predict severe neurotoxicity in ALL patients treated with CAR-T cells as early as day 1 after CAR-T cell administration, which is generally before normal physical signs and symptoms of neurotoxicity develop. The ability to predict severe neurotoxicity early (e.g., early following treatment permits can mean that subjects may be treated with an intervention, e.g. an agent that treats neurotoxicity, to prevent or reduce the severity of neurotoxicity. Further, the subjects can optionally be tested again at one or more timepoints following the intervention to reevaluate the prediction based on the additional measured values or to determine whether the intervention has reduced or ameliorated the risk or development of neurotoxicity.

Example 3: Assessment of Cytokine Levels Predictive of Toxicity from Administered CAR-Expressing Autologous T Cells Autologous T cells expressing a chimeric antigen-receptor (CAR) specific for CD19 were administered to 127 adult human subjects with CD19+ acute lymphoblastic leukemia (ALL), Non-Hodgkin Lymphoma (NHL) or chronic lymphocytic leukemia (CLL), including subjects in the studies as described in Example 1 and 2. The CAR and autologous CAR-expressing cells were generated substantially as described in Example 1.

CAR-expressing T cells were administered at a dose of either $2 \times 10^5$ cells/kg, $2 \times 10^6$ cells/kg or $2 \times 10^7$ cells/kg. Prior to administration of the cells, a preconditioning chemotherapeutic treatment of cyclophosphamide (cy, dose of about 30-60 mg/kg) was, with or without fludarabine (flu, dose of about 25 mg/m$^2$, administered three to five times daily).

The incidence and grade of cytokine release syndrome (CRS) was determined according to Lee et al, Blood. 2014; 124(2):188-95, and neurotoxicity (NT) was determined as described in Examples 1 and 2 above. Clinical and laboratory parameters and biomarker levels were assessed, prior to infusion of CAR+ T cells, and through 28 after infusion. Parameters that were assessed include body temperature (° C.), absolute neutrophil count (ANC)/4, monocyte count/4, heart rate (beats/min), platelet count/4, and levels of ferritin (ng/mL), albumin (g/dL), fibrinogen (mg/dL), C-reactive protein (mg/L), IL-15, IL-6, IL-2, IFN-γ, IL-8, IL-10 and soluble TNF receptor type 1. One hundred and nine (109) subjects (45 ALL, 47 NHL, 17 CLL) completed toxicity and response assessment.

Seventy-one percent (71%) of subjects developed CRS (44% grade 1-2; 22% grade 3-4; and 5% grade 5). Pressors were required in 21% of the subjects who developed grade 3-4 CRS. Severe neurotoxicity (NCI-CTCAE v4.03 grade≥3) was observed in 25% of subjects, all of whom developed a fever before manifesting NT. The median duration of all-cause hospitalization from the start of lymphodepletion was 7, 6, and 10 days for subjects with ALL, NHL and CLL, respectively.

In NHL and CLL subjects, $2 \times 10^7$ CAR-T cells/kg after Cy/Flu resulted in toxicity (5/9 of subjects developed grade 4-5 CRS), and $2 \times 10^6$ CAR-T cells/kg was identified as the maximum tolerated dose in NHL and CLL. Among twenty-six (26) NHL subjects (22 with aggressive histology) treated with cy/flu and $2 \times 10^6$ CAR+ T cells/kg, the objective response rate (ORR) was 73% and the complete response (CR) rate 46%. No subjects had grade 5 CRS or required pressors, and only 12% of subjects experienced either grade 3-4 CRS and/or severe NT (grade≥3 NT). Among thirteen (13) CLL subjects treated with cy/flu preconditioning and $2 \times 10^5$ or $2 \times 10^6$ CAR+ T cells/kg, the ORR (as measured by CT+/−PET) was 85%. Eleven (11) (85%) exhibited complete elimination of marrow disease by flow cytometry. Overall, 38% of subjects achieved CR, including one subject who had residual CLL after first infusion with CAR+ T cells and achieved CR after a second CAR+ T cell infusion. No subjects exhibited grade 4-5 CRS or required pressors, and 23% of the subjects exhibited either grade 3 CRS and/or grade≥3 NT.

In subjects with ALL, the incidence of CRS and NT correlated with the percentage of marrow blasts and CAR-T cell dose; further dose modification was carried out for subjects with 5% marrow blasts, in whom $2 \times 10^6$ CAR-T cells/kg was deemed to be excessive in this study (56% grade 4-5 CRS; 56% grade 4-5 NT; n=9). CRS and NT was mitigated in subjects with 5% blasts by administering $2 \times 10^5$ CAR-T cells/kg resulting in 6% grade 4 CRS, 17% grade 3; and 17% grade 3-4 NT; n=18). Efficacy was not compromised with the T cell dose reduction for the high tumor burden cohort with 89% of subjects achieving a bone marrow CR by high-resolution flow cytometry.

Average levels of certain factors (particular clinical and laboratory measurements) were assessed over time following cy/flu lymphodepletion and CAR+ T cell administration, for subjects with grade 0-2 CRS as compared to those for the subjects with grade≥3 CRS. The results from subjects with ALL and NHL are shown in FIGS. 8A-8I.

Compared to subjects observed to exhibit grade 0-2 CRS, in those who over the course of treatment were observed to exhibit grade≥3 CRS, significantly higher peak levels of IL-15, IL-6, IL-2, IFN-γ, C-reactive protein and ferritin were observed in both ALL and NHL cohorts. In univariate analysis, the levels of IL-15, IL-6, IL-8, IL-10, soluble TNF receptor type 1 (sTNFR1) and IFN-γ were significantly higher on day 1 following administration of CAR-T cells in subjects in the ALL and NHL cohorts that went on to develop grade≥3 CRS. Similar observations were made in subjects that exhibited or did not exhibit severe NT.

The results showed that levels of certain factors, such as certain biomarkers in blood samples derived from the subjects, as early as day 1 following CAR+ T cell administration, could predict and/or identify subjects at risk for developing severe CRS in ALL and NHL cohorts as early as day 1 after CAR+ T cell administration, and can be used to identify subjects for early intervention, e.g., with an agent that treats CRS and/or neurotoxicity, to prevent or reduce the severity of CRS. In some embodiments, such biomarkers and/or combinations thereof are assessed and/or their assessment used to predict risk of toxicity or toxicities developing, and in connection with early intervention methods, to reduce or minimize toxicity that can be associated with CAR+ T cell therapy, e.g., CRS and/or NT. Thus in some embodiments, the methods facilitate enhanced safety and/or efficacy of CAR+ T cell therapy. Further, the subjects in some embodiments are optionally tested again at one or more timepoints following the intervention to reevaluate the prediction based on the additional measured values or to determine whether the intervention has reduced or ameliorated the risk or development of CRS and/or neurotoxicity.

Example 4: Cytokine Levels Predictive of Cytokine Release Syndrome (CRS) Outcomes Across Adult ALL, NHL and CLL Patient Cohorts Following Administration of CAR-Expressing T Cells in ALL, NHL and CLL Patients Autologous T cells expressing a chimeric antigen receptor (CAR) specifically binding to CD19 were administered to 133 adult human subjects with B cell malignancies (CD19+ acute lymphoblastic leukemia (ALL; 47 subjects), Non-Hodgkin Lymphoma (NHL; 62 subjects) or chronic lymphocytic leukemia (CLL; 24 subjects)), including subjects among those described in Examples 1-3. The CAR and autologous CAR-expressing cells were generated substantially as described in Example 1. CAR-expressing T cells were administered at one of 3 dose levels following lymphodepletion chemotherapy essentially as described in Example 3.

Incidence and grade of cytokine release syndrome (CRS) and neurotoxicity, and correlative biomarkers, were analyzed in all subjects (ALL, NHL and CLL) through at least 28 days after infusion. The incidence and grade of cytokine release syndrome (CRS) were determined according to Lee et al, Blood. 2014; 124(2):188-95, and incidence and grade of neurotoxicity (NT) were determined as described in Examples 1-3 above. Additional clinical and laboratory parameters were assessed, prior to infusion of CAR+ T cells, and through approximately 28 after infusion.

After cy/flu lymphodepletion, 4/7 subjects receiving $2\times10^7$ CAR+ T cells/kg dose developed grade 4-5 CRS; $2\times10^6$ CAR+ T cells/kg was identified in this study as the maximum tolerated dose. Of thirty-three (33) subjects with ALL that were treated with cy/flu and either $2\times10^5$ or $2\times10^6$ CAR+ T cells/kg, 88% achieved clearance of bone marrow disease by high-resolution flow cytometry. Of twenty-four (24) subjects with NHL treated with cy/flu and $2\times10^6$ CAR+ T cells/kg, the overall response rate (ORR) was 75% and the complete response (CR) rate was 46%. Of fifteen (15) subjects with CLL treated with cy/flu and $2\times10^6$ CAR+ T cells/kg, 80% cleared marrow disease by high-resolution flow cytometry, and lymph node response (deemed to be CR/PR when assessed according to the IWCLL 2008 criteria) was observed in 67% of the subjects.

Seventy-one percent (71%) of subjects developed CRS (26.3% grade 1, 33.8% grade 2, 3.8% grade 3, 3.8% grade 4, 3.8% grade 5). Nine (9) of 10 subjects with grade 4-5 CRS, and two (2) subjects with grade 2-3 CRS, required pressors. The median duration of all-cause hospitalization from the start of lymphodepletion was 0, 9, and 18 days for subjects with grade 0, 1-3, and 4-5 CRS, respectively.

A. Characteristics Associated with Toxicity

Baseline characteristics (including age, sex, Karnofsky Performance score, number of prior therapies, % of marrow disease, % of blood burden of disease, % of antigen-expressing cells in the marrow, platelet count/4 of blood, and eosinophil count/4 of blood) and therapy-related characteristics (including features of treatment, e.g., dosage, and outcomes such as number of days of hospital stay, and grade of CRS and neurotoxicity) were determined for each of the subjects. Table 8 sets forth the median values (and ranges) for these baseline characteristics for subjects within the indicated cohorts. For each row, separate columns indicate values for subsets of patients who went on to exhibit indicated grade (or lack thereof) of cytokine release syndrome (CRS). Table 8 also lists univariate p-values for individual characteristics and their association with grade of cytokine release syndrome. Table 9 sets forth values for the therapy related characteristics.

TABLE 8

Patient baseline characteristics.

| CRS Grade | 0 | 1-3 | 4-5 | Total | p value |
|---|---|---|---|---|---|
| Number of Patients, n (%) | 38 (28.6) | 85 (63.9) | 10 (7.5) | 133 | |
| Age (years) | | | | | 0.6 |
| Median | 56 | 54 | 53.5 | | |
| Range | 27, 70 | 20, 73 | 20, 70 | 20, 73 | |
| Sex, n (%) | | | | | 0.3 |
| Male | 26 (28.9) | 58 (64.4) | 6 (6.7) | 90 | |
| Female | 12 (27.9) | 27 (62.8) | 4 (9.3) | 43 | |
| Karnofsky Performance, n (%) | | | | | 0.3 |
| 60-70 | 2 (14.3) | 10 (71.4) | 2 (14.3) | 14 (10.5) | |
| 80-90 | 30 (30.6) | 62 (63.3) | 6 (6.1) | 98 (73.7) | |
| 100 | 6 (50) | 5 (41.7) | 1 (8.3) | 12 (9.0) | |
| Missing | 0 | 8 | 1 | 9 (6.8) | |
| Disease Type, n (%) | | | | | 0.5 |
| ALL | 12 (25.5) | 31 (66) | 4 (8.5) | 47 (35.3) | |
| CLL | 4 (16.7) | 18 (75) | 2 (8.3) | 24 (18.0) | |
| NHL | 22 (35.5) | 36 (58) | 4 (6.5) | 62 (46.6) | |
| Prior Lines of Therapy, n | | | | | 0.043 |
| Median | 3.0 | 4.0 | 4.5 | 4.0 | |
| Range | 1, 9 | 1, 11 | 2, 9 | 1, 11 | |
| Prior Transplant, n (%) | | | | | 0.3 |
| Allogeneic | 2 (7.1) | 25 (89.3) | 1 (3.6) | 28 (21.1) | |
| Autologous | 9 (36.0) | 14 (56.0) | 2 (8.0) | 25 (18.8) | |
| Marrow Disease, % | | | | | 0.0002 |
| Median | 0 | 17 | 21.2 | 1.3 | |
| Range | 0, 79 | 0, 97 | 0, 89.8 | 0, 97 | |
| Not involved, n (%) | 21 (42.9) | 27 (55.1) | 1 (2.0) | 49 (36.8) | |
| Blood Burden of Disease, % | | | | | 0.0002 |
| Mean | 4.6 | 14.8 | 6.4 | 11.3 | |
| Range | 0, 92 | 0, 90.1 | 0, 39.3 | 0, 92 | |
| CD19+ Cells in Marrow, % | | | | | 0.0009 |
| Median | 3.7 | 19.5 | 21.7 | 8.8 | |
| Range | 0, 79 | 0, 98.7 | 0.3, 89.8 | 0, 98.7 | |
| Platelet Count, 1000/µL | | | | | 0.002 |
| Median | 97.5 | 69 | 32 | 77 | |
| Range | 19, 251 | 1, 553 | 5, 162 | 1, 553 | |
| Eosinophil Count, 1000/µL | | | | | 0.002 |
| Median | 0.05 | 0.02 | 0.00 | 0.02 | |
| Range | 0, 0.28 | 0, 0.68 | 0, 0.03 | 0, 0.68 | |

TABLE 9

Therapy related characteristics.

| CRS Grade | 0 | 1-3 | 4-5 | Total | p value |
|---|---|---|---|---|---|
| Number of Patients, n (%) | 38 (28.6) | 85 (63.9) | 10 (7.5) | 133 | |
| Lymphodepletion, n (%) | | | | | 0.5875 |
| Cy/Flu | 29 (27.9) | 66 (63.5) | 9 (8.6) | 104 (78.2) | |
| Non-Cy/Flu | 9 (31.0) | 19 (65.5) | 1 (3.4) | 29 (21.8) | |
| CAR-T Cell Dose, n (%) | | | | | 0.0019 |
| $2 \times 10^5$ cells/kg | 10 (28.6) | 25 (71.4) | 0 (0.0) | 35 (26.3) | |
| $2 \times 10^6$ cells/kg | 25 (29.1) | 56 (65.1) | 5 (5.8) | 86 (64.7) | |
| $2 \times 10^7$ cells/kg | 3 (25.0) | 4 (33.3) | 5 (41.7) | 12 (9.0) | |
| Days in Hospital, n | | | | | <0.001 |
| Median | 0 | 9 | 18 | 7 | |
| Range | 0, 227 | 0, 96 | 3, 98 | 0, 227 | |
| Neurotoxicity, n (%) | | | | | <0.001 |
| Grade 0 | 33 (86.8) | 49 (57.6) | 0 (0.0) | 82 (61.7) | |
| Grade 1-2 | 5 (13.2) | 18 (21.2) | 0 (0.0) | 23 (17.3) | |
| Grade 3-5 | 0 (0.0) | 18 (21.2) | 10 (100.0) | 28 (21.0) | |

Multivariable proportional odds models were performed to assess impact of baseline factors and dosage on the likelihood of occurrence and severity of CRS (Grade 0, 1-3 or 4-5), where log 10 values were used to transform data as appropriate with 0.001 substituting for values of 0.2-sided P-values were calculated based on Kruskal-Wallis test for continuous variables, and based on Fisher's Exact test for categorical variables. Results of multivariate analysis of baseline characteristics are shown in Table 10 below. The results showed that high marrow burden of disease and higher CAR+ T cell dose level correlated with the occurrence and severity of CRS. The data are consistent with the use of certain baseline parameters as predictive of risk of grade of CRS.

TABLE 10

Summary of Multivariate Analysis

| Variable | P-value |
|---|---|
| Disease Type | 0.3 |
| Planned Dose Level | 0.0004 |
| Prior Therapies | 0.18 |
| Eosinophils (log10) | 0.057 |
| Platelet (log10) | 0.4 |
| Baseline Marrow % (log10) | 0.0007 |

B. Biomarkers Associated with Toxicity

Levels of IFN-γ, IL-2, IL-6, IL-8, IL-10, IL-15, IL-18, IL-2 receptor alpha (IL-2Ra), soluble IL-6 receptor (sIL-6R), monocyte chemoattractant protein-1 (MCP-1), tumor necrosis factor receptor p55 (TNFRp55), tumor necrosis factor receptor p75 (TNFRp75), T-cell immunoglobulin and mucin-domain containing-3 (TIM-3), B cell-activating factor belonging to TNF family (BAFF), macrophage inflammatory protein 1 beta (MIP-1β), ferritin, C-reactive protein (CRP), soluble Fas (sFAS), IL-22, IL-7, transforming growth factor type 1 (TGF1) and tumor necrosis factor alpha (TNFα) were measured (detected) at various time points in the serum of subjects following cy/flu lymphodepletion and CAR+ T cell administration.

Figure 9A:
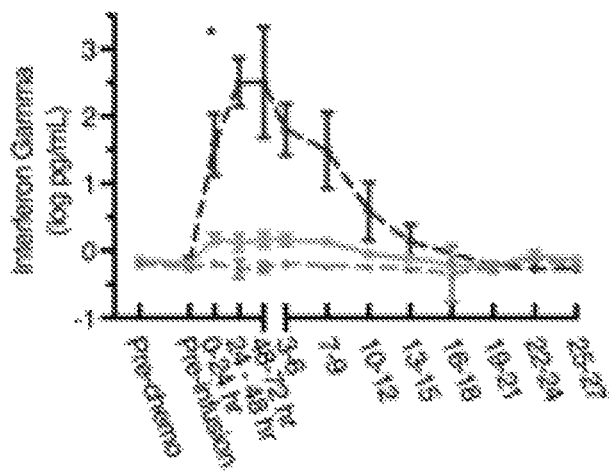
FIGS. 9A-9Q show results for various biomarkers, measured over time in subjects with ALL, NHL or CLL, following treatment with anti-CD19 CAR T cell infusion. Results are shown for groups of subjects who were observed to exhibit Grade 0 CRS (triangles), Grade 1-3 CRS (square) or Grade 4-5 CRS (circles) following the treatment. The biomarkers included IFN-γ (FIG. 9A), IL-2 (FIG. 9B), IL-6 (FIG. 9C), IL-8 (FIG. 9D), IL-10 (FIG. 9E), IL-15 (FIG. 9F), IL-18 (FIG. 9G), IL-2Ra (FIG. 9H), sIL-6R (FIG. 9I), MCP-1 (FIG. 9J), TNFRp55 (FIG. 9K), TNFRp75 (FIG. 9L), TIM3 (FIG. 9M), BAFF (FIG. 9N), MIP-1β (FIG. 9O) and CRP (FIG. 9P) and Ferritin (FIG. 9Q) ** represents $p<0.0001$ and * represents $p<0.05$.
Figure 9B:
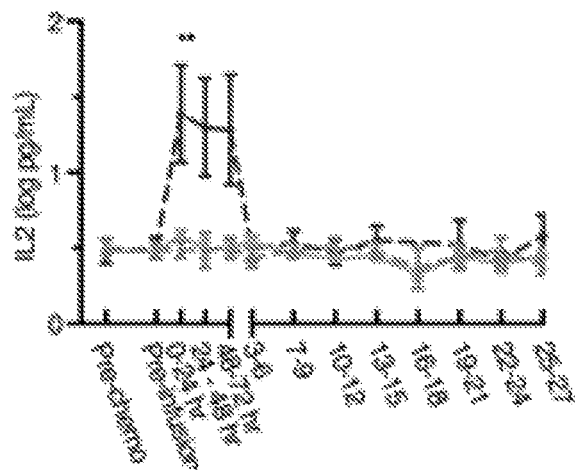
Figure 9C:
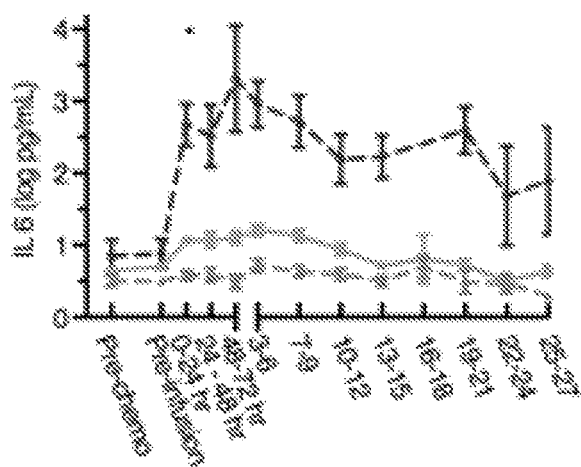
Figure 9D:
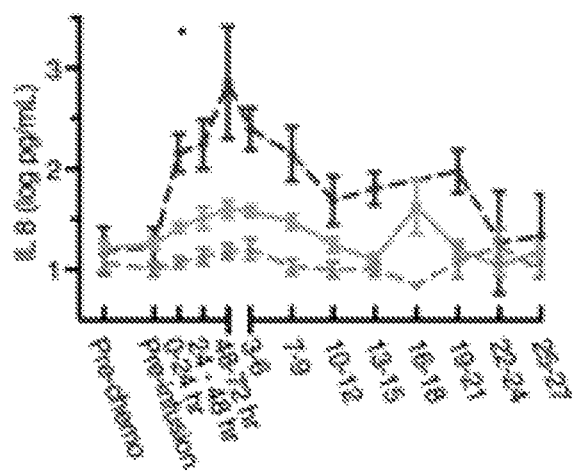
Figure 9E:
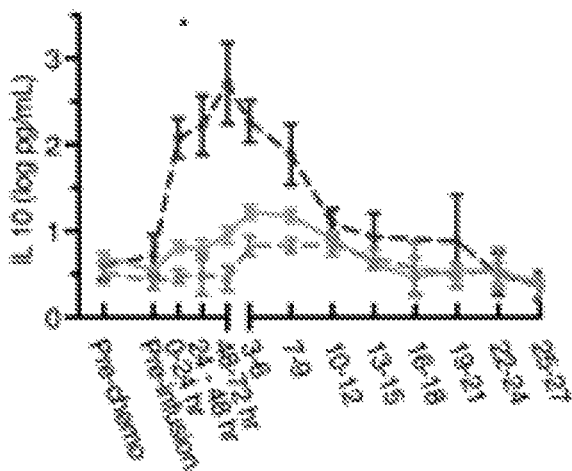
Figure 9F:
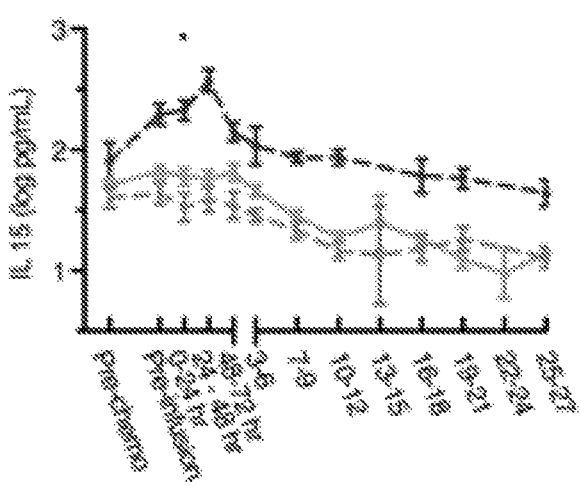
Figure 9G:
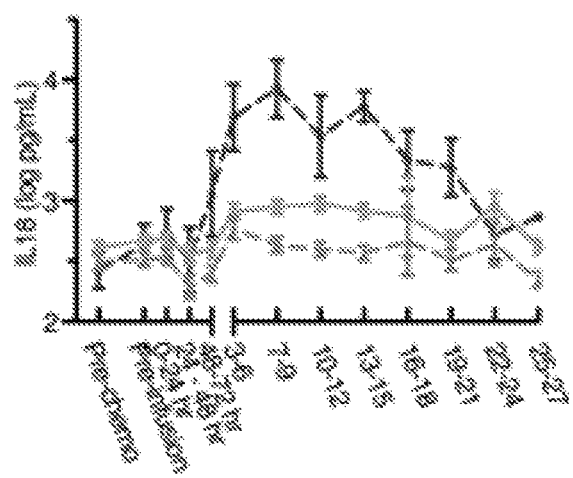
Figure 9H:
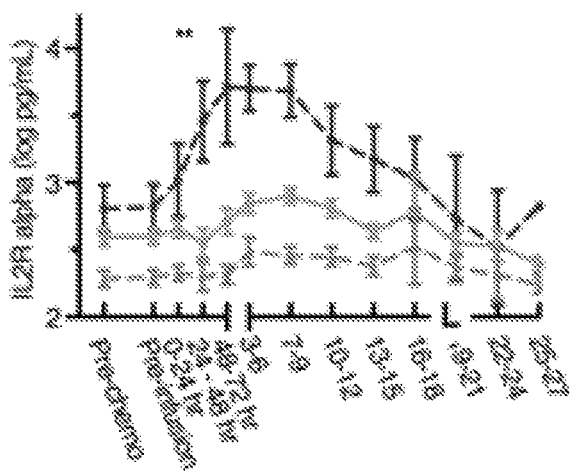
Figure 9I:
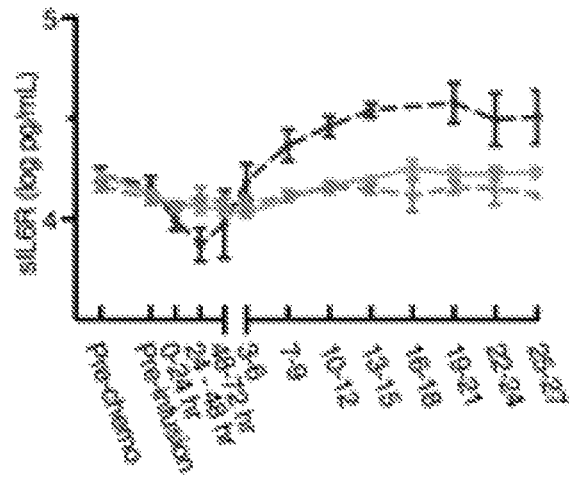
Figure 9J:
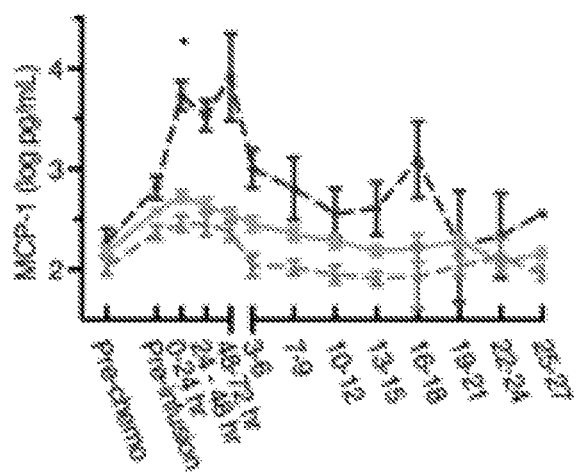
Figure 9K:
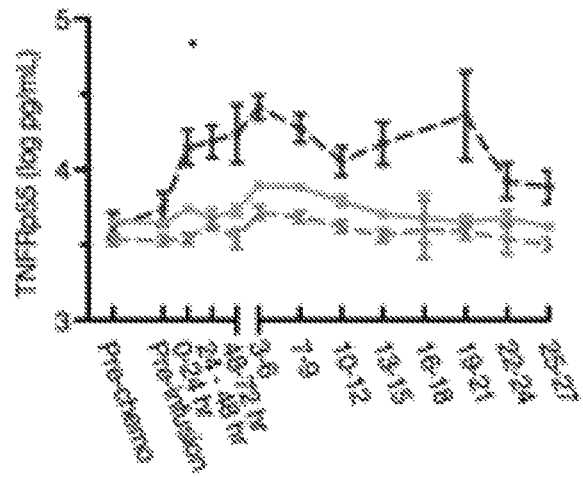
Figure 9L:
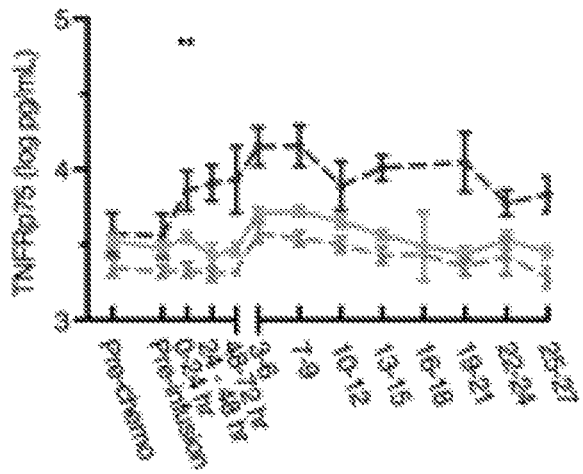
Figure 9M:
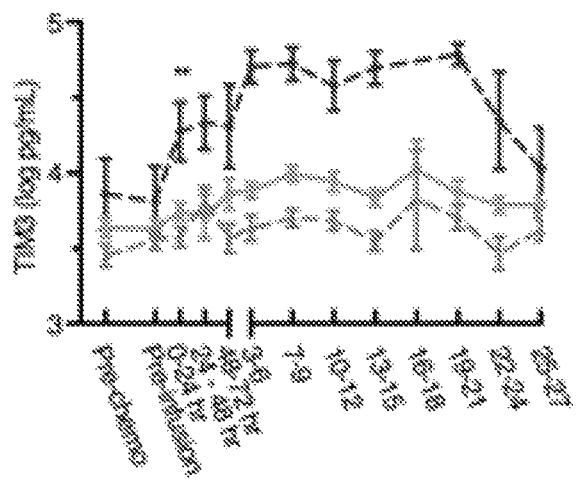
Figure 9N:
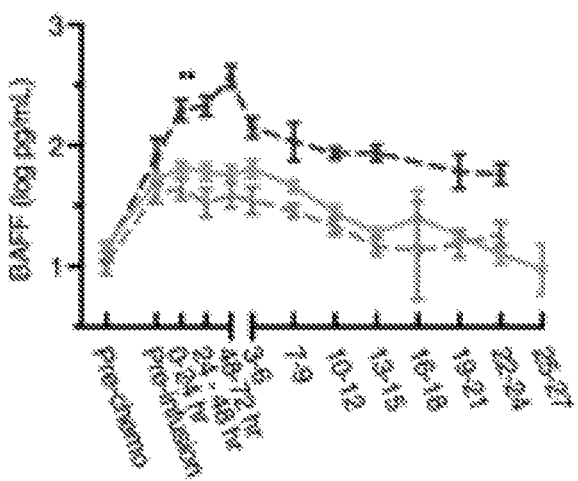
Figure 9O:
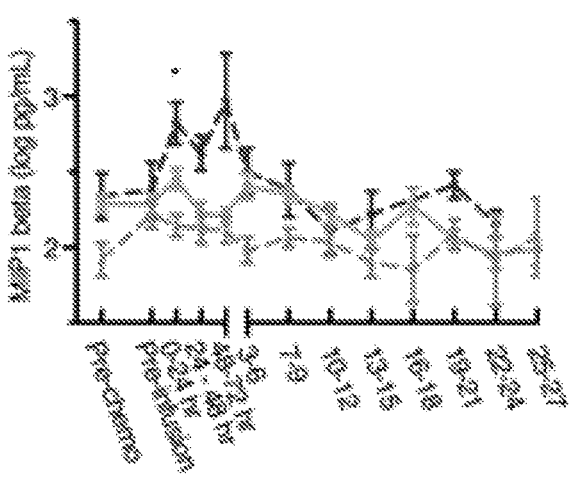
Figure 9P:
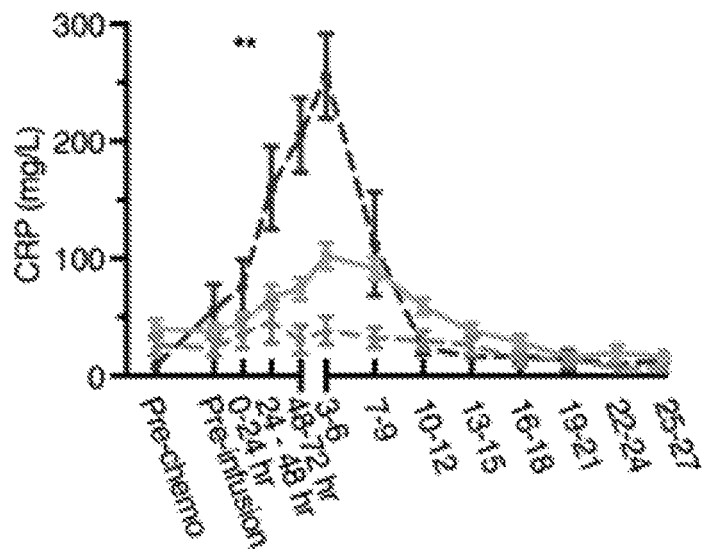
Figure 9Q:
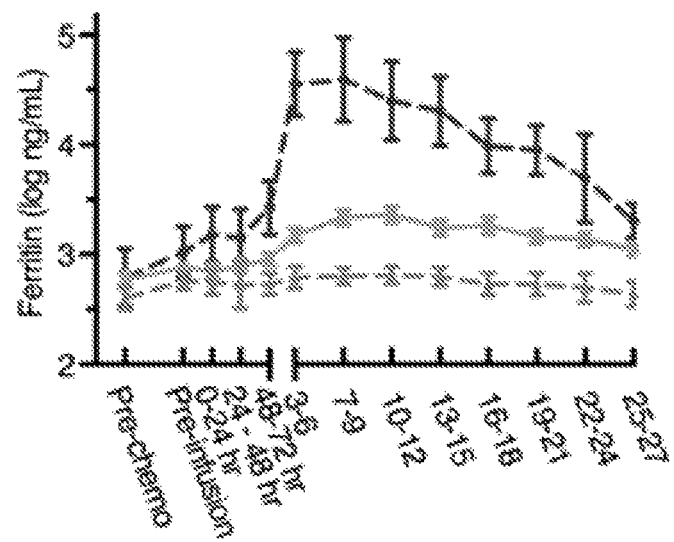
Figure 10A:
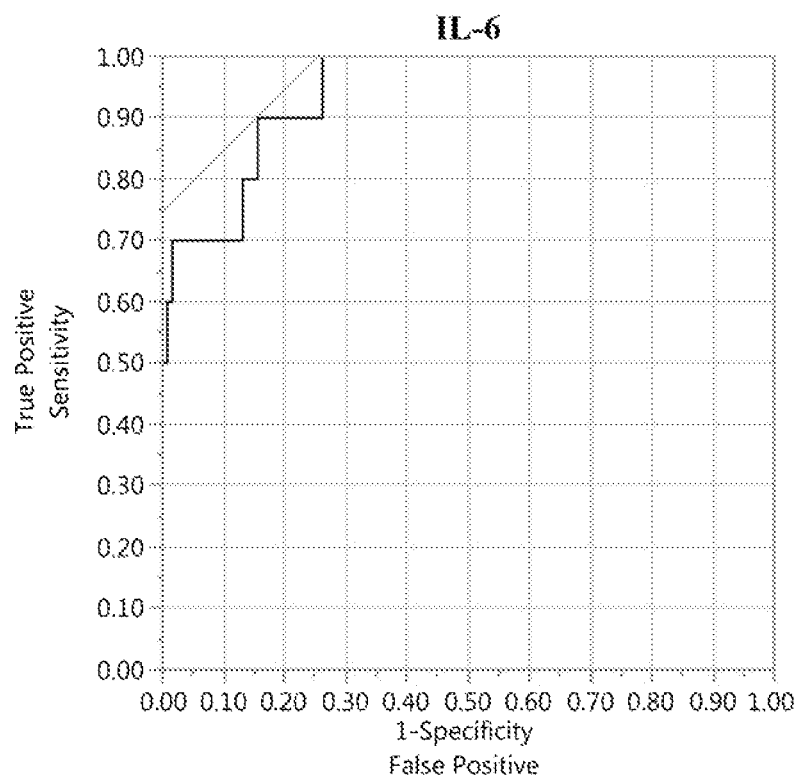
FIGS. 10A-10D show receiver operating characteristic (ROC) curves of the sensitivity and specificity of various cytokine markers as predictors of CRS in subjects with ALL, NHL or CLL, after treatment with anti-CD19 CART cell infusion.
Figure 10B:
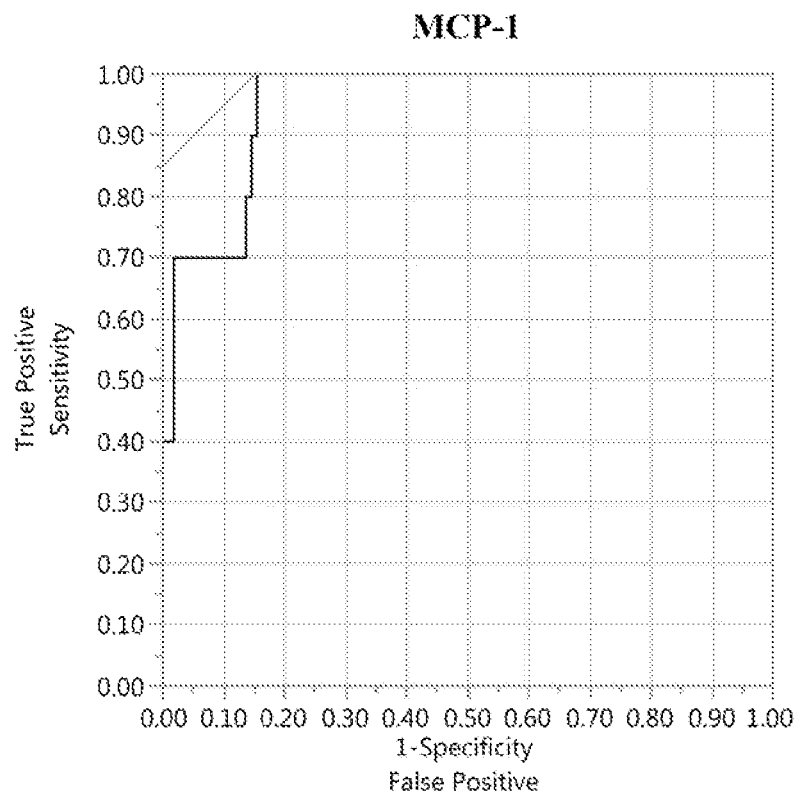
Figure 10C:
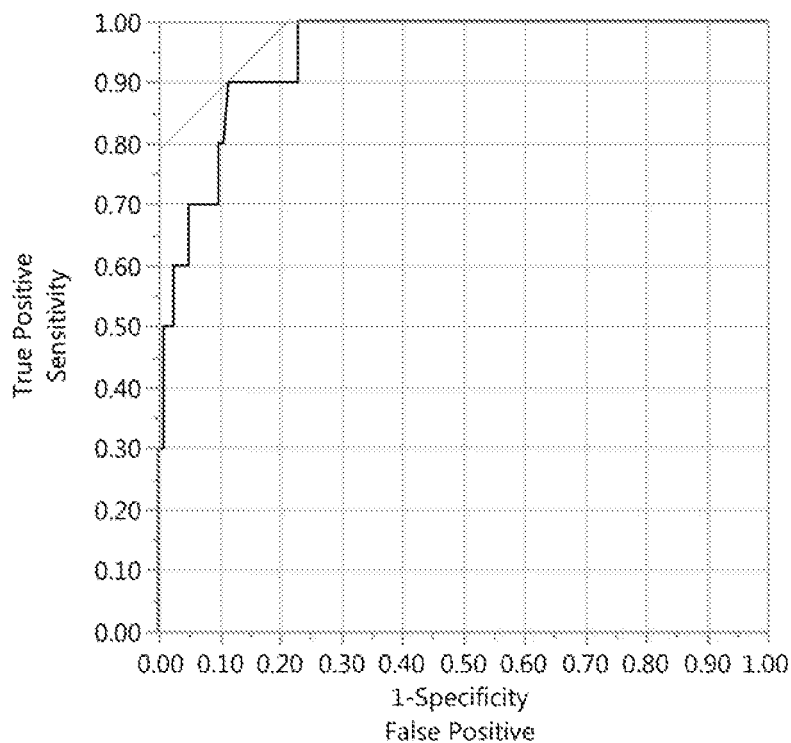
Figure 10D:
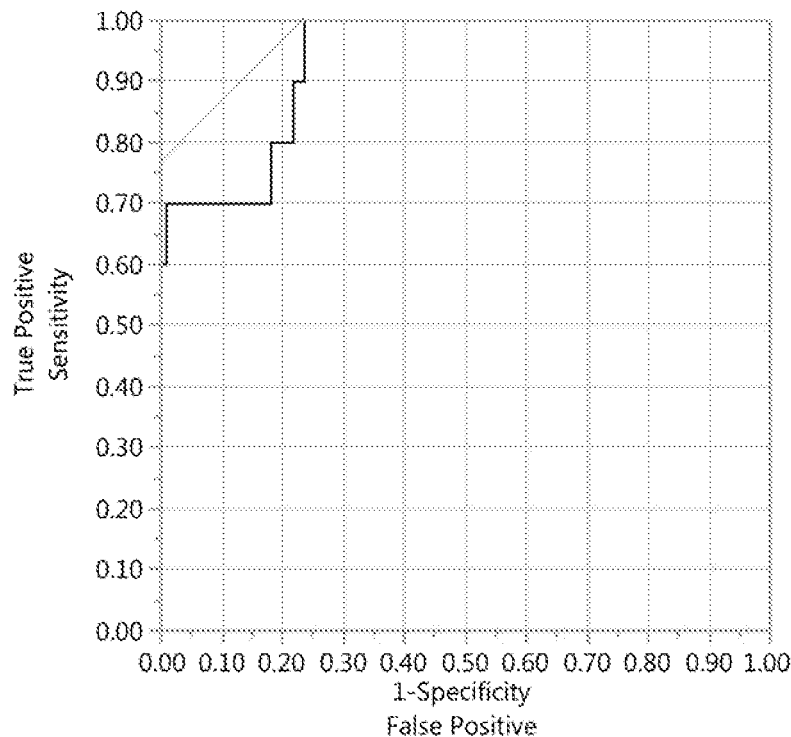

FIGS. 9A-9R depict the kinetics of cytokines in subjects that developed grade 0, grade 1-3 or grade 4-5 CRS. As shown, within 48 hours after infusion of CAR+ T cells, grade 4-5 CRS was associated with significantly higher levels of IFN-γ (FIG. 9A), IL-2 (FIG. 9B), IL-6 (FIG. 9C), IL-8 (FIG. 9D), IL-10 (FIG. 9E), IL-15 (FIG. 9F), IL-2Ra (FIG. 9H), MCP-1 (FIG. 9J), TNFRp55 (FIG. 9K), TNFRp75 (FIG. 9L), TIM3 (FIG. 9M), BAFF (FIG. 9N), MIP-1β (FIG. 9O) and CRP (FIG. 9P). Elevated levels of IL-18 (FIG. 9G), sIL-6R (FIG. 9I) and Ferritin (FIG. 9R) also were associated with grade 4-5 CRS, but increased at later time points. In this study, sFAS, IL-22, IL-7, TGF1, and TNF-α levels were not associated with CRS or severe CRS.

To further assess the accuracy of measuring a cytokine as a marker predictive of grade 4-5 CRS, receiver operating characteristic (ROC) analysis was performed for peak values of IL-6, IL-10, IL-15 and MCP-1 in blood from time period between infusion and 48 hours post-infusion of CAR+ T cell. The ROC curves are shown in FIGS. 10A-10D. For each cytokine, the ROC for IL-6, IL-10, IL-15 and MCP-1 were used to calculate the Youden Index (i.e. reference or cut-off value associated with maximal specificity and sensitivity) and the AUC sensitivity and specificity associated with each cut-off reference value. Table 11 summarizes the results. The results showed that a reference value or cut-off for IL-6 of greater than 26.1 pg/mL, for MCP-1 of greater than 1343.5 pg/mL, for IL-10 of greater than 30.3 pg/mL and for IL-15 of greater than 89.6 pg/mL, each individually, resulted in accuracy of prediction with an AUC of greater than 0.94. The results were consistent with the utility of levels of certain factors, such as certain biomarkers, e.g., IL-6, IL-10, IL-15 and MCP-1, in blood samples derived from the subjects, as early as within 48 hours following CAR+ T cell administration, to predict and/or identify subjects at risk for developing greater severity CRS (grade 4-5) in subjects with ALL, NHL or CLL. In some embodiments, such biomarkers and/or panels thereof can be used to identify subjects for early intervention, e.g., with an agent that treats CRS, to prevent or reduce the severity of CRS, and/or in connection with therapeutic methods involving such intervention.

TABLE 11

Summary of Accuracy and Performance of Cytokine Biomarkers for Predicting Severe CRS in ALL, NHL and CLL Patients

| | IL-6 | MCP-1 | IL-10 | IL-15 |
|---|---|---|---|---|
| AUC | 0.94 | 0.95 | 0.94 | 0.95 |
| Reference Value (pg/mL) | 26.1 | 1343.5 | 30.3 | 89.6 |
| Sensitivity | 0.90 | 1.00 | 0.90 | 1.00 |
| Specificity | 0.84 | 0.85 | 0.89 | 0.76 |
| PPV | 41 | 37 | 39 | 27.8 |
| NPV | 97 | 100 | 99 | 100 |

C. Absolute Number of CAR+ T Cells

The relationship between the absolute number of $CD4^+$ and $CD8^+$ CAR-T cells in the blood and the probability of response, grade 2-5 CRS, and grade 2-5 neurotoxicity in NLL, AHL and CLL was determined. Response in CLL subjects was determined either based on marrow response (measured by flow cytometry) or lymph node response in accord with IWCLL criteria (CR+PR). Response in NHL subjects was classified either as a CR or ORR (PR+CR). Bone marrow disease clearance in ALL subjects was determined using high-resolution flow cytometry.

Figure 11A:
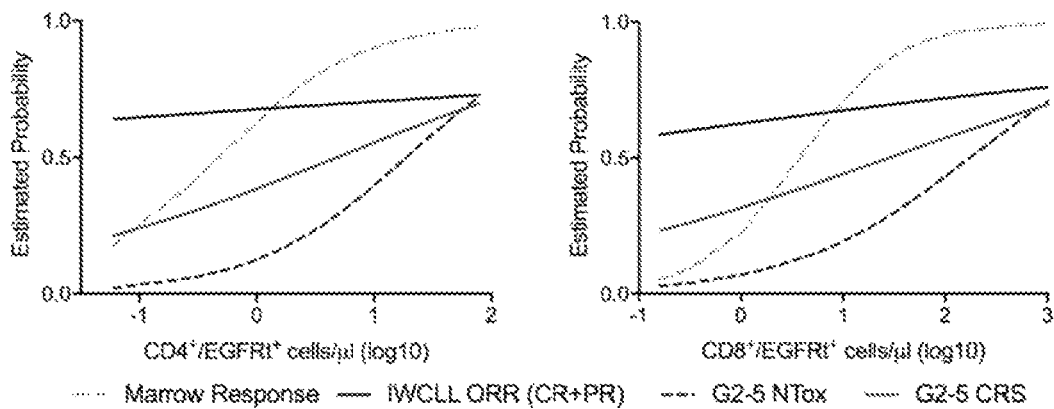
FIGS. 11A-11C show a curve of estimated probability plotted against number of peak CD4+/EGFRt+ CAR-T cells (log 10, left panel) and peak CD8+/EGFRt+ CAR-T cells (log 10, right panel), in groups of subjects with different responses or subjects that exhibited different toxicities after treatment with anti-CD19 CAR T cell infusion.
Figure 11B:
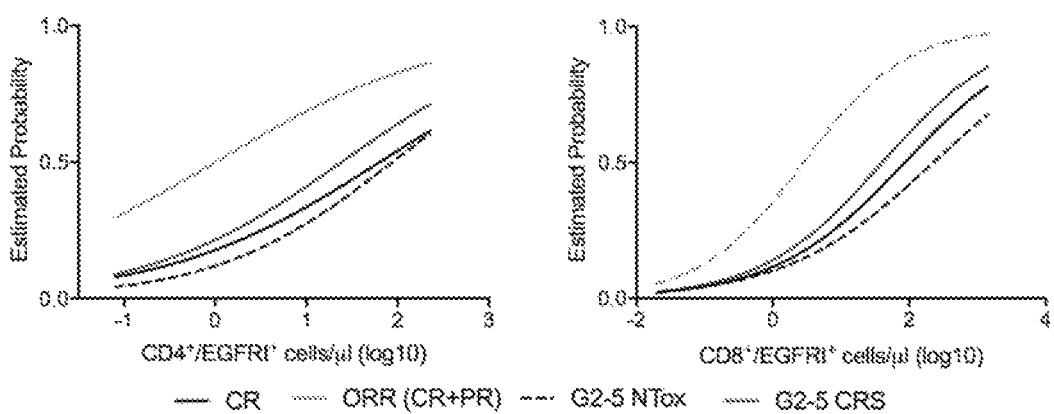
Figure 11C:
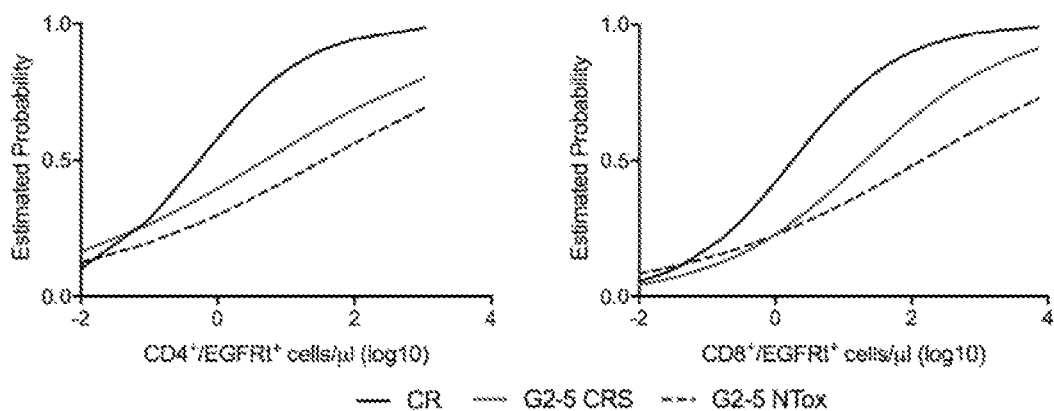

The probabilities of response, CRS and neurotoxicity to CAR-T cell peak for CD4+ or CD8+ CAR+ T cells in CLL are shown in FIG. 11A, in NHL are shown in FIG. 11B and in ALL are shown in 11C.

D. Onset and Kinetics of Parameters Associated with Toxicity

The time to onset of first symptoms for CRS (as determined by a fever of over 38° C.) and time to onset of grade 3 neurotoxicity were determined in subjects having received CAR-T cell therapy.

Figure 12A:
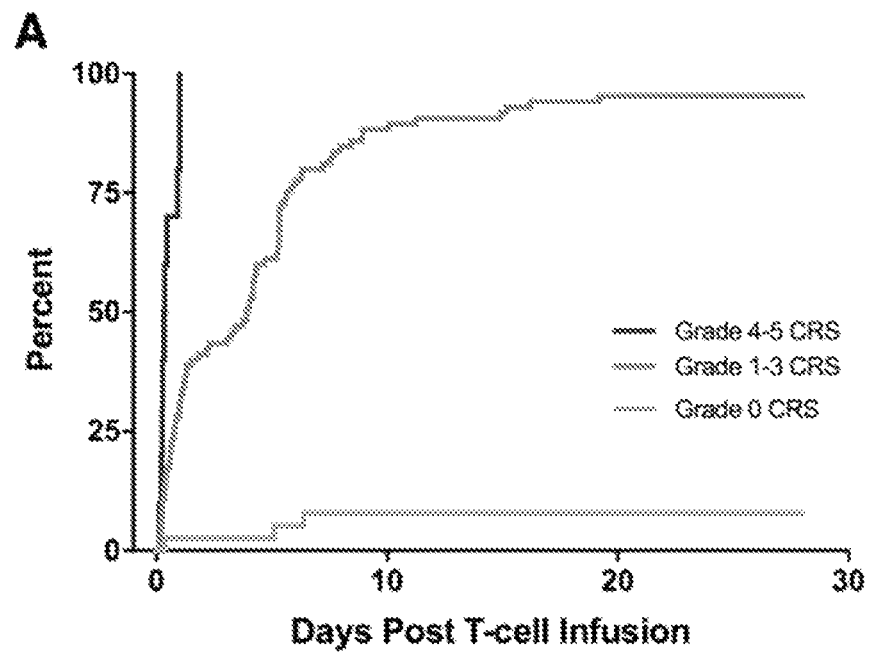
Figure 12B:
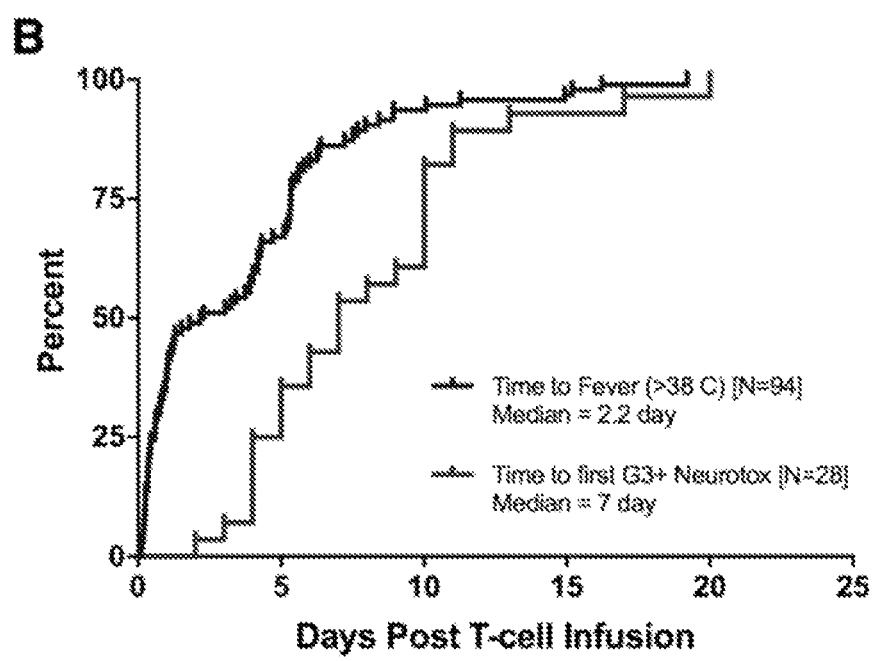

FIG. 12A shows the percent of subjects having developed a first fever of over 38° C. over time after CAR-T cell infusion. As shown, when correlating the time to first fever in subjects that developed grade 0, 1-3 or 4-5 CRS, the onset of first fever occurred earlier in subjects who developed severe CRS. FIG. 12B depicts the percent of subjects who, at various time points after CAR-T cell infusion, developed a fever or grade 3 or higher neurotoxicity. Among the 98 subjects that developed a fever, the median time to fever was 2.2 days, and among the 28 subjects that developed grade 3 or higher neurotoxicity, the median onset of neurotoxicity was 7 days.

For the ten (10) subjects who developed a grade 4 or grade 5 CRS, the kinetics of development of CRS were assessed for the occurrence of grade 0, 1, 2, 3, 4 or 5 CRS over time, including in subjects who developed onset of severe neurotoxicity (grade 3 or higher) or who had received an intervening therapy (steroid and/or tocilizumab dose) for the toxicity. The data showed that onset of severe CRS in these patients was preceded by mild to moderate CRS.

Figure 13A:
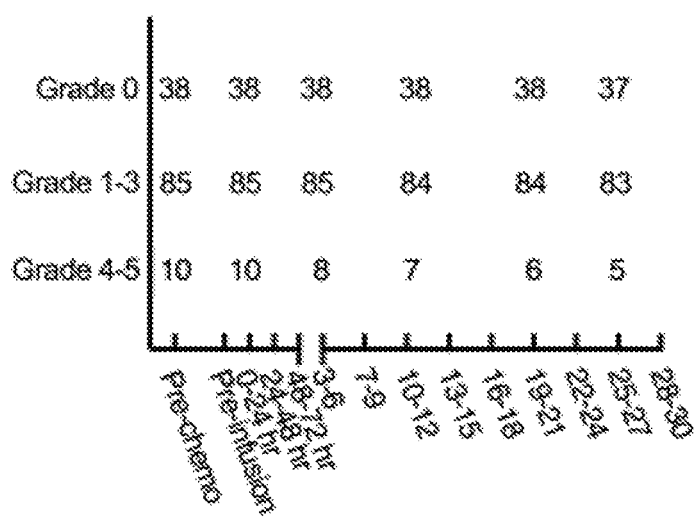
FIGS. 13A-13I show results for vital signs and hemodynamic parameters, measured over time in subjects with ALL, NHL or CLL, following treatment with anti-CD19 CAR T cell infusion. Results are shown for groups of subjects who were observed to exhibit Grade 0 CRS (triangles), Grade 1-3 CRS (square) or Grade 4-5 CRS (circles) following the treatment. The parameters included number of subjects at risk (FIG. 13A), absolute maximum temperature (° C.
Figure 13B:
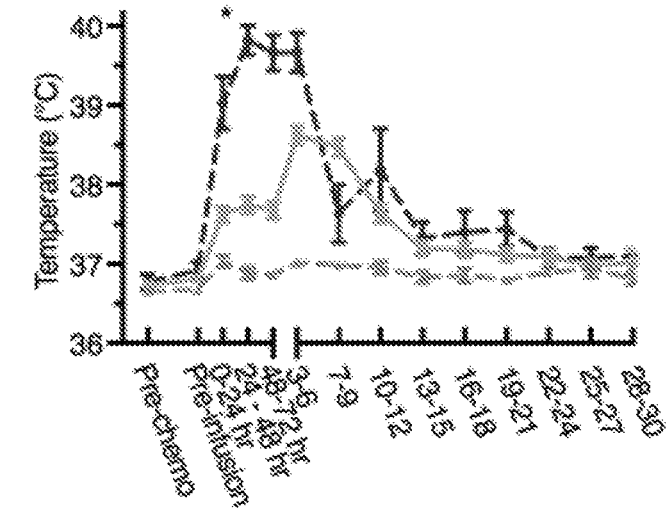
Figure 13C:
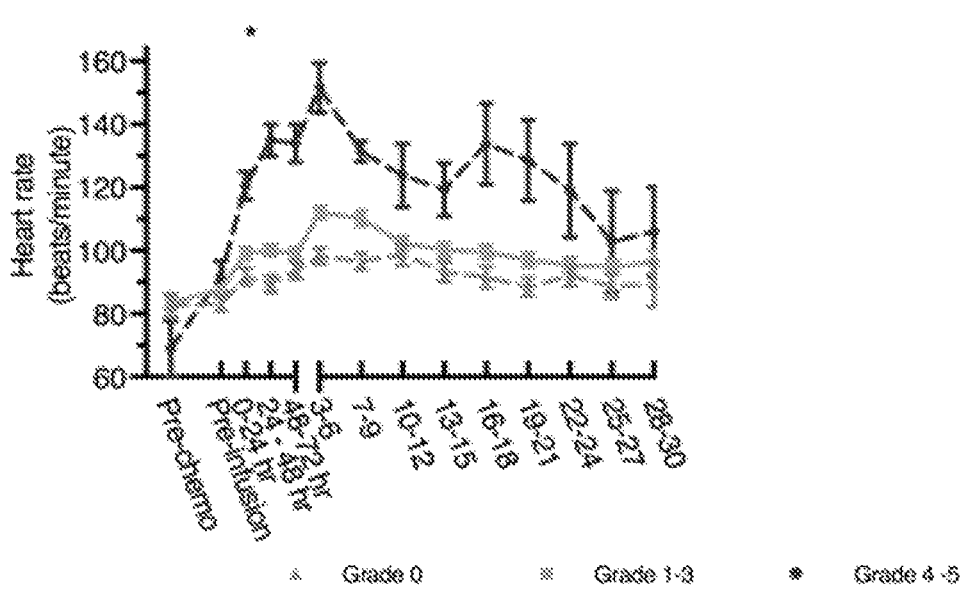
Figures 13D, 13E, 13F:
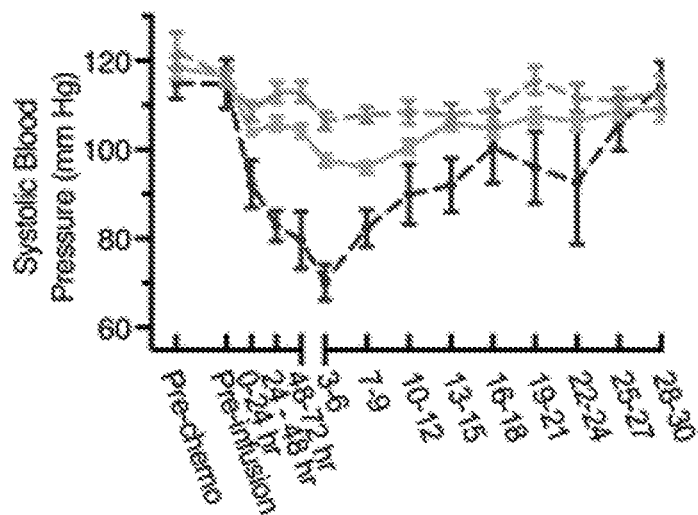
Figure 13G:
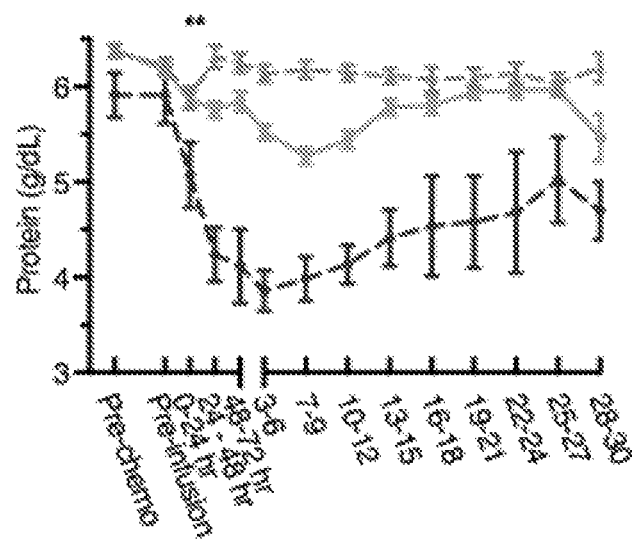
Figure 13H:
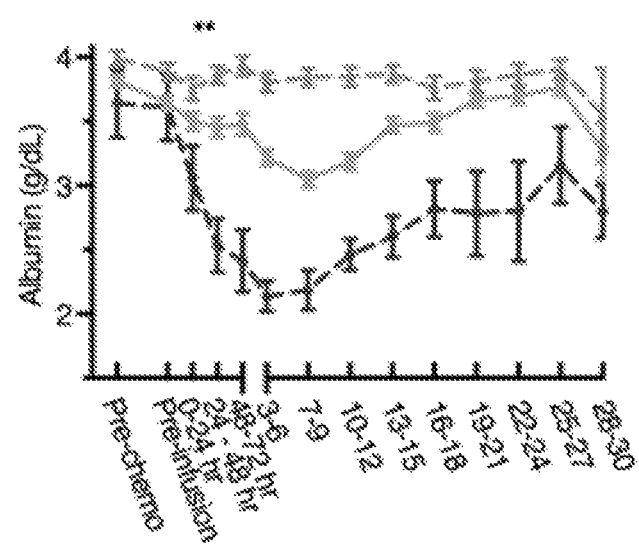
Figure 13I:
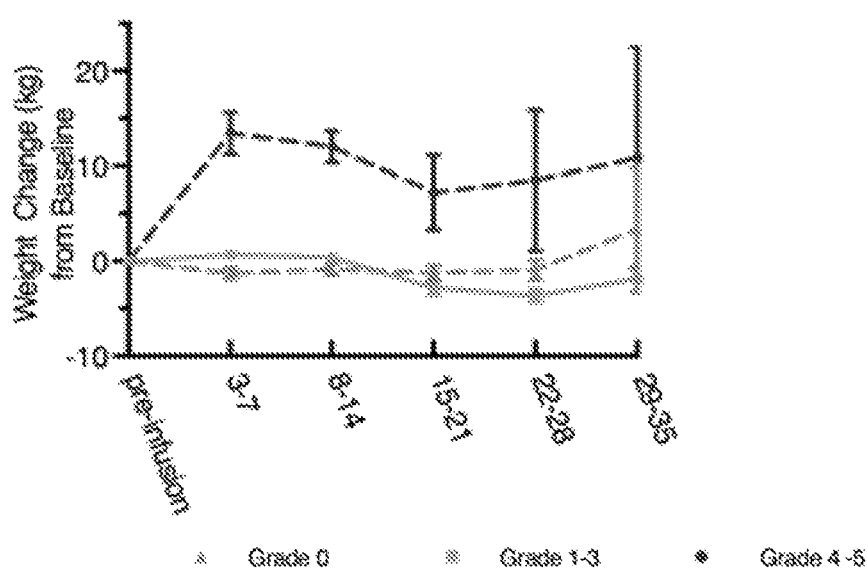
Figure 14A:
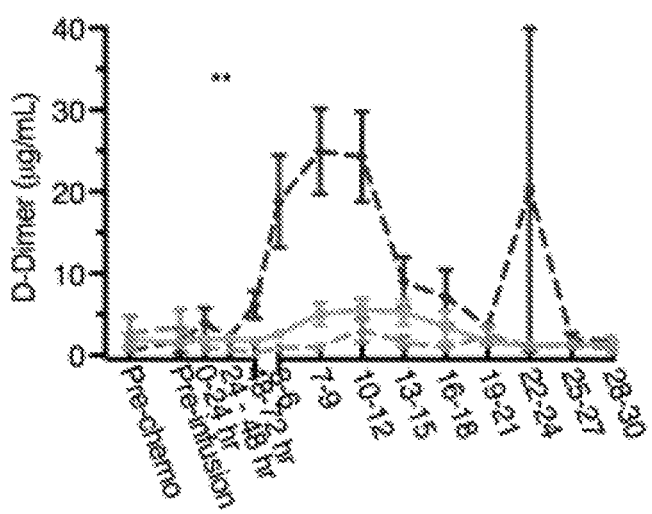
FIGS. 14A-14E show results for coagulation factors, measured over time in subjects with ALL, NHL or CLL, following treatment with anti-CD19 CART cell infusion. Results are shown for groups of subjects who were observed to exhibit Grade 0 CRS (triangles), Grade 1-3 CRS (square) or Grade 4-5 CRS (circles) following the treatment. The parameters included levels of D-dimer (μg/mL.
Figure 14B:
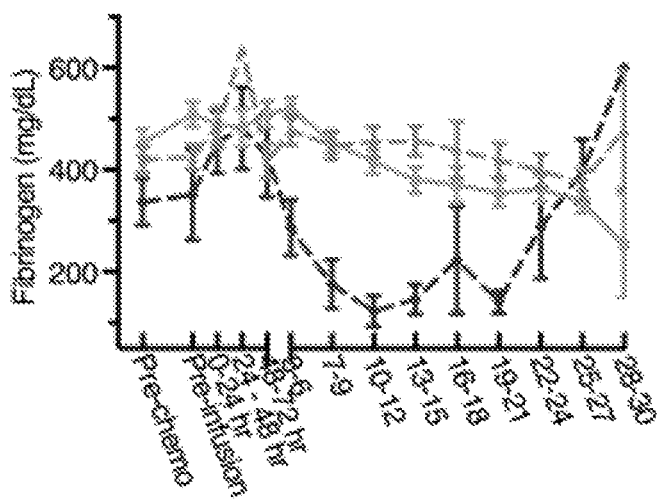
Figure 14C:
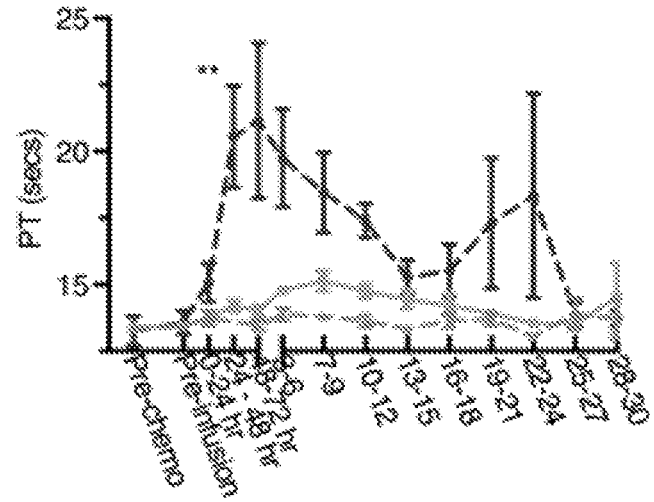
Figures 14D, 14E:
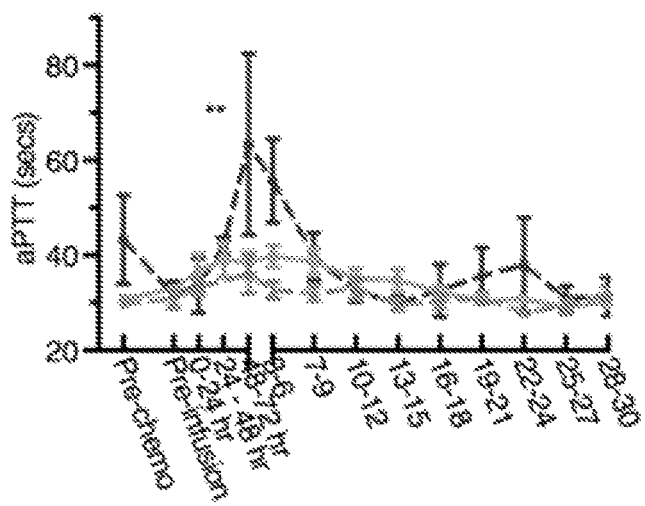
Figure 15A:
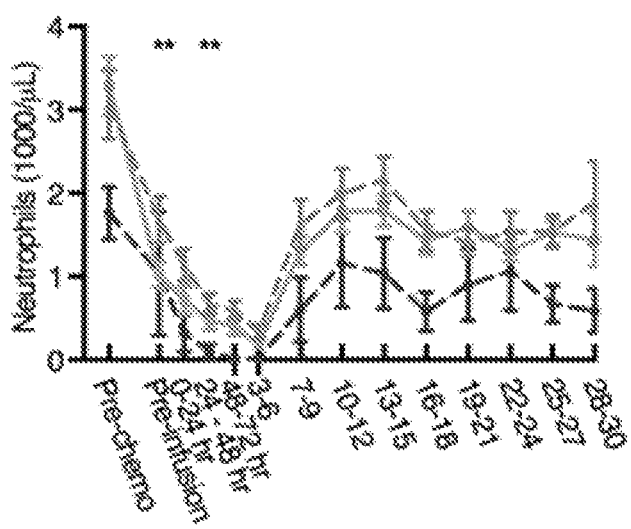
FIGS. 15A-15E show results for various blood counts, measured over time in subjects with ALL, NHL or CLL, following treatment with anti-CD19 CAR T cell infusion. Results are shown for groups of subjects who were observed to exhibit Grade 0 CRS (triangles), Grade 1-3 CRS (square) or Grade 4-5 CRS (circles) following the treatment. The parameters included neutrophil count (1000/μL.
Figure 15B:
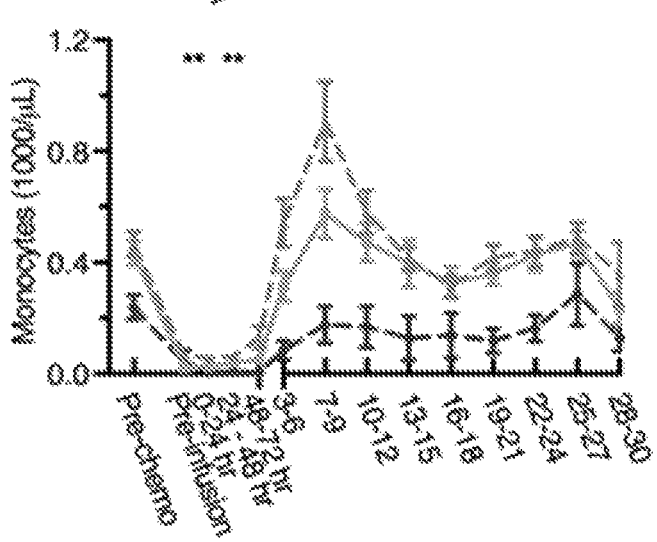
Figure 15C:
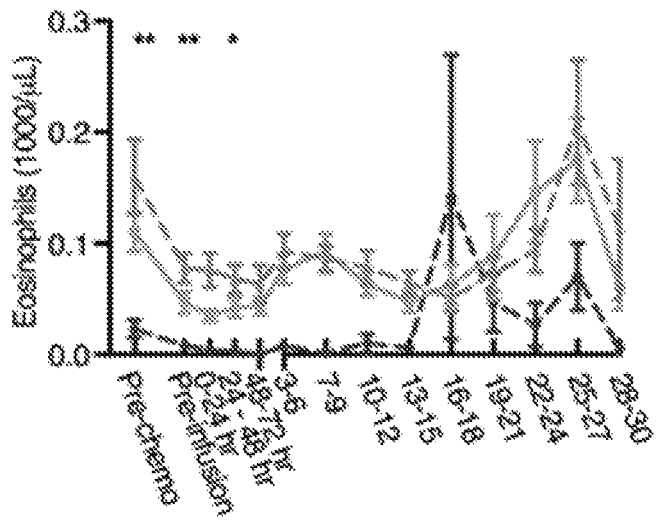
Figure 15D:
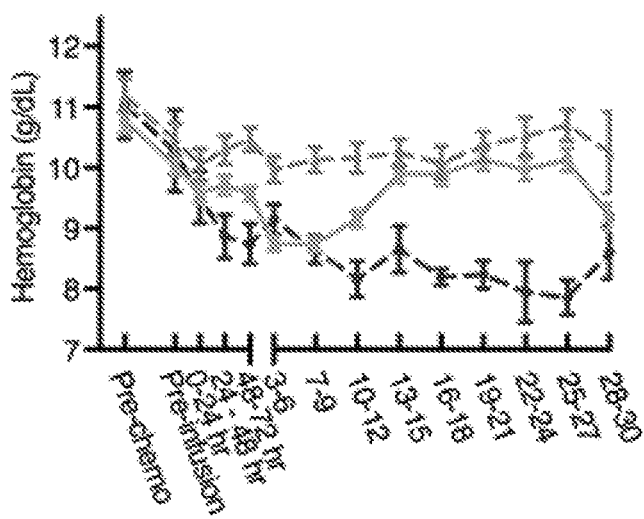
Figure 15E:
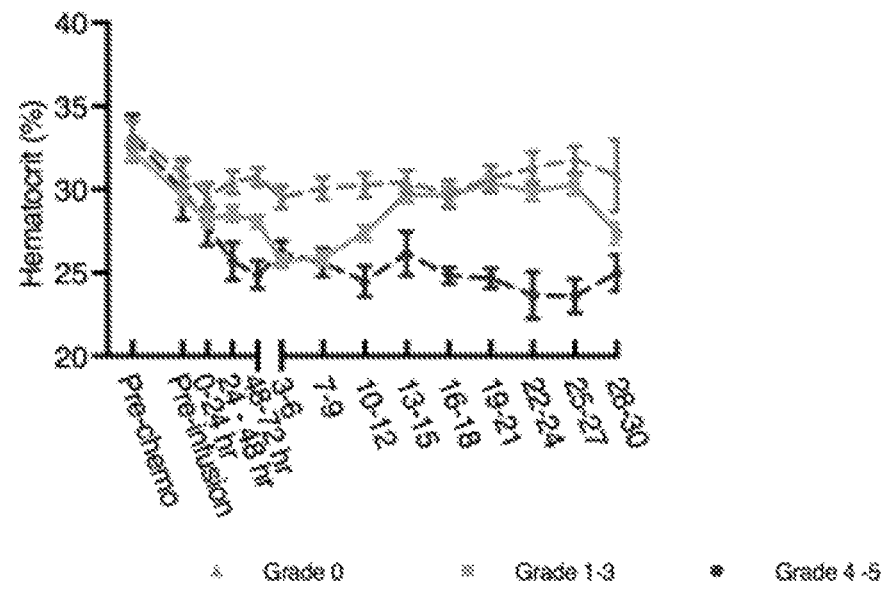
Figure 16A:
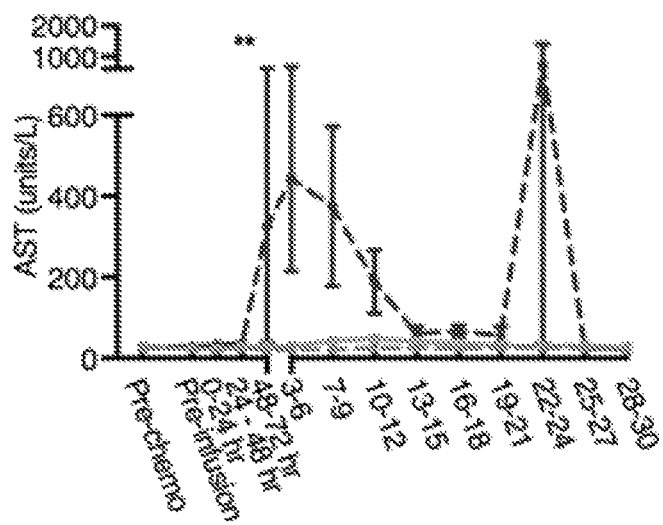
FIGS. 16A-16E show results for levels of various hepatic and renal factors, measured over time in subjects with ALL, NHL or CLL, following treatment with anti-CD19 CART cell infusion. Results are shown for groups of subjects who were observed to exhibit Grade 0 CRS (triangles), Grade 1-3 CRS (square) or Grade 4-5 CRS (circles) following the treatment. The parameters included aspartate transaminase (AST; units/L.
Figure 16B:
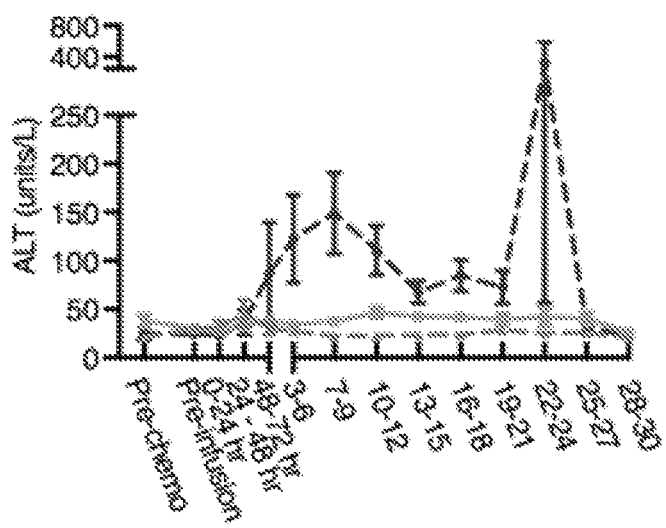
Figure 16C:
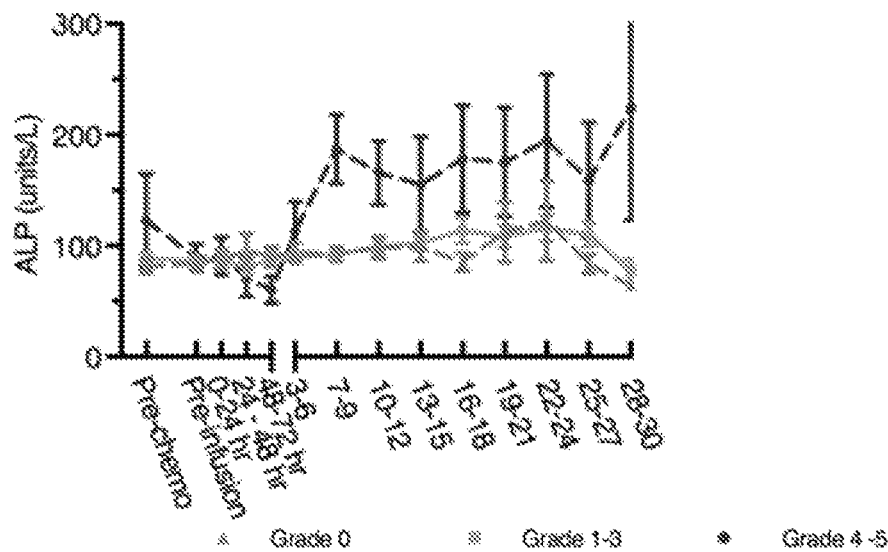
Figure 16D:
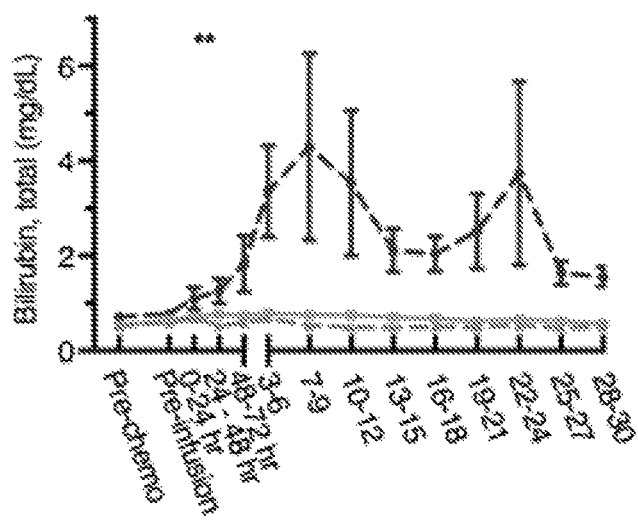
Figure 16E:
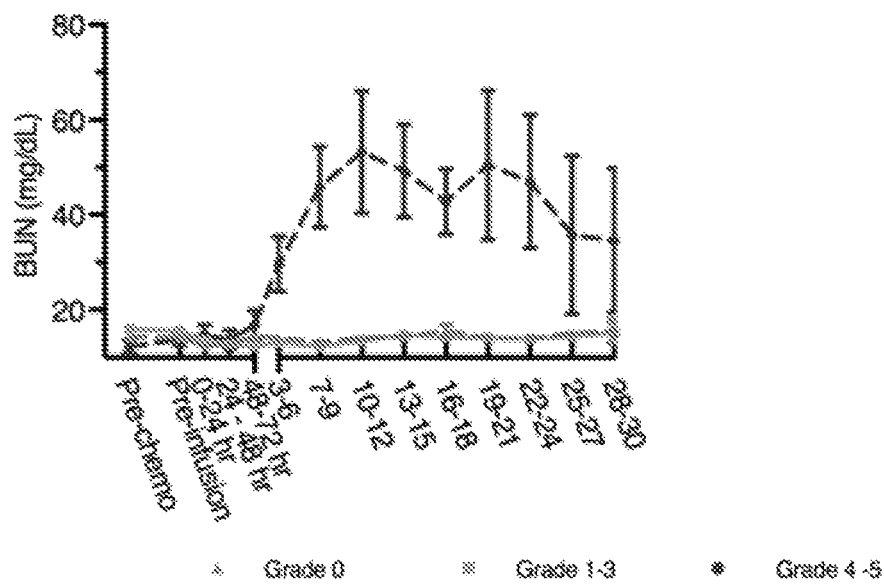

Additional parameters, including hemodynamic parameters, coagulopathy, blood counts, and hepatic and renal function, were monitored over time for correlation to development of grade 0, 1-3 or 4-5 CRS after infusion of CAR+ T cells. FIG. 13A depicts the number of patients at risk for grade 0, grade 1-3 or grade 4-5 toxicity over time. Kinetics for occurrence of fever (temperature) (FIG. 13B), hemodynamic changes (FIG. 13C-F depicting heart rate, systolic blood pressure, diastolic blood pressure or respiratory rate, respectively) or hypoaluminemia and weight gain (FIG. 13G-I, depicting total protein, albumin or weight change, respectively), prior to and post-infusion with CAR+ T cells, showed that development of grade 4-5 CRS was associated with high temperature (fever), higher respiratory rate, early hemodynamic changes, capillary leak (e.g., hypoalbuminemia) and significant weight gain (* $p<0.0001$,  $p<0.05$). As shown in FIGS. 14A-E, kinetics for occurrence of parameters associated with coagulopathy after CAR-T cell infusion showed that the severity of coagulopathy correlated with grade 4-5 CRS ( $p<0.05$). In this study, all subjects represented in FIG. 14E received Cy/Flu lymphodepletion. There also was increased transfusion requirements, as determined by number of units of packed red blood cell counts (pRBCs), platelets or cryoprecipiate, in subjects who developed grade 4-5 CRS. As shown in FIG. 15A-15C, occurrence of cytopenia in subjects having received Cy/Flu lymphodepletion was associated with grade 4-5 CRS, as evidence by persistence of neurtropenia (FIG. 15A), monocytopenia (FIG. 15B) and low eosionophils (FIG. 15C) after the chemotherapy-induced nadir in these subjects compared with subjects with grade 0 or grade 1-3 CRS (* $p<0.00001$,  $p<0.05$). FIG. 15D and FIG. 15E also depict kinetics of hemoglobin (g/dL) and hematocrit percentage (%), respectively, in subjects having developed grade 0, 1-3 or 4-5 CRS after CAR-T cell infusion. Kinetics for occurrence of parameters associated with hepatic (FIG. 16A-D) and renal (FIG. 16E) dysfunction, prior to and post-CAR+ T cell infusion, was associated with grade 4-5 CRS ( $p<0.05$). As shown in FIGS. 17A and 17B, elevation of AST/ALT at day 22-24 in grade 4-5 group was due to one patient who developed late hepatotoxicity.

In sum, Grade 4-5 CRS was associated with earlier onset of fever, early hemodynamic instability, as well as hypoalbuminemia and weight gain consistent with capillary leak syndrome, and more significant coagulopathy and cytopenias that correlated with the higher severity (grade 4-5) of CRS.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
| --- | --- | --- |
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) homo sapiens |
| 3 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer Homo sapiens |

| SEQ ID NO. | SEQUENCE | DESCRIPTION |
|---|---|---|
| 4 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2-CH3 spacer<br>*Homo sapiens* |
| 5 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAGT SVTCTLNHPSLPPQRLMALREPAAQAPVKLSLNLLASSDPPEAASWLLC EVSGFSPPNILLMWLEDQREVNTSGFAPARPPPQPGSTTFWAWSVLRVP APPSPQPATYTCVVSHEDSRTLLNASRSLEVSYVTDH | IgD-hinge-Fc<br>*Homo sapiens* |
| 6 | LEGGGEGRGSLLTCGDVEENPGPR | T2A<br>artificial |
| 7 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | tEGFR<br>artificial |
| 8 | FWVLVVVGGVLACYSLLVTVAFIIFWV | CD28 (amino acids 153-179 of Accession No. P10747)<br>*Homo sapiens* |
| 9 | IEVMYPPPYLDNEKSNGTIIHVKGKHLCPSPLFPGPSKPFWVLVVVGGV LACYSLLVTVAFIIFWV | CD28 (amino acids 114-179 of Accession No. P10747)<br>*Homo sapiens* |
| 10 | RSKRSRLLHSDYMNMTPRRPGPTRKHYQPYAPPRDFAAYRS | CD28 (amino acids 180-220 of P10747)<br>*Homo sapiens* |
| 11 | RSKRSRGGHSDYMNMTPRRPGPTRKHYQPYAPPRDFAAYRS | CD28 (LL to GG)<br>*Homo sapiens* |
| 12 | KRGRKKLLYIFKQPFMRPVQTTQEEDGCSCRFPEEEEGGCEL | 4-1BB (amino acids 214-255 of Q07011.1)<br>*Homo sapiens* |
| 13 | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta<br>*Homo sapiens* |
| 14 | RVKFSRSAEPPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta<br>*Homo sapiens* |
| 15 | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta<br>*Homo sapiens* |
| 16 | RKVCNGIGIGEFKDSLSINATNIKHFKNCTSISGDLHILPVAFRGDSFT HTPPLDPQELDILKTVKEITGFLLIQAWPENRTDLHAFENLEIIRGRTK QHGQFSLAVVSLNITSLGLRSLKEISDGDVIISGNKNLCYANTINWKKL FGTSGQKTKIISNRGENSCKATGQVCHALCSPEGCWGPEPRDCVSCRNV SRGRECVDKCNLLEGEPREFVENSECIQCHPECLPQAMNITCTGRGPDN CIQCAHYIDGPHCVKTCPAGVMGENNTLVWKYADAGHVCHLCHPNCTYG CTGPGLEGCPTNGPKIPSIATGMVGALLLLLVVALGIGLFM | tEGFR<br>artificial |

The invention claimed is:

1. A method of ameliorating the development of toxicity in a subject, the method comprising administering an agent or therapy that is capable of treating, preventing, delaying, or attenuating the development of a toxicity to a subject, wherein the agent or therapy is a corticosteroid or is an anti-IL-6 receptor (anti-IL-6R) antibody or antigen-binding fragment thereof; and wherein the subject is determined to be at risk of developing the toxicity by a method comprising:

(a) detecting a concentration or relative concentration for a biomarker or, individually, for each biomarker in a panel of biomarkers in a biological sample, wherein:
the biomarker or one or more of the biomarkers in the panel of biomarkers, individually, is or comprises a cytokine selected from among transforming growth factor beta (TGF-beta), interleukin 6 (IL-6), interleukin 10 (IL-10), interleukin 15 (IL-15), interferon gamma (IFN-gamma) and monocyte chemoattractant protein-1 (MCP-1); and the biological sample is obtained or has been obtained from the subject no more than 14 days after administration of a cell therapy comprising a dose of T cells expressing a chimeric antigen receptor (CAR) for treating a disease or condition in the subject, wherein the disease or condition is a non-Hodgkin lymphoma (NHL) or acute lymphoblastic leukemia (ALL) or chronic lymphocytic leukemia (CLL); and (b) comparing the concentration or relative concentration detected for the biomarker, or for each of the biomarkers in the panel, individually, to a reference value, wherein the subject is one in which the comparison indicates that the subject is at risk of developing the toxicity, wherein the toxicity is severe neurotoxicity and/or is a grade 3 or higher neurotoxicity.

2. The method of claim 1, wherein the biological sample is obtained or has been obtained from the subject no more than 3 days, no more than 2 days, or no more than 1 day after administration of a cell therapy for treating a disease or condition in the subject.

3. The method of claim 1, wherein the method comprises detecting a concentration or relative concentration of each biomarker in a panel of biomarkers, wherein the panel of biomarkers comprises at least TGF-β and IL-6.

4. The method of claim 1, wherein the biological sample is derived from the subject at a time at which the subject does or did not exhibit a physical sign or symptom of neurotoxicity or cytokine release syndrome (CRS).

5. The method of claim 1, wherein the method comprises detecting a concentration or relative concentration of each biomarker in a panel of biomarkers, wherein the panel of biomarkers comprises at least IL-15 and IL-6.

6. The method of claim 1, wherein the biomarker or panel of biomarkers comprises IL-6.

7. The method of claim 4, wherein neurotoxicity a severe neurotoxicity.

8. The method of claim 1, wherein the biomarker or panel of biomarkers comprise one or a combination of cytokines comprising at least one cytokine selected from among TGF-beta, IL-6 and IL-15 and the comparison indicates that the subject is at risk for developing the toxicity if the detected concentration or relative concentration for at least one of the cytokines meets a classification selected from: (i) for TGF-beta, less than a TGF-beta reference value; (ii) for IL-6, greater than a IL-6 reference value; and/or (iii) for IL-15, greater than a IL-15 reference value.

9. The method of claim 8, wherein the biomarker or panel of biomarkers comprise a first and second cytokine selected from among: TGF-beta and IL-6, TGF-beta and IL-15, or IL-6 and IL-15, and the comparison indicates that the subject is at risk for developing the toxicity
if the detected concentration or relative concentration for each of the first and second cytokines, individually, meets the classification.

10. The method of claim 8, wherein a concentration or relative concentration of each of TGF-beta, IL-6 and IL-15 are detected, and wherein:
if the detected concentration or relative concentration for all three cytokines meet the classification, then the comparison indicates the subject is at risk for the toxicity; or if the detected concentration or relative concentration for at least two of the cytokines meet the classification, then the comparison indicates the subject is at risk for the toxicity.

11. The method of claim 8, wherein:
the TGF-beta reference value is within a range from 5.5 pg/mL to 15.00 pg/mL (log 2 scale) or from 45 pg/mL to 33000 pg/mL;
the IL-6 reference value is within a range from 2.6 pg/mL to 5.4 pg/mL (log 2 scale) or from 6.00 pg/mL to 41.0 pg/mL; and/or
the IL-15 reference value is within a range from 6.1 pg/mL to 7.1 pg/mL (log 2 scale) or from 69.0 pg/mL to 135.0 pg/mL.

12. The method of claim 8, wherein the disease or condition in the subject is a non-Hodgkin lymphoma (NHL).

13. The method of claim 1, wherein the biomarker or panel of biomarkers comprise one or a combination of cytokines comprising at least one cytokine selected from among MCP-1, IL-6 and IL15, and the comparison indicates that the subject is at risk for developing the toxicity, if the detected concentration or relative concentration for at least one of the cytokines meets a classification selected from: (i) for MCP-1, greater than a MCP-1 reference value; (ii) for IL-6, greater than a IL-6 reference value; and/or (iii) for IL-15, greater than a IL-15 reference value.

14. The method of claim 13, wherein
if the detected concentration or relative concentration for at least two of the cytokines or all three cytokines meet the classification, the comparison indicates the subject is at risk of the toxicity.

15. The method of claim 14, wherein:
the IL-6 reference value is within a range, or is a range, from 2.0 pg/mL to 4.0 pg/mL (log 2 scale) or from 6.00 pg/mL to 12.0 pg/mL; and/or
the IL-15 reference value is within a range, or is a range, from 5.0 pg/mL to 6.5 pg/mL (log 2 scale) or from 40.0 pg/mL to 90.0 pg/mL; and/or
the MCP-1 reference value is within a range, or is a range, from 7.00 pg/mL to 12.0 pg/mL (log 2 scale) or from 700 pg/mL to 1400 pg/mL.

16. The method of claim 13, wherein the disease or condition in the subject is acute lymphoblastic leukemia (ALL).

17. The method of claim 8, further comprising:
detecting a concentration or relative concentration for IL-10 or IFN-gamma in a sample from the subject, wherein the biological sample is or has been derived from the subject no more than three days after the administration of the cells; and
identifying the subject as at risk of developing neurotoxicity if the detected concentration or relative concentration of IL-10 and/or IFN-gamma meets a classification selected from: iv) the concentration or relative concentration for IL-10 is greater than a IL-10 reference value; or v) the concentration or relative concentration for IFN-gamma is greater than a IFN-gamma reference value.

18. The method of claim 13, further comprising:
detecting a concentration or relative concentration for IL-10 or IFN-gamma in a sample from the subject, wherein the biological sample is or has been derived from the subject no more than three days after the administration of the cells; and
identifying the subject as at risk of developing neurotoxicity if the detected concentration or relative concentration of IL-10 and/or IFN-gamma meets a classification selected from: iv) the concentration or relative concentration for IL-10 is greater than a IL-10 reference value; or v) the concentration or relative concentration for IFN-gamma is greater than a IFN-gamma reference value.

19. The method of claim 17, wherein:
the IL-10 reference value is a reference value that is at least 3.0 pg/mL (log 2 scale) or is at least 10.0 pg/mL; and/or
the IFN-gamma reference value is a reference value that is at least 4.0 pg/mL (log 2 scale) or is at least 18.0 pg/mL.

20. The method of claim 1, wherein the biomarker or panel of biomarkers comprise one or a combination of cytokines comprising at least one cytokine selected from among IL-6, MCP-1, IL-10 and IL-15, and the comparison indicates that the subject is at risk for developing the toxicity if the detected concentration or relative concentration for at least one of the cytokines meets a classification selected from: (i) the concentration or relative concentration for IL-6 is greater than an IL-6 reference value; (ii) the concentration or relative concentration for MCP-1 is greater than a MCP-1 reference value; and/or (iii) the concentration or relative concentration for IL-10 is greater than a IL-10 reference value; and/or the concentration or relative concentration for IL-15 is greater than a IL-15 reference value.

21. The method of claim 20, wherein:
the IL-6 reference value is a reference value that is at least 26.0 pg/mL; and/or
the MCP-1 reference value is a reference value that is at least 1343.0 pg/mL; and/or
the IL-10 reference value is a reference value that is at least 30.0 pg/mL; and/or
the IL-15 reference value is a reference value that is at least 89.0 pg/mL.

22. The method claim 1, wherein the biological sample is obtained or has been obtained from the subject within 2 days after administration of the cell therapy.

23. The method of claim 1, wherein the biological sample is obtained or has been obtained from the subject at 1 day after administration of the cell therapy.

24. The method of claim 1, wherein the agent is tocilizumab, sarilumab, or a corticosteroid.

25. The method of claim 1, wherein the method further comprises, after administration of the agent, monitoring the efficacy of the agent on the treatment, prevention, delay, or attenuation of toxicity.

26. The method of claim 1, wherein the biological sample is a bodily fluid from the subject selected from whole blood, serum or plasma.

27. The method of claim 1, wherein the biological sample is a serum sample.

28. The method of claim 11, wherein the disease or condition in the subject is NHL.

29. The method of claim 28, wherein the biological sample is obtained or has been obtained from the subject no more than at 1 day after administration of the cell therapy.

30. The method of claim 14, wherein the disease or condition in the subject is ALL.

31. The method of claim 30, wherein the biological sample is obtained or has been obtained from the subject no more than at or about 1 day after administration of the cell therapy.

* * * * *

SEQUENCE LISTING

<160> NUMBER OF SEQ ID NOS: 16

<210> SEQ ID NO 1
<211> LENGTH: 12
<212> TYPE: PRT
<213> ORGANISM: Homo sapiens
<220> FEATURE:
<223> OTHER INFORMATION: spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 2
gaatctaagt acggaccgcc ctgccccct tgccct                          36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

```
Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
                130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
                20                  25                  30

Thr Thr Arg Asn Thr Gly Arg Gly Gly Glu Glu Lys Lys Lys Glu Lys
                35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
                115                 120                 125

Ser Gln Ser Gln His Ser Arg Leu Thr Leu Pro Arg Ser Leu Trp Asn
                130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175
```

```
Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
            275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
```

-continued

```
                165                 170                 175
Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
            210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
                260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
            355

<210> SEQ ID NO 8
<211> LENGTH: 27
<212> TYPE: PRT
<213> ORGANISM: Homo sapiens
<220> FEATURE:
<223> OTHER INFORMATION: CD28

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val
65
```

<210> SEQ ID NO 10
<211> LENGTH: 41
<212> TYPE: PRT
<213> ORGANISM: Homo sapiens
<220> FEATURE:
<223> OTHER INFORMATION: CD28

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Artificial Sequence
<220> FEATURE:
<223> OTHER INFORMATION: CD28 (LL to GG)

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Homo sapiens
<220> FEATURE:
<223> OTHER INFORMATION: CD3zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

```
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 14
<211> LENGTH: 112
<212> TYPE: PRT
<213> ORGANISM: Homo sapiens
<220> FEATURE:
<223> OTHER INFORMATION: CD3zeta

<400> SEQUENCE: 14

```
Arg Val Lys Phe Ser Arg Ser Ala Glu Pro Pro Ala Tyr Gln Gln Gly
  1               5                  10                  15

Gln Asn Gln Leu Tyr Asn Glu Leu Asn Leu Gly Arg Arg Glu Glu Tyr
                 20                  25                  30

Asp Val Leu Asp Lys Arg Arg Gly Arg Asp Pro Glu Met Gly Gly Lys
             35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 15
<211> LENGTH: 112
<212> TYPE: PRT
<213> ORGANISM: Homo sapiens
<220> FEATURE:
<223> OTHER INFORMATION: CD3zeta

<400> SEQUENCE: 15

```
Arg Val Lys Phe Ser Arg Ser Ala Asp Ala Pro Ala Tyr Lys Gln Gly
  1               5                  10                  15

Gln Asn Gln Leu Tyr Asn Glu Leu Asn Leu Gly Arg Arg Glu Glu Tyr
                 20                  25                  30

Asp Val Leu Asp Lys Arg Arg Gly Arg Asp Pro Glu Met Gly Gly Lys
             35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 16
<211> LENGTH: 335

-continued

```
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```